(12) United States Patent
Yang et al.

(10) Patent No.: US 9,839,698 B2
(45) Date of Patent: Dec. 12, 2017

(54) LIGHT-SWITCHABLE GENE EXPRESSION SYSTEM

(75) Inventors: Yi Yang, Shanghai (CN); Xue Wang, Shanghai (CN); Xianjun Chen, Shanghai (CN)

(73) Assignee: EAST CHINA UNIVERSITY OF SCIENCE AND TECHNOLOGY, Xuhui District, Shanghai (CN)

( * ) Notice: Subject to any disclaimer, the term of this patent is extended or adjusted under 35 U.S.C. 154(b) by 0 days.

(21) Appl. No.: 14/001,865

(22) PCT Filed: Feb. 27, 2012

(86) PCT No.: PCT/CN2012/071679
§ 371 (c)(1),
(2), (4) Date: Aug. 27, 2013

(87) PCT Pub. No.: WO2012/116621
PCT Pub. Date: Sep. 7, 2012

(65) Prior Publication Data
US 2013/0345294 A1    Dec. 26, 2013

(30) Foreign Application Priority Data
Feb. 28, 2011 (CN) .......... 2011 1 0048142

(51) Int. Cl.
C12N 15/63 (2006.01)
A61K 48/00 (2006.01)
C12N 15/85 (2006.01)

(52) U.S. Cl.
CPC .......... *A61K 48/0083* (2013.01); *C12N 15/63* (2013.01); *C12N 15/85* (2013.01); *C07K 2319/00* (2013.01); *C12N 2830/001* (2013.01)

(58) Field of Classification Search
None
See application file for complete search history.

(56) References Cited

U.S. PATENT DOCUMENTS

2012/0237966 A1* 9/2012 Dolmetsch et al. ............ 435/29
2014/0325692 A1* 10/2014 Gardner et al. ................ 800/13

FOREIGN PATENT DOCUMENTS

WO    WO02097137         12/2002
WO    WO2005093075 A1    10/2005

OTHER PUBLICATIONS

Shimizu-Sato et al., A light-switchable gene promoter system, Nature biotechnology, vol. 20, pp. 1041-1044, Sep. 3, 2002 (Sep. 3, 2002).*
Oh et al. (Bacteriol. 2009; 191: 2419-2420).*
Rivera-Cancel et al. (Biochemistry. 2012; 51: 10024-10034).*
Strickland et al. (PNAS. Aug. 5, 2008; 105(31): 10709-10714).*
Yazawa et al. (Nature Biotechnology. Oct 2009. 27(10): 941-945, and online methods, doi:10.1038/nbt.1569).*
Mizutani et al. (The EMBO Journal. 2003; 22(9): 2178-2187).*
www.uspto.gov/sites/default/files/documents/112b_workshop.pptx (downloaded Feb. 21, 2016).*
Wang et al. Nature Methods 9, 266-269 (2012).*
Maria Papatriantafyllou. Nature Reviews Molecular Cell Biology 13, 210 (Apr. 2012).*
Sae Shimizu-Dato et al., A light-switchable gene promoter system, Nature biotechnology, vol. 20, pp. I041-1044, Sep. 3, 2002(Sep. 3, 2002), See p. 1041 and fig. 1.
IMasayuki Yazawa et al., Induction of protein-protein interactions in live cells using light, Nat Biotechnol., vol. 27, No. 10, pp. 941-945 and "Online Methods", Oct. 4, 2009(Oct. 4, 2009), See the whole document.
Thomas Drepper et al., Lights on and action! Controlling microbial gene expression by light, Appl Microbiol Biotechnol, vol. 90, No. 1, pp. 23-40 !J[,Feb. 20, 2011(Feb. 20, 2011), See the whole document.
Matthew J Kennedy et al., Rapid blue-light-mediated induction of protein interactions in living cells, Nature Methods, vol. 7 , No. 12, pp. 973-975 and "Online Methods", Oct. 31, 2010(Oct. 31, 2010), See the whole document.

* cited by examiner

*Primary Examiner* — Scott Long
(74) *Attorney, Agent, or Firm* — Global IP Services; Tianhua Gu

(57) ABSTRACT

Provided is a light-switchable gene expression system, comprising: a) a recombinant light-switchable transcription factor-encoding gene, said recombinant light-switchable transcription factor comprising a first polypeptide as the DNA bonding domain, a second polypeptide as the photosensitive domain, and a third polypeptide as the transcription regulatory domain; b) a target transcription unit comprising at least one reaction element recognized and bound by the first polypeptide, a promoter regulated by the third polypeptide and a nucleotide sequence to be transcribed. Also provided is an eukaryotic expression vector comprising said light-switchable gene expression system, and a method for regulating gene expression in a host cell by using the light-switchable gene expression system. Also provided is a reagent kit containing different elements of the light-switchable gene expression system. The light-switchable gene expression system has a quick, effective and powerful induction with little or no toxicity. It is safer than other inducers, and can spatiotemporally control gene expression.

12 Claims, 14 Drawing Sheets

SEQUENCE LISTING

<160> NUMBER OF SEQ ID NOS: 250

<210> SEQ ID NO 1
<211> LENGTH: 441
<212> TYPE: DNA
<213> ORGANISM: Saccharomy cescerevisiae

```
<400> SEQUENCE: 1
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120 tctcccaaaa ccaaaaggtc tccgctgact agggcacatc tgacagaagt ggaatcaagg    180
ctagaaagac tggaacagct atttctactg attttcctc gagaagacct tgacatgatt     240
ttgaaaatgg attctttaca ggatataaaa gcattgttaa caggattatt tgtacaagat    300
aatgtgaata agatgccgt cacagataga ttggcttcag tggagactga tatgcctcta    360
acattgagac agcatagaat aagtgcgaca tcatcatcgg aagagagtag taacaaaggt    420
caaagacagt tgactgtatc g                                              441

<210> SEQ ID NO 2
<211> LENGTH: 147
<212> TYPE: PRT
<213> ORGANISM: Saccharomy cescerevisiae

<400> SEQUENCE: 2

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145

<210> SEQ ID NO 3
<211> LENGTH: 858
<212> TYPE: DNA
<213> ORGANISM: Artificial sequence
<220> FEATURE:
<223> OTHER INFORMATION: Synthetic

<400> SEQUENCE: 3
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120 tctcccaaaa ccaaaaggtc tccgctgact agggcacatc tgacagaagt ggaatcaagg    180
ctagaaagac tggaaagatc catcgccacc agatctcata cgctctacgc tcccggcggt    240
tatgacatta tgggctatct gattcagatt atgaacaggc aaaccccca gtagaactg      300 ggacctgttg acacgtcatg cgctctgatt ctgtgcgacc tgaagcaaaa agacacgcca    360
attgtgtacg cctcggaagc ttttctctat atgacaggat acagcaatgc ggaggtcttg    420
```

```
gggagaaact gccgttttct tcagtcaccc gacggaatgg tcaagccgaa atcgacaagg    480
aagtacgtcg actccaacac gatcaatacg atgaggaaag cgattgatag gaacgccgag    540
gtgcaggttg aggtggtcaa ttttaagaag aacggccaac ggtttgtcaa cttcttgacg    600
atgattccgg tgcgagatga aacaggggaa taccggtaca gcatgggttt ccagtgcgaa    660
acggaactgc agtacccata cgatgttcca gattacgctg aattcccggg gatctcgacg    720
gcccccccga ccgatgtcag cctggggac gagctccact tagacggcga ggacgtggcg     780
atggcgcatg ccgacgcgct agacgatttc gatctggaca tgttggggga cggggattcc    840
ccgggtccgg gatcgcca                                                  858
```

<210> SEQ ID NO 4
<211> LENGTH: 286
<212> TYPE: PRT
<213> ORGANISM: Artificial sequence
<220> FEATURE:
<223> OTHER INFORMATION: Synthetic

<400> SEQUENCE: 4

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Asn Arg Pro Asn Pro
                85                  90                  95

Gln Val Glu Leu Gly Pro Val Asp Thr Ser Cys Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Leu Gln
    210                 215                 220

Tyr Pro Tyr Asp Val Pro Asp Tyr Ala Glu Phe Pro Gly Ile Ser Thr
225                 230                 235                 240

Ala Pro Pro Thr Asp Val Ser Leu Gly Asp Glu Leu His Leu Asp Gly
                245                 250                 255

Glu Asp Val Ala Met Ala His Ala Asp Ala Leu Asp Asp Phe Asp Leu
            260                 265                 270

Asp Met Leu Gly Asp Gly Asp Ser Pro Gly Pro Gly Ser Pro
        275                 280                 285
```

<210> SEQ ID NO 5
<211> LENGTH: 261
<212> TYPE: DNA
<213> ORGANISM: E.coli

<400> SEQUENCE: 5

```
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc g                                               261
```

<210> SEQ ID NO 6
<211> LENGTH: 87
<212> TYPE: PRT
<213> ORGANISM: E.coli

<400> SEQUENCE: 6

```
Met Lys Ala Leu Thr Ala Arg Gln Gln Glu Val Phe Asp Leu Ile Arg
1               5                   10                  15
Asp His Ile Ser Gln Thr Gly Met Pro Pro Thr Arg Ala Glu Ile Ala
            20                  25                  30
Gln Arg Leu Gly Phe Arg Ser Pro Asn Ala Ala Glu Glu His Leu Lys
        35                  40                  45
Ala Leu Ala Arg Lys Gly Val Ile Glu Ile Val Ser Gly Ala Ser Arg
    50                  55                  60
Gly Ile Arg Leu Leu Gln Glu Glu Glu Glu Gly Leu Pro Leu Val Gly
65                  70                  75                  80
Arg Val Ala Ala Gly Glu Pro
            85
```

<210> SEQ ID NO 7
<211> LENGTH: 1182
<212> TYPE: DNA
<213> ORGANISM: Artificial sequence
<220> FEATURE:
<223> OTHER INFORMATION: Synthetic

<400> SEQUENCE: 7

```
atggataaag cggaattaat tcccgagcct ccaaaaaaga agagaaaggt cgaattgggt      60
accgccgccg gtggtggctc tggaggcatg aaagcgttaa cggccaggca acaagaggtg     120
tttgatctca tccgtgatca catcagccag acaggtatgc cgccgacgcg tgcggaaatc     180
gcgcagcgtt tggggttccg ttccccaaac gcggctgaag aacatctgaa ggcgctggca     240
cgcaaaggcg ttattgaaat tgtttccggc gcatcacgcg ggattcgtct gttgcaggaa     300
gaggaagaag ggttgccgct ggtaggtcgt gtggctgccg gtgaaccgag atctcatacg     360
ctctacgctc ccgcggtta tgacattatg gctatctga ttcagattat gaagaggcca      420
aaccccaag tagaactggg acctgttgac acgtcagttg ctctgattct gtgcgacctg     480
aagcaaaag acacgccaat tgtgtacgcc tcggaagctt ttctctatat gacaggatac     540
agcaatgcgg aggtcttggg gagaaactgc cgtttttctt agtcacccga cggaatggtc     600
aagccgaaat cgacaaggaa gtacgtcgac tccaacacga tcaatacgat gaggaaagcg     660
attgatagga acgccgaggt gcaggttgag gtggtcaatt ttaagaagaa cggccaacgg     720
```

```
tttgtcaact tcttgacgat gattccggtg cgagatgaaa caggggaata ccggtacagc    780
atgggtttcc agtgcgaaac ggaaggatcc ggcggtggtg gatcaggtgg aggtggctcc    840
aattttaatc aaagtgggaa tattgctgat agctcattgt ccttcacttt cactaacagt    900
agcaacggtc cgaacctcat aacaactcaa acaaattctc aagcgctttc acaaccaatt    960
gcctcctcta acgttcatga taacttcatg aataatgaaa tcacggctag taaaattgat   1020
gatggtaata attcaaaacc actgtcacct ggttggacgg accaaactgc gtataacgcg   1080
tttggaatca ctacagggat gtttaatacc actacaatgg atgatgtata aactatcta   1140 ttcgatgatg aagataccccc accaaaccca aaaaagagt aa                      1182
```

<210> SEQ ID NO 8
<211> LENGTH: 393
<212> TYPE: PRT
<213> ORGANISM: Artificial sequence
<220> FEATURE:
<223> OTHER INFORMATION: Synthetic

<400> SEQUENCE: 8

```
Met Asp Lys Ala Glu Leu Ile Pro Glu Pro Lys Lys Lys Arg Lys
1               5                   10                  15

Val Glu Leu Gly Thr Ala Ala Gly Gly Ser Gly Gly Met Lys Ala
                20                  25                  30

Leu Thr Ala Arg Gln Gln Glu Val Phe Asp Leu Ile Arg Asp His
            35                  40                  45      Ile

Ser Gln Thr Gly Met Pro Pro Thr Arg Ala Glu Ile Ala Gln Arg Leu
50                  55                  60

Gly Phe Arg Ser Pro Asn Ala Ala Glu Glu His Leu Lys Ala Leu Ala
65                  70                  75                  80

Arg Lys Gly Val Ile Glu Ile Val Ser Gly Ala Ser Arg Gly Ile Arg
                85                  90                  95

Leu Leu Gln Glu Glu Glu Gly Leu Pro Leu Val Gly Arg Val Ala
            100                 105                 110

Ala Gly Glu Pro Arg Ser His Thr Leu Tyr Ala Pro Gly Gly Tyr Asp
            115                 120                 125

Ile Met Gly Tyr Leu Ile Gln Ile Met Lys Arg Pro Asn Pro Gln Val
130                 135                 140

Glu Leu Gly Pro Val Asp Thr Ser Val Ala Leu Ile Leu Cys Asp Leu
145                 150                 155                 160

Lys Gln Lys Asp Thr Pro Ile Val Tyr Ala Ser Glu Ala Phe Leu Tyr
                165                 170                 175

Met Thr Gly Tyr Ser Asn Ala Glu Val Leu Gly Arg Asn Cys Arg Phe
            180                 185                 190

Leu Gln Ser Pro Asp Gly Met Val Lys Pro Lys Ser Thr Arg Lys Tyr
            195                 200                 205

Val Asp Ser Asn Thr Ile Asn Thr Met Arg Lys Ala Ile Asp Arg Asn
        210                 215                 220

Ala Glu Val Gln Val Glu Val Asn Phe Lys Lys Asn Gly Gln Arg
225                 230                 235                 240

Phe Val Asn Phe Leu Thr Met Ile Pro Val Arg Asp Glu Thr Gly Glu
                245                 250                 255

Tyr Arg Tyr Ser Met Gly Phe Gln Cys Glu Thr Glu Gly Ser Gly Gly
            260                 265                 270

Gly Gly Ser Gly Gly Gly Gly Ser Asn Phe Asn Gln Ser Gly Asn Ile
```

```
            275                 280                 285
Ala Asp Ser Ser Leu Ser Phe Thr Phe Thr Asn Ser Ser Asn Gly Pro
        290                 295                 300

Asn Leu Ile Thr Thr Gln Thr Asn Ser Gln Ala Leu Ser Gln Pro Ile
305                 310                 315                 320

Ala Ser Ser Asn Val His Asp Asn Phe Met Asn Asn Glu Ile Thr Ala
                325                 330                 335

Ser Lys Ile Asp Asp Gly Asn Asn Ser Lys Pro Leu Ser Pro Gly Trp
            340                 345                 350

Thr Asp Gln Thr Ala Tyr Asn Ala Phe Gly Ile Thr Thr Gly Met Phe
                355                 360                 365

Asn Thr Thr Thr Met Asp Asp Val Tyr Asn Tyr Leu Phe Asp Asp Glu
        370                 375                 380

Asp Thr Pro Pro Asn Pro Lys Lys Glu
385                 390

<210> SEQ ID NO 9
<211> LENGTH: 186
<212> TYPE: DNA
<213> ORGANISM: E.coli

<400> SEQUENCE: 9
atgaaaccag taacgttata cgatgtcgca gagtatgccg gtgtctctta tcagaccgtt      60
tcccgcgtgg tgaaccaggc cagccacgtt tctgcgaaaa cgcgggaaaa agtggaagcg     120
gcgatggcgg agctgaatta cattcccaac cgcgtggcac aacaactggc gggcaaacag     180
tcgttg                                                                186

<210> SEQ ID NO 10
<211> LENGTH: 62
<212> TYPE: PRT
<213> ORGANISM: E.coli

<400> SEQUENCE: 10

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu
    50                  55                  60

<210> SEQ ID NO 11
<211> LENGTH: 1107
<212> TYPE: DNA
<213> ORGANISM: Artificial sequence
<220> FEATURE:
<223> OTHER INFORMATION: Synthetic

<400> SEQUENCE: 11
atggataaag cggaattaat tcccgagcct ccaaaaaaga agagaaaggt cgaattgggt      60
accgccgccg gtggtggctc tgaggcatg aaaccagtaa cgttatacga tgtcgcagag     120
tatgccggtg tctcttatca gaccgtttcc cgcgtggtga accaggccag ccacgtttct     180
gcgaaaacgc gggaaaaagt ggaagcggcg atggcggagc tgaattacat tcccaaccgc     240
gtggcacaac aactggcggg caaacagtcg ttgagatctc tacgctctac gctcccggc     300
```

```
ggttatgaca ttatgggcta tctgattcag attatgaaga ggccaaaccc ccaagtagaa    360
ctgggacctg ttgacacgtc agttgctctg attctgtgcg acctgaagca aaaagacacg    420
ccaattgtgt acgcctcgga agcttttctc tatatgacag gatacagcaa tgcggaggtc    480
ttggggagaa actgccgttt tcttcagtca cccgacggaa tggtcaagcc gaaatcgaca    540
aggaagtacg tcgactccaa cacgatcaat acgatgagga aagcgattga taggaacgcc    600
gaggtgcagg ttgaggtggt caattttaag aagaacggcc aacggtttgt caacttcttg    660
acgatgattc cggtgcgaga tgaaacaggg gaataccggt acagcatggg tttccagtgc    720
gaaacggaag gatccggcgg tggtggatca ggtggaggtg gctccaattt taatcaaagt    780
gggaatattg ctgatagctc attgtccttc actttcacta cagtagcaa cggtccgaac    840
ctcataacaa ctcaaacaaa ttctcaagcg ctttcacaac caattgcctc ctctaacgtt    900
catgataact tcatgaataa tgaaatcacg gctagtaaaa ttgatgatgg taataattca    960
aaaccactgt cacctggttg gacggaccaa actgcgtata acgcgtttgg aatcactaca   1020
gggatgttta taccactac aatggatgat gtatataact atctattcga tgatgaagat   1080
accccaccaa acccaaaaaa agagtaa                                      1107
```

<210> SEQ ID NO 12
<211> LENGTH: 368
<212> TYPE: PRT
<213> ORGANISM: Artificial sequence
<220> FEATURE:
<223> OTHER INFORMATION: Synthetic

<400> SEQUENCE: 12

```
Met Asp Lys Ala Glu Leu Ile Pro Glu Pro Pro Lys Lys Arg Lys
1               5                   10                  15

Val Glu Leu Gly Thr Ala Ala Gly Gly Gly Ser Gly Gly Met Lys Pro
            20                  25                  30

Val Thr Leu Tyr Asp Val Ala Glu Tyr Ala Gly Val Ser Tyr Gln Thr
        35                  40                  45

Val Ser Arg Val Val Asn Gln Ala Ser His Val Ser Ala Lys Thr Arg
    50                  55                  60

Glu Lys Val Glu Ala Ala Met Ala Glu Leu Asn Tyr Ile Pro Asn Arg
65                  70                  75                  80

Val Ala Gln Gln Leu Ala Gly Lys Gln Ser Leu Arg Ser His Thr Leu
                85                  90                  95

Tyr Ala Pro Gly Gly Tyr Asp Ile Met Gly Tyr Leu Ile Gln Ile Met
            100                 105                 110

Lys Arg Pro Asn Pro Gln Val Glu Leu Gly Pro Val Asp Thr Ser Val
        115                 120                 125

Ala Leu Ile Leu Cys Asp Leu Lys Gln Lys Asp Thr Pro Ile Val Tyr
    130                 135                 140

Ala Ser Glu Ala Phe Leu Tyr Met Thr Gly Tyr Ser Asn Ala Glu Val
145                 150                 155                 160

Leu Gly Arg Asn Cys Arg Phe Leu Gln Ser Pro Asp Gly Met Val Lys
                165                 170                 175

Pro Lys Ser Thr Arg Lys Tyr Val Asp Ser Asn Thr Ile Asn Thr Met
            180                 185                 190

Arg Lys Ala Ile Asp Arg Asn Ala Glu Val Gln Val Glu Val Val Asn
        195                 200                 205

Phe Lys Lys Asn Gly Gln Arg Phe Val Asn Phe Leu Thr Met Ile Pro
    210                 215                 220
```

```
Val Arg Asp Glu Thr Gly Glu Tyr Arg Tyr Ser Met Gly Phe Gln Cys
225                 230                 235                 240

Glu Thr Glu Gly Ser Gly Gly Gly Ser Gly Gly Gly Gly Gly Ser Asn
            245                 250                 255

Phe Asn Gln Ser Gly Asn Ile Ala Asp Ser Ser Leu Ser Phe Thr Phe
        260                 265                 270

Thr Asn Ser Ser Asn Gly Pro Asn Leu Ile Thr Thr Gln Thr Asn Ser
    275                 280                 285

Gln Ala Leu Ser Gln Pro Ile Ala Ser Ser Asn Val His Asp Asn Phe
290                 295                 300

Met Asn Asn Glu Ile Thr Ala Ser Lys Ile Asp Asp Gly Asn Asn Ser
305                 310                 315                 320

Lys Pro Leu Ser Pro Gly Trp Thr Asp Gln Thr Ala Tyr Asn Ala Phe
                325                 330                 335

Gly Ile Thr Thr Gly Met Phe Asn Thr Thr Thr Met Asp Asp Val Tyr
            340                 345                 350

Asn Tyr Leu Phe Asp Asp Glu Asp Thr Pro Pro Asn Pro Lys Lys Glu
        355                 360                 365
```

<210> SEQ ID NO 13
<211> LENGTH: 189
<212> TYPE: DNA
<213> ORGANISM: E.coli

<400> SEQUENCE: 13

```
atgtctaggc tagataagag caaagtcatc aattccgcgt tggaattact taacgaagta      60
ggtattgagg gtttgactac gagaaaacta gcgcaaaaat tgggtgtgga acaaccaaca     120
ctatactggc acgttaagaa taaacgtgca ttattagacg cattagccat cgagatgctg     180
gatagacac                                                              189
```

<210> SEQ ID NO 14
<211> LENGTH: 63
<212> TYPE: PRT
<213> ORGANISM: E.coli

<400> SEQUENCE: 14

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His
    50                  55                  60
```

<210> SEQ ID NO 15
<211> LENGTH: 1116
<212> TYPE: DNA
<213> ORGANISM: Artificial sequence
<220> FEATURE:
<223> OTHER INFORMATION: Synthetic

<400> SEQUENCE: 15

```
atggataaag cggaattaat tcccgagcct ccaaaaaaga agagaaaggt cgaattgggt      60
accgccgccg gtggtggctc tggaggcatg tctaggctag ataagagcaa agtcatcaat     120
tccgcgttgg aattacttaa cgaagtaggt attgagggtt tgactacgag aaaactagcg     180
```

-continued

```
caaaaattgg gtgtggaaca accaacacta tactggcacg ttaagaataa acgtgcatta    240
ttagacgcat tagccatcga gatgctggat agacacggca ccagatctca tacgctctac    300
gctcccggcg ttatgacat tatgggctat ctgattcaga ttatgaagag gccaaacccc     360
caagtagaac tgggacctgt tgacacgtca gttgctctga ttctgtgcga cctgaagcaa    420
aaagacacgc caattgtgta cgcctcggaa gcttttctct atatgacagg atacagcaat    480
gcggaggtct tggggagaaa ctgccgtttt cttcagtcac ccgacggaat ggtcaagccg    540
aaatcgacaa ggaagtacgt cgactccaac acgatcaata cgatgaggaa agcgattgat    600
aggaacgccg aggtgcaggt tgaggtggtc aattttaaga agaacggcca acggtttgtc    660
aacttcttga cgatgattcc ggtgcgagat gaaacagggg aataccggta cagcatgggt    720
ttccagtgcg aaacggaagg atccggcggt ggtggatcag gtggaggtgg ctccaatttt    780
aatcaaagtg ggaatattgc tgatagctca ttgtccttca ctttcactaa cagtagcaac    840
ggtccgaacc tcataacaac tcaaacaaat tctcaagcgc tttcacaacc aattgcctcc    900
tctaacgttc atgataactt catgaataat gaaatcacgg ctagtaaaat tgatgatggt    960
aataattcaa aaccactgtc acctggttgg acggaccaaa ctgcgtataa cgcgtttgga   1020
atcactacag ggatgtttaa taccactaca atggatgatg tatataacta tctattcgat   1080
gatgaagata ccccaccaaa cccaaaaaaa gagtaa                              1116
```

<210> SEQ ID NO 16  
<211> LENGTH: 371  
<212> TYPE: PRT  
<213> ORGANISM: Artificial sequence  
<220> FEATURE:  
<223> OTHER INFORMATION: Synthetic

<400> SEQUENCE: 16

```
Met Asp Lys Ala Glu Leu Ile Pro Glu Pro Pro Lys Lys Arg Lys
1               5                  10                 15

Val Glu Leu Gly Thr Ala Ala Gly Gly Ser Gly Gly Met Ser Arg
            20                  25                  30

Leu Asp Lys Ser Lys Val Ile Asn Ser Ala Leu Glu Leu Leu Asn Glu
        35                  40                  45

Val Gly Ile Glu Gly Leu Thr Thr Arg Lys Leu Ala Gln Lys Leu Gly
50                  55                  60

Val Glu Gln Pro Thr Leu Tyr Trp His Val Lys Asn Lys Arg Ala Leu
65                  70                  75                  80

Leu Asp Ala Leu Ala Ile Glu Met Leu Asp Arg His Gly Thr Arg Ser
                85                  90                  95

His Thr Leu Tyr Ala Pro Gly Gly Tyr Asp Ile Met Gly Tyr Leu Ile
                100                 105                 110

Gln Ile Met Lys Arg Pro Asn Pro Gln Val Glu Leu Gly Pro Val Asp
            115                 120                 125

Thr Ser Val Ala Leu Ile Leu Cys Asp Leu Lys Gln Lys Asp Thr Pro
    130                 135                 140

Ile Val Tyr Ala Ser Glu Ala Phe Leu Tyr Met Thr Gly Tyr Ser Asn
145                 150                 155                 160

Ala Glu Val Leu Gly Arg Asn Cys Arg Phe Leu Gln Ser Pro Asp Gly
                165                 170                 175

Met Val Lys Pro Lys Ser Thr Arg Lys Tyr Val Asp Ser Asn Thr Ile
                180                 185                 190
```

```
Asn Thr Met Arg Lys Ala Ile Asp Arg Asn Ala Glu Val Gln Val Glu
            195                 200                 205

Val Val Asn Phe Lys Lys Asn Gly Gln Arg Phe Val Asn Phe Leu Thr
    210                 215                 220

Met Ile Pro Val Arg Asp Glu Thr Gly Glu Tyr Arg Tyr Ser Met Gly
225                 230                 235                 240

Phe Gln Cys Glu Thr Glu Gly Ser Gly Gly Gly Ser Gly Gly Gly
                245                 250                 255

Gly Ser Asn Phe Asn Gln Ser Gly Asn Ile Ala Asp Ser Ser Leu Ser
            260                 265                 270

Phe Thr Phe Thr Asn Ser Ser Asn Gly Pro Asn Leu Ile Thr Thr Gln
        275                 280                 285

Thr Asn Ser Gln Ala Leu Ser Gln Pro Ile Ala Ser Ser Asn Val His
    290                 295                 300

Asp Asn Phe Met Asn Asn Glu Ile Thr Ala Ser Lys Ile Asp Asp Gly
305                 310                 315                 320

Asn Asn Ser Lys Pro Leu Ser Pro Gly Trp Thr Asp Gln Thr Ala Tyr
                325                 330                 335

Asn Ala Phe Gly Ile Thr Thr Gly Met Phe Asn Thr Thr Thr Met Asp
            340                 345                 350

Asp Val Tyr Asn Tyr Leu Phe Asp Asp Glu Asp Thr Pro Pro Asn Pro
        355                 360                 365

Lys Lys Glu
    370

<210> SEQ ID NO 17
<211> LENGTH: 306
<212> TYPE: DNA
<213> ORGANISM: Bacteriophage lambda

<400> SEQUENCE: 17
atgtctacca agaagaaacc tttaactcaa gaacaattgg aggatgctag aaggttgaag      60
gccatctacg aaaagaaaaa gaatgagtta gggctatctc aggaaagtgt ggccgacaag     120
atgggaatgg gccaatcagg tgttggtgct tgttcaacg ggataaacgc attaaatgcc      180
tacaatgctg ccttactggc aaagatattg aaggtatctg tagaagagtt ctcaccttct     240
attgctcgtg aaatctatga aatgtatgag gcggttagca tgcagccgtc tttgaggtca     300
gaatat                                                                306

<210> SEQ ID NO 18
<211> LENGTH: 102
<212> TYPE: PRT
<213> ORGANISM: Bacteriophage lambda

<400> SEQUENCE: 18

Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Ala Lys Ile Leu Lys Val Ser Val Glu Glu Phe Ser Pro Ser
65                  70                  75                  80
```

Ile Ala Arg Glu Ile Tyr Glu Met Tyr Glu Ala Val Ser Met Gln Pro
                85                  90                  95

Ser Leu Arg Ser Glu Tyr
            100

<210> SEQ ID NO 19
<211> LENGTH: 1227
<212> TYPE: DNA
<213> ORGANISM: Artificial sequence
<220> FEATURE:
<223> OTHER INFORMATION: Synthetic

<400> SEQUENCE: 19
atggataaag cggaattaat tcccgagcct ccaaaaaaga agagaaaggt cgaattgggt      60
accgccgccg gtggtggctc tggaggcatg tctaccaaga gaaacctttt aactcaagaa     120
caattggagg atgctagaag gttgaaggcc atctacgaaa agaaaagaa tgagttaggg      180 ctatctcagg aaagtgtggc cgacaagatg gaatgggcc aatcaggtgt tggtgctttg      240
ttcaacggga taaacgcatt aaatgcctac aatgctgcct actggcaaa gatattgaag      300 gtatctgtag aagagttctc accttctatt gctcgtgaaa tctatgaaat gtatgaggcg     360
gttagcatgc agccgtcttt gaggtcagaa tatagatctc atacgctcta cgctcccggc     420
ggttatgaca ttatgggcta tctgattcag attatgaaga ggccaaaccc ccaagtagaa     480
ctgggacctg ttgacacgtc agttgctctg attctgtgcg acctgaagca aaaagacacg     540
ccaattgtgt acgcctcgga agcttttctc tatatgacag gatacagcaa tgcggaggtc     600
ttggggagaa actgccgttt tcttcagtca cccgacggaa tggtcaagcc gaaatcgaca     660
aggaagtacg tcgactccaa cacgatcaat acgatgagga aagcgattga taggaacgcc     720
gaggtgcagg ttgaggtggt caattttaag aagaacggcc aacggtttgt caacttcttg     780
acgatgattc cggtgcgaga tgaaacaggg gaataccggt acagcatggg tttccagtgc     840
gaaacggaag atccggcgg tggtggatca ggtggaggtg gctccaattt taatcaaagt     900
gggaatattg ctgatagctc attgtccttc actttcacta acagtagcaa cggtccgaac     960
ctcataacaa ctcaaacaaa ttctcaagcg ctttcacaac caattgcctc ctctaacgtt    1020
catgataact tcatgaataa tgaaatcacg gctagtaaaa ttgatgatgg taataattca    1080
aaaccactgt cacctggttg gacgaccaa actgcgtata acgcgtttgg aatcactaca    1140
gggatgttta ataccactac aatggatgat gtatataact atctattcga tgatgaagat    1200
accccaccaa acccaaaaaa agagtaa                                        1227

<210> SEQ ID NO 20
<211> LENGTH: 408
<212> TYPE: PRT
<213> ORGANISM: Artificial sequence
<220> FEATURE:
<223> OTHER INFORMATION: Synthetic

<400> SEQUENCE: 20

Met Asp Lys Ala Glu Leu Ile Pro Glu Pro Pro Lys Lys Arg Lys
1               5                   10                  15

Val Glu Leu Gly Thr Ala Ala Gly Gly Gly Ser Gly Gly Met Ser Thr
                20                  25                  30

Lys Lys Lys Pro Leu Thr Gln Glu Gln Leu Glu Asp Ala Arg Arg Leu
            35                  40                  45

Lys Ala Ile Tyr Glu Lys Lys Lys Asn Glu Leu Gly Leu Ser Gln Glu
        50                  55                  60

```
Ser Val Ala Asp Lys Met Gly Met Gly Gln Ser Gly Val Gly Ala Leu
 65                  70                  75                  80

Phe Asn Gly Ile Asn Ala Leu Asn Ala Tyr Asn Ala Ala Leu Leu Ala
                 85                  90                  95

Lys Ile Leu Lys Val Ser Val Glu Glu Phe Ser Pro Ser Ile Ala Arg
            100                 105                 110

Glu Ile Tyr Glu Met Tyr Glu Ala Val Ser Met Gln Pro Ser Leu Arg
        115                 120                 125

Ser Glu Tyr Arg Ser His Thr Leu Tyr Ala Pro Gly Tyr Asp Ile
    130                 135                 140

Met Gly Tyr Leu Ile Gln Ile Met Lys Arg Pro Asn Pro Gln Val Glu
145                 150                 155                 160

Leu Gly Pro Val Asp Thr Ser Val Ala Leu Ile Leu Cys Asp Leu Lys
                165                 170                 175

Gln Lys Asp Thr Pro Ile Val Tyr Ala Ser Glu Ala Phe Leu Tyr Met
            180                 185                 190

Thr Gly Tyr Ser Asn Ala Glu Val Leu Gly Arg Asn Cys Arg Phe Leu
        195                 200                 205

Gln Ser Pro Asp Gly Met Val Lys Pro Lys Ser Thr Arg Lys Tyr Val
    210                 215                 220

Asp Ser Asn Thr Ile Asn Thr Met Arg Lys Ala Ile Asp Arg Asn Ala
225                 230                 235                 240

Glu Val Gln Val Glu Val Val Asn Phe Lys Lys Asn Gly Gln Arg Phe
                245                 250                 255

Val Asn Phe Leu Thr Met Ile Pro Val Arg Asp Glu Thr Gly Glu Tyr
            260                 265                 270

Arg Tyr Ser Met Gly Phe Gln Cys Glu Thr Glu Gly Ser Gly Gly Gly
        275                 280                 285

Gly Ser Gly Gly Gly Gly Ser Asn Phe Asn Gln Ser Gly Asn Ile Ala
    290                 295                 300

Asp Ser Ser Leu Ser Phe Thr Phe Thr Asn Ser Ser Asn Gly Pro Asn
305                 310                 315                 320

Leu Ile Thr Thr Gln Thr Asn Ser Gln Ala Leu Ser Gln Pro Ile Ala
                325                 330                 335

Ser Ser Asn Val His Asp Asn Phe Met Asn Asn Glu Ile Thr Ala Ser
            340                 345                 350

Lys Ile Asp Asp Gly Asn Asn Ser Lys Pro Leu Ser Pro Gly Trp Thr
        355                 360                 365

Asp Gln Thr Ala Tyr Asn Ala Phe Gly Ile Thr Thr Gly Met Phe Asn
    370                 375                 380

Thr Thr Thr Met Asp Asp Val Tyr Asn Tyr Leu Phe Asp Asp Glu Asp
385                 390                 395                 400

Thr Pro Pro Asn Pro Lys Lys Glu
                405
```

<210> SEQ ID NO 21
<211> LENGTH: 561
<212> TYPE: DNA
<213> ORGANISM: Neurospora crassa

<400> SEQUENCE: 21
atgagccata ccgtgaactc gagcaccatg aacccatggg aggttgaggc gtatcagcaa    60
taccactatg accctcgaac cgcgcccacg gccaaccctc tcttcttcca tacgctctac   120

```
gctcccggcg gttatgacat tatgggctat ctgattcaga ttatgaacag gccaaacccc      180
caagtagaac tgggacctgt tgacacgtca tgcgctctga ttctgtgcga cctgaagcaa      240
aaagacacgc caattgtgta cgcctcggaa gctttctct atatgacagg atacagcaat       300
gcggaggtct tggggagaaa ctgccgtttt cttcagtcac ccgacggaat ggtcaagccg      360
aaatcgacaa ggaagtacgt cgactccaac acgatcaata cgatgaggaa agcgattgat     420
aggaacgccg aggtgcaggt tgaggtggtc aattttaaga gaacggcca acggtttgtc       480 aacttcttga cgatgattcc ggtgcgagat gaaacagggg aataccggta cagcatgggt     540
ttccagtgcg aaacggaatg a                                                561

<210> SEQ ID NO 22
<211> LENGTH: 186
<212> TYPE: PRT
<213> ORGANISM: Neurospora crassa

<400> SEQUENCE: 22

Met Ser His Thr Val Asn Ser Ser Thr Met Asn Pro Trp Glu Val Glu
1               5                   10                  15

Ala Tyr Gln Gln Tyr His Tyr Asp Pro Arg Thr Ala Pro Thr Ala Asn
            20                  25                  30

Pro Leu Phe Phe His Thr Leu Tyr Ala Pro Gly Gly Tyr Asp Ile Met
        35                  40                  45

Gly Tyr Leu Ile Gln Ile Met Asn Arg Pro Asn Pro Gln Val Glu Leu
    50                  55                  60

Gly Pro Val Asp Thr Ser Cys Ala Leu Ile Leu Cys Asp Leu Lys Gln
65                  70                  75                  80

Lys Asp Thr Pro Ile Val Tyr Ala Ser Glu Ala Phe Leu Tyr Met Thr
                85                  90                  95

Gly Tyr Ser Asn Ala Glu Val Leu Gly Arg Asn Cys Arg Phe Leu Gln
            100                 105                 110

Ser Pro Asp Gly Met Val Lys Pro Lys Ser Thr Arg Lys Tyr Val Asp
        115                 120                 125

Ser Asn Thr Ile Asn Thr Met Arg Lys Ala Ile Asp Arg Asn Ala Glu
    130                 135                 140

Val Gln Val Glu Val Val Asn Phe Lys Lys Asn Gly Gln Arg Phe Val
145                 150                 155                 160

Asn Phe Leu Thr Met Ile Pro Val Arg Asp Glu Thr Gly Glu Tyr Arg
                165                 170                 175

Tyr Ser Met Gly Phe Gln Cys Glu Thr Glu
            180                 185

<210> SEQ ID NO 23
<211> LENGTH: 450
<212> TYPE: DNA
<213> ORGANISM: Neurospora crassa

<400> SEQUENCE: 23
catacgctct acgctcccgg cggttatgac attatgggct atctgattca gattatgaac      60
aggccaaacc cccaagtaga actgggacct gttgacacgt cagttgctct gattctgtgc     120
gacctgaagc aaaaagacac gccaattgtg tacgcctcgg aagcttttct ctatatgaca     180
ggatacagca atgcggaggt cttggggaga aactgccgtt tcttcagtc acccgacgga      240 atggtcaagc cgaaatcgac aaggaagtac gtcgactcca cacgatcaa tacgatgagg      300 aaagcgattg ataggaacgc cgaggtgcag gttgaggtgg tcaattttaa gaagaacggc     360
```

```
caacggtttg tcaacttctt gacgatgatt ccggtgcgag atgaaacagg ggaataccgg    420
tacagcatgg gtttccagtg cgaaacggaa                                    450
```

<210> SEQ ID NO 24
<211> LENGTH: 150
<212> TYPE: PRT
<213> ORGANISM: Neurospora crassa

<400> SEQUENCE: 24

```
His Thr Leu Tyr Ala Pro Gly Gly Tyr Asp Ile Met Gly Tyr Leu Ile
1               5                   10                  15

Gln Ile Met Asn Arg Pro Asn Pro Gln Val Glu Leu Gly Pro Val Asp
            20                  25                  30

Thr Ser Val Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150
```

<210> SEQ ID NO 25
<211> LENGTH: 450
<212> TYPE: DNA
<213> ORGANISM: Neurospora crassa

<400> SEQUENCE: 25

```
catacgctct acgctcccgg cggttatgac attatgggct atctgattca gattatgaag    60
aggccaaacc cccaagtaga actgggacct gttgacacgt catgcgctct gattctgtgc   120
gacctgaagc aaaagacac gccaattgtg tacgcctcgg aagcttttct ctatatgaca   180
ggatacagca atgcggaggt cttggggaga aactgccgtt tcttcagtc acccgacgga   240 atggtcaagc cgaaatcgac aaggaagtac gtcgactcca acacgatcaa tacgatgagg   300
aaagcgattg ataggaacgc cgaggtgcag gttgaggtgg tcaattttaa gaagaacggc   360
caacggtttg tcaacttctt gacgatgatt ccggtgcgag atgaaacagg ggaataccgg   420
tacagcatgg gtttccagtg cgaaacggaa                                    450
```

<210> SEQ ID NO 26
<211> LENGTH: 150
<212> TYPE: PRT
<213> ORGANISM: Neurospora crassa

<400> SEQUENCE: 26

```
His Thr Leu Tyr Ala Pro Gly Gly Tyr Asp Ile Met Gly Tyr Leu Ile
1               5                   10                  15

Gln Ile Met Lys Arg Pro Asn Pro Gln Val Glu Leu Gly Pro Val Asp
            20                  25                  30
```

```
                20                  25                  30
Thr Ser Cys Ala Leu Ile Leu Cys Asp Leu Lys Gln Lys Asp Thr Pro
            35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 27
<211> LENGTH: 450
<212> TYPE: DNA
<213> ORGANISM: Neurospora crassa

<400> SEQUENCE: 27
catacgctct acgctcccgg cggttatgac attatgggct atctgattca gattatgaac    60
aggccaaacc cccaagtaga actgggacct gttgacacgt catgcgctct gattctgtgc   120
gacctgaagc aaaaagacac gccaattgtg tacgcctcgg aagcttttct ctatatgaca   180
ggatacagca atgcggaggt cttggggaga aactgccgtt tcttcagtc acccgacgga    240
atggtcaagc cgaaatcgac aaggaagtac gtcgactcca acacgatcaa tacgatgagg   300
aaagcgattg ataggaacgc cgaggtgcag gttgaggtgg tcaattttaa gaagaacggc   360
caacggtttg tcaacttctt gacgatgatt ccggtgcgag atgaaacagg ggaataccgg   420
tacagcatgg gtttccagtg cgaaacggaa                                    450

<210> SEQ ID NO 28
<211> LENGTH: 150
<212> TYPE: PRT
<213> ORGANISM: Neurospora crassa

<400> SEQUENCE: 28

His Thr Leu Tyr Ala Pro Gly Gly Tyr Asp Ile Met Gly Tyr Leu Ile
1               5                   10                  15

Gln Ile Met Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110
```

```
Val Val Asn Phe Lys Lys Asn Gly Gln Arg Phe Val Asn Phe Leu Thr
            115                 120                 125

Met Ile Pro Val Arg Asp Glu Thr Gly Glu Tyr Arg Tyr Ser Met Gly
        130                 135                 140

Phe Gln Cys Glu Thr Glu
145                 150

<210> SEQ ID NO 29
<211> LENGTH: 450
<212> TYPE: DNA
<213> ORGANISM: Neurospora crassa

<400> SEQUENCE: 29
catacgctct acgctcccgg cggttatgac attatgggct ggctgattca gattatgaac      60
aggccaaacc cccaagtaga actgggacct gttgacacgt catgcgctct gattctgtgc     120
gacctgaagc aaaaagacac gccaattgtg tacgcctcgg aagcttttct ctatatgaca     180
ggatacagca atgcggaggt cttggggaga aactgccgtt ttcttcagtc acccgacgga     240
atggtcaagc cgaaatcgac aaggaagtac gtcgactcca acacgatcaa tacgatgagg     300
aaagcgattg ataggaacgc cgaggtgcag gttgaggtgg tcaattttaa gaagaacggc     360
caacggtttg tcaacttctt gacgatgatt ccggtgcgag atgaaacagg ggaataccgg     420
tacagcatgg gtttccagtg cgaaacggaa                                      450

<210> SEQ ID NO 30
<211> LENGTH: 150
<212> TYPE: PRT
<213> ORGANISM: Neurospora crassa

<400> SEQUENCE: 30

His Thr Leu Tyr Ala Pro Gly Gly Tyr Asp Ile Met Gly Trp Leu Ile
1               5                   10                  15

Gln Ile Met Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
            115                 120                 125

Met Ile Pro Val Arg Asp Glu Thr Gly Glu Tyr Arg Tyr Ser Met Gly
        130                 135                 140

Phe Gln Cys Glu Thr Glu
145                 150

<210> SEQ ID NO 31
<211> LENGTH: 1503
<212> TYPE: DNA
<213> ORGANISM: Artificial sequence
<220> FEATURE:
<223> OTHER INFORMATION: Synthetic
```

<400> SEQUENCE: 31

```
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaacaggc aaacccccca agtagaactg     300
ggacctgttg acacgtcatg cgctctgatt ctgtgcgacc tgaagcaaaa agacacgcca     360
attgtgtacg cctcggaagc ttttctctat atgacaggat acagcaatgc ggaggtcttg     420
gggagaaaact gccgttttct tcagtcaccc gacggaatgg tcaagccgaa atcgacaagg     480
aagtacgtcg actccaacac gatcaatacg atgaggaaag cgattgatag aacgccgag     540
gtgcaggttg aggtggtcaa ttttaagaag aacggccaac ggtttgtcaa cttcttgacg     600
atgattccgg tgcgagatga acaggggaa taccggtaca gcatgggttt ccagtgcgaa     660
acggaactgc agtacccata cgatgttcca gattacgctg aattccagta cctgccagat     720
acagacgatc gtcaccggat tgaggagaaa cgtaaaagga catatgagac cttcaagagc     780
atcatgaaga gagtccttt cagcggaccc accgaccccc ggcctccacc tcgacgcatt     840
gctgtgcctt cccgcagctc agcttctgtc cccaagccag caccccagcc ctatcccttt     900
acgtcatccc tgagcaccat caactatgat gagtttccca ccatggtgtt ccttctgggg     960
cagatcagcc aggcctcggc cttggccccg gcccctcccc aagtcctgcc ccaggctcca    1020
gccctgccc tgctccagc catggtatca gctctgcc aggccccagc ccctgtccca    1080
gtcctagccc caggccctcc tcaggctgtg gccccacctg ccccaagcc cacccaggct    1140
ggggaaggaa cgctgtcaga ggccctgctg cagctgcagt ttgatgatga agacctgggg    1200
gccttgcttg caacagcac agacccagct gtgttcacag acctggcatc cgtcgacaac    1260
tccgagtttc agcagctgct gaaccagggc atacctgtgg ccccccacac aactgagccc    1320
atgctgatgg agtaccctga ggctataact cgcctagtga caggggccca gaggcccccc    1380
gacccagctc ctgctccact gggggccccg gggctcccca atggcctcct ttcaggagat    1440
gaagacttct cctccattgc ggacatggac ttctcagccc tgctgagtca gatcagctcc    1500
taa                                                                 1503
```

<210> SEQ ID NO 32
<211> LENGTH: 500
<212> TYPE: PRT
<213> ORGANISM: Artificial sequence
<220> FEATURE:
<223> OTHER INFORMATION: Synthetic

<400> SEQUENCE: 32

```
Met Lys Leu Leu Ser Ser Ile Glu Gln Ala Cys Asp Ile Cys Arg Leu
1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80
```

```
Tyr Asp Ile Met Gly Tyr Leu Ile Gln Ile Met Asn Arg Pro Asn Pro
                85                  90                  95
Gln Val Glu Leu Gly Pro Val Asp Thr Ser Cys Ala Leu Ile Leu Cys
            100                 105                 110
Asp Leu Lys Gln Lys Asp Thr Pro Ile Val Tyr Ala Ser Glu Ala Phe
        115                 120                 125
Leu Tyr Met Thr Gly Tyr Ser Asn Ala Glu Val Leu Gly Arg Asn Cys
    130                 135                 140
Arg Phe Leu Gln Ser Pro Asp Gly Met Val Lys Pro Lys Ser Thr Arg
145                 150                 155                 160
Lys Tyr Val Asp Ser Asn Thr Ile Asn Thr Met Arg Lys Ala Ile Asp
                165                 170                 175
Arg Asn Ala Glu Val Gln Val Glu Val Val Asn Phe Lys Lys Asn Gly
            180                 185                 190
Gln Arg Phe Val Asn Phe Leu Thr Met Ile Pro Val Arg Asp Glu Thr
        195                 200                 205
Gly Glu Tyr Arg Tyr Ser Met Gly Phe Gln Cys Glu Thr Glu Leu Gln
    210                 215                 220
Tyr Pro Tyr Asp Val Pro Asp Tyr Ala Glu Phe Gln Tyr Leu Pro Asp
225                 230                 235                 240
Thr Asp Asp Arg His Arg Ile Glu Glu Lys Arg Lys Arg Thr Tyr Glu
                245                 250                 255
Thr Phe Lys Ser Ile Met Lys Lys Ser Pro Phe Ser Gly Pro Thr Asp
            260                 265                 270
Pro Arg Pro Pro Arg Arg Ile Ala Val Pro Ser Arg Ser Ser Ala
        275                 280                 285
Ser Val Pro Lys Pro Ala Pro Gln Pro Tyr Pro Phe Thr Ser Ser Leu
    290                 295                 300
Ser Thr Ile Asn Tyr Asp Glu Phe Pro Thr Met Val Phe Pro Ser Gly
305                 310                 315                 320
Gln Ile Ser Gln Ala Ser Ala Leu Ala Pro Ala Pro Pro Gln Val Leu
                325                 330                 335
Pro Gln Ala Pro Ala Pro Ala Pro Ala Pro Ala Met Val Ser Ala Leu
            340                 345                 350
Ala Gln Ala Pro Ala Pro Val Pro Val Leu Ala Pro Gly Pro Pro Gln
        355                 360                 365
Ala Val Ala Pro Pro Ala Pro Lys Pro Thr Gln Ala Gly Glu Gly Thr
    370                 375                 380
Leu Ser Glu Ala Leu Leu Gln Leu Gln Phe Asp Asp Glu Asp Leu Gly
385                 390                 395                 400
Ala Leu Leu Gly Asn Ser Thr Asp Pro Ala Val Phe Thr Asp Leu Ala
                405                 410                 415
Ser Val Asp Asn Ser Glu Phe Gln Gln Leu Leu Asn Gln Gly Ile Pro
            420                 425                 430
Val Ala Pro His Thr Thr Glu Pro Met Leu Met Glu Tyr Pro Glu Ala
        435                 440                 445
Ile Thr Arg Leu Val Thr Gly Ala Gln Arg Pro Pro Asp Pro Ala Pro
    450                 455                 460
Ala Pro Leu Gly Ala Pro Gly Leu Pro Asn Gly Leu Leu Ser Gly Asp
465                 470                 475                 480
Glu Asp Phe Ser Ser Ile Ala Asp Met Asp Phe Ser Ala Leu Leu Ser
                485                 490                 495
Gln Ile Ser Ser
```

<210> SEQ ID NO 33
<211> LENGTH: 1503
<212> TYPE: DNA
<213> ORGANISM: Artificial sequence
<220> FEATURE:
<223> OTHER INFORMATION: Synthetic

<400> SEQUENCE: 33

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcgt     240
tatgacatta tgggctatct gattcagatt atgaacaggc caaaccccca agtagaactg     300
ggacctgttg acacgtcagt cgctctgatt ctgtgcgacc tgaagcaaaa agacacgcca     360
attgtgtacg cctcggaagc ttttctctat atgacaggat acagcaatgc ggaggtcttg     420
gggagaaaact gccgttttct tcagtcaccc gacggaatgg tcaagccgaa atcgacaagg     480
aagtacgtcg actccaacac gatcaatacg atgaggaaag cgattgatag aacgccgag      540
gtgcaggttg aggtggtcaa ttttaagaag aacggccaac ggtttgtcaa cttcttgacg     600
atgattccgg tgcgagatga acagggaa taccggtaca gcatgggttt ccagtgcgaa     660
acggaactgc agtacccata cgatgttcca gattacgctg aattccagta cctgccagat     720
acagacgatc gtcaccggat tgaggagaaa cgtaaaagga catatgagac cttcaagagc     780
atcatgaaga gagtcctttt cagcggaccc accgaccccc ggcctccacc tcgacgcatt     840
gctgtgcctt cccgcagctc agcttctgtc cccaagccag caccccagcc ctatcccttt     900
acgtcatccc tgagcaccat caactatgat gagtttccca ccatggtgtt tccttctggg     960
cagatcagcc aggcctcggc cttggccccg gcccctcccc aagtcctgcc ccaggctcca    1020
gcccctgccc ctgctccagc catggtatca gctctggccc aggcccagc cctgtccca     1080
gtcctagccc caggccctcc tcaggctgtg gccccacctg cccccaagcc cacccaggct    1140
ggggaaggaa cgctgtcaga ggccctgctg cagctgcagt ttgatgatga agacctgggg    1200
gccttgcttg caacagcac agacccagct gtgttcacag acctggcatc cgtcgacaac    1260
tccgagtttc agcagctgct gaaccagggc atacctgtgg ccccacac aactgagccc    1320
atgctgatgg agtaccctga ggctataact cgcctagtga caggggccca gaggcccccc    1380
gacccagctc ctgctccact ggggggcccg gggctcccca atggcctcct ttcaggagat    1440
gaagacttct cctccattgc ggacatggac ttctcagccc tgctgagtca gatcagctcc    1500
taa                                                                  1503
```

<210> SEQ ID NO 34
<211> LENGTH: 500
<212> TYPE: PRT
<213> ORGANISM: Artificial sequence
<220> FEATURE:
<223> OTHER INFORMATION: Synthetic

<400> SEQUENCE: 34

```
Met Lys Leu Leu Ser Ser Ile Glu Gln Ala Cys Asp Ile Cys Arg Leu
1               5                   10                  15
Lys Lys Leu Lys Cys Ser Lys Glu Lys Pro Lys Cys Ala Lys Cys Leu
            20                  25                  30
```

```
Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
 50                  55                  60

Glu Arg Ser Ile Ala Thr Arg Ser His Thr Leu Tyr Ala Pro Gly Gly
 65                  70                  75                  80

Tyr Asp Ile Met Gly Tyr Leu Ile Gln Ile Met Asn Arg Pro Asn Pro
                 85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
            115                 120                 125

Leu Tyr Met Thr Gly Tyr Ser Asn Ala Glu Val Leu Gly Arg Asn Cys
            130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
            195                 200                 205

Gly Glu Tyr Arg Tyr Ser Met Gly Phe Gln Cys Glu Thr Glu Leu Gln
            210                 215                 220

Tyr Pro Tyr Asp Val Pro Asp Tyr Ala Glu Phe Gln Tyr Leu Pro Asp
225                 230                 235                 240

Thr Asp Asp Arg His Arg Ile Glu Glu Lys Arg Lys Arg Thr Tyr Glu
                245                 250                 255

Thr Phe Lys Ser Ile Met Lys Lys Ser Pro Phe Ser Gly Pro Thr Asp
                260                 265                 270

Pro Arg Pro Pro Arg Arg Ile Ala Val Pro Ser Arg Ser Ser Ala
            275                 280                 285

Ser Val Pro Lys Pro Ala Pro Gln Pro Tyr Pro Phe Thr Ser Ser Leu
            290                 295                 300

Ser Thr Ile Asn Tyr Asp Glu Phe Pro Thr Met Val Phe Pro Ser Gly
305                 310                 315                 320

Gln Ile Ser Gln Ala Ser Ala Leu Ala Pro Ala Pro Gln Val Leu
                325                 330                 335

Pro Gln Ala Pro Ala Pro Ala Pro Ala Met Val Ser Ala Leu
            340                 345                 350

Ala Gln Ala Pro Ala Pro Val Pro Val Leu Ala Pro Gly Pro Pro Gln
            355                 360                 365

Ala Val Ala Pro Pro Ala Pro Lys Pro Thr Gln Ala Gly Glu Gly Thr
370                 375                 380

Leu Ser Glu Ala Leu Leu Gln Leu Gln Phe Asp Asp Glu Asp Leu Gly
385                 390                 395                 400

Ala Leu Leu Gly Asn Ser Thr Asp Pro Ala Val Phe Thr Asp Leu Ala
                405                 410                 415

Ser Val Asp Asn Ser Glu Phe Gln Gln Leu Leu Asn Gln Gly Ile Pro
                420                 425                 430

Val Ala Pro His Thr Thr Glu Pro Met Leu Met Glu Tyr Pro Glu Ala
            435                 440                 445
```

Ile Thr Arg Leu Val Thr Gly Ala Gln Arg Pro Asp Pro Ala Pro
450                 455                 460

Ala Pro Leu Gly Ala Pro Gly Leu Pro Asn Gly Leu Leu Ser Gly Asp
465                 470                 475                 480

Glu Asp Phe Ser Ser Ile Ala Asp Met Asp Phe Ser Ala Leu Leu Ser
                485                 490                 495

Gln Ile Ser Ser
            500

<210> SEQ ID NO 35
<211> LENGTH: 1503
<212> TYPE: DNA
<213> ORGANISM: Artificial sequence
<220> FEATURE:
<223> OTHER INFORMATION: Synthetic

<400> SEQUENCE: 35

| | | | | | |
|---|---|---|---|---|---|
| atgaagctac | tgtcttctat | cgaacaagca | tgcgatattt | gccgacttaa | aaagctcaag | 60 |
| tgctccaaag | aaaaaccgaa | gtgcgccaag | tgtctgaaga | caactggga | gtgtcgctac | 120 |
| tctcccaaaa | ccaaaaggtc | tccgctgact | agggcacatc | tgacagaagt | ggaatcaagg | 180 |
| ctagaaagac | tggaaagatc | catcgccacc | agatctcata | cgctctacgc | tcccggcggt | 240 |
| tatgacatta | tgggctatct | gattcagatt | atgaagaggc | caaaccccca | agtagaactg | 300 |
| ggacctgttg | acacgtcatg | cgctctgatt | ctgtgcgacc | tgaagcaaaa | agacacgcca | 360 |
| attgtgtacg | cctcggaagc | ttttctctat | atgacaggat | acagcaatgc | ggaggtcttg | 420 |
| gggagaaact | gccgttttct | tcagtcaccc | gacggaatgg | tcaagccgaa | atcgacaagg | 480 |
| aagtacgtcg | actccaacac | gatcaatacg | atgaggaaag | cgattgatag | aacgccgag | 540 |
| gtgcaggttg | aggtggtcaa | ttttaagaag | aacggccaac | ggtttgtcaa | cttcttgacg | 600 |
| atgattccgg | tgcgagatga | aacaggggaa | taccggtaca | gcatgggttt | ccagtgcgaa | 660 |
| acggaactgc | agtacccata | cgatgttcca | gattacgctg | aattccagta | cctgccagat | 720 |
| acagacgatc | gtcaccggat | tgaggagaaa | cgtaaaagga | catatgagac | cttcaagagc | 780 |
| atcatgaaga | agagtccttt | cagcggaccc | accgaccccc | ggcctccacc | tcgacgcatt | 840 |
| gctgtgcctt | cccgcagctc | agcttctgtc | cccaagccag | caccccagcc | ctatcccttt | 900 |
| acgtcatccc | tgagcaccat | caactatgat | gagtttccca | ccatggtgtt | tccttctggg | 960 |
| cagatcagcc | aggcctcggc | cttggccccg | gcccctcccc | aagtcctgcc | ccaggctcca | 1020 |
| gcccctgccc | ctgctccagc | catggtatca | gctctggccc | aggccccagc | ccctgtccca | 1080 |
| gtcctagccc | caggccctcc | tcaggctgtg | gccccacctg | ccccaagcc | acccaggct | 1140 |
| ggggaaggaa | cgctgtcaga | ggccctgctg | cagctgcagt | tgatgatga | agacctgggg | 1200 |
| gccttgcttg | caacagcac | agaccagct | gtgttcacag | acctggcatc | cgtcgacaac | 1260 |
| tccgagtttc | agcagctgct | gaaccagggc | atacctgtgg | ccccccacac | aactgagccc | 1320 |
| atgctgatgg | agtaccctga | ggctataact | cgcctagtga | caggggccca | gaggcccccc | 1380 |
| gacccagctc | ctgctccact | ggggccccg | gggctcccca | atggcctcct | ttcaggagat | 1440 |
| gaagacttct | cctccattgc | ggacatggac | ttctcagccc | tgctgagtca | gatcagctcc | 1500 |
| taa | | | | | | 1503 |

<210> SEQ ID NO 36
<211> LENGTH: 426
<212> TYPE: PRT
<213> ORGANISM: Artificial sequence
<220> FEATURE:
<223> OTHER INFORMATION: Synthetic

<400> SEQUENCE: 36

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Leu Gln Tyr Pro Tyr Asp Val Pro Asp Tyr Ala Glu Phe
145                 150                 155                 160

Gln Tyr Leu Pro Asp Thr Asp Asp Arg His Arg Ile Glu Glu Lys Arg
                165                 170                 175

Lys Arg Thr Tyr Glu Thr Phe Lys Ser Ile Met Lys Lys Ser Pro Phe
            180                 185                 190

Ser Gly Pro Thr Asp Pro Arg Pro Pro Arg Arg Ile Ala Val Pro
        195                 200                 205

Ser Arg Ser Ser Ala Ser Val Pro Lys Pro Ala Pro Gln Pro Tyr Pro
    210                 215                 220

Phe Thr Ser Ser Leu Ser Thr Ile Asn Tyr Asp Glu Phe Pro Thr Met
225                 230                 235                 240

Val Phe Pro Ser Gly Gln Ile Ser Gln Ala Ser Ala Leu Ala Pro Ala
                245                 250                 255

Pro Pro Gln Val Leu Pro Gln Ala Pro Ala Pro Ala Pro Ala Pro Ala
            260                 265                 270

Met Val Ser Ala Leu Ala Gln Ala Pro Ala Pro Val Pro Val Leu Ala
        275                 280                 285

Pro Gly Pro Pro Gln Ala Val Ala Pro Pro Ala Pro Lys Pro Thr Gln
    290                 295                 300

Ala Gly Glu Gly Thr Leu Ser Glu Ala Leu Leu Gln Leu Gln Phe Asp
305                 310                 315                 320

Asp Glu Asp Leu Gly Ala Leu Leu Gly Asn Ser Thr Asp Pro Ala Val
                325                 330                 335

Phe Thr Asp Leu Ala Ser Val Asp Asn Ser Glu Phe Gln Gln Leu Leu
            340                 345                 350

Asn Gln Gly Ile Pro Val Ala Pro His Thr Thr Glu Pro Met Leu Met
        355                 360                 365

Glu Tyr Pro Glu Ala Ile Thr Arg Leu Val Thr Gly Ala Gln Arg Pro
    370                 375                 380

Pro Asp Pro Ala Pro Ala Pro Leu Gly Ala Val Pro Gly Leu Pro Asn
385                 390                 395                 400

Gly Leu Leu Ser Gly Asp Glu Asp Phe Ser Ser Ile Ala Asp Met Asp
            405                 410                 415

Phe Ser Ala Leu Leu Ser Gln Ile Ser Ser
            420                 425

<210> SEQ ID NO 37
<211> LENGTH: 1503
<212> TYPE: DNA
<213> ORGANISM: Artificial sequence
<220> FEATURE:
<223> OTHER INFORMATION: Synthetic

<400> SEQUENCE: 37

| | | | | | | |
|---|---|---|---|---|---|---|
| atgaagctac | tgtcttctat | cgaacaagca | tgcgatattt | gccgacttaa | aaagctcaag | 60 |
| tgctccaaag | aaaaaccgaa | gtgcgccaag | tgtctgaaga | caactggga | gtgtcgctac | 120 |
| tctcccaaaa | ccaaaaggtc | tccgctgact | agggcacatc | tgacagaagt | ggaatcaagg | 180 |
| ctagaaagac | tggaaagatc | catcgccacc | agatctcata | cgctctacgc | tcccggcggt | 240 |
| tatgacatta | tgggctatct | gattcagatt | atgaagaggc | caaaccccca | agtagaactg | 300 |
| ggacctgttg | acacgtcagt | cgctctgatt | ctgtgcgacc | tgaagcaaaa | agacacgcca | 360 |
| attgtgtacg | cctcggaagc | ttttctctat | atgacaggat | acagcaatgc | ggaggtcttg | 420 |
| gggagaaact | gccgttttct | tcagtcaccc | gacggaatgg | tcaagccgaa | atcgacaagg | 480 |
| aagtacgtcg | actccaacac | gatcaatacg | atgaggaaag | cgattgatag | gaacgccgag | 540 |
| gtgcaggttg | aggtggtcaa | ttttaagaag | aacggccaac | ggtttgtcaa | cttcttgacg | 600 |
| atgattccgg | tgcgagatga | aacaggggaa | taccggtaca | gcatgggttt | ccagtgcgaa | 660 |
| acggaactgc | agtacccata | cgatgttcca | gattacgctg | aattccagta | cctgccagat | 720 |
| acagacgatc | gtcaccggat | tgaggagaaa | cgtaaaagga | catatgagac | cttcaagagc | 780 |
| atcatgaaga | gagtcctttt | cagcggaccc | accgaccccc | ggcctccacc | tcgacgcatt | 840 |
| gctgtgcctt | cccgcagctc | agcttctgtc | cccaagccag | caccccagcc | ctatcccttt | 900 |
| acgtcatccc | tgagcaccat | caactatgat | gagtttccca | ccatggtgtt | tccttctggg | 960 |
| cagatcagcc | aggcctcggc | cttggccccg | gcccctcccc | aagtcctgcc | ccaggctcca | 1020 |
| gccccctgccc | ctgctccagc | catggtatca | gctctggccc | aggccccagc | cctgtccca | 1080 |
| gtcctagccc | caggccctcc | tcaggctgtg | gccccacctg | cccccaagcc | cacccaggct | 1140 |
| ggggaaggaa | cgctgtcaga | ggccctgctg | cagctgcagt | ttgatgatga | agacctgggg | 1200 |
| gccttgcttg | gcaacagcac | agacccagct | gtgttcacag | acctggcatc | cgtcgacaac | 1260 |
| tccgagtttc | agcagctgct | gaaccagggc | atacctgtgg | ccccccacac | aactgagccc | 1320 |
| atgctgatgg | agtaccctga | ggctataact | cgcctagtga | caggggccca | gaggcccccc | 1380 |
| gacccagctc | ctgctccact | gggggccccg | gggctcccca | atggcctcct | ttcaggagat | 1440 |
| gaagacttct | cctccattgc | ggacatggac | ttctcagccc | tgctgagtca | gatcagctcc | 1500 |
| taa | | | | | | 1503 |

<210> SEQ ID NO 38
<211> LENGTH: 500
<212> TYPE: PRT
<213> ORGANISM: Artificial sequence
<220> FEATURE:
<223> OTHER INFORMATION: Synthetic

<400> SEQUENCE: 38

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
            115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Leu Gln
    210                 215                 220

Tyr Pro Tyr Asp Val Pro Asp Tyr Ala Glu Phe Gln Tyr Leu Pro Asp
225                 230                 235                 240

Thr Asp Asp Arg His Arg Ile Glu Glu Lys Arg Lys Arg Thr Tyr Glu
                245                 250                 255

Thr Phe Lys Ser Ile Met Lys Lys Ser Pro Phe Ser Gly Pro Thr Asp
            260                 265                 270

Pro Arg Pro Pro Arg Arg Ile Ala Val Pro Ser Arg Ser Ser Ala
            275                 280                 285

Ser Val Pro Lys Pro Ala Pro Gln Pro Tyr Pro Phe Thr Ser Ser Leu
    290                 295                 300

Ser Thr Ile Asn Tyr Asp Glu Phe Pro Thr Met Val Phe Pro Ser Gly
305                 310                 315                 320

Gln Ile Ser Gln Ala Ser Ala Leu Ala Pro Ala Pro Pro Gln Val Leu
            325                 330                 335

Pro Gln Ala Pro Ala Pro Ala Pro Ala Pro Ala Met Val Ser Ala Leu
            340                 345                 350

Ala Gln Ala Pro Ala Pro Val Pro Val Leu Ala Pro Gly Pro Pro Gln
            355                 360                 365

Ala Val Ala Pro Pro Ala Pro Lys Pro Thr Gln Ala Gly Glu Gly Thr
    370                 375                 380

Leu Ser Glu Ala Leu Leu Gln Leu Gln Phe Asp Asp Glu Asp Leu Gly
385                 390                 395                 400

Ala Leu Leu Gly Asn Ser Thr Asp Pro Ala Val Phe Thr Asp Leu Ala
                405                 410                 415

Ser Val Asp Asn Ser Glu Phe Gln Gln Leu Leu Asn Gln Gly Ile Pro
```

```
                420            425            430
Val Ala Pro His Thr Thr Glu Pro Met Leu Met Glu Tyr Pro Glu Ala
            435                440               445

Ile Thr Arg Leu Val Thr Gly Ala Gln Arg Pro Pro Asp Pro Ala Pro
    450                455                460

Ala Pro Leu Gly Ala Pro Gly Leu Pro Asn Gly Leu Leu Ser Gly Asp
465             470                475                    480

Glu Asp Phe Ser Ser Ile Ala Asp Met Asp Phe Ser Ala Leu Leu Ser
                485                490                495

Gln Ile Ser Ser
            500

<210> SEQ ID NO 39
<211> LENGTH: 1503
<212> TYPE: DNA
<213> ORGANISM: Artificial sequence
<220> FEATURE:
<223> OTHER INFORMATION: Synthetic

<400> SEQUENCE: 39
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120 tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctggct gattcagatt atgaacaggc caaaccccca agtagaactg     300
ggacctgttg acacgtcatg cgctctgatt ctgtgcgacc tgaagcaaaa agacacgcca     360
attgtgtacg cctcggaagc ttttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag gaacgccgag     540
gtgcaggttg aggtggtcaa ttttaagaag aacggccaac ggtttgtcaa cttcttgacg     600
atgattccgg tgcgagatga aacaggggaa taccggtaca gcatgggttt ccagtgcgaa     660
acggaactgc agtacccata cgatgttcca gattacgctg aattccagta cctgccagat     720
acagacgatc gtcaccggat tgaggagaaa cgtaaaagga catatgagac cttcaagagc     780
atcatgaaga gagtcctttt cagcggaccc accgaccccc ggcctccacc tcgacgcatt     840
gctgtgcctt cccgcagctc agcttctgtc cccaagccag caccccagcc ctatcccttt     900
acgtcatccc tgagcaccat caactatgat gagtttccca ccatggtgtt tccttctggg     960
cagatcagcc aggcctcggc cttggccccg gcccctcccc aagtcctgcc ccaggctcca    1020
gcccctgccc tgctccagc catggtatca gctctggccc aggccccagc ccctgtccca    1080
gtcctagccc caggccctcc tcaggctgtg gccccacctg ccccaagcc cacccaggct    1140 ggggaaggaa cgctgtcaga ggccctgctg cagctgcagt tgatgatga agacctgggg    1200 gccttgcttg gcaacagcac agacccagct gtgttcacag acctggcatc cgtcgacaac    1260
tccgagtttc agcagctgct gaaccagggc atacctgtgg ccccccacac aactgagccc    1320
atgctgatgg agtaccctga ggctataact cgcctagtga caggggccca gaggcccccc    1380
gacccagctc ctgctccact gggggccccg gggctcccca tggcctcctt caggagat     1440 gaagacttct cctccattgc ggacatggac ttctcagccc tgctgagtca gatcagctcc    1500
taa                                                                  1503
```

<210> SEQ ID NO 40
<211> LENGTH: 500
<212> TYPE: PRT
<213> ORGANISM: Artificial sequence
<220> FEATURE:
<223> OTHER INFORMATION: Synthetic

<400> SEQUENCE: 40

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Trp Leu Ile Gln Ile Met Asn Arg Pro Asn Pro
                85                  90                  95

Gln Val Glu Leu Gly Pro Val Asp Thr Ser Cys Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Leu Gln
    210                 215                 220

Tyr Pro Tyr Asp Val Pro Asp Tyr Ala Glu Phe Gln Tyr Leu Pro Asp
225                 230                 235                 240

Thr Asp Asp Arg His Arg Ile Glu Glu Lys Arg Lys Arg Thr Tyr Glu
                245                 250                 255

Thr Phe Lys Ser Ile Met Lys Lys Ser Pro Phe Ser Gly Pro Thr Asp
            260                 265                 270

Pro Arg Pro Pro Arg Arg Ile Ala Val Pro Ser Arg Ser Ser Ala
        275                 280                 285

Ser Val Pro Lys Pro Ala Pro Gln Pro Tyr Pro Phe Thr Ser Ser Leu
    290                 295                 300

Ser Thr Ile Asn Tyr Asp Glu Phe Pro Thr Met Val Phe Pro Ser Gly
305                 310                 315                 320

Gln Ile Ser Gln Ala Ser Ala Leu Ala Pro Ala Pro Pro Gln Val Leu
                325                 330                 335

Pro Gln Ala Pro Ala Pro Ala Pro Ala Met Val Ser Ala Leu
            340                 345                 350

Ala Gln Ala Pro Ala Pro Val Pro Val Leu Ala Pro Gly Pro Pro Gln
        355                 360                 365
```

Ala Val Ala Pro Pro Ala Pro Lys Pro Thr Gln Ala Gly Glu Gly Thr
370                 375                 380

Leu Ser Glu Ala Leu Leu Gln Leu Gln Phe Asp Asp Glu Asp Leu Gly
385                 390                 395                 400

Ala Leu Leu Gly Asn Ser Thr Asp Pro Ala Val Phe Thr Asp Leu Ala
                405                 410                 415

Ser Val Asp Asn Ser Glu Phe Gln Gln Leu Leu Asn Gln Gly Ile Pro
                420                 425                 430

Val Ala Pro His Thr Thr Glu Pro Met Leu Met Glu Tyr Pro Glu Ala
            435                 440                 445

Ile Thr Arg Leu Val Thr Gly Ala Gln Arg Pro Pro Asp Pro Ala Pro
450                 455                 460

Ala Pro Leu Gly Ala Pro Gly Leu Pro Asn Gly Leu Leu Ser Gly Asp
465                 470                 475                 480

Glu Asp Phe Ser Ser Ile Ala Asp Met Asp Phe Ser Ala Leu Leu Ser
                485                 490                 495

Gln Ile Ser Ser
        500

<210> SEQ ID NO 41
<211> LENGTH: 432
<212> TYPE: DNA
<213> ORGANISM: Avena sativa

<400> SEQUENCE: 41
ttcttggcta ctacacttga acgtattgag aagaactttg tcattactga cccaaggttg      60
ccagataatc ccattatatt cgcgtccgat agtttcttgc agttgacaga atatagccgt     120
gaagaaattt tgggaagaaa ctgcaggttt ctacaaggtc ctgaaactga tcgcgcgaca     180
gtgagaaaaa ttagagatgc catagataac caaacagagg tcactgttca gctgattaat     240
tatacaaaga gtggtaaaaa gttctggaac ctctttcact tgcagcctat gcgagatcag     300
aagggagatg tccagtactt tattggggtt cagttggatg aactgagca tgtccgagat      360 gctgccgaga gagggagt catgctgatt aagaaaactg cagaaaatat tgatgaggcg      420
gcaaaagaac tt                                                         432

<210> SEQ ID NO 42
<211> LENGTH: 144
<212> TYPE: PRT
<213> ORGANISM: Avena sativa

<400> SEQUENCE: 42

Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
                20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
        50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
                100                 105                 110

Asp Gly Thr Glu His Val Arg Asp Ala Ala Glu Arg Glu Gly Val Met
        115                 120                 125

Leu Ile Lys Lys Thr Ala Glu Asn Ile Asp Glu Ala Ala Lys Glu Leu
    130                 135                 140

<210> SEQ ID NO 43
<211> LENGTH: 1467
<212> TYPE: DNA
<213> ORGANISM: Artificial sequence
<220> FEATURE:
<223> OTHER INFORMATION: Synthetic

<400> SEQUENCE: 43

```
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctttct tggctactac acttgaacgt     240
attgagaaga actttgtcat tactgaccca aggttgccag ataatcccat tatattcgcg     300
tccgatagtt tcttgcagtt gacagaatat agccgtgaag aaattttggg aagaaactgc     360
aggtttctac aaggtcctga aactgatcgc gcgacagtga gaaaaattag gatgccata     420
gataaccaaa cagaggtcac tgttcagctg attaattata caaagagtgg taaaaagttc     480
tggaacctct ttcacttgca gcctatgcga gatcagaagg gagatgtcca gtactttatt     540
ggggttcagt tggatggaac tgagcatgtc cgagatgctg ccgagagaga gggagtcatg     600
ctgattaaga aaactgcaga aaatattgat gaggcggcaa agaacttgg tggcggatca     660
ggtgaattcc agtacctgcc agatacagac gatcgtcacc ggattgagga gaaacgtaaa     720
aggacatatg agaccttcaa gagcatcatg aagaagagtc ctttcagcgg acccaccgac     780
ccccggcctc cacctcgacg cattgctgtg ccttcccgca gctcagcttc tgtccccaag     840
ccagcacccc agccctatcc ctttacgtca tccctgagca ccatcaacta tgatgagttt     900
cccaccatgg tgtttccttc tgggcagatc agccaggcct cggccttggc cccggccccT     960
ccccaagtcc tgcccaggc tccagcccct gccctgctc cagccatggt atcagctctg    1020
gcccaggccc cagcccctgt cccagtccta gccccaggcc ctcctcaggc tgtgggccca    1080
cctgccccca gcccacccaa ggctggggaa ggaacgctgt cagaggccct gctgcagctg    1140
cagtttgatg atgaagacct ggggggccttg cttggcaaca gcacagaccc agctgtgttc    1200
acagacctgg catccgtcga caactccgag tttcagcagc tgctgaacca gggcataccT    1260
gtggccccc acacaactga gcccatgctg atggagtacc ctgaggctat aactcgccta    1320
gtgacagggg cccagaggcc ccccgaccca gctcctgctc cactgggggc cccggggctc    1380
cccaatggcc tcctttcagg agatgaagac ttctcctcca ttgcggacat ggacttctca    1440
gccctgctga gtcagatcag ctcctaa                                          1467
```

<210> SEQ ID NO 44
<211> LENGTH: 488
<212> TYPE: PRT
<213> ORGANISM: Artificial sequence
<220> FEATURE:
<223> OTHER INFORMATION: Synthetic

<400> SEQUENCE: 44

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
 50                  55                  60

Glu Arg Ser Ile Ala Thr Arg Ser Phe Leu Ala Thr Thr Leu Glu Arg
 65                  70                  75                  80

Ile Glu Lys Asn Phe Val Ile Thr Asp Pro Arg Leu Pro Asp Asn Pro
                85                  90                  95

Ile Ile Phe Ala Ser Asp Ser Phe Leu Gln Leu Thr Glu Tyr Ser Arg
                100                 105                 110

Glu Glu Ile Leu Gly Arg Asn Cys Arg Phe Leu Gln Gly Pro Glu Thr
                115                 120                 125

Asp Arg Ala Thr Val Arg Lys Ile Arg Asp Ala Ile Asp Asn Gln Thr
 130                 135                 140

Glu Val Thr Val Gln Leu Ile Asn Tyr Thr Lys Ser Gly Lys Lys Phe
145                 150                 155                 160

Trp Asn Leu Phe His Leu Gln Pro Met Arg Asp Gln Lys Gly Asp Val
                165                 170                 175

Gln Tyr Phe Ile Gly Val Gln Leu Asp Gly Thr Glu His Val Arg Asp
                180                 185                 190

Ala Ala Glu Arg Glu Gly Val Met Leu Ile Lys Lys Thr Ala Glu Asn
                195                 200                 205

Ile Asp Glu Ala Ala Lys Glu Leu Gly Gly Ser Gly Glu Phe Gln
 210                 215                 220

Tyr Leu Pro Asp Thr Asp Asp Arg His Arg Ile Glu Glu Lys Arg Lys
225                 230                 235                 240

Arg Thr Tyr Glu Thr Phe Lys Ser Ile Met Lys Lys Ser Pro Phe Ser
                245                 250                 255

Gly Pro Thr Asp Pro Arg Pro Pro Arg Arg Ile Ala Val Pro Ser
                260                 265                 270

Arg Ser Ser Ala Ser Val Pro Lys Pro Ala Pro Gln Pro Tyr Pro Phe
 275                 280                 285

Thr Ser Ser Leu Ser Thr Ile Asn Tyr Asp Glu Phe Pro Thr Met Val
 290                 295                 300

Phe Pro Ser Gly Gln Ile Ser Gln Ala Ser Ala Leu Ala Pro Ala Pro
305                 310                 315                 320

Pro Gln Val Leu Pro Gln Ala Pro Ala Pro Ala Pro Ala Pro Ala Met
                325                 330                 335

Val Ser Ala Leu Ala Gln Ala Pro Ala Pro Val Pro Val Leu Ala Pro
                340                 345                 350

Gly Pro Pro Gln Ala Val Ala Pro Pro Ala Pro Lys Pro Thr Gln Ala
                355                 360                 365

Gly Glu Gly Thr Leu Ser Glu Ala Leu Leu Gln Leu Gln Phe Asp Asp
                370                 375                 380

Glu Asp Leu Gly Ala Leu Leu Gly Asn Ser Thr Asp Pro Ala Val Phe
385                 390                 395                 400

Thr Asp Leu Ala Ser Val Asp Asn Ser Glu Phe Gln Gln Leu Leu Asn
                405                 410                 415

Gln Gly Ile Pro Val Ala Pro His Thr Thr Glu Pro Met Leu Met Glu
                420                 425                 430

Tyr Pro Glu Ala Ile Thr Arg Leu Val Thr Gly Ala Gln Arg Pro Pro
            435                 440                 445

Asp Pro Ala Pro Ala Pro Leu Gly Ala Pro Gly Leu Pro Asn Gly Leu
    450                 455                 460

Leu Ser Gly Asp Glu Asp Phe Ser Ser Ile Ala Asp Met Asp Phe Ser
465                 470                 475                 480

Ala Leu Leu Ser Gln Ile Ser Ser
                485

<210> SEQ ID NO 45
<211> LENGTH: 339
<212> TYPE: DNA
<213> ORGANISM: Arabidopsis thaliana

<400> SEQUENCE: 45
cagaattttg tgataactga tgcaagcttg ccggataatc ccatcgtcta tgcaagccga      60 ggcttttttaa cgctaactgg ttattcccctt gatcagattc taggtcgaaa ctgtcgtttc    120
cttcaaggcc ctgaaacaga tccacgagct gtcgataaga tccgaaatgc catcacaaaa    180
ggagtggaca catcagtgtg tcttcttaat taccgtcaag atggtacaac cttttggaat    240
ctgttttttg ttgctggtct acgagattca aagggcaata ttgttaacta tgttggtgtg    300
cagagtaaag tttctgaaga ttacgccaag ttgctagtg                            339

<210> SEQ ID NO 46
<211> LENGTH: 113
<212> TYPE: PRT
<213> ORGANISM: Arabidopsis thaliana

<400> SEQUENCE: 46

Gln Asn Phe Val Ile Thr Asp Ala Ser Leu Pro Asp Asn Pro Ile Val
1               5                   10                  15

Tyr Ala Ser Arg Gly Phe Leu Thr Leu Thr Gly Tyr Ser Leu Asp Gln
            20                  25                  30

Ile Leu Gly Arg Asn Cys Arg Phe Leu Gln Gly Pro Glu Thr Asp Pro
        35                  40                  45

Arg Ala Val Asp Lys Ile Arg Asn Ala Ile Thr Lys Gly Val Asp Thr
    50                  55                  60

Ser Val Cys Leu Leu Asn Tyr Arg Gln Asp Gly Thr Thr Phe Trp Asn
65                  70                  75                  80

Leu Phe Phe Val Ala Gly Leu Arg Asp Ser Lys Gly Asn Ile Val Asn
                85                  90                  95

Tyr Val Gly Val Gln Ser Lys Val Ser Glu Asp Tyr Ala Lys Leu Leu
            100                 105                 110

Val

<210> SEQ ID NO 47
<211> LENGTH: 1377
<212> TYPE: DNA
<213> ORGANISM: Artificial sequence
<220> FEATURE:
<223> OTHER INFORMATION: Synthetic

<400> SEQUENCE: 47
atgaagctac tgtcttctat cgaacaagca tgcgatattt gccgacttaa aaagctcaag      60
tgctccaaag aaaaccgaa gtgcgccaag tgtctgaaga caactggga gtgtcgctac       120 tctcccaaaa ccaaaaggtc tccgctgact agggcacatc tgacagaagt ggaatcaagg    180

```
ctagaaagac tggaaagatc tcagaatttt gtgataactg atgcaagctt gccggataat    240
cccatcgtct atgcaagccg aggcttttta acgctaactg gttattccct tgatcagatt    300
ctaggtcgaa actgtcgttt ccttcaaggc cctgaaacag atccacgagc tgtcgataag    360
atccgaaatg ccatcacaaa aggagtggac acatcagtgt gtcttcttaa ttaccgtcaa    420
gatggtacaa cctttggaa tctgtttttt gttgctggtc tacgagattc aaagggcaat     480
attgttaact atgttggtgt gcagagtaaa gtttctgaag attacgccaa gttgctagtg    540
ctgcagtacc catacgatgt tccagattac gctgaattcc agtacctgcc agatacagac    600
gatcgtcacc ggattgagga gaaacgtaaa aggacatatg agaccttcaa gagcatcatg    660
aagaagagtc ctttcagcgg acccaccgac ccccggcctc cacctcgacg cattgctgtg    720
ccttcccgca gctcagcttc tgtccccaag ccagcacccc agccctatcc ctttacgtca    780
tccctgagca ccatcaacta tgatgagttt cccaccatgg tgtttccttc tgggcagatc    840
agccaggcct cggccttggc cccggcccct cccaagtcc tgcccaggc tccagcccct    900 gcccctgctc cagccatggt atcagctctg gcccaggccc cagcccctgt cccagtccta    960
gccccaggcc ctcctcaggc tgtggcccca cctgcccca agcccaccca ggctggggaa    1020
ggaacgctgt cagaggccct gctgcagctg cagtttgatg atgaagacct gggggccttg    1080
cttggcaaca gcacagaccc agctgtgttc acagacctgg catccgtcga caactccgag    1140
tttcagcagc tgctgaacca gggcatacct gtggcccccc acacaactga gcccatgctg    1200
atggagtacc ctgaggctat aactcgccta gtgacagggg cccagaggcc ccccgaccca    1260
gctcctgctc cactggggcc cccggggctc cccaatggcc tcctttcagg agatgaagac    1320
ttctcctcca ttgcggacat ggacttctca gccctgctga gtcagatcag ctcctaa       1377
```

<210> SEQ ID NO 48
<211> LENGTH: 458
<212> TYPE: PRT
<213> ORGANISM: Artificial sequence
<220> FEATURE:
<223> OTHER INFORMATION: Synthetic

<400> SEQUENCE: 48

```
Met Lys Leu Leu Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Gln Asn Phe Val Ile Thr Asp Ala Ser Leu Pro Asp Asn
65                  70                  75                  80

Pro Ile Val Tyr Ala Ser Arg Gly Phe Leu Thr Leu Thr Gly Tyr Ser
                85                  90                  95

Leu Asp Gln Ile Leu Gly Arg Asn Cys Arg Phe Leu Gln Gly Pro Glu
            100                 105                 110

Thr Asp Pro Arg Ala Val Asp Lys Ile Arg Asn Ala Ile Thr Lys Gly
        115                 120                 125

Val Asp Thr Ser Val Cys Leu Leu Asn Tyr Arg Gln Asp Gly Thr Thr
    130                 135                 140

Phe Trp Asn Leu Phe Phe Val Ala Gly Leu Arg Asp Ser Lys Gly Asn
145                 150                 155                 160
```

Ile Val Asn Tyr Val Gly Val Gln Ser Lys Val Ser Glu Asp Tyr Ala
                165                 170                 175

Lys Leu Leu Val Leu Gln Tyr Pro Tyr Asp Val Pro Asp Tyr Ala Glu
            180                 185                 190

Phe Gln Tyr Leu Pro Asp Thr Asp Asp Arg His Arg Ile Glu Glu Lys
        195                 200                 205

Arg Lys Arg Thr Tyr Glu Thr Phe Lys Ser Ile Met Lys Lys Ser Pro
210                 215                 220

Phe Ser Gly Pro Thr Asp Pro Arg Pro Pro Arg Arg Ile Ala Val
225                 230                 235                 240

Pro Ser Arg Ser Ser Ala Ser Val Pro Lys Pro Ala Pro Gln Pro Tyr
                245                 250                 255

Pro Phe Thr Ser Ser Leu Ser Thr Ile Asn Tyr Asp Glu Phe Pro Thr
            260                 265                 270

Met Val Phe Pro Ser Gly Gln Ile Ser Gln Ala Ser Ala Leu Ala Pro
        275                 280                 285

Ala Pro Pro Gln Val Leu Pro Gln Ala Pro Ala Pro Ala Pro Ala Pro
290                 295                 300

Ala Met Val Ser Ala Leu Ala Gln Ala Pro Ala Pro Val Pro Val Leu
305                 310                 315                 320

Ala Pro Gly Pro Pro Gln Ala Val Ala Pro Ala Pro Lys Pro Thr
                325                 330                 335

Gln Ala Gly Glu Gly Thr Leu Ser Glu Ala Leu Leu Gln Leu Gln Phe
            340                 345                 350

Asp Asp Glu Asp Leu Gly Ala Leu Leu Gly Asn Ser Thr Asp Pro Ala
        355                 360                 365

Val Phe Thr Asp Leu Ala Ser Val Asp Asn Ser Glu Phe Gln Gln Leu
370                 375                 380

Leu Asn Gln Gly Ile Pro Val Ala Pro His Thr Thr Glu Pro Met Leu
385                 390                 395                 400

Met Glu Tyr Pro Glu Ala Ile Thr Arg Leu Val Thr Gly Ala Gln Arg
                405                 410                 415

Pro Pro Asp Pro Ala Pro Ala Pro Leu Gly Ala Pro Gly Leu Pro Asn
            420                 425                 430

Gly Leu Leu Ser Gly Asp Glu Asp Phe Ser Ser Ile Ala Asp Met Asp
        435                 440                 445

Phe Ser Ala Leu Leu Ser Gln Ile Ser Ser
    450                 455

<210> SEQ ID NO 49
<211> LENGTH: 795
<212> TYPE: DNA
<213> ORGANISM: Homo sapiens

<400> SEQUENCE: 49
cagtacctgc cagatacaga cgatcgtcac cggattgagg agaaacgtaa aaggacatat    60
gagaccttca agagcatcat gaagaagagt cctttcagcg acccaccga ccccggcct    120 ccacctcgac gcattgctgt gccttcccgc agctcagctt ctgtcccaa gccagcaccc    180 cagccctatc cctttacgtc atccctgagc accatcaact atgatgagtt tccaccatg    240 gtgtttcctt ctgggcagat cagccaggcc tcggccttgg ccccggcccc tccccaagtc    300
ctgccccagg ctccagcccc tgcccctgct ccagccatgg tatcagctct ggcccaggcc    360
ccagcccctg tcccagtcct agccccaggc cctcctcagg ctgtggcccc acctgccccc    420

-continued

```
aagcccaccc aggctgggga aggaacgctg tcagaggccc tgctgcagct gcagtttgat      480
gatgaagacc tgggggcctt gcttggcaac agcacagacc cagctgtgtt cacagacctg      540
gcatccgtcg acaactccga gtttcagcag ctgctgaacc agggcatacc tgtggccccc      600
cacacaactg agcccatgct gatggagtac cctgaggcta taactcgcct agtgacaggg      660
gcccagaggc cccccgaccc agctcctgct ccactggggg ccccggggct ccccaatggc      720
ctcctttcag gagatgaaga cttctcctcc attgcggaca tggacttctc agccctgctg      780
agtcagatca gctcc                                                       795
```

<210> SEQ ID NO 50
<211> LENGTH: 266
<212> TYPE: PRT
<213> ORGANISM: Homo sapiens

<400> SEQUENCE: 50

```
Gln Tyr Leu Pro Asp Thr Asp Asp Arg His Arg Ile Glu Glu Lys Arg
1               5                   10                  15

Lys Arg Thr Tyr Glu Thr Phe Lys Ser Ile Met Lys Lys Ser Pro Phe
            20                  25                  30

Ser Gly Pro Thr Asp Pro Arg Pro Pro Arg Arg Ile Ala Val Pro
        35                  40                  45

Ser Arg Ser Ser Ala Ser Val Pro Lys Pro Ala Pro Gln Pro Tyr Pro
    50                  55                  60

Phe Thr Ser Ser Leu Ser Thr Ile Asn Tyr Asp Glu Phe Pro Thr Met
65                  70                  75                  80

Val Phe Pro Ser Gly Gln Ile Ser Gln Ala Ser Ala Leu Ala Pro Ala
                85                  90                  95

Pro Pro Gln Val Leu Pro Gln Ala Pro Ala Pro Ala Pro Ala Pro Ala
            100                 105                 110

Met Val Ser Ala Leu Ala Gln Ala Pro Ala Pro Val Pro Val Leu Ala
        115                 120                 125

Pro Gly Pro Pro Gln Ala Val Ala Pro Ala Pro Lys Pro Thr Gln
    130                 135                 140

Ala Gly Glu Gly Thr Leu Ser Glu Ala Leu Leu Gln Leu Gln Phe Asp
145                 150                 155                 160

Asp Glu Asp Leu Gly Ala Leu Leu Gly Asn Ser Thr Asp Pro Ala Val
                165                 170                 175

Phe Thr Asp Leu Ala Ser Val Asp Asn Ser Glu Phe Gln Gln Leu Leu
            180                 185                 190

Asn Gln Gly Ile Pro Val Ala Pro His Thr Thr Glu Pro Met Leu Met
        195                 200                 205

Glu Tyr Pro Glu Ala Ile Thr Arg Leu Val Thr Gly Ala Gln Arg Pro
    210                 215                 220

Pro Asp Pro Ala Pro Ala Pro Leu Gly Ala Val Pro Gly Leu Pro Asn
225                 230                 235                 240

Gly Leu Leu Ser Gly Asp Glu Asp Phe Ser Ser Ile Ala Asp Met Asp
                245                 250                 255

Phe Ser Ala Leu Leu Ser Gln Ile Ser Ser
            260                 265
```

<210> SEQ ID NO 51
<211> LENGTH: 138
<212> TYPE: DNA
<213> ORGANISM: Herpes simplex virus

<400> SEQUENCE: 51

```
tcgacggccc ccccgaccga tgtcagcctg ggggacgagc tccacttaga cggcgaggac    60
gtggcgatgg cgcatgccga cgcgctagac gatttcgatc tggacatgtt gggggacggg   120
gattccccgg gtccggga                                                 138
```

<210> SEQ ID NO 52
<211> LENGTH: 46
<212> TYPE: PRT
<213> ORGANISM: Herpes simplex virus

<400> SEQUENCE: 52

```
Ser Thr Ala Pro Pro Thr Asp Val Ser Leu Gly Asp Glu Leu His Leu
1               5                   10                  15
Asp Gly Glu Asp Val Ala Met Ala His Ala Asp Ala Leu Asp Asp Phe
            20                  25                  30
Asp Leu Asp Met Leu Gly Asp Gly Asp Ser Pro Gly Pro Gly
        35                  40                  45
```

<210> SEQ ID NO 53
<211> LENGTH: 339
<212> TYPE: DNA
<213> ORGANISM: Saccharomy cescerevisiae

<400> SEQUENCE: 53

```
aattttaatc aaagtgggaa tattgctgat agctcattgt ccttcacttt cactaacagt    60
agcaacggtc cgaacctcat aacaactcaa acaaattctc aagcgctttc acaaccaatt   120
gcctcctcta acgttcatga taacttcatg aataatgaaa tcacggctag taaaattgat   180
gatggtaata attcaaaacc actgtcacct ggttggacgg accaaactgc gtataacgcg   240
tttggaatca ctacagggat gtttaatacc actacaatgg atgatgtata taactatcta   300
ttcgatgatg aagatacccc accaaaccca aaaaaagag                         339
```

<210> SEQ ID NO 54
<211> LENGTH: 113
<212> TYPE: PRT
<213> ORGANISM: Saccharomy cescerevisiae

<400> SEQUENCE: 54

```
Asn Phe Asn Gln Ser Gly Asn Ile Ala Asp Ser Ser Leu Ser Phe Thr
1               5                   10                  15
Phe Thr Asn Ser Ser Asn Gly Pro Asn Leu Ile Thr Thr Gln Thr Asn
            20                  25                  30
Ser Gln Ala Leu Ser Gln Pro Ile Ala Ser Ser Asn Val His Asp Asn
        35                  40                  45
Phe Met Asn Asn Glu Ile Thr Ala Ser Lys Ile Asp Asp Gly Asn Asn
    50                  55                  60
Ser Lys Pro Leu Ser Pro Gly Trp Thr Asp Gln Thr Ala Tyr Asn Ala
65                  70                  75                  80
Phe Gly Ile Thr Thr Gly Met Phe Asn Thr Thr Thr Met Asp Asp Val
                85                  90                  95
Tyr Asn Tyr Leu Phe Asp Asp Glu Asp Thr Pro Pro Asn Pro Lys Lys
            100                 105                 110
Glu
```

<210> SEQ ID NO 55

<211> LENGTH: 192
<212> TYPE: DNA
<213> ORGANISM: Homo sapiens

<400> SEQUENCE: 55

```
gtgtcagtga catttgaaga tgtggctgtg ctctttactc gggacgagtg gaagaagctg      60
gatctgtctc agagaagcct gtaccgtgag gtgatgctgg agaattacag caacctggcc     120
tccatggcag gattcctgtt taccaaacca aaggtgatct ccctgttgca gcaaggagag     180
gatccctggt aa                                                         192
```

<210> SEQ ID NO 56
<211> LENGTH: 63
<212> TYPE: PRT
<213> ORGANISM: Homo sapiens

<400> SEQUENCE: 56

```
Val Ser Val Thr Phe Glu Asp Val Ala Val Leu Phe Thr Arg Asp Glu
 1               5                  10                  15

Trp Lys Lys Leu Asp Leu Ser Gln Arg Ser Leu Tyr Arg Glu Val Met
            20                  25                  30

Leu Glu Asn Tyr Ser Asn Leu Ala Ser Met Ala Gly Phe Leu Phe Thr
        35                  40                  45

Lys Pro Lys Val Ile Ser Leu Leu Gln Gln Gly Glu Asp Pro Trp
    50                  55                  60
```

<210> SEQ ID NO 57
<211> LENGTH: 918
<212> TYPE: DNA
<213> ORGANISM: Artificial sequence
<220> FEATURE:
<223> OTHER INFORMATION: Synthetic

<400> SEQUENCE: 57

```
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaaacga cctgaaacag aaagtcatga ccacagatc tcatacgctc      240
tacgctcccg gcggttatga cattatgggc tatctgattc agattatgaa caggccaaac     300
ccccaagtag aactgggacc tgttgacacg tcagttgctc tgattctgtg cgacctgaag     360
caaaaagaca cgccaattgt gtacgcctcg gaagcttttc tctatatgac aggatacagc     420
aatgcggagg tcttggggag aaactgccgt tttcttcagt cacccgacgg aatggtcaag     480
ccgaaatcga caaggaagta cgtcgactcc aacacgatca atacgatgag gaaagcgatt     540
gataggaacg ccgaggtgca ggttgaggtg gtcaattta agaagaacgg ccaacggttt      600
gtcaacttct tgacgatgat tccggtgcga atgaaacag gggaataccg gtacagcatg      660
ggttccagt gcgaaacgga actgcagtac ccatacgatg ttccagatta cgctgaattc      720
ctagcagtgt cagtgacatt tgaagatgtg gctgtgctct tactcgggac gagtggaag      780
aagctggatc tgtctcagag aagcctgtac cgtgaggtga tgctggagaa ttacagcaac     840
ctggcctcca tggcaggatt cctgtttacc aaaccaaagg tgatctcct gttgcagcaa      900
ggagaggatc cctggtaa                                                   918
```

<210> SEQ ID NO 58
<211> LENGTH: 305

<212> TYPE: PRT
<213> ORGANISM: Artificial sequence
<220> FEATURE:
<223> OTHER INFORMATION: Synthetic

<400> SEQUENCE: 58

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Asn Asp Leu Lys Gln Lys Val Met Asn His Arg Ser His Thr Leu
65                  70                  75                  80

Tyr Ala Pro Gly Gly Tyr Asp Ile Met Gly Tyr Leu Ile Gln Ile Met
                85                  90                  95

Asn Arg Pro Asn Pro Gln Val Glu Leu Gly Pro Val Asp Thr Ser Val
            100                 105                 110

Ala Leu Ile Leu Cys Asp Leu Lys Gln Lys Asp Thr Pro Ile Val Tyr
        115                 120                 125

Ala Ser Glu Ala Phe Leu Tyr Met Thr Gly Tyr Ser Asn Ala Glu Val
    130                 135                 140

Leu Gly Arg Asn Cys Arg Phe Leu Gln Ser Pro Asp Gly Met Val Lys
145                 150                 155                 160

Pro Lys Ser Thr Arg Lys Tyr Val Asp Ser Asn Thr Ile Asn Thr Met
                165                 170                 175

Arg Lys Ala Ile Asp Arg Asn Ala Glu Val Gln Val Glu Val Val Asn
            180                 185                 190

Phe Lys Lys Asn Gly Gln Arg Phe Val Asn Phe Leu Thr Met Ile Pro
        195                 200                 205

Val Arg Asp Glu Thr Gly Glu Tyr Arg Tyr Ser Met Gly Phe Gln Cys
    210                 215                 220

Glu Thr Glu Leu Gln Tyr Pro Tyr Asp Val Pro Asp Tyr Ala Glu Phe
225                 230                 235                 240

Leu Ala Val Ser Val Thr Phe Glu Asp Val Ala Val Leu Phe Thr Arg
                245                 250                 255

Asp Glu Trp Lys Lys Leu Asp Leu Ser Gln Arg Ser Leu Tyr Arg Glu
            260                 265                 270

Val Met Leu Glu Asn Tyr Ser Asn Leu Ala Ser Met Ala Gly Phe Leu
        275                 280                 285

Phe Thr Lys Pro Lys Val Ile Ser Leu Leu Gln Gln Gly Glu Asp Pro
    290                 295                 300

Trp
305
```

<210> SEQ ID NO 59
<211> LENGTH: 1509
<212> TYPE: DNA
<213> ORGANISM: Artificial sequence
<220> FEATURE:
<223> OTHER INFORMATION: Synthetic

<400> SEQUENCE: 59

```
atgaagctac tgtcttctat cgaacaagca tgcgatattt gccgacttaa aaagctcaag    60
```

```
tgctccaaag aaaaaccgaa gtgcgccaag tgtctgaaga caactggga gtgtcgctac      120 tctcccaaaa ccaaaaggtc tccgctgact agggcacatc tgacagaagt ggaatcaagg      180
ctagaaagac tggaaggtgg cagatccatc gccaccagat ctcatacgct ctacgctccc      240
ggcggttatg acattatggg ctatctgatt cagattatga acaggccaaa ccccccaagta     300 gaactgggac ctgttgacac gtcatgcgct ctgattctgt gcgacctgaa gcaaaaagac      360
acgccaattg tgtacgcctc ggaagctttt ctctatatga caggatacag caatgcggag      420
gtcttgggga gaaactgccg tttttcttcag tcacccgacg gaatggtcaa gccgaaatcg    480
acaaggaagt acgtcgactc aaacacgatc aatacgatga ggaaagcgat tgataggaac     540
gccgaggtgc aggttgaggt ggtcaatttt aagaagaacg ccaacggtt tgtcaacttc      600 ttgacgatga ttccggtgcg agatgaaaca ggggaatacc ggtacagcat gggtttccag     660
tgcgaaacgg aactgcagta cccatacgat gttccagatt acgctgaatt ccagtacctg     720
ccagatacag acgatcgtca ccggattgag gagaaacgta aaggacata tgagaccttc      780 aagagcatca tgaagaagag tcctttcagc ggacccaccg accccggcc tccacctcga     840 cgcattgctg tgccttcccg cagctcagct tctgtcccca agccagcacc ccagccctat     900 cccttttacgt catccctgag caccatcaac tatgatgagt tcccaccat ggtgtttcct     960 tctgggcaga tcagccaggc ctcggccttg gccccggccc ctccccaagt cctgccccag    1020
gctccagccc ctgcccctgc tccagccatg gtatcagctc tggcccaggc ccagccccct    1080
gtcccagtcc tagccccagg ccctcctcag gctgtggccc cacctgcccc caagcccacc    1140
caggctgggg aaggaacgct gtcagaggcc ctgctgcagc tgcagtttga tgatgaagac    1200
ctgggggcct tgcttggcaa cagcacagac ccagctgtgt tcacagacct ggcatccgtc    1260
gacaactccg agtttcagca gctgctgaac cagggcatac ctgtggcccc ccacacaact    1320
gagcccatgc tgatggagta ccctgaggct ataactcgcc tagtgacagg ggcccagagg    1380
ccccccgacc cagctcctgc tccactgggg gccccggggc tccccaatgg cctcctttca    1440
ggagatgaag acttctcctc cattgcggac atggacttct cagccctgct gagtcagatc    1500
agctcctaa                                                            1509
```

<210> SEQ ID NO 60
<211> LENGTH: 502
<212> TYPE: PRT
<213> ORGANISM: Artificial sequence
<220> FEATURE:
<223> OTHER INFORMATION: Synthetic

<400> SEQUENCE: 60

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gly Gly Arg Ser Ile Ala Thr Arg Ser His Thr Leu Tyr Ala Pro
65                  70                  75                  80

Gly Gly Tyr Asp Ile Met Gly Tyr Leu Ile Gln Ile Met Asn Arg Pro
                85                  90                  95

Asn Pro Gln Val Glu Leu Gly Pro Val Asp Thr Ser Cys Ala Leu Ile
```

```
            100                 105                 110
Leu Cys Asp Leu Lys Gln Lys Asp Thr Pro Ile Val Tyr Ala Ser Glu
            115                 120                 125

Ala Phe Leu Tyr Met Thr Gly Tyr Ser Asn Ala Glu Val Leu Gly Arg
            130                 135                 140

Asn Cys Arg Phe Leu Gln Ser Pro Asp Gly Met Val Lys Pro Lys Ser
145                 150                 155                 160

Thr Arg Lys Tyr Val Asp Ser Asn Thr Ile Asn Thr Met Arg Lys Ala
                165                 170                 175

Ile Asp Arg Asn Ala Glu Val Gln Val Glu Val Val Asn Phe Lys Lys
                180                 185                 190

Asn Gly Gln Arg Phe Val Asn Phe Leu Thr Met Ile Pro Val Arg Asp
            195                 200                 205

Glu Thr Gly Glu Tyr Arg Tyr Ser Met Gly Phe Gln Cys Glu Thr Glu
            210                 215                 220

Leu Gln Tyr Pro Tyr Asp Val Pro Asp Tyr Ala Glu Phe Gln Tyr Leu
225                 230                 235                 240

Pro Asp Thr Asp Asp Arg His Arg Ile Glu Glu Lys Arg Lys Arg Thr
                245                 250                 255

Tyr Glu Thr Phe Lys Ser Ile Met Lys Lys Ser Pro Phe Ser Gly Pro
                260                 265                 270

Thr Asp Pro Arg Pro Pro Arg Arg Ile Ala Val Pro Ser Arg Ser
            275                 280                 285

Ser Ala Ser Val Pro Lys Pro Ala Pro Gln Pro Tyr Pro Phe Thr Ser
            290                 295                 300

Ser Leu Ser Thr Ile Asn Tyr Asp Glu Phe Pro Thr Met Val Phe Pro
305                 310                 315                 320

Ser Gly Gln Ile Ser Gln Ala Ser Ala Leu Ala Pro Ala Pro Pro Gln
            325                 330                 335

Val Leu Pro Gln Ala Pro Ala Pro Ala Pro Ala Met Val Ser
            340                 345                 350

Ala Leu Ala Gln Ala Pro Ala Pro Val Pro Val Leu Ala Pro Gly Pro
            355                 360                 365

Pro Gln Ala Val Ala Pro Pro Ala Pro Lys Pro Thr Gln Ala Gly Glu
            370                 375                 380

Gly Thr Leu Ser Glu Ala Leu Leu Gln Leu Gln Phe Asp Asp Glu Asp
385                 390                 395                 400

Leu Gly Ala Leu Leu Gly Asn Ser Thr Asp Pro Ala Val Phe Thr Asp
                405                 410                 415

Leu Ala Ser Val Asp Asn Ser Glu Phe Gln Gln Leu Leu Asn Gln Gly
                420                 425                 430

Ile Pro Val Ala Pro His Thr Thr Glu Pro Met Leu Met Glu Tyr Pro
                435                 440                 445

Glu Ala Ile Thr Arg Leu Val Thr Gly Ala Gln Arg Pro Pro Asp Pro
            450                 455                 460

Ala Pro Ala Pro Leu Gly Ala Pro Gly Leu Pro Asn Gly Leu Leu Ser
465                 470                 475                 480

Gly Asp Glu Asp Phe Ser Ser Ile Ala Asp Met Asp Phe Ser Ala Leu
                485                 490                 495

Leu Ser Gln Ile Ser Ser
            500

<210> SEQ ID NO 61
```

<211> LENGTH: 1518
<212> TYPE: DNA
<213> ORGANISM: Artificial sequence
<220> FEATURE:
<223> OTHER INFORMATION: Synthetic

<400> SEQUENCE: 61

```
atgaagctac tgtcttctat cgaacaagca tgcgatattt gccgacttaa aaagctcaag    60
tgctccaaag aaaaaccgaa gtgcgccaag tgtctgaaga caactggga gtgtcgctac   120
tctcccaaaa ccaaaaggtc tccgctgact agggcacatc tgacagaagt ggaatcaagg   180
ctagaaagac tggaaggtgg tggaggatcc agatccatcg ccaccagatc tcatacgctc   240
tacgctcccg gcggttatga cattatgggc tatctgattc agattatgaa caggccaaac   300
ccccaagtag aactgggacc tgttgacacg tcatgcgctc tgattctgtg cgacctgaag   360
caaaagaca cgccaattgt gtacgcctcg gaagcttttc tctatatgac aggatacagc   420
aatgcggagg tcttggggag aaactgccgt tttcttcagt cacccgacgg aatggtcaag   480
ccgaaatcga caaggaagta cgtcgactcc aacacgatca atacgatgag gaaagcgatt   540
gataggaacg ccgaggtgca ggttgaggtg gtcaatttta agaagaacgg ccaacggttt   600
gtcaacttct tgacgatgat tccggtgcga gatgaaacag gggaataccg gtacagcatg   660
ggtttccagt gcgaaacgga actgcagtac ccatacgatg ttccagatta cgctgaattc   720
cagtacctgc cagatacaga cgatcgtcac cggattgagg agaaacgtaa aaggacatat   780
gagaccttca gagcatcat gaagaagagt cctttcagcg acccaccga ccccgggcct   840
ccacctcgac gcattgctgt gccttcccgc agctcagctt ctgtcccaa gcagcaccc   900
cagccctatc cctttacgtc atccctgagc accatcaact atgatgagtt tcccaccatg   960
gtgtttcctt ctgggcagat cagccaggcc tcggccttgg ccccggcccc tccccaagtc  1020
ctgccccagg ctccagcccc tgcccctgct ccagccatgg tatcagctct ggcccaggcc  1080
ccagcccctg tccagtcct agccccaggc cctcctcagg ctgtggcccc acctgccccc  1140
aagcccaccc aggctgggga aggaacgctg tcagaggccc tgctgcagct gcagtttgat  1200
gatgaagacc tggggccctt gcttggcaac agcacagacc cagctgtgtt cacagacctg  1260
gcatccgtcg acaactccga gtttcagcag ctgctgaacc agggcatacc tgtggccccc  1320
cacacaactg agcccatgct gatggagtac cctgaggcta taactcgcct agtgacaggg  1380
gcccagaggc ccccgacccc agctcctgct ccactggggg ccccggggct ccccaatggc  1440
ctcctttcag gagatgaaga cttctcctcc attgcggaca tggacttctc agccctgctg  1500
agtcagatca gctcctaa                                                1518
```

<210> SEQ ID NO 62
<211> LENGTH: 505
<212> TYPE: PRT
<213> ORGANISM: Artificial sequence
<220> FEATURE:
<223> OTHER INFORMATION: Synthetic

<400> SEQUENCE: 62

```
Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45
```

```
Leu Thr Arg Ala His Leu Thr Glu Val Glu Ser Arg Leu Glu Arg Leu
 50                  55                  60

Glu Gly Gly Gly Ser Arg Ser Ile Ala Thr Arg Ser His Thr Leu
 65                  70                  75                  80

Tyr Ala Pro Gly Gly Tyr Asp Ile Met Gly Tyr Leu Ile Gln Ile Met
                 85                  90                  95

Asn Arg Pro Asn Pro Gln Val Glu Leu Gly Pro Val Asp Thr Ser Cys
                100                 105                 110

Ala Leu Ile Leu Cys Asp Leu Lys Gln Lys Asp Thr Pro Ile Val Tyr
                115                 120                 125

Ala Ser Glu Ala Phe Leu Tyr Met Thr Gly Tyr Ser Asn Ala Glu Val
        130                 135                 140

Leu Gly Arg Asn Cys Arg Phe Leu Gln Ser Pro Asp Gly Met Val Lys
145                 150                 155                 160

Pro Lys Ser Thr Arg Lys Tyr Val Asp Ser Asn Thr Ile Asn Thr Met
                165                 170                 175

Arg Lys Ala Ile Asp Arg Asn Ala Glu Val Gln Val Glu Val Val Asn
                180                 185                 190

Phe Lys Lys Asn Gly Gln Arg Phe Val Asn Phe Leu Thr Met Ile Pro
        195                 200                 205

Val Arg Asp Glu Thr Gly Glu Tyr Arg Tyr Ser Met Gly Phe Gln Cys
210                 215                 220

Glu Thr Glu Leu Gln Tyr Pro Tyr Asp Val Pro Asp Tyr Ala Glu Phe
225                 230                 235                 240

Gln Tyr Leu Pro Asp Thr Asp Asp Arg His Arg Ile Glu Glu Lys Arg
                245                 250                 255

Lys Arg Thr Tyr Glu Thr Phe Lys Ser Ile Met Lys Lys Ser Pro Phe
                260                 265                 270

Ser Gly Pro Thr Asp Pro Arg Pro Pro Arg Arg Ile Ala Val Pro
        275                 280                 285

Ser Arg Ser Ser Ala Ser Val Pro Lys Pro Ala Pro Gln Pro Tyr Pro
        290                 295                 300

Phe Thr Ser Ser Leu Ser Thr Ile Asn Tyr Asp Glu Phe Pro Thr Met
305                 310                 315                 320

Val Phe Pro Ser Gly Gln Ile Ser Gln Ala Ser Ala Leu Ala Pro Ala
                325                 330                 335

Pro Pro Gln Val Leu Pro Gln Ala Pro Ala Pro Ala Pro Ala Pro Ala
                340                 345                 350

Met Val Ser Ala Leu Ala Gln Ala Pro Ala Pro Val Pro Val Leu Ala
                355                 360                 365

Pro Gly Pro Pro Gln Ala Val Ala Pro Ala Pro Lys Pro Thr Gln
        370                 375                 380

Ala Gly Glu Gly Thr Leu Ser Glu Ala Leu Leu Gln Leu Gln Phe Asp
385                 390                 395                 400

Asp Glu Asp Leu Gly Ala Leu Leu Gly Asn Ser Thr Asp Pro Ala Val
                405                 410                 415

Phe Thr Asp Leu Ala Ser Val Asp Asn Ser Glu Phe Gln Gln Leu Leu
                420                 425                 430

Asn Gln Gly Ile Pro Val Ala Pro His Thr Thr Glu Pro Met Leu Met
                435                 440                 445

Glu Tyr Pro Glu Ala Ile Thr Arg Leu Val Thr Gly Ala Gln Arg Pro
                450                 455                 460

Pro Asp Pro Ala Pro Ala Pro Leu Gly Ala Pro Gly Leu Pro Asn Gly
```

465             470              475              480
Leu Leu Ser Gly Asp Glu Asp Phe Ser Ile Ala Asp Met Asp Phe
                485              490              495

Ser Ala Leu Leu Ser Gln Ile Ser Ser
            500              505

<210> SEQ ID NO 63
<211> LENGTH: 1518
<212> TYPE: DNA
<213> ORGANISM: Artificial sequence
<220> FEATURE:
<223> OTHER INFORMATION: Synthetic

<400> SEQUENCE: 63

| | | | | | |
|---|---|---|---|---|---|
| atgaagctac | tgtcttctat | cgaacaagca | tgcgatattt | gccgacttaa | aaagctcaag | 60 |
| tgctccaaag | aaaaaccgaa | gtgcgccaag | tgtctgaaga | caactggga | gtgtcgctac | 120 |
| tctcccaaaa | ccaaaaggtc | tccgctgact | agggcacatc | tgacagaagt | ggaatcaagg | 180 |
| ctagaaagac | tggaaaacga | cctgaaacag | aaagtcatga | ccacagatc | tcatacgctc | 240 |
| tacgctcccg | gcggttatga | cattatgggc | tatctgattc | agattatgaa | caggccaaac | 300 |
| ccccaagtag | aactgggacc | tgttgacacg | tcatgcgctc | tgattctgtg | cgacctgaag | 360 |
| caaaaagaca | cgccaattgt | gtacgcctcg | gaagctttc | tctatatgac | aggatacagc | 420 |
| aatgcggagg | tcttggggag | aaactgccgt | tttcttcagt | cacccgacgg | aatggtcaag | 480 |
| ccgaaatcga | caaggaagta | cgtcgactcc | aacacgatca | atacgatgag | gaaagcgatt | 540 |
| gataggaacg | ccgaggtgca | ggttgaggtg | gtcaatttta | gaagaacgg | ccaacggttt | 600 |
| gtcaacttct | tgacgatgat | tccggtgcga | gatgaaacag | gggaataccg | gtacagcatg | 660 |
| ggtttccagt | gcgaaacgga | actgcagtac | ccatacgatg | ttccagatta | cgctgaattc | 720 |
| cagtacctgc | cagatacaga | cgatcgtcac | cggattgagg | agaaacgtaa | aaggacatat | 780 |
| gagaccttca | gagcatcat | gaagaagagt | cctttcagcg | gacccaccga | ccccggcct | 840 |
| ccacctcgac | gcattgctgt | gccttcccgc | agctcagctt | ctgtccccaa | gccagcaccc | 900 |
| cagcccctatc | cctttacgtc | atccctgagc | accatcaact | atgatgagtt | ccccaccatg | 960 |
| gtgtttcctt | ctgggcagat | cagccaggcc | tcggccttgg | ccccggcccc | tccccaagtc | 1020 |
| ctgccccagg | ctccagcccc | tgccctgct | ccagccatgg | tatcagctct | ggcccaggcc | 1080 |
| ccagcccctg | tcccagtcct | agcccaggc | cctcctcagg | ctgtggcccc | acctgccccc | 1140 |
| aagcccaccc | aggctgggga | aggaacgctg | tcagaggccc | tgctgcagct | gcagtttgat | 1200 |
| gatgaagacc | tgggggcctt | gcttggcaac | agcacagacc | cagctgtgtt | cacagacctg | 1260 |
| gcatccgtcg | acaactccga | gtttcagcag | ctgctgaacc | agggcatacc | tgtggccccc | 1320 |
| cacacaactg | agcccatgct | gatggagtac | cctgaggcta | taactcgcct | agtgacaggg | 1380 |
| gcccagaggc | cccccgaccc | agctcctgct | ccactggggg | cccgggggct | ccccaatggc | 1440 |
| ctcctttcag | gagatgaaga | cttctcctcc | attgcggaca | tggacttctc | agccctgctg | 1500 |
| agtcagatca | gctcctaa | | | | | 1518 |

<210> SEQ ID NO 64
<211> LENGTH: 505
<212> TYPE: PRT
<213> ORGANISM: Artificial sequence
<220> FEATURE:
<223> OTHER INFORMATION: Synthetic

<400> SEQUENCE: 64

-continued

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Asn Asp Leu Lys Gln Lys Val Met Asn His Arg Ser His Thr Leu
65                  70                  75                  80

Tyr Ala Pro Gly Gly Tyr Asp Ile Met Gly Tyr Leu Ile Gln Ile Met
                85                  90                  95

Asn Arg Pro Asn Pro Gln Val Glu Leu Gly Pro Val Asp Thr Ser Cys
            100                 105                 110

Ala Leu Ile Leu Cys Asp Leu Lys Gln Lys Asp Thr Pro Ile Val Tyr
        115                 120                 125

Ala Ser Glu Ala Phe Leu Tyr Met Thr Gly Tyr Ser Asn Ala Glu Val
    130                 135                 140

Leu Gly Arg Asn Cys Arg Phe Leu Gln Ser Pro Asp Gly Met Val Lys
145                 150                 155                 160

Pro Lys Ser Thr Arg Lys Tyr Val Asp Ser Asn Thr Ile Asn Thr Met
                165                 170                 175

Arg Lys Ala Ile Asp Arg Asn Ala Glu Val Gln Val Glu Val Val Asn
            180                 185                 190

Phe Lys Lys Asn Gly Gln Arg Phe Val Asn Phe Leu Thr Met Ile Pro
        195                 200                 205

Val Arg Asp Glu Thr Gly Glu Tyr Arg Tyr Ser Met Gly Phe Gln Cys
    210                 215                 220

Glu Thr Glu Leu Gln Tyr Pro Tyr Asp Val Pro Asp Tyr Ala Glu Phe
225                 230                 235                 240

Gln Tyr Leu Pro Asp Thr Asp Asp Arg His Arg Ile Glu Glu Lys Arg
                245                 250                 255

Lys Arg Thr Tyr Glu Thr Phe Lys Ser Ile Met Lys Lys Ser Pro Phe
            260                 265                 270

Ser Gly Pro Thr Asp Pro Arg Pro Pro Arg Arg Ile Ala Val Pro
        275                 280                 285

Ser Arg Ser Ser Ala Ser Val Pro Lys Pro Ala Pro Gln Pro Tyr Pro
    290                 295                 300

Phe Thr Ser Ser Leu Ser Thr Ile Asn Tyr Asp Glu Phe Pro Thr Met
305                 310                 315                 320

Val Phe Pro Ser Gly Gln Ile Ser Gln Ala Ser Ala Leu Ala Pro Ala
                325                 330                 335

Pro Pro Gln Val Leu Pro Gln Ala Pro Ala Pro Ala Pro Ala Pro Ala
            340                 345                 350

Met Val Ser Ala Leu Ala Gln Ala Pro Ala Pro Val Pro Val Leu Ala
        355                 360                 365

Pro Gly Pro Pro Gln Ala Val Ala Pro Ala Pro Lys Pro Thr Gln
    370                 375                 380

Ala Gly Glu Gly Thr Leu Ser Glu Ala Leu Leu Gln Leu Gln Phe Asp
385                 390                 395                 400

Asp Glu Asp Leu Gly Ala Leu Leu Gly Asn Ser Thr Asp Pro Ala Val
                405                 410                 415
```

```
Phe Thr Asp Leu Ala Ser Val Asp Asn Ser Glu Phe Gln Gln Leu Leu
            420                 425                 430

Asn Gln Gly Ile Pro Val Ala Pro His Thr Thr Glu Pro Met Leu Met
        435                 440                 445

Glu Tyr Pro Glu Ala Ile Thr Arg Leu Val Thr Gly Ala Gln Arg Pro
    450                 455                 460

Pro Asp Pro Ala Pro Ala Pro Leu Gly Ala Pro Gly Leu Pro Asn Gly
465                 470                 475                 480

Leu Leu Ser Gly Asp Glu Asp Phe Ser Ser Ile Ala Asp Met Asp Phe
                485                 490                 495

Ser Ala Leu Leu Ser Gln Ile Ser Ser
            500                 505

<210> SEQ ID NO 65
<211> LENGTH: 72
<212> TYPE: PRT
<213> ORGANISM: Simian vacuolating virus 40

<400> SEQUENCE: 65

Ala Thr Gly Gly Ala Thr Ala Ala Ala Gly Cys Gly Gly Ala Ala Thr
1               5                   10                  15

Thr Ala Ala Thr Thr Cys Cys Cys Gly Ala Gly Cys Cys Thr Cys Cys
                20                  25                  30

Ala Ala Ala Ala Ala Gly Ala Gly Ala Gly Ala Ala Ala Ala Ala Gly
            35                  40                  45

Gly Thr Cys Gly Ala Ala Thr Thr Gly Gly Gly Thr Ala Cys Cys Gly
        50                  55                  60

Cys Cys Gly Cys Gly Gly Thr
65                  70

<210> SEQ ID NO 66
<211> LENGTH: 24
<212> TYPE: PRT
<213> ORGANISM: Simian vacuolating virus 40

<400> SEQUENCE: 66

Met Asp Lys Ala Glu Leu Ile Pro Glu Pro Lys Lys Lys Arg Lys
1               5                   10                  15

Val Glu Leu Gly Thr Ala Ala Gly
            20

<210> SEQ ID NO 67
<211> LENGTH: 19
<212> TYPE: PRT
<213> ORGANISM: Saccharomy cescerevisiae

<400> SEQUENCE: 67

Cys Gly Gly Arg Asn Asn Arg Cys Tyr Asn Tyr Asn Tyr Asn Cys Asn
1               5                   10                  15

Cys Cys Gly

<210> SEQ ID NO 68
<211> LENGTH: 9
<212> TYPE: DNA
<213> ORGANISM: E.coli
<220> FEATURE:
<221> NAME/KEY: misc_feature
<222> LOCATION: (5)..(5)
<223> OTHER INFORMATION: n is a, c, g, or t

<400> SEQUENCE: 68
``` ctgtnacag                                                                9

<210> SEQ ID NO 69
<211> LENGTH: 21
<212> TYPE: DNA
<213> ORGANISM: E.coli

<400> SEQUENCE: 69
gaattgtgag cgctcacaat t                                                 21

<210> SEQ ID NO 70
<211> LENGTH: 19
<212> TYPE: DNA
<213> ORGANISM: E.coli

<400> SEQUENCE: 70
tccctatcag tgatagaga                                                    19

<210> SEQ ID NO 71
<211> LENGTH: 64
<212> TYPE: DNA
<213> ORGANISM: Bacteriophage lambda

<400> SEQUENCE: 71
tatcaccgca aggagataaat atctaacacc gtgcgtgttg actattttac ctctggcggt      60
gata                                                                    64

<210> SEQ ID NO 72
<211> LENGTH: 42
<212> TYPE: DNA
<213> ORGANISM: adenovirus

<400> SEQUENCE: 72 cgggggggcta taaaaggggg tgggggcgtt cgtcctcact ct                         42

<210> SEQ ID NO 73
<211> LENGTH: 344
<212> TYPE: DNA
<213> ORGANISM: Simian vacuolating virus 40

<400> SEQUENCE: 73
ctgtggaatg tgtgtcagtt agggtgtgga aagtccccag gctccccagc aggcagaagt       60
atgcaaagca tgcatctcaa ttagtcagca accaggtgtg gaaagtcccc aggctcccca     120
gcaggcagaa gtatgcaaag catgcatctc aattagtcag caaccatagt cccgccccta    180
actccgccca tcccgcccct aactccgccc agttccgccc attctccgcc ccatggctga    240 ctaattttt ttatttatgc agaggccgag gccgcctctg cctctgagct attccagaag     300
tagtgaggag gcttttttgg aggcctaggc ttttgcaaaa agct                      344

<210> SEQ ID NO 74
<211> LENGTH: 451
<212> TYPE: DNA
<213> ORGANISM: Saccharomy cescerevisiae

<400> SEQUENCE: 74
acggattaga agccgccgag cgggtgacag ccctccgaag gaagactctc ctccgtgcgt       60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180

```
ctggccccac aaaccttcaa atgaacgaat caaattaaca accataggat gataatgcga    240 ttagttttt agccttattt ctggggtaat taatcagcga agcgatgatt tttgatctat     300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac c                                   451

<210> SEQ ID NO 75
<211> LENGTH: 120
<212> TYPE: DNA
<213> ORGANISM: Cytomegalovirus

<400> SEQUENCE: 75
gtaggcgtgt acggtgggag gcctatataa gcagagctcg tttagtgaac cgtcagatcg    60
cctggagacg ccatccacgc tgttttgacc tccatagaag acaccgggac cgatccagcc    120

<210> SEQ ID NO 76
<211> LENGTH: 1653
<212> TYPE: DNA
<213> ORGANISM: firefly

<400> SEQUENCE: 76
atggaagacg ccaaaaacat aaagaaaggc ccggcgccat tctatccgct ggaagatgga    60
accgctggag agcaactgca taaggctatg aagagatacg ccctggttcc tggaacaatt    120
gcttttacag atgcacatat cgaggtggac atcacttacg ctgagtactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgggcatt    360
tcgcagccta ccgtggtgtt cgtttccaaa aaggggttgc aaaaaatttt gaacgtgcaa    420
aaaaagctcc caatcatcca aaaaattatt atcatggatt ctaaaacgga ttaccaggga    480
tttcagtcga tgtacacgtt cgtcacatct catctacctc ccggttttaa tgaatacgat    540
tttgtgccag agtccttcga tagggacaag acaattgcac tgatcatgaa ctcctctgga    600
tctactggtc tgcctaaagg tgtcgctctg cctcatagaa ctgcctgcgt gagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tcccctctct    960
aaggaagtcg gggaagcggt tgccaagagg ttccatctgc caggtatcag gcaaggatat    1020
gggctcactg agactacatc agctattctg attacacccg agggggatga taaaccgggc    1080
gcggtcggta aagttgttcc attttttgaa gcgaaggttg tggatctgga taccgggaaa    1140
acgctgggcg ttaatcaaag aggcgaactg tgtgtgagag gtcctatgat tatgtccggt    1200
tatgtaaaca atccggaagc gaccaacgcc ttgattgaca aggatggatg gctacattct    1260
ggagacatag cttactggga cgaagacgaa cacttcttca tcgttgaccg cctgaagtct    1320
ctgattaagt acaaaggcta tcaggtggct cccgctgaat tggaatccat cttgctccaa    1380 cacccccaaca tcttcgacgc aggtgtcgca ggtcttcccg acgatgacgc cggtgaactt    1440
cccgccgccg ttgttgtttt ggagcacgga aagacgatga cggaaaaaga gatcgtggat    1500
```

```
tacgtcgcca gtcaagtaac aaccgcgaaa aagttgcgcg gaggagttgt gtttgtggac    1560
gaagtaccga aggtcttac cggaaaactc gacgcaagaa aaatcagaga gatcctcata    1620
aaggccaaga agggcggaaa gatcgccgtg taa                                 1653
```

<210> SEQ ID NO 77
<211> LENGTH: 550
<212> TYPE: PRT
<213> ORGANISM: firefly

<400> SEQUENCE: 77

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
```

```
              340            345              350
Pro Glu Gly Asp Asp Lys Pro Gly Ala Val Gly Lys Val Val Pro Phe
            355                360                 365

Phe Glu Ala Lys Val Val Asp Leu Asp Thr Gly Lys Thr Leu Gly Val
        370                375                 380

Asn Gln Arg Gly Glu Leu Cys Val Arg Gly Pro Met Ile Met Ser Gly
385                 390                395                 400

Tyr Val Asn Asn Pro Glu Ala Thr Asn Ala Leu Ile Asp Lys Asp Gly
                405                410                 415

Trp Leu His Ser Gly Asp Ile Ala Tyr Trp Asp Glu Asp His Phe
            420                425                 430

Phe Ile Val Asp Arg Leu Lys Ser Leu Ile Lys Tyr Lys Gly Tyr Gln
        435                440                 445

Val Ala Pro Ala Glu Leu Glu Ser Ile Leu Leu Gln His Pro Asn Ile
    450                455                 460

Phe Asp Ala Gly Val Ala Gly Leu Pro Asp Asp Ala Gly Glu Leu
465                470                475                 480

Pro Ala Ala Val Val Val Leu Glu His Gly Lys Thr Met Thr Glu Lys
            485                490                 495

Glu Ile Val Asp Tyr Val Ala Ser Gln Val Thr Ala Lys Lys Leu
            500                505                 510

Arg Gly Gly Val Val Phe Val Asp Glu Val Pro Lys Gly Leu Thr Gly
        515                520                 525

Lys Leu Asp Ala Arg Lys Ile Arg Glu Ile Leu Ile Lys Ala Lys Lys
530                535                 540

Gly Gly Lys Ile Ala Val
545                 550

<210> SEQ ID NO 78
<211> LENGTH: 558
<212> TYPE: DNA
<213> ORGANISM: Gaussia princeps

<400> SEQUENCE: 78
atgggagtca aagttctgtt tgccctgatc tgcatcgctg tggccgaggc caagcccacc      60
gagaacaacg aagacttcaa catcgtggcc gtggccagca acttcgcgac cacggatctc     120
gatgctgacc gcgggaagtt gcccggcaag aagctgccgc tggaggtgct caaagagatg     180
gaagccaatg cccggaaagc tggctgcacc aggggctgtc tgatctgcct gtcccacatc     240
aagtgcacgc ccaagatgaa gaagttcatc ccaggacgct gccacaccta cgaaggcgac     300
aaagagtccg cacagggcgg cataggcgag gcgatcgtcg acattcctga gattcctggg     360
ttcaaggact ggagcccat ggagcagttc atcgcacagg tcgatctgtg tgtggactgc     420
acaactggct gcctcaaagg gcttgccaac gtgcagtgtt ctgacctgct caagaagtgg     480
ctgccgcaac gctgtgcgac ctttgccagc aagatccagg ccaggtggaa caagatcaag     540
ggggccggtg gtgactaa                                                  558

<210> SEQ ID NO 79
<211> LENGTH: 185
<212> TYPE: PRT
<213> ORGANISM: Gaussia princeps

<400> SEQUENCE: 79

Met Gly Val Lys Val Leu Phe Ala Leu Ile Cys Ile Ala Val Ala Glu
1               5                   10                  15
```

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185

<210> SEQ ID NO 80
<211> LENGTH: 711
<212> TYPE: DNA
<213> ORGANISM: Artificial sequence
<220> FEATURE:
<223> OTHER INFORMATION: Synthetic

<400> SEQUENCE: 80
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact cccctccga cggccccgta      420 atgcagaaga gaccatgggc ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaagta g              711

<210> SEQ ID NO 81
<211> LENGTH: 236
<212> TYPE: PRT
<213> ORGANISM: Artificial sequence
<220> FEATURE:
<223> OTHER INFORMATION: Synthetic

<400> SEQUENCE: 81

Met Val Ser Lys Gly Glu Glu Asp Asn Met Ala Ile Ile Lys Glu Phe

```
1               5                   10                  15
Met Arg Phe Lys Val His Met Glu Gly Ser Val Asn Gly His Glu Phe
                20                  25                  30
Glu Ile Glu Gly Glu Gly Gly Arg Pro Tyr Glu Gly Thr Gln Thr
                35                  40                  45
Ala Lys Leu Lys Val Thr Lys Gly Gly Pro Leu Pro Phe Ala Trp Asp
 50                      55                  60
Ile Leu Ser Pro Gln Phe Met Tyr Gly Ser Lys Ala Tyr Val Lys His
 65                      70                  75                  80
Pro Ala Asp Ile Pro Asp Tyr Leu Lys Leu Ser Phe Pro Glu Gly Phe
                85                  90                  95
Lys Trp Glu Arg Val Met Asn Phe Glu Asp Gly Gly Val Val Thr Val
                100                 105                 110
Thr Gln Asp Ser Ser Leu Gln Asp Gly Glu Phe Ile Tyr Lys Val Lys
                115                 120                 125
Leu Arg Gly Thr Asn Phe Pro Ser Asp Gly Pro Val Met Gln Lys Lys
                130                 135                 140
Thr Met Gly Trp Glu Ala Ser Ser Glu Arg Met Tyr Pro Glu Asp Gly
145                     150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
                180                 185                 190
Gln Leu Pro Gly Ala Tyr Asn Val Asn Ile Lys Leu Asp Ile Thr Ser
                195                 200                 205
His Asn Glu Asp Tyr Thr Ile Val Glu Gln Tyr Glu Arg Ala Glu Gly
                210                 215                 220
Arg His Ser Thr Gly Gly Met Asp Glu Leu Tyr Lys
225                     230                 235
```

<210> SEQ ID NO 82
<211> LENGTH: 720
<212> TYPE: DNA
<213> ORGANISM: Artificial sequence
<220> FEATURE:
<223> OTHER INFORMATION: Synthetic

<400> SEQUENCE: 82

```
atggtgagca agcagatcct gaagaacacc ggcctgcagg agatcatgag cttcaaggtg    60
aacctggagg gcgtggtgaa caaccacgtg ttcaccatgg agggctgcgg caagggcaac   120
atcctgttcg gcaaccagct ggtgcagatc cgcgtgacca agggcgcccc cctgcccttc   180
gccttcgaca tcctgagccc cgccttccag tacggcaacc gcaccttcac caagtacccc   240
gaggacatca gcgacttctt catccagagc ttccccgccg gcttcgtgta cgagcgcacc   300
ctgcgctacg aggacggcgg cctggtggag atccgcagcg acatcaacct gatcgaggag   360
atgttcgtgt accgcgtgga gtacaagggc cgcaacttcc ccaacgacgg ccccgtgatg   420
aagaagacca tcaccggcct gcagcccagc ttcgaggtgg tgtacatgaa cgacggcgtg   480
ctggtgggcc aggtgatcct ggtgtaccgc ctgaacagcg gcaagttcta cagctgccac   540
atgcgcaccc tgatgaagag caagggcgtg gtgaaggact cccccgagta ccacttcatc   600
cagcaccgcc tggagaagac ctacgtggag gacggcggct tcgtggagca gcacgagacc   660
gccatcgccc agctgaccag cctgggcaag cccctgggca gcctgcacga gtgggtgtaa   720
```

<210> SEQ ID NO 83
<211> LENGTH: 239
<212> TYPE: PRT
<213> ORGANISM: Artificial sequence
<220> FEATURE:
<223> OTHER INFORMATION: Synthetic

<400> SEQUENCE: 83

```
Met Val Ser Lys Gln Ile Leu Lys Asn Thr Gly Leu Gln Glu Ile Met
1               5                   10                  15

Ser Phe Lys Val Asn Leu Glu Gly Val Val Asn His Val Phe Thr
                20                  25                  30

Met Glu Gly Cys Gly Lys Gly Asn Ile Leu Phe Gly Asn Gln Leu Val
            35                  40                  45

Gln Ile Arg Val Thr Lys Gly Ala Pro Leu Pro Phe Ala Phe Asp Ile
        50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

<210> SEQ ID NO 84
<211> LENGTH: 768
<212> TYPE: DNA
<213> ORGANISM: Artificial sequence
<220> FEATURE:
<223> OTHER INFORMATION: Synthetic

<400> SEQUENCE: 84

```
atgggcagca gccatcatca tcatcatcac agcagcggcc tggtgccgcg cggcagccat      60
atggctagca tgactggtgg acagcaaatg ggtcgcagcg ctatgaagct actgtcttct     120
atcgaacaag catgcgatat ttgccgactt aaaaagctca gtgctccaa gaaaaaccg      180 aagtgcgcca agtgtctgaa gaacaactgg gagtgtcgct actctcccaa aaccaaaagg     240
tctccgctga ctagggcaca tctgacagaa gtggaatcaa ggctagaaag actggaaaga     300
tccatcgcca ccagatctca tacgctctac gctcccggcg ttatgacat tatgggctat      360 ctgattcaga ttatgaacag gccaaacccc caagtagaac tgggacctgt tgacacgtca     420
tgcgctctga ttctgtgcga cctgaagcaa aaagacacgc caattgtgta cgcctcggaa     480
```

-continued

```
gcttttctct atatgacagg atacagcaat gcggaggtct tggggagaaa ctgccgtttt    540
cttcagtcac ccgacggaat ggtcaagccg aaatcgacaa ggaagtacgt cgactccaac    600
acgatcaata cgatgaggaa agcgattgat aggaacgccg aggtgcaggt tgaggtggtc    660
aattttaaga agaacggcca acggtttgtc aacttcttga cgatgattcc ggtgcgagat    720
gaaacagggg aataccggta cagcatgggt ttccagtgcg aaacggaa                 768
```

```
<210> SEQ ID NO 85
<211> LENGTH: 256
<212> TYPE: PRT
<213> ORGANISM: Artificial sequence
<220> FEATURE:
<223> OTHER INFORMATION: Synthetic

<400> SEQUENCE: 85
```

Met Gly Ser Ser His His His His His Ser Ser Gly Leu Val Pro
1               5                   10                  15

Arg Gly Ser His Met Ala Ser Met Thr Gly Gln Gln Met Gly Arg
                20                  25                  30

Ser Ala Met Lys Leu Leu Ser Ser Ile Glu Gln Ala Cys Asp Ile Cys
                35                  40                  45

Arg Leu Lys Lys Leu Lys Cys Ser Lys Glu Lys Pro Lys Cys Ala Lys
    50                  55                  60

Cys Leu Lys Asn Asn Trp Glu Cys Arg Tyr Ser Pro Lys Thr Lys Arg
65                  70                  75                  80

Ser Pro Leu Thr Arg Ala His Leu Thr Glu Val Glu Ser Arg Leu Glu
                85                  90                  95

Arg Leu Glu Arg Ser Ile Ala Thr Arg Ser His Thr Leu Tyr Ala Pro
            100                 105                 110

Gly Gly Tyr Asp Ile Met Gly Tyr Leu Ile Gln Ile Met Asn Arg Pro
        115                 120                 125

Asn Pro Gln Val Glu Leu Gly Pro Val Asp Thr Ser Cys Ala Leu Ile
    130                 135                 140

Leu Cys Asp Leu Lys Gln Lys Asp Thr Pro Ile Val Tyr Ala Ser Glu
145                 150                 155                 160

Ala Phe Leu Tyr Met Thr Gly Tyr Ser Asn Ala Glu Val Leu Gly Arg
                165                 170                 175

Asn Cys Arg Phe Leu Gln Ser Pro Asp Gly Met Val Lys Pro Lys Ser
            180                 185                 190

Thr Arg Lys Tyr Val Asp Ser Asn Thr Ile Asn Thr Met Arg Lys Ala
        195                 200                 205

Ile Asp Arg Asn Ala Glu Val Gln Val Glu Val Asn Phe Lys Lys
    210                 215                 220

Asn Gly Gln Arg Phe Val Asn Phe Leu Thr Met Ile Pro Val Arg Asp
225                 230                 235                 240

Glu Thr Gly Glu Tyr Arg Tyr Ser Met Gly Phe Gln Cys Glu Thr Glu
                245                 250                 255

```
<210> SEQ ID NO 86
<211> LENGTH: 1844
<212> TYPE: DNA
<213> ORGANISM: Artificial sequence
<220> FEATURE:
<223> OTHER INFORMATION: Synthetic

<400> SEQUENCE: 86
```

| | |
|---|---|
| tctagacgga gtactgtcct ccgagcggag tactgtcctc cgactcgagc ggagtactgt | 60 |
| cctccgatcg gagtactgtc ctccgcgaat tccggagtac tgtcctccga agacgctagc | 120 |
| ggggggctat aaaaggggggt gggggcgttc gtcctcactc tagatctgcg atctaagtaa | 180 |
| gcttggccac catggaagac gccaaaaaca taaagaaagg cccggcgcca ttctatccgc | 240 |
| tggaagatgg aaccgctgga gagcaactgc ataaggctat gaagagatac gccctggttc | 300 |
| ctggaacaat tgcttttaca gatgcacata tcgaggtgga catcacttac gctgagtact | 360 |
| tcgaaatgtc cgttcggttg gcagaagcta tgaaacgata tgggctgaat acaaatcaca | 420 |
| gaatcgtcgt atgcagtgaa aactctcttc aattctttat gccggtgttg ggcgcgttat | 480 |
| ttatcggagt tgcagttgcg cccgcgaacg acatttataa tgaacgtgaa ttgctcaaca | 540 |
| gtatgggcat ttcgcagcct accgtggtgt tcgtttccaa aaaggggttg caaaaaattt | 600 |
| tgaacgtgca aaaaaagctc ccaatcatcc aaaaaattat tatcatggat tctaaaacgg | 660 |
| attaccaggg atttcagtcg atgtacacgt tcgtcacatc tcatctacct cccggtttta | 720 |
| atgaatacga ttttgtgcca gagtccttcg atagggacaa gacaattgca ctgatcatga | 780 |
| actcctctgg atctactggt ctgcctaaag gtgtcgctct gcctcataga actgcctgcg | 840 |
| tgagattctc gcatgccaga gatcctattt ttggcaatca aatcattccg gatactgcga | 900 |
| ttttaagtgt tgttccattc catcacggtt ttggaatgtt tactacactc ggatatttga | 960 |
| tatgtggatt tcgagtcgtc ttaatgtata gatttgaaga gagctgtttt ctgaggagcc | 1020 |
| ttcaggatta caagattcaa agtgcgctgc tggtgccaac cctattctcc ttcttcgcca | 1080 |
| aaagcactct gattgacaaa tacgatttat ctaatttaca cgaaattgct tctggtggcg | 1140 |
| ctcccctctc taaggaagtc ggggaagcgg ttgccaagag gttccatctg ccaggtatca | 1200 |
| ggcaaggata tgggctcact gagactacat cagctattct gattacaccc gagggggatg | 1260 |
| ataaaccggg cgcggtcggt aaagttgttc cattttttga agcgaaggtt gtggatctgg | 1320 |
| ataccgggaa aacgctgggc gttaatcaaa gaggcgaact gtgtgtgaga ggtcctatga | 1380 |
| ttatgtccgg ttatgtaaac aatccggaag cgaccaacgc cttgattgac aaggatggat | 1440 |
| ggctacattc tggagacata gcttactggg acgaagacga acacttcttc atcgttgacc | 1500 |
| gcctgaagtc tctgattaag tacaaaggct atcaggtggc tcccgctgaa ttggaatcca | 1560 |
| tcttgctcca acaccccaac atcttcgacg caggtgtcgc aggtcttccc gacgatgacg | 1620 |
| ccggtgaact tcccgccgcc gttgttgttt tggagcacgg aaagacgatg acggaaaaag | 1680 |
| agatcgtgga ttacgtcgcc agtcaagtaa caaccgcgaa aaagttgcgc ggaggagttg | 1740 |
| tgtttgtgga cgaagtaccg aaaggtctta ccggaaaact cgacgcaaga aaaatcagag | 1800 |
| agatcctcat aaaggccaag aagggcggaa agatcgccgt gtaa | 1844 |

<210> SEQ ID NO 87
<211> LENGTH: 911
<212> TYPE: DNA
<213> ORGANISM: Artificial sequence
<220> FEATURE:
<223> OTHER INFORMATION: Synthetic

<400> SEQUENCE: 87

| | |
|---|---|
| tctagacgga gtactgtcct ccgagcggag tactgtcctc cgactcgagc ggagtactgt | 60 |
| cctccgatcg gagtactgtc ctccgcgaat tccggagtac tgtcctccga agacgctagc | 120 |
| ggggggctat aaaaggggggt gggggcgttc gtcctcactc tagatctgcg atctaagtaa | 180 |
| gcttggccac catggtgagc aagcagatcc tgaagaacac cggcctgcag gagatcatga | 240 |

```
gcttcaaggt gaacctggag ggcgtggtga acaaccacgt gttcaccatg gagggctgcg      300
gcaagggcaa catcctgttc ggcaaccagc tggtgcagat ccgcgtgacc aagggcgccc      360
ccctgccctt cgccttcgac atcctgagcc ccgccttcca gtacggcaac cgcaccttca      420
ccaagtaccc cgaggacatc agcgacttct tcatccagag cttccccgcc ggcttcgtgt      480
acgagcgcac cctgcgctac gaggacggcg gcctggtgga gatccgcagc gacatcaacc      540
tgatcgagga gatgttcgtg taccgcgtgg agtacaaggg ccgcaacttc cccaacgacg      600
gccccgtgat gaagaagacc atcaccggcc tgcagcccag cttcgaggtg gtgtacatga      660 acgacgcgt gctggtgggc caggtgatcc tggtgtaccg cctgaacagc ggcaagttct      720
acagctgcca catgcgcacc ctgatgaaga gcaagggcgt ggtgaaggac ttccccgagt      780
accacttcat ccagcaccgc ctggagaaga cctacgtgga ggacggcggc ttcgtggagc      840
agcacgagac cgccatcgcc cagctgacca gcctgggcaa gcccctgggc agcctgcacg      900
agtgggtgta a                                                          911
```

```
<210> SEQ ID NO 88
<211> LENGTH: 902
<212> TYPE: DNA
<213> ORGANISM: Artificial sequence
<220> FEATURE:
<223> OTHER INFORMATION: Synthetic

<400> SEQUENCE: 88
tctagacgga gtactgtcct ccgagcggag tactgtcctc cgactcgagc ggagtactgt      60
cctccgatcg gagtactgtc ctccgcgaat tccggagtac tgtcctccga agacgctagc      120 gggggctat aaaaggggt gggggcgttc gtcctcactc tagatctgcg atctaagtaa       180
gcttggccac catggtgagc aagggcgagg aggataacat ggccatcatc aaggagttca      240
tgcgcttcaa ggtgcacatg gagggctccg tgaacggcca cgagttcgag atcgagggcg      300
agggcgaggg ccgcccctac gagggcaccc agaccgccaa gctgaaggtg accaagggtg      360
gccccctgcc cttcgcctgg gacatcctgt cccctcagtt catgtacggc tccaaggcct      420
acgtgaagca ccccgccgac atccccgact acttgaagct gtccttcccc gagggcttca      480
agtgggagcg cgtgatgaac ttcgaggacg gcggcgtggt gaccgtgacc caggactcct      540
ccctgcagga cggcgagttc atctacaagg tgaagctgcg cggcaccaac ttcccctccg      600
acggccccgt aatgcagaag aagaccatgg gctgggaggc ctcctccgag cggatgtacc      660
ccgaggacgg cgccctgaag ggcgagatca agcagaggct gaagctgaag gacggcggcc      720
actacgacgc tgaggtcaag accacctaca aggccaagaa gcccgtgcag ctgcccggcg      780
cctacaacgt caacatcaag ttggacatca cctcccacaa cgaggactac accatcgtgg      840
aacagtacga acgcgccgag ggccgccact ccaccggcgg catggacgag ctgtacaagt      900
ag                                                                   902
```

```
<210> SEQ ID NO 89
<211> LENGTH: 749
<212> TYPE: DNA
<213> ORGANISM: Artificial sequence
<220> FEATURE:
<223> OTHER INFORMATION: Synthetic

<400> SEQUENCE: 89
tctagacgga gtactgtcct ccgagcggag tactgtcctc cgactcgagc ggagtactgt      60
```

```
cctccgatcg gagtactgtc ctccgcgaat tccggagtac tgtcctccga agacgctagc    120 gggggctat aaaagggggt gggggcgttc gtcctcactc tagatctgcg atctaagtaa    180
gcttggccac catgggagtc aaagttctgt ttgccctgat ctgcatcgct gtggccgagg    240
ccaagcccac cgagaacaac gaagacttca acatcgtggc cgtggccagc aacttcgcga    300
ccacggatct cgatgctgac cgcgggaagt tgcccggcaa gaagctgccg ctggaggtgc    360
tcaaagagat ggaagccaat gcccggaaag ctggctgcac caggggctgt ctgatctgcc    420
tgtcccacat caagtgcacg cccaagatga agaagttcat cccaggacgc tgccacacct    480
acgaaggcga caaagagtcc gcacagggcg gcataggcga ggcgatcgtc gacattcctg    540
agattcctgg gttcaaggac ttggagccca tggagcagtt catcgcacag gtcgatctgt    600
gtgtggactg cacaactggc tgcctcaaag ggcttgccaa cgtgcagtgt tctgacctgc    660
tcaagaagtg gctgccgcaa cgctgtgcga cctttgccag caagatccag ggccaggtgg    720
acaagatcaa gggggccggt ggtgactaa                                     749

<210> SEQ ID NO 90
<211> LENGTH: 2221
<212> TYPE: DNA
<213> ORGANISM: Artificial sequence
<220> FEATURE:
<223> OTHER INFORMATION: Synthetic

<400> SEQUENCE: 90
ctgtggaatg tgtgtcagtt agggtgtgga aagtccccag gctccccagc aggcagaagt     60
atgcaaagca tgcatctcaa ttagtcagca accaggtgtg gaaagtcccc aggctcccca    120
gcaggcagaa gtatgcaaag catgcatctc aattagtcag caaccatagt cccgccccta    180
actccgccca tcccgcccct aactccgccc agttccgccc attctccgcc ccatggctga    240 ctaattttt ttatttatgc agaggccgag gccgcctctg cctctgagct attccagaag    300
tagtgaggag gctttttttgg aggcctaggc ttttgcaaaa agctggtacc gagtttctag    360
acggagtact gtcctccgag cggagtactg tcctccgact cgagcggagt actgtcctcc    420
gatcggagta ctgtcctccg cgaattccgg agtactgtcc tccgaagacg ctagcggggg    480
gctataaaag ggggtggggg cgttcgtcct cactctagat ctgcgatcta agtaagcttg    540
gcattccggt actgttggta aagccaccat ggaagacgcc aaaaacataa agaaaggccc    600
ggcgccattc tatccgctgg aagatggaac cgctggagag caactgcata aggctatgaa    660
gagatacgcc ctggttcctg gaacaattgc ttttacagat gcacatatcg aggtggacat    720
cacttacgct gagtacttcg aaatgtccgt tcggttggca gaagctatga aacgatatgg    780
gctgaataca aatcacagaa tcgtcgtatg cagtgaaaac tctcttcaat tctttatgcc    840
ggtgttgggc gcgttattta tcggagttgc agttgcgccc gcgaacgaca tttataatga    900
acgtgaattg ctcaacagta tgggcatttc gcagcctacc gtggtgttcg tttccaaaaa    960
ggggttgcaa aaaatttttga acgtgcaaaa aagctcccaa tcatccaaa aaattattat   1020 catggattct aaaacggatt accagggatt tcagtcgatg tacacgttcg tcacatctca   1080
tctacctccc ggttttaatg aatacgattt tgtgccagag tccttcgata gggacaagac   1140
aattgcactg atcatgaact cctctggatc tactggtctg cctaaaggtg tcgctctgcc   1200
tcatagaact gcctgcgtga gattctcgca tgccagagat cctatttttg gcaatcaaat   1260
cattccggat actgcgattt taagtgttgt tccattccat cacggttttg gaatgtttac   1320
tacactcgga tatttgatat gtggatttcg agtcgtctta atgtatagat ttgaagaaga   1380
```

-continued

```
gctgtttctg aggagccttc aggattacaa gattcaaagt gcgctgctgg tgccaaccct    1440
attctccttc ttcgccaaaa gcactctgat tgacaaatac gatttatcta atttacacga    1500
aattgcttct ggtggcgctc ccctctctaa ggaagtcggg gaagcggttg ccaagaggtt    1560
ccatctgcca ggtatcaggc aaggatatgg gctcactgag actacatcag ctattctgat    1620
tacacccgag ggggatgata aaccgggcgc ggtcggtaaa gttgttccat tttttgaagc    1680
gaaggttgtg gatctggata ccgggaaaac gctgggcgtt aatcaaagag gcgaactgtg    1740
tgtgagaggt cctatgatta tgtccggtta tgtaaacaat ccggaagcga ccaacgcctt    1800
gattgacaag gatggatggc tacattctgg agacatagct tactgggacg aagacgaaca    1860
cttcttcatc gttgaccgcc tgaagtctct gattaagtac aaaggctatc aggtggctcc    1920
cgctgaattg gaatccatct tgctccaaca ccccaacatc ttcgacgcag gtgtcgcagg    1980
tcttcccgac gatgacgccg gtgaacttcc cgccgccgtt gttgttttgg agcacggaaa    2040
gacgatgacg gaaaaagaga tcgtggatta cgtcgccagt caagtaacaa ccgcgaaaaa    2100
gttgcgcgga ggagttgtgt ttgtggacga agtaccgaaa ggtcttaccg aaaaactcga    2160
cgcaagaaaa atcagagaga tcctcataaa ggccaagaag ggcggaaaga tcgccgtgta    2220
a                                                                    2221
```

<210> SEQ ID NO 91
<211> LENGTH: 333
<212> TYPE: DNA
<213> ORGANISM: Homo sapiens

<400> SEQUENCE: 91

```
atggccctgt ggatgcggct gctcccactg ctcgccctcc tggctctgtg gggccctgac     60
cccgccgctg cattcgtgaa ccagcacctg tgcggctccc acctcgtgga ggctctgtat    120
ctggtctgcg gagaaagggg cttcttttac acccccagga ccaagagaga ggccgaagac    180
ctgcaagtgg gccaggtgga gctgggcgga ggccctggcg ctggaagcct ccagcctctg    240
gccctggagg gctcccggca gaagcggggc attgtggagc agtgctgtac cagcatctgt    300
agcctgtatc agctggagaa ctactgcaat tag                                 333
```

<210> SEQ ID NO 92
<211> LENGTH: 110
<212> TYPE: PRT
<213> ORGANISM: Homo sapiens

<400> SEQUENCE: 92

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser Asp Leu Val Glu Ala Leu Tyr Leu Val Cys Gly Glu Arg Gly Phe
        35                  40                  45

Phe Tyr Thr Pro Arg Thr Lys Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Arg Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 93
<211> LENGTH: 720
<212> TYPE: DNA
<213> ORGANISM: Aequorea victoria

<400> SEQUENCE: 93

```
atggtgagta aaggagaaga acttttcact ggagttgtcc caattcttgt tgaattagat    60
ggtgatgtta atgggcacaa attttctgtc agtggagagg gtgaaggtga tgcaacatac   120
ggaaaactta cccttaaatt tatttgcact actggaaaac tacctgttcc atggccaaca   180
cttgtcacta ctttcggtta tggtctacaa tgctttgcta tacccagat catatgaaa    240
caacatgact ttttcaagag tgccatgccc gaaggttatg tacaggaaag aactatatt    300
ttcaaagatg acgggaacta caagacacgt gctgaagtca agtttgaagg tgataccctt   360
gttaatagaa tcgagttaaa aggtattgat tttaagaag atggaaacat tcttggacac   420
aaattggaat acaactataa ctcacacaat gtatacatca tggcagacaa acaaaagaat   480
ggaatcaaag ttaacttcaa aattagacac aacattgaag atggaagcgt tcaactagca   540
gaccattatc aacaaaatac tccaattggc gatggccctg tccttttacc agacaaccat   600
tacctgtcct atcaatctgc cctttcgaaa gatcccaacg aaaagagaga ccacatggtc   660
cttcttgagt ttgtaacagc tgctgggatt acactcggca tggatgaact atacaaataa   720
```

<210> SEQ ID NO 94
<211> LENGTH: 239
<212> TYPE: PRT
<213> ORGANISM: Aequorea victoria

<400> SEQUENCE: 94

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205
```

Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys
225                 230                 235

<210> SEQ ID NO 95
<211> LENGTH: 3051
<212> TYPE: DNA
<213> ORGANISM: E.coli

<400> SEQUENCE: 95

| | | | | | |
|---|---|---|---|---|---|
| atggtcgttt | tacaacgtcg | tgactgggaa | aaccctggcg | ttacccaact | taatcgcctt | 60 |
| gcagcacatc | cccctttcgc | cagctggcgt | aatagcgaag | aggcccgcac | cgatcgccct | 120 |
| tcccaacagt | tgcgcagcct | gaatggcgaa | tggcgctttg | cctggtttcc | ggcaccagaa | 180 |
| gcggtgccgg | aaagctggct | ggagtgcgat | cttcctgagg | ccgatactgt | cgtcgtcccc | 240 |
| tcaaactggc | agatgcacgg | ttacgatgcg | cccatctaca | ccaacgtaac | ctatcccatt | 300 |
| acggtcaatc | cgccgtttgt | tcccacggag | aatccgacgg | gttgttactc | gctcacattt | 360 |
| aatgttgatg | aaagctggct | acaggaaggc | cagacgcgaa | ttattttga | tggcgttaac | 420 |
| tcggcgtttc | atctgtggtg | caacgggcgc | tgggtcggtt | acggccagga | cagtcgtttg | 480 |
| ccgtctgaat | ttgacctgag | cgcatttttta | cgcgccggag | aaaaccgcct | cgcggtgatg | 540 |
| gtgctgcgtt | ggagtgacgg | cagttatctg | gaagatcagg | atatgtggcg | gatgagcggc | 600 |
| attttccgtg | acgtctcgtt | gctgcataaa | ccgactacac | aaatcagcga | tttccatgtt | 660 |
| gccactcgct | ttaatgatga | tttcagccgc | gctgtactgg | aggctgaagt | tcagatgtgc | 720 |
| ggcgagttgc | gtgactacct | acgggtaaca | gtttctttat | ggcagggtga | aacgcaggtc | 780 |
| gccagcggca | ccgcgccttt | cggcggtgaa | attatcgatg | agcgtggtgg | ttatgccgat | 840 |
| cgcgtcacac | tacgtctgaa | cgtcgaaaac | ccgaaactgt | ggagcgccga | aatcccgaat | 900 |
| ctctatcgtg | cggtggttga | actgcacacc | gccgacggca | cgctgattga | agcagaagcc | 960 |
| tgcgatgtcg | gtttccgcga | ggtgcggatt | gaaaatggtc | tgctgctgct | gaacggcaag | 1020 |
| ccgttgctga | ttcgaggcgt | taaccgtcac | gagcatcatc | ctctgcatgg | tcaggtcatg | 1080 |
| gatgagcaga | cgatggtgca | ggatatcctg | ctgatgaagc | agaacaactt | taacgccgtg | 1140 |
| cgctgttcgc | attatccgaa | ccatccgctg | tggtacacgc | tgtgcgaccg | ctacggcctg | 1200 |
| tatgtggtgg | atgaagccaa | tattgaaacc | cacggcatgg | tgccaatgaa | tcgtctgacc | 1260 |
| gatgatccgc | gctggctacc | ggcgatgagc | gaacgcgtaa | cgcgaatggt | gcagcgcgat | 1320 |
| cgtaatcacc | cgagtgtgat | catctggtcg | ctggggaatg | aatcaggcca | cggcgctaat | 1380 |
| cacgacgcgc | tgtatcgctg | gatcaaatct | gtcgatcctt | cccgcccggt | gcagtatgaa | 1440 |
| ggcggcggag | ccgacaccac | ggccaccgat | attatttgcc | cgatgtacgc | gcgcgtggat | 1500 |
| gaagaccagc | ccttcccggc | tgtgccgaaa | tggtccatca | aaaaatggct | ttcgctacct | 1560 |
| ggagagacgc | gcccgctgat | cctttgcgaa | tacgcccacg | cgatgggtaa | cagtcttggc | 1620 |
| ggtttcgcta | aatactggca | ggcgtttcgt | cagtatcccc | gtttacaggg | cggcttcgtc | 1680 |
| tgggactggg | tggatcagtc | gctgattaaa | tatgatgaaa | acggcaaccc | gtggtcggct | 1740 |
| tacggcggtg | attttggcga | tacgccgaac | gatcgccagt | tctgtatgaa | cggtctggtc | 1800 |
| tttgccgacc | gcacgccgca | tccagcgctg | acggaagcaa | acaccagca | gcagtttttc | 1860 |
| cagttccgtt | tatccgggca | aaccatcgaa | gtgaccagcg | aatacctgtt | ccgtcatagc | 1920 |

```
gataacgagc tcctgcactg gatggtggcg ctggatggta agccgctggc aagcggtgaa   1980
gtgcctctgg atgtcgctcc acaaggtaaa cagttgattg aactgcctga actaccgcag   2040
ccggagagcg ccgggcaact ctggctcaca gtacgcgtag tgcaaccgaa cgcgaccgca   2100
tggtcagaag ccgggcacat cagcgcctgg cagcagtggc gtctggcgga aaacctcagt   2160
gtgacgctcc ccgccgcgtc ccacgccatc ccgcatctga ccaccagcga aatggatttt   2220
tgcatcgagc tgggtaataa gcgttggcaa tttaaccgcc agtcaggctt tctttcacag   2280
atgtggattg cgataaaaa caactgctg acgccgctgc gcgatcagtt cacccgtgca   2340
ccgctggata cgacattgg cgtaagtgaa gcgacccgca ttgaccctaa cgcctgggtc   2400
gaacgctgga aggcggcggg ccattaccag gccgaagcag cgttgttgca gtgcacggca   2460
gatacacttg ctgatgcggt gctgattacg accgctcacg cgtggcagca tcaggggaaa   2520
accttattta tcagccggaa aacctaccgg attgatggta gtggtcaaat ggcgattacc   2580
gttgatgttg aagtggcgag cgatacaccg catccggcgc ggattggcct gaactgccag   2640
ctggcgcagg tagcagagcg ggtaaactgg ctcggattag ggccgcaaga aaactatccc   2700
gaccgcctta ctgccgcctg ttttgaccgc tgggatctgc cattgtcaga catgtatacc   2760
ccgtacgtct ccccgagcga aaacggtctg cgctgcggga cgcgcgaatt gaattatggc   2820
ccacaccagt ggcgcggcga cttccagttc aacatcagcc gctacagtca acagcaactg   2880
atggaaaacca gccatcgcca tctgctgcac gcggaagaag cacatggct gaatatcgac   2940
ggtttccata tggggattgg tggcgacgac tcctggagcc cgtcagtatc ggcggaattc   3000
cagctgagcg ccggtcgcta ccattaccag ttggtctggt gtcaaaaata a            3051

<210> SEQ ID NO 96
<211> LENGTH: 1016
<212> TYPE: PRT
<213> ORGANISM: E.coli

<400> SEQUENCE: 96

Met Val Val Leu Gln Arg Arg Asp Trp Glu Asn Pro Gly Val Thr Gln
1               5                   10                  15

Leu Asn Arg Leu Ala Ala His Pro Pro Phe Ala Ser Trp Arg Asn Ser
            20                  25                  30

Glu Glu Ala Arg Thr Asp Arg Pro Ser Gln Gln Leu Arg Ser Leu Asn
        35                  40                  45

Gly Glu Trp Arg Phe Ala Trp Phe Pro Ala Pro Glu Ala Val Pro Glu
    50                  55                  60

Ser Trp Leu Glu Cys Asp Leu Pro Glu Ala Asp Thr Val Val Val Pro
65                  70                  75                  80

Ser Asn Trp Gln Met His Gly Tyr Asp Ala Pro Ile Tyr Thr Asn Val
                85                  90                  95

Thr Tyr Pro Ile Thr Val Asn Pro Pro Phe Val Pro Thr Glu Asn Pro
            100                 105                 110

Thr Gly Cys Tyr Ser Leu Thr Phe Asn Val Asp Glu Ser Trp Leu Gln
        115                 120                 125

Glu Gly Gln Thr Arg Ile Ile Phe Asp Gly Val Asn Ser Ala Phe His
    130                 135                 140

Leu Trp Cys Asn Gly Arg Trp Val Gly Tyr Gly Gln Asp Ser Arg Leu
145                 150                 155                 160

Pro Ser Glu Phe Asp Leu Ser Ala Phe Leu Arg Ala Gly Glu Asn Arg
                165                 170                 175
```

-continued

```
Leu Ala Val Met Val Leu Arg Trp Ser Asp Gly Ser Tyr Leu Glu Asp
            180                 185                 190

Gln Asp Met Trp Arg Met Ser Gly Ile Phe Arg Asp Val Ser Leu Leu
        195                 200                 205

His Lys Pro Thr Thr Gln Ile Ser Asp Phe His Val Ala Thr Arg Phe
    210                 215                 220

Asn Asp Asp Phe Ser Arg Ala Val Leu Glu Ala Glu Val Gln Met Cys
225                 230                 235                 240

Gly Glu Leu Arg Asp Tyr Leu Arg Val Thr Val Ser Leu Trp Gln Gly
                245                 250                 255

Glu Thr Gln Val Ala Ser Gly Thr Ala Pro Phe Gly Gly Glu Ile Ile
            260                 265                 270

Asp Glu Arg Gly Gly Tyr Ala Asp Arg Val Thr Leu Arg Leu Asn Val
        275                 280                 285

Glu Asn Pro Lys Leu Trp Ser Ala Glu Ile Pro Asn Leu Tyr Arg Ala
    290                 295                 300

Val Val Glu Leu His Thr Ala Asp Gly Thr Leu Ile Glu Ala Glu Ala
305                 310                 315                 320

Cys Asp Val Gly Phe Arg Glu Val Arg Ile Glu Asn Gly Leu Leu Leu
                325                 330                 335

Leu Asn Gly Lys Pro Leu Leu Ile Arg Gly Val Asn Arg His Glu His
            340                 345                 350

His Pro Leu His Gly Gln Val Met Asp Glu Gln Thr Met Val Gln Asp
        355                 360                 365

Ile Leu Leu Met Lys Gln Asn Asn Phe Asn Ala Val Arg Cys Ser His
    370                 375                 380

Tyr Pro Asn His Pro Leu Trp Tyr Thr Leu Cys Asp Arg Tyr Gly Leu
385                 390                 395                 400

Tyr Val Val Asp Glu Ala Asn Ile Glu Thr His Gly Met Val Pro Met
                405                 410                 415

Asn Arg Leu Thr Asp Asp Pro Arg Trp Leu Pro Ala Met Ser Glu Arg
            420                 425                 430

Val Thr Arg Met Val Gln Arg Asp Arg Asn His Pro Ser Val Ile Ile
        435                 440                 445

Trp Ser Leu Gly Asn Glu Ser Gly His Gly Ala Asn His Asp Ala Leu
    450                 455                 460

Tyr Arg Trp Ile Lys Ser Val Asp Pro Ser Arg Pro Val Gln Tyr Glu
465                 470                 475                 480

Gly Gly Gly Ala Asp Thr Thr Ala Thr Asp Ile Ile Cys Pro Met Tyr
                485                 490                 495

Ala Arg Val Asp Glu Asp Gln Pro Phe Pro Ala Val Pro Lys Trp Ser
            500                 505                 510

Ile Lys Lys Trp Leu Ser Leu Pro Gly Glu Thr Arg Pro Leu Ile Leu
        515                 520                 525

Cys Glu Tyr Ala His Ala Met Gly Asn Ser Leu Gly Gly Phe Ala Lys
    530                 535                 540

Tyr Trp Gln Ala Phe Arg Gln Tyr Pro Arg Leu Gln Gly Gly Phe Val
545                 550                 555                 560

Trp Asp Trp Val Asp Gln Ser Leu Ile Lys Tyr Asp Glu Asn Gly Asn
                565                 570                 575

Pro Trp Ser Ala Tyr Gly Gly Asp Phe Gly Asp Thr Pro Asn Asp Arg
            580                 585                 590

Gln Phe Cys Met Asn Gly Leu Val Phe Ala Asp Arg Thr Pro His Pro
```

```
                595                 600                 605
Ala Leu Thr Glu Ala Lys His Gln Gln Gln Phe Phe Gln Phe Arg Leu
610                 615                 620

Ser Gly Gln Thr Ile Glu Val Thr Ser Glu Tyr Leu Phe Arg His Ser
625                 630                 635                 640

Asp Asn Glu Leu Leu His Trp Met Val Ala Leu Asp Gly Lys Pro Leu
                645                 650                 655

Ala Ser Gly Glu Val Pro Leu Asp Val Ala Pro Gln Gly Lys Gln Leu
                660                 665                 670

Ile Glu Leu Pro Glu Leu Pro Gln Pro Glu Ser Ala Gly Gln Leu Trp
                675                 680                 685

Leu Thr Val Arg Val Val Gln Pro Asn Ala Thr Ala Trp Ser Glu Ala
690                 695                 700

Gly His Ile Ser Ala Trp Gln Gln Trp Arg Leu Ala Glu Asn Leu Ser
705                 710                 715                 720

Val Thr Leu Pro Ala Ala Ser His Ala Ile Pro His Leu Thr Thr Ser
                725                 730                 735

Glu Met Asp Phe Cys Ile Glu Leu Gly Asn Lys Arg Trp Gln Phe Asn
                740                 745                 750

Arg Gln Ser Gly Phe Leu Ser Gln Met Trp Ile Gly Asp Lys Lys Gln
                755                 760                 765

Leu Leu Thr Pro Leu Arg Asp Gln Phe Thr Arg Ala Pro Leu Asp Asn
770                 775                 780

Asp Ile Gly Val Ser Glu Ala Thr Arg Ile Asp Pro Asn Ala Trp Val
785                 790                 795                 800

Glu Arg Trp Lys Ala Ala Gly His Tyr Gln Ala Glu Ala Ala Leu Leu
                805                 810                 815

Gln Cys Thr Ala Asp Thr Leu Ala Asp Ala Val Leu Ile Thr Thr Ala
                820                 825                 830

His Ala Trp Gln His Gln Gly Lys Thr Leu Phe Ile Ser Arg Lys Thr
                835                 840                 845

Tyr Arg Ile Asp Gly Ser Gly Gln Met Ala Ile Thr Val Asp Val Glu
850                 855                 860

Val Ala Ser Asp Thr Pro His Pro Ala Arg Ile Gly Leu Asn Cys Gln
865                 870                 875                 880

Leu Ala Gln Val Ala Glu Arg Val Asn Trp Leu Gly Leu Gly Pro Gln
                885                 890                 895

Glu Asn Tyr Pro Asp Arg Leu Thr Ala Ala Cys Phe Asp Arg Trp Asp
                900                 905                 910

Leu Pro Leu Ser Asp Met Tyr Thr Pro Tyr Val Phe Pro Ser Glu Asn
                915                 920                 925

Gly Leu Arg Cys Gly Thr Arg Glu Leu Asn Tyr Gly Pro His Gln Trp
                930                 935                 940

Arg Gly Asp Phe Gln Phe Asn Ile Ser Arg Tyr Ser Gln Gln Gln Leu
945                 950                 955                 960

Met Glu Thr Ser His Arg His Leu Leu His Ala Glu Glu Gly Thr Trp
                965                 970                 975

Leu Asn Ile Asp Gly Phe His Met Gly Ile Gly Gly Asp Ser Trp
                980                 985                 990

Ser Pro Ser Val Ser Ala Glu Phe Gln Leu Ser Ala Gly Arg Tyr His
                995                 1000                1005

Tyr Gln Leu Val Trp Cys Gln Lys
                1010                1015
```

<210> SEQ ID NO 97
<211> LENGTH: 435
<212> TYPE: DNA
<213> ORGANISM: Saccharomy cescerevisiae

<400> SEQUENCE: 97

```
atgtccgaat atcagccaag tttatttgct ttaaatccaa tgggtttctc accattggat      60
ggttctaaat caaccaacga aaatgtatct gcttccactt ctactgccaa accaatggtt     120
ggccaattga ttttgataa attcatcaag actgaagagg atccaattat caaacaggat     180
accccttcga accttgattt tgattttgct cttccacaaa cggcaactgc acctgatgcc     240
aagaccgttt tgccaattcc ggagctagat gacgctgtag tggaatcttt cttttcgtca     300
agcactgatt caactccaat gtttgagtat gaaaacctag aagacaactc taagaatgg     360
acatccttgt ttgacaatga cattccagtt accactgacg atgtttcatt ggctgataag     420
gcaattgaat cctaa                                                     435
```

<210> SEQ ID NO 98
<211> LENGTH: 144
<212> TYPE: PRT
<213> ORGANISM: Saccharomy cescerevisiae

<400> SEQUENCE: 98

```
Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
        115                 120                 125

Pro Val Thr Thr Asp Asp Val Ser Leu Ala Asp Lys Ala Ile Glu Ser
    130                 135                 140
```

<210> SEQ ID NO 99
<211> LENGTH: 1029
<212> TYPE: DNA
<213> ORGANISM: Artificial sequence
<220> FEATURE:
<223> OTHER INFORMATION: Synthetic

<400> SEQUENCE: 99

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaagaggc caaacccca gtagaactg     300
```

```
ggacctgttg acacgtcagt tgctctgatt ctgtgcgacc tgaagcaaaa agacacgcca    360
attgtgtacg cctcggaagc tttctctat  atgacaggat acagcaatgc ggaggtcttg    420
gggagaaact gccgttttct tcagtcaccc gacggaatgg tcaagccgaa atcgacaagg    480
aagtacgtcg actccaacac gatcaatacg atgaggaaag cgattgatag gaacgccgag    540
gtgcaggttg aggtggtcaa ttttaagaag aacggccaac ggtttgtcaa cttcttgacg    600
atgattccgg tgcgagatga aacaggggaa taccggtaca gcatgggttt ccagtgcgaa    660
acggaaggat ccggtggagg tggctccaat tttaatcaaa gtgggaatat tgctgatagc    720
tcattgtcct tcactttcac taacagtagc aacggtccga acctcataac aactcaaaca    780
aattctcaag cgctttcaca accaattgcc tcctctaacg ttcatgataa cttcatgaat    840
aatgaaatca cggctagtaa aattgatgat ggtaataatt caaaaccact gtcacctggt    900
tggacggacc aaaactgcgta taacgcgttt ggaatcacta cagggatgtt taataccact    960
acaatggatg atgtatataa ctatctattc gatgatgaag ataccccacc aaacccaaaa   1020
aaagagtaa                                                           1029
```

<210> SEQ ID NO 100
<211> LENGTH: 342
<212> TYPE: PRT
<213> ORGANISM: Artificial sequence
<220> FEATURE:
<223> OTHER INFORMATION: Synthetic

<400> SEQUENCE: 100

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220
```

Gly Gly Gly Gly Ser Asn Phe Asn Gln Ser Gly Asn Ile Ala Asp Ser
225                 230                 235                 240

Ser Leu Ser Phe Thr Phe Thr Asn Ser Ser Asn Gly Pro Asn Leu Ile
            245                 250                 255

Thr Thr Gln Thr Asn Ser Gln Ala Leu Ser Gln Pro Ile Ala Ser Ser
        260                 265                 270

Asn Val His Asp Asn Phe Met Asn Asn Glu Ile Thr Ala Ser Lys Ile
    275                 280                 285

Asp Asp Gly Asn Asn Ser Lys Pro Leu Ser Pro Gly Trp Thr Asp Gln
290                 295                 300

Thr Ala Tyr Asn Ala Phe Gly Ile Thr Thr Gly Met Phe Asn Thr Thr
305                 310                 315                 320

Thr Met Asp Asp Val Tyr Asn Tyr Leu Phe Asp Asp Glu Asp Thr Pro
                325                 330                 335

Pro Asn Pro Lys Lys Glu
            340

<210> SEQ ID NO 101
<211> LENGTH: 1044
<212> TYPE: DNA
<213> ORGANISM: Artificial sequence
<220> FEATURE:
<223> OTHER INFORMATION: Synthetic

<400> SEQUENCE: 101
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaagaggc aaacccccca gtagaactg      300 ggacctgttg acacgtcagt tgctctgatt ctgtgcgacc tgaagcaaaa agacacgcca     360
attgtgtacg cctcggaagc ttttctctat atgacaggat acagcaatgc ggaggtcttg     420 gggagaaaact gccgtttttct tcagtcaccc gacggaatgg tcaagccgaa atcgacaagg     480
aagtacgtcg actccaacac gatcaatacg atgaggaaag cgattgatag aacgccgag      540 gtgcaggttg aggtggtcaa ttttaagaag acggccaac ggtttgtcaa cttcttgacg      600
atgattccgg tgcgagatga acaggggaa taccggtaca gcatgggttt ccagtgcgaa      660
acggaaggat ccggcggtgg tggatcaggt ggaggtggct ccaattttaa tcaaagtggg     720
aatattgctg atagctcatt gtccttcact ttcactaaca gtagcaacgg tccgaacctc     780
ataacaactc aaacaaattc tcaagcgctt tcacaaccaa ttgcctcctc taacgttcat     840
gataacttca tgaataatga aatcacggct agtaaaattg atgatggtaa taattcaaaa     900
ccactgtcac tggttggac ggaccaaact gcgtataacg cgtttggaat cactacaggg     960
atgtttaata ccactacaat ggatgatgta tataactatc tattcgatga tgaagatacc    1020
ccaccaaacc caaaaaaaga gtaa                                            1044

<210> SEQ ID NO 102
<211> LENGTH: 347
<212> TYPE: PRT
<213> ORGANISM: Artificial sequence
<220> FEATURE:
<223> OTHER INFORMATION: Synthetic

<400> SEQUENCE: 102

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
                100                 105                 110

Asp Leu Lys Gln Lys Asp Thr Pro Ile Val Tyr Ala Ser Glu Ala Phe
            115                 120                 125

Leu Tyr Met Thr Gly Tyr Ser Asn Ala Glu Val Leu Gly Arg Asn Cys
        130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Gly Gly Gly Ser Gly Gly Gly Ser Asn Phe Asn Gln Ser Gly
225                 230                 235                 240

Asn Ile Ala Asp Ser Ser Leu Ser Phe Thr Phe Thr Asn Ser Ser Asn
                245                 250                 255

Gly Pro Asn Leu Ile Thr Thr Gln Thr Asn Ser Gln Ala Leu Ser Gln
            260                 265                 270

Pro Ile Ala Ser Ser Asn Val His Asp Asn Phe Met Asn Asn Glu Ile
        275                 280                 285

Thr Ala Ser Lys Ile Asp Asp Gly Asn Asn Ser Lys Pro Leu Ser Pro
    290                 295                 300

Gly Trp Thr Asp Gln Thr Ala Tyr Asn Ala Phe Gly Ile Thr Thr Gly
305                 310                 315                 320

Met Phe Asn Thr Thr Met Asp Asp Val Tyr Asn Tyr Leu Phe Asp
                325                 330                 335

Asp Glu Asp Thr Pro Pro Asn Pro Lys Lys Glu
            340                 345

<210> SEQ ID NO 103
<211> LENGTH: 1038
<212> TYPE: DNA
<213> ORGANISM: Artificial sequence
<220> FEATURE:
<223> OTHER INFORMATION: Synthetic

<400> SEQUENCE: 103
atgaagctac tgtcttctat cgaacaagca tgcgatattt gccgacttaa aaagctcaag    60
```

```
tgctccaaag aaaaaccgaa gtgcgccaag tgtctgaaga caactgggga gtgtcgctac     120
tctcccaaaa ccaaaggtc tccgctgact agggcacatc tgacagaagt ggaatcaagg      180
ctagaaagac tggaaagatc catcgccacc agatctcata cgctctacgc tcccggcggt    240
tatgacatta tgggctatct gattcagatt atgaagaggc caaaccccca agtagaactg    300
ggacctgttg acacgtcagt tgctctgatt ctgtgcgacc tgaagcaaaa agacacgcca    360
attgtgtacg cctcggaagc ttttctctat atgacaggat acagcaatgc ggaggtcttg    420
gggagaaact gccgttttct tcagtcaccc gacggaatgg tcaagccgaa atcgacaagg    480
aagtacgtcg actccaacac gatcaatacg atgaggaaag cgattgatag gaacgccgag    540
gtgcaggttg aggtggtcaa ttttaagaag aacggccaac ggtttgtcaa cttcttgacg    600
atgattccgg tgcgagatga aacagggggaa taccggtaca gcatgggttt ccagtgcgaa    660
acggaaggat ccggtggatc aggtggaggt ggctccaatt ttaatcaaag tgggaatatt    720
gctgatagct cattgtcctt cactttcact aacagtagca acggtccgaa cctcataaca    780
actcaaacaa attctcaagc gctttcacaa ccaattgcct cctctaacgt tcatgataac    840
ttcatgaata atgaaatcac ggctagtaaa attgatgatg gtaataattc aaaaccactg    900
tcacctggtt ggacggacca aactgcgtat aacgcgtttg gaatcactac agggatgttt    960
aataccacta caatggatga tgtatataac tatctattcg atgatgaaga taccccacca   1020
aacccaaaaa aagagtaa                                                 1038
```

<210> SEQ ID NO 104
<211> LENGTH: 345
<212> TYPE: PRT
<213> ORGANISM: Artificial sequence
<220> FEATURE:
<223> OTHER INFORMATION: Synthetic

<400> SEQUENCE: 104

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190
```

Gln Arg Phe Val Asn Phe Leu Thr Met Ile Pro Val Arg Asp Glu Thr
    195                 200                 205

Gly Glu Tyr Arg Tyr Ser Met Gly Phe Gln Cys Glu Thr Glu Gly Ser
    210                 215                 220

Gly Gly Ser Gly Gly Gly Ser Asn Phe Asn Gln Ser Gly Asn Ile
225                 230                 235                 240

Ala Asp Ser Ser Leu Ser Phe Thr Phe Thr Asn Ser Ser Asn Gly Pro
                245                 250                 255

Asn Leu Ile Thr Thr Gln Thr Asn Ser Gln Ala Leu Ser Gln Pro Ile
                260                 265                 270

Ala Ser Ser Asn Val His Asp Asn Phe Met Asn Asn Glu Ile Thr Ala
                275                 280                 285

Ser Lys Ile Asp Asp Gly Asn Asn Ser Lys Pro Leu Ser Pro Gly Trp
    290                 295                 300

Thr Asp Gln Thr Ala Tyr Asn Ala Phe Gly Ile Thr Thr Gly Met Phe
305                 310                 315                 320

Asn Thr Thr Thr Met Asp Asp Val Tyr Asn Tyr Leu Phe Asp Asp Glu
                325                 330                 335

Asp Thr Pro Pro Asn Pro Lys Lys Glu
                340                 345

<210> SEQ ID NO 105
<211> LENGTH: 1050
<212> TYPE: DNA
<213> ORGANISM: Artificial sequence
<220> FEATURE:
<223> OTHER INFORMATION: Synthetic

<400> SEQUENCE: 105
atgaagctac tgtcttctat cgaacaagca tgcgatattt gccgacttaa aaagctcaag      60
tgctccaaag aaaaaccgaa gtgcgccaag tgtctgaaga caactgggag tgtcgctac     120 tctcccaaaa ccaaaaggtc tccgctgact agggcacatc tgacagaagt ggaatcaagg    180 ctagaaaagac tggaaagatc catcgccacc agatctcata cgctctacgc tcccggcggt   240
tatgacatta tgggctatct gattcagatt atgaagaggc aaaccccca gtagaactg      300 ggacctgttg acacgtcagt tgctctgatt ctgtgcgacc tgaagcaaaa agacacgcca    360
attgtgtacg cctcggaagc ttttctctat atgacaggat acagcaatgc ggaggtcttg    420 gggagaaaact gccgtttct tcagtcaccc gacggaatgg tcaagccgaa atcgacaagg   480
aagtacgtcg actccaacac gatcaatacg atgaggaaag cgattgatag aacgccgag    540 gtgcaggttg aggtggtcaa ttttaagaag aacggccaac ggtttgtcaa cttcttgacg   600
atgattccgg tgcgagatga acagggaa taccggtaca gcatgggttt ccagtgcgaa    660
acggaaggat ccggaagcgg cggtggtgga tcaggtggag gtggctccaa ttttaatcaa   720
agtgggaata ttgctgatag ctcattgtcc ttcactttca ctaacagtag caacggtccg   780
aacctcataa caactcaaac aaattctcaa gcgctttcac aaccaattgc tcctctaac   840 gttcatgata acttcatgaa taatgaaatc acggctagta aaattgatga tggtaataat   900
tcaaaaccac tgtcacctgg ttggacggac caaactgcgt ataacgcgtt tggaatcact   960
acagggatgt ttaataccac tacaatggat gatgtatata actatctatt cgatgatgaa  1020 gatacccccac caaacccaaa aaagagtaa                                    1050

<210> SEQ ID NO 106

<211> LENGTH: 349
<212> TYPE: PRT
<213> ORGANISM: Artificial sequence
<220> FEATURE:
<223> OTHER INFORMATION: Synthetic

<400> SEQUENCE: 106

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Ser Gly Gly Gly Ser Gly Gly Gly Ser Asn Phe Asn Gln
225                 230                 235                 240

Ser Gly Asn Ile Ala Asp Ser Ser Leu Ser Phe Thr Phe Thr Asn Ser
                245                 250                 255

Ser Asn Gly Pro Asn Leu Ile Thr Thr Gln Thr Asn Ser Gln Ala Leu
            260                 265                 270

Ser Gln Pro Ile Ala Ser Ser Asn Val His Asp Asn Phe Met Asn Asn
        275                 280                 285

Glu Ile Thr Ala Ser Lys Ile Asp Asp Gly Asn Asn Ser Lys Pro Leu
    290                 295                 300

Ser Pro Gly Trp Thr Asp Gln Thr Ala Tyr Asn Ala Phe Gly Ile Thr
305                 310                 315                 320

Thr Gly Met Phe Asn Thr Thr Thr Met Asp Asp Val Tyr Asn Tyr Leu
                325                 330                 335

Phe Asp Asp Glu Asp Thr Pro Asn Pro Lys Lys Glu
            340                 345

<210> SEQ ID NO 107
<211> LENGTH: 1059
<212> TYPE: DNA
<213> ORGANISM: Artificial sequence
<220> FEATURE:
<223> OTHER INFORMATION: Synthetic

<400> SEQUENCE: 107

```
atgaagctac tgtcttctat cgaacaagca tgcgatattt gccgacttaa aaagctcaag    60
tgctccaaag aaaaaccgaa gtgcgccaag tgtctgaaga caactggga gtgtcgctac    120
tctcccaaaa ccaaaaggtc tccgctgact agggcacatc tgacagaagt ggaatcaagg   180
ctagaaagac tggaaagatc catcgccacc agatctcata cgctctacgc tcccggcggt   240
tatgacatta tgggctatct gattcagatt atgaagaggc caaaccccca gtagaactg    300
ggacctgttg acacgtcagt tgctctgatt ctgtgcgacc tgaagcaaaa agacacgcca   360
attgtgtacg cctcggaagc ttttctctat atgacaggat acagcaatgc ggaggtcttg   420
gggagaaact gccgttttct tcagtcaccc gacggaatgg tcaagccgaa atcgacaagg   480
aagtacgtcg actccaacac gatcaatacg atgaggaaag cgattgatag aacgccgag    540
gtgcaggttg aggtggtcaa tttttaagaag aacggccaac ggtttgtcaa cttcttgacg  600
atgattccgg tgcgagatga acaggggaa taccggtaca gcatgggttt ccagtgcgaa    660
acggaaggat ccggtggcgg cggaagcggc ggtggtggat caggtggagg tggctccaat   720
tttaatcaaa gtgggaatat tgctgatagc tcattgtcct tcactttcac taacagtagc   780
aacggtccga acctcataac aactcaaaca aattctcaag cgctttcaca accaattgcc   840
tcctctaacg ttcatgataa cttcatgaat aatgaaatca cggctagtaa aattgatgat   900
ggtaataatt caaaaccact gtcacctggt tggacggacc aaactgcgta taacgcgttt   960
ggaatcacta cagggatgtt taataccact acaatggatg atgtatataa ctatctattc  1020
gatgatgaag ataccccacc aaacccaaaa aaagagtaa                         1059
```

<210> SEQ ID NO 108
<211> LENGTH: 352
<212> TYPE: PRT
<213> ORGANISM: Artificial sequence
<220> FEATURE:
<223> OTHER INFORMATION: Synthetic

<400> SEQUENCE: 108

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
```

```
            145                 150                 155                 160
Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Gly Gly Gly Ser Gly Gly Gly Ser Gly Gly Gly Ser Asn
225                 230                 235                 240

Phe Asn Gln Ser Gly Asn Ile Ala Asp Ser Ser Leu Ser Phe Thr Phe
                245                 250                 255

Thr Asn Ser Ser Asn Gly Pro Asn Leu Ile Thr Thr Gln Thr Asn Ser
            260                 265                 270

Gln Ala Leu Ser Gln Pro Ile Ala Ser Ser Asn Val His Asp Asn Phe
        275                 280                 285

Met Asn Asn Glu Ile Thr Ala Ser Lys Ile Asp Asp Gly Asn Asn Ser
    290                 295                 300

Lys Pro Leu Ser Pro Gly Trp Thr Asp Gln Thr Ala Tyr Asn Ala Phe
305                 310                 315                 320

Gly Ile Thr Thr Gly Met Phe Asn Thr Thr Met Asp Asp Val Tyr
                325                 330                 335

Asn Tyr Leu Phe Asp Asp Glu Asp Thr Pro Pro Asn Pro Lys Lys Glu
            340                 345                 350

<210> SEQ ID NO 109
<211> LENGTH: 1068
<212> TYPE: DNA
<213> ORGANISM: Artificial sequence
<220> FEATURE:
<223> OTHER INFORMATION: Synthetic

<400> SEQUENCE: 109
atgaagctac tgtcttctat cgaacaagca tgcgatattt gccgacttaa aaagctcaag      60
tgctccaaag aaaaaccgaa gtgcgccaag tgtctgaaga caactgggag gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaagaggc aaaccccca agtagaactg      300 ggacctgttg acacgtcagt tgctctgatt ctgtgcgacc tgaagcaaaa agacacgcca     360
attgtgtacg cctcggaagc ttttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag aacgccgag      540 gtgcaggttg aggtggtcaa ttttaagaag aacggccaac ggtttgtcaa cttcttgacg     600
atgattccgg tgcgagatga aacaggggaa taccggtaca gcatgggttt ccagtgcgaa     660
acggaaggat ccggcggagg tgggggctcc ggaagcggcg gtggtggatc aggtggaggt     720
ggctccaatt ttaatcaaag tggaatatt gctgatagct cattgtcctt cactttcact      780
aacagtagca acggtccgaa cctcataaca actcaaacaa attctcaagc gctttcacaa     840
ccaattgcct cctctaacgt tcatgataac ttcatgaata tgaaaatcac ggctagtaaa     900
attgatgatg gtaataattc aaaaccactg tcacctggtt ggacggacca aactgcgtat     960
```

```
aacgcgtttg gaatcactac agggatgttt aataccacta caatggatga tgtatataac    1020
tatctattcg atgatgaaga tacccccacca aacccaaaaa aagagtaa                1068
```

<210> SEQ ID NO 110
<211> LENGTH: 355
<212> TYPE: PRT
<213> ORGANISM: Artificial sequence
<220> FEATURE:
<223> OTHER INFORMATION: Synthetic

<400> SEQUENCE: 110

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Gly Gly Gly Ser Gly Ser Gly Gly Gly Ser Gly Gly Gly
225                 230                 235                 240

Gly Ser Asn Phe Asn Gln Ser Gly Asn Ile Ala Asp Ser Ser Leu Ser
                245                 250                 255

Phe Thr Phe Thr Asn Ser Ser Asn Gly Pro Asn Leu Ile Thr Thr Gln
            260                 265                 270

Thr Asn Ser Gln Ala Leu Ser Gln Pro Ile Ala Ser Ser Asn Val His
        275                 280                 285

Asp Asn Phe Met Asn Asn Glu Ile Thr Ala Ser Lys Ile Asp Asp Gly
    290                 295                 300

Asn Asn Ser Lys Pro Leu Ser Pro Gly Trp Thr Asp Gln Thr Ala Tyr
305                 310                 315                 320

Asn Ala Phe Gly Ile Thr Thr Gly Met Phe Asn Thr Thr Thr Met Asp
                325                 330                 335

Asp Val Tyr Asn Tyr Leu Phe Asp Asp Glu Asp Thr Pro Pro Asn Pro
```

```
                 340             345             350
Lys Lys Glu
        355

<210> SEQ ID NO 111
<211> LENGTH: 861
<212> TYPE: DNA
<213> ORGANISM: Artificial sequence
<220> FEATURE:
<223> OTHER INFORMATION: Synthetic

<400> SEQUENCE: 111
atgaagctac tgtcttctat cgaacaagca tgcgatattt gccgacttaa aaagctcaag    60
tgctccaaag aaaaaccgaa gtgcgccaag tgtctgaaga caactgggga gtgtcgctac   120
tctcccaaaa ccaaaaggtc tccgctgact agggcacatc tgacagaagt ggaatcaagg   180
ctagaaagac tggaaagatc catcgccacc agatctcata cgctctacgc tcccggcggt   240
tatgacatta tgggctatct gattcagatt atgaacaggc caaaccccca agtagaactg   300
ggacctgttg acacgtcatg cgctctgatt ctgtgcgacc tgaagcaaaa agacacgcca   360
attgtgtacg cctcggaagc ttttctctat atgacaggat acagcaatgc ggaggtcttg   420 gggagaaaact gccgttttct tcagtcaccc gacggaatgg tcaagccgaa atcgacaagg   480
aagtacgtcg actccaacac gatcaatacg atgaggaaag cgattgatag aacgccgag    540 gtgcaggttg aggtggtcaa ttttaagaag aacggccaac ggtttgtcaa cttcttgacg   600
atgattccgg tgcgagatga aacaggggaa taccggtaca gcatgggttt ccagtgcgaa   660
acggaactgc agtacccata cgatgttcca gattacgctg aattcccggg gatctcgacg   720
gcccccccga ccgatgtcag cctggggaac gagctccact agacggcga ggacgtggcg    780 atggcgcatg ccgacgcgct agacgatttc gatctggaca tgttggggga cggggattcc   840
ccgggtccgg gatcgccata a                                              861

<210> SEQ ID NO 112
<211> LENGTH: 286
<212> TYPE: PRT
<213> ORGANISM: Artificial sequence
<220> FEATURE:
<223> OTHER INFORMATION: Synthetic

<400> SEQUENCE: 112

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Asn Arg Pro Asn Pro
                85                  90                  95

Gln Val Glu Leu Gly Pro Val Asp Thr Ser Cys Ala Leu Ile Leu Cys
            100                 105                 110

Asp Leu Lys Gln Lys Asp Thr Pro Ile Val Tyr Ala Ser Glu Ala Phe
        115                 120                 125
```

| | | | | | | | | | | | |
|---|---|---|---|---|---|---|---|---|---|---|---|
| Leu | Tyr | Met | Thr | Gly | Tyr | Ser | Asn | Ala | Glu | Val | Leu | Gly | Arg | Asn | Cys |
| 130 | | | | | 135 | | | | | 140 | |

Leu Tyr Met Thr Gly Tyr Ser Asn Ala Glu Val Leu Gly Arg Asn Cys
            130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Leu Gln
    210                 215                 220

Tyr Pro Tyr Asp Val Pro Asp Tyr Ala Glu Phe Pro Gly Ile Ser Thr
225                 230                 235                 240

Ala Pro Pro Thr Asp Val Ser Leu Gly Asp Glu Leu His Leu Asp Gly
                245                 250                 255

Glu Asp Val Ala Met Ala His Ala Asp Ala Leu Asp Asp Phe Asp Leu
            260                 265                 270

Asp Met Leu Gly Asp Gly Asp Ser Pro Gly Pro Gly Ser Pro
        275                 280                 285

<210> SEQ ID NO 113
<211> LENGTH: 1143
<212> TYPE: DNA
<213> ORGANISM: Artificial sequence
<220> FEATURE:
<223> OTHER INFORMATION: Synthetic

<400> SEQUENCE: 113

```
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaagaggc aaaccccca agtagaactg      300
ggacctgttg acacgtcagt tgctctgatt ctgtgcgacc tgaagcaaaa agacacgcca     360
attgtgtacg cctcggaagc ttttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag aacgccgag      540
gtgcaggttg aggtggtcaa ttttaagaag aacggccaac ggtttgtcaa cttcttgacg     600
atgattccgg tgcgagatga aacaggggaa taccggtaca gcatgggttt ccagtgcgaa     660
acggaaggat ccggcggtgg tggatcaggt ggaggtggct ccgaattcat gtccgaatat     720
cagccaagtt tatttgcttt aaatccaatg ggtttctcac cattggatgg ttctaaatca     780
accaacgaaa atgtatctgc ttccacttct actgccaaac caatggttgg ccaattgatt     840
tttgataaat tcatcaagac tgaagaggat ccaattatca acaggatac cccttcgaac      900
cttgattttg attttgctct tccacaaacg gcaactgcac ctgatgccaa gaccgttttg     960
ccaattccgg agctagatga cgctgtagtg gaatctttct tttcgtcaag cactgattca    1020
actccaatgt ttgagtatga aaacctagaa gacaactcta agaatggac atccttgttt     1080
gacaatgaca ttccagttac cactgacgat gtttcattgg ctgataaggc aattgaatcc    1140
taa                                                                  1143
```

<210> SEQ ID NO 114
<211> LENGTH: 380
<212> TYPE: PRT
<213> ORGANISM: Artificial sequence
<220> FEATURE:
<223> OTHER INFORMATION: Synthetic

<400> SEQUENCE: 114

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Gly Gly Gly Ser Gly Gly Gly Ser Glu Phe Met Ser Glu Tyr
225                 230                 235                 240

Gln Pro Ser Leu Phe Ala Leu Asn Pro Met Gly Phe Ser Pro Leu Asp
                245                 250                 255

Gly Ser Lys Ser Thr Asn Glu Asn Val Ser Ala Ser Thr Ser Thr Ala
            260                 265                 270

Lys Pro Met Val Gly Gln Leu Ile Phe Asp Lys Phe Ile Lys Thr Glu
        275                 280                 285

Glu Asp Pro Ile Ile Lys Gln Asp Thr Pro Ser Asn Leu Asp Phe Asp
    290                 295                 300

Phe Ala Leu Pro Gln Thr Ala Thr Ala Pro Asp Ala Lys Thr Val Leu
305                 310                 315                 320

Pro Ile Pro Glu Leu Asp Asp Ala Val Val Glu Ser Phe Phe Ser Ser
                325                 330                 335

Ser Thr Asp Ser Thr Pro Met Phe Glu Tyr Glu Asn Leu Glu Asp Asn
            340                 345                 350

Ser Lys Glu Trp Thr Ser Leu Phe Asp Asn Asp Ile Pro Val Thr Thr
        355                 360                 365
```

Asp Asp Val Ser Leu Ala Asp Lys Ala Ile Glu Ser
        370                 375                 380

<210> SEQ ID NO 115
<211> LENGTH: 1044
<212> TYPE: DNA
<213> ORGANISM: Artificial sequence
<220> FEATURE:
<223> OTHER INFORMATION: Synthetic

<400> SEQUENCE: 115

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaacaggc caaaccccca agtagaactg     300
ggacctgttg acacgtcatg cgctctgatt ctgtgcgacc tgaagcaaaa agacacgcca     360
attgtgtacg cctcggaagc tttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag gaacgccgag     540
gtgcaggttg aggtggtcaa ttttaagaag aacggccaac ggtttgtcaa cttcttgacg     600
atgattccgg tgcgagatga aacaggggaa taccggtaca gcatgggttt ccagtgcgaa     660
acggaaggat ccggcggtgg tggatcaggt ggaggtggct ccaattttaa tcaaagtggg     720
aatattgctg atagctcatt gtccttcact ttcactaaca gtagcaacgg tccgaacctc     780
ataacaactc aaacaaattc tcaagcgctt tcacaaccaa ttgcctcctc taacgttcat     840
gataacttca tgaataatga aatcacggct agtaaaattg atgatggtaa taattcaaaa     900
ccactgtcac ctggttggac ggaccaaact gcgtataacg cgtttggaat cactacaggg     960
atgtttaata ccactacaat ggatgatgta tataactatc tattcgatga tgaagatacc    1020
ccaccaaacc caaaaaaaga gtaa                                             1044
```

<210> SEQ ID NO 116
<211> LENGTH: 347
<212> TYPE: PRT
<213> ORGANISM: Artificial sequence
<220> FEATURE:
<223> OTHER INFORMATION: Synthetic

<400> SEQUENCE: 116

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Asn Arg Pro Asn Pro
                85                  90                  95

Gln Val Glu Leu Gly Pro Val Asp Thr Ser Cys Ala Leu Ile Leu Cys

```
              100                 105                 110
Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
                180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
        210                 215                 220

Gly Gly Gly Gly Ser Gly Gly Gly Ser Asn Phe Asn Gln Ser Gly
225                 230                 235                 240

Asn Ile Ala Asp Ser Ser Leu Ser Phe Thr Phe Thr Asn Ser Ser Asn
                245                 250                 255

Gly Pro Asn Leu Ile Thr Thr Gln Thr Asn Ser Gln Ala Leu Ser Gln
                260                 265                 270

Pro Ile Ala Ser Ser Asn Val His Asp Asn Phe Met Asn Asn Glu Ile
        275                 280                 285

Thr Ala Ser Lys Ile Asp Asp Gly Asn Asn Ser Lys Pro Leu Ser Pro
290                 295                 300

Gly Trp Thr Asp Gln Thr Ala Tyr Asn Ala Phe Gly Ile Thr Thr Gly
305                 310                 315                 320

Met Phe Asn Thr Thr Thr Met Asp Val Tyr Asn Tyr Leu Phe Asp
                325                 330                 335

Asp Glu Asp Thr Pro Pro Asn Pro Lys Lys Glu
                340                 345

<210> SEQ ID NO 117
<211> LENGTH: 1044
<212> TYPE: DNA
<213> ORGANISM: Artificial sequence
<220> FEATURE:
<223> OTHER INFORMATION: Synthetic

<400> SEQUENCE: 117
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaacaggc aaaccccca agtagaactg      300 ggacctgttg acacgtcagt tgctctgatt ctgtgcgacc tgaagcaaaa agacacgcca     360
attgtgtacg cctcggaagc ttttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag aacgccgag     540 gtgcaggttg aggtggtcaa ttttaagaag acggccaac ggtttgtcaa cttcttgacg      600
atgattccgg tgcgagatga aacaggggaa taccggtaca gcatgggttt ccagtgcgaa     660
```

```
acggaaggat ccggcggtgg tggatcaggt ggaggtggct ccaattttaa tcaaagtggg    720
aatattgctg atagctcatt gtccttcact ttcactaaca gtagcaacgg tccgaacctc    780
ataacaactc aaacaaattc tcaagcgctt tcacaaccaa ttgcctcctc taacgttcat    840
gataacttca tgaataatga aatcacggct agtaaaattg atgatggtaa taattcaaaa    900
ccactgtcac ctggttggac ggaccaaact gcgtataacg cgtttggaat cactacaggg    960
atgtttaata ccactacaat ggatgatgta tataactatc tattcgatga tgaagatacc   1020
ccaccaaacc caaaaaaaga gtaa                                          1044
```

<210> SEQ ID NO 118
<211> LENGTH: 347
<212> TYPE: PRT
<213> ORGANISM: Artificial sequence
<220> FEATURE:
<223> OTHER INFORMATION: Synthetic

<400> SEQUENCE: 118

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Asn Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Gly Gly Gly Ser Gly Gly Gly Gly Ser Asn Phe Asn Gln Ser Gly
225                 230                 235                 240

Asn Ile Ala Asp Ser Ser Leu Ser Phe Thr Phe Thr Asn Ser Ser Asn
                245                 250                 255

Gly Pro Asn Leu Ile Thr Thr Gln Thr Asn Ser Gln Ala Leu Ser Gln
            260                 265                 270

Pro Ile Ala Ser Ser Asn Val His Asp Asn Phe Met Asn Asn Glu Ile
        275                 280                 285

Thr Ala Ser Lys Ile Asp Asp Gly Asn Asn Ser Lys Pro Leu Ser Pro
```

```
                290                 295                 300
Gly Trp Thr Asp Gln Thr Ala Tyr Asn Ala Phe Gly Ile Thr Thr Gly
305                 310                 315                 320

Met Phe Asn Thr Thr Thr Met Asp Asp Val Tyr Asn Tyr Leu Phe Asp
                325                 330                 335

Asp Glu Asp Thr Pro Pro Asn Pro Lys Lys Glu
            340                 345
```

<210> SEQ ID NO 119
<211> LENGTH: 1044
<212> TYPE: DNA
<213> ORGANISM: Artificial sequence
<220> FEATURE:
<223> OTHER INFORMATION: Synthetic

<400> SEQUENCE: 119

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctggct gattcagatt atgaacaggc aaaccccca gtagaactg      300
ggacctgttg acacgtcatg cgctctgatt ctgtgcgacc tgaagcaaaa agacacgcca     360
attgtgtacg cctcggaagc ttttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag aacgccgag     540
gtgcaggttg aggtggtcaa ttttaagaag aacggccaac ggtttgtcaa cttcttgacg     600
atgattccgg tgcgagatga acaggggaa taccggtaca gcatgggttt ccagtgcgaa     660
acggaaggat ccggcggtgg tggatcaggt ggaggtggct ccaattttaa tcaaagtggg     720
aatattgctg atagctcatt gtccttcact ttcactaaca gtagcaacgg tccgaacctc     780
ataacaactc aaacaaattc tcaagcgctt tcacaaccaa ttgcctcctc taacgttcat     840
gataacttca tgaataatga aatcacggct agtaaaattg atgatggtaa taattcaaaa     900
ccactgtcac ctggttggac ggaccaaact gcgtataacg cgtttggaat cactacaggg     960
atgtttaata ccactacaat ggatgatgta tataactatc tattcgatga tgaagatacc    1020
ccaccaaacc caaaaaaaga gtaa                                           1044
```

<210> SEQ ID NO 120
<211> LENGTH: 347
<212> TYPE: PRT
<213> ORGANISM: Artificial sequence
<220> FEATURE:
<223> OTHER INFORMATION: Synthetic

<400> SEQUENCE: 120

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60
```

```
Glu Arg Ser Ile Ala Thr Arg Ser His Thr Leu Tyr Ala Pro Gly Gly
 65                  70                  75                  80

Tyr Asp Ile Met Gly Trp Leu Ile Gln Ile Met Asn Arg Pro Asn Pro
                 85                  90                  95

Gln Val Glu Leu Gly Pro Val Asp Thr Ser Cys Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Gly Ser
    210                 215                 220

Gly Gly Gly Gly Ser Gly Gly Gly Ser Asn Phe Asn Gln Ser Gly
225                 230                 235                 240

Asn Ile Ala Asp Ser Ser Leu Ser Phe Thr Phe Thr Asn Ser Ser Asn
                245                 250                 255

Gly Pro Asn Leu Ile Thr Thr Gln Thr Asn Ser Gln Ala Leu Ser Gln
            260                 265                 270

Pro Ile Ala Ser Ser Asn Val His Asp Asn Phe Met Asn Asn Glu Ile
        275                 280                 285

Thr Ala Ser Lys Ile Asp Asp Gly Asn Asn Ser Lys Pro Leu Ser Pro
    290                 295                 300

Gly Trp Thr Asp Gln Thr Ala Tyr Asn Ala Phe Gly Ile Thr Thr Gly
305                 310                 315                 320

Met Phe Asn Thr Thr Thr Met Asp Asp Val Tyr Asn Tyr Leu Phe Asp
                325                 330                 335

Asp Glu Asp Thr Pro Pro Asn Pro Lys Lys Glu
            340                 345

<210> SEQ ID NO 121
<211> LENGTH: 1026
<212> TYPE: DNA
<213> ORGANISM: Artificial sequence
<220> FEATURE:
<223> OTHER INFORMATION: Synthetic

<400> SEQUENCE: 121
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctttct ggctactac  acttgaacgt     240 attgagaaga actttgtcat tactgaccca aggttgccag ataatcccat tatattcgcg     300
tccgatagtt tcttgcagtt gacagaatat agccgtgaag aaattttggg aagaaactgc     360
aggtttctac aaggtcctga aactgatcgc gcgacagtga aaaaattag  agatgccata     420 gataaccaaa cagaggtcac tgttcagctg attaattata caaagagtgg taaaaagttc     480
```

```
tggaacctct ttcacttgca gcctatgcga gatcagaagg gagatgtcca gtactttatt    540 gggggttcagt tggatggaac tgagcatgtc cgagatgctg ccgagagaga gggagtcatg    600
ctgattaaga aaactgcaga aaatattgat gaggcggcaa agaacttgg atccggcggt    660 ggtggatcag gtggaggtgg ctccaatttt aatcaaagtg gaatattgc tgatagctca    720 ttgtccttca ctttcactaa cagtagcaac ggtccgaacc tcataacaac tcaaacaaat    780
tctcaagcgc tttcacaacc aattgcctcc tctaacgttc atgataactt catgaataat    840
gaaatcacgg ctagtaaaat tgatgatggt aataattcaa aaccactgtc acctggttgg    900
acggaccaaa ctgcgtataa cgcgtttgga atcactacag gatgttttaa taccactaca    960
atggatgatg tatataacta tctattcgat gatgaagata ccccaccaaa cccaaaaaaa   1020
gagtaa                                                              1026
```

<210> SEQ ID NO 122
<211> LENGTH: 341
<212> TYPE: PRT
<213> ORGANISM: Artificial sequence
<220> FEATURE:
<223> OTHER INFORMATION: Synthetic

<400> SEQUENCE: 122

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser Phe Leu Ala Thr Thr Leu Glu Arg
65                  70                  75                  80

Ile Glu Lys Asn Phe Val Ile Thr Asp Pro Arg Leu Pro Asp Asn Pro
                85                  90                  95

Ile Ile Phe Ala Ser Asp Ser Phe Leu Gln Leu Thr Glu Tyr Ser Arg
            100                 105                 110

Glu Glu Ile Leu Gly Arg Asn Cys Arg Phe Leu Gln Gly Pro Glu Thr
        115                 120                 125

Asp Arg Ala Thr Val Arg Lys Ile Arg Asp Ala Ile Asp Asn Gln Thr
    130                 135                 140

Glu Val Thr Val Gln Leu Ile Asn Tyr Thr Lys Ser Gly Lys Lys Phe
145                 150                 155                 160

Trp Asn Leu Phe His Leu Gln Pro Met Arg Asp Gln Lys Gly Asp Val
                165                 170                 175

Gln Tyr Phe Ile Gly Val Gln Leu Asp Gly Thr Glu His Val Arg Asp
            180                 185                 190

Ala Ala Glu Arg Glu Gly Val Met Leu Ile Lys Lys Thr Ala Glu Asn
        195                 200                 205

Ile Asp Glu Ala Ala Lys Glu Leu Gly Ser Gly Gly Gly Ser Gly
    210                 215                 220

Gly Gly Gly Ser Asn Phe Asn Gln Ser Gly Asn Ile Ala Asp Ser Ser
225                 230                 235                 240

Leu Ser Phe Thr Phe Thr Asn Ser Asn Gly Pro Asn Leu Ile Thr
                245                 250                 255
```

```
Thr Gln Thr Asn Ser Gln Ala Leu Ser Gln Pro Ile Ala Ser Ser Asn
        260                 265                 270

Val His Asp Asn Phe Met Asn Asn Glu Ile Thr Ala Ser Lys Ile Asp
    275                 280                 285

Asp Gly Asn Asn Ser Lys Pro Leu Ser Pro Gly Trp Thr Asp Gln Thr
        290                 295                 300

Ala Tyr Asn Ala Phe Gly Ile Thr Thr Gly Met Phe Asn Thr Thr Thr
305                 310                 315                 320

Met Asp Asp Val Tyr Asn Tyr Leu Phe Asp Asp Glu Asp Thr Pro Pro
                325                 330                 335

Asn Pro Lys Lys Glu
        340

<210> SEQ ID NO 123
<211> LENGTH: 1241
<212> TYPE: DNA
<213> ORGANISM: Artificial sequence
<220> FEATURE:
<223> OTHER INFORMATION: Synthetic

<400> SEQUENCE: 123
cggattagaa gccgccgagc gggtgacagc cctccgaagg aagactctcc tccgtgcgtc      60
ctcgtcttca ccggtcgcgt tcctgaaacg cagatgtgcc tcgcgccgca ctgctccgaa     120
caataaagat tctacaatac tagcttttat ggttatgaag aggaaaaatt ggcagtaacc     180
tggccccaca aaccttcaaa tgaacgaatc aaattaacaa ccataggatg ataatgcgat     240 tagttttttta gccttatttc tggggtaatt aatcagcgaa gcgatgattt ttgatctatt    300
aacagatata taaatgcaaa aactgcataa ccactttaac taatactttc aacattttcg     360
gtttgtatta cttcttattc aaatgtaata aaagtatcaa caaaaaattg ttaatatacc     420
tctatacttt aacgtcaagg agaaaaaacc ccggatcgga ctactagcag ctgtaatacg     480
actcactata gggaatatta gctcgcccg gatccaaaaa aatggtgagt aaaggagaag       540
aacttttcac tggagttgtc ccaattcttg ttgaattaga tggtgatgtt aatgggcaca     600
aattttctgt cagtggagag ggtgaaggtg atgcaacata cggaaaactt acccttaaat     660
ttatttgcac tactggaaaa ctacctgttc catggccaac acttgtcact actttcggtt     720
atggtctaca atgctttgct agataccccag atcatatgaa acaacatgac ttttttcaaga   780 gtgccatgcc cgaaggttat gtacaggaaa gaactatatt tttcaaagat gacgggaact     840
acaagacacg tgctgaagtc aagtttgaag gtgataccct tgttaataga atcgagttaa     900
aaggtattga ttttaaagaa gatggaaaca ttcttggaca caaattggaa tacaactata    960
actcacacaa tgtatacatc atggcagaca acaaaagaa tggaatcaaa gttaacttca    1020
aaattagaca caacattgaa gatggaagcg ttcaactagc agaccattat caacaaaata    1080
ctccaattgg cgatggccct gtccttttac cagacaacca ttacctgtcc tatcaatctg    1140 cccttttcgaa agatcccaac gaaaagagag accacatggt ccttcttgag tttgtaacag   1200
ctgctgggat tacactcggc atggatgaac tatacaaata a                        1241

<210> SEQ ID NO 124
<211> LENGTH: 1140
<212> TYPE: DNA
<213> ORGANISM: Artificial sequence
<220> FEATURE:
<223> OTHER INFORMATION: Synthetic

<400> SEQUENCE: 124
```

```
cgcgccgcac tgctccgaac aataaagatt ctacaatact agcttttatg gttatgaaga     60
ggaaaaattg gcagtaacct ggccccacaa accttcaaat gaacgaatca aattaacaac    120
cataggatga taatgcgatt agttttttag ccttatttct ggggtaatta atcagcgaag    180
cgatgatttt tgatctatta acagatatat aaatgcaaaa actgcataac cactttaact    240
aatactttca acattttcgg tttgtattac ttcttattca aatgtaataa agtatcaac     300 aaaaaattgt taatataccct ctatacttta acgtcaagga gaaaaaaccc cggatcggac   360
tactagcagc tgtaatacga ctcactatag gaatattaa gctcgcccgg atccaaaaaa    420
atggtgagta aaggagaaga acttttcact ggagttgtcc caattcttgt tgaattagat    480
ggtgatgtta atgggcacaa attttctgtc agtggagagg gtgaaggtga tgcaacatac    540
ggaaaactta cccttaaatt tatttgcact actggaaaac tacctgttcc atggccaaca    600
cttgtcacta ctttcggtta tggtctacaa tgctttgcta gatacccaga tcatatgaaa    660
caacatgact ttttcaagag tgccatgccc gaaggttatg tacaggaaag aactatattt    720
ttcaaagatg acgggaacta caagacacgt gctgaagtca agtttgaagg tgatacccttt  780 gttaatagaa tcgagttaaa aggtattgat tttaaagaag atggaaacat tcttggacac    840
aaattggaat acaactataa ctcacacaat gtatacatca tggcagacaa acaaaagaat    900
ggaatcaaag ttaacttcaa aattagacac aacattgaag atggaagcgt tcaactagca    960
gaccattatc aacaaaatac tccaattggc gatggccctg tccttttacc agacaaccat   1020
tacctgtcct atcaatctgc cctttcgaaa gatcccaacg aaaagagaga ccacatggtc   1080
cttcttgagt ttgtaacagc tgctgggatt acactcggca tggatgaact atacaaataa   1140
```

<210> SEQ ID NO 125
<211> LENGTH: 1204
<212> TYPE: DNA
<213> ORGANISM: Artificial sequence
<220> FEATURE:
<223> OTHER INFORMATION: Synthetic

<400> SEQUENCE: 125

```
cggaagactc tcctccgtgc gtcctcgtct tcaccggtcg cgttcctgaa acgcagatgt     60
gcctcgcgcc gcactgctcc gaacaataaa gattctacaa tactagcttt tatggttatg   120
aagaggaaaa attggcagta acctggcccc acaaaccttc aaatgaacga atcaaattaa   180
caaccatagg atgataatgc gattagtttt ttagccttat ttctggggta attaatcagc   240
gaagcgatga ttttgatctt attaacagat atataaatgc aaaaactgca taaccacttt    300
aactaatact ttcaacattt tcggtttgta ttacttctta ttcaaatgta ataaagtat    360 caacaaaaaa ttgttaatat accctctatac tttaacgtca aggagaaaaa accccggatc   420
ggactactag cagctgtaat acgactcact atagggaata ttaagctcgc ccggatccaa    480
aaaaatggtg agtaaaggag aagaactttt cactggagtt gtcccaattc ttgttgaatt   540
agatggtgat gttaatgggc acaaattttc tgtcagtgga gagggtgaag gtgatgcaac   600
atacggaaaa cttacccctta aatttatttg cactactgga aaactacctg ttccatggcc   660
aacacttgtc actactttcg gttatggtct acaatgcttt gctagatacc cagatcatat   720
gaaacaacat gactttttca agagtgccat gcccgaaggt tatgtacagg aaagaactat   780
atttttcaaa gatgacggga actacaagac acgtgctgaa gtcaagtttg aaggtgatac    840
ccttgttaat agaatcgagt taaaaggtat tgattttaaa gaagatggaa acattcttgg    900
```

| | |
|---|---|
| acacaaattg gaatacaact ataactcaca caatgtatac atcatggcag acaaacaaaa | 960 |
| gaatggaatc aaagttaact tcaaaattag acacaacatt gaagatggaa gcgttcaact | 1020 |
| agcagaccat tatcaacaaa atactccaat tggcgatggc cctgtccttt taccagacaa | 1080 |
| ccattacctg tcctatcaat ctgccctttc gaaagatccc aacgaaaaga gagaccacat | 1140 |
| ggtccttctt gagtttgtaa cagctgctgg gattacactc ggcatggatg aactatacaa | 1200 |
| ataa | 1204 |

<210> SEQ ID NO 126
<211> LENGTH: 1223
<212> TYPE: DNA
<213> ORGANISM: Artificial sequence
<220> FEATURE:
<223> OTHER INFORMATION: Synthetic

<400> SEQUENCE: 126

| | |
|---|---|
| gcgggtgaca gccctccgaa ggaagactct cctccgtgcg tcctcgtctt caccggtcgc | 60 |
| gttcctgaaa cgcagatgtg cctcgcgccg cactgctccg aacaataaag attctacaat | 120 |
| actagctttt atggttatga agaggaaaaa ttggcagtaa cctggcccca caaaccttca | 180 |
| aatgaacgaa tcaaattaac aaccatagga tgataatgcg attagttttt tagccttatt | 240 |
| tctggggtaa ttaatcagcg aagcgatgat ttttgatcta ttaacagata tataaatgca | 300 |
| aaaactgcat aaccacttta actaatactt tcaacatttt cggtttgtat tacttcttat | 360 |
| tcaaatgtaa taaagtatc aacaaaaaat tgttaatata cctctatact ttaacgtcaa | 420 |
| ggagaaaaaa ccccggatcg gactactagc agctgtaata cgactcacta tagggaatat | 480 |
| taagctcgcc cggatccaaa aaaatggtga gtaaaggaga agaactttc actggagttg | 540 |
| tcccaattct tgttgaatta gatggtgatg ttaatgggca caattttct gtcagtggag | 600 |
| agggtgaagg tgatgcaaca tacggaaaac ttacccttaa atttatttgc actactggaa | 660 |
| aactacctgt tccatggcca acacttgtca ctactttcgg ttatggtcta caatgctttg | 720 |
| ctagataccc agatcatatg aaacaacatg actttttcaa gagtgccatg cccgaaggtt | 780 |
| atgtacagga agaactata ttttcaaag atgacgggaa ctacaagaca cgtgctgaag | 840 |
| tcaagtttga aggtgatacc cttgttaata gaatcgagtt aaaaggtatt gattttaaag | 900 |
| aagatggaaa cattcttgga cacaaattgg aatacaacta taactcacac aatgtataca | 960 |
| tcatggcaga caaacaaaag aatggaatca agttaactt caaaattaga cacaacattg | 1020 |
| aagatggaag cgttcaacta gcagaccatt atcaacaaaa tactccaatt ggcgatggcc | 1080 |
| ctgtcctttt accagacaac cattacctgt cctatcaatc tgcccttcg aaagatccca | 1140 |
| acgaaaagag agaccacatg gtccttcttg agtttgtaac agctgctggg attacactcg | 1200 |
| gcatggatga actatacaaa taa | 1223 |

<210> SEQ ID NO 127
<211> LENGTH: 1136
<212> TYPE: DNA
<213> ORGANISM: Artificial sequence
<220> FEATURE:
<223> OTHER INFORMATION: Synthetic

<400> SEQUENCE: 127

| | |
|---|---|
| ggcgttcgtc ctcactgtat gatcatacag tctgtatata tatacagtac tgtatgatca | 60 |
| tacaggttcc tgaaacgcag atgtgcctac tgtatatata tacagtaaca ataaagattc | 120 |
| aagctttaat gcgattagtt ttttagccctt atttctgggg taattaatca gcgaagcgat | 180 |

```
gatttttgat ctattaacag atatataaat gcaaaaactg cataaccact ttaactaata    240
ctttcaacat tttcggtttg tattacttct tattcaaatg taataaaagt atcaacaaaa    300
aattgttaat atacctctat actttaacgt caaggagaaa aaacccccgga tcggactact   360 agcagctgta atacgactca ctatagggaa tattaagctc gcccggatcc aaaaaaatgg    420
tgagtaaagg agaagaactt ttcactggag ttgtcccaat tcttgttgaa ttagatggtg    480
atgttaatgg gcacaaattt tctgtcagtg gagagggtga aggtgatgca acatacggaa    540
aacttaccct taaatttatt tgcactactg gaaaactacc tgttccatgg ccaacacttg    600
tcactacttt cggttatggt ctacaatgct tgctagata cccagatcat atgaaacaac     660 atgactttt caagagtgcc atgcccgaag ttatgtaca ggaagaact atattttca       720 aagatgacgg gaactacaag acacgtgctg aagtcaagtt tgaaggtgat acccttgtta    780
atagaatcga gttaaaaggt attgatttta aagaagatgg aaacattctt ggacacaaat    840
tggaatacaa ctataactca cacaatgtat acatcatggc agacaaacaa agaatggaa    900 tcaaagttaa cttcaaaatt agacacaaca ttgaagatgg aagcgttcaa ctagcagacc    960
attatcaaca aaatactcca attggcgatg gccctgtcct tttaccagac aaccattacc   1020
tgtcctatca atctgccctt tcgaaagatc ccaacgaaaa gagagaccac atggtccttc   1080
ttgagtttgt aacagctgct gggattacac tcggcatgga tgaactatac aaataa       1136
```

<210> SEQ ID NO 128
<211> LENGTH: 1109
<212> TYPE: DNA
<213> ORGANISM: Artificial sequence
<220> FEATURE:
<223> OTHER INFORMATION: Synthetic

<400> SEQUENCE: 128

```
aattgtgagc ggataacaat tgtaattgtg agcggataac aattatttga attgtgagcg     60
gataacaatt gtaattgtga gcggataaca attaagcttt aatgcgatta gttttttagc    120
cttatttctg gggtaattaa tcagcgaagc gatgattttt gatctattaa cagatatata    180
aatgcaaaaa ctgcataacc actttaacta atactttcaa cattttcggt ttgtattact    240
tcttattcaa atgtaataaa agtatcaaca aaaaattgtt aatatacctc tatactttaa    300
cgtcaaggag aaaaaacccc ggatcggact actagcagct gtaatacgac tcactatagg    360
gaatattaag ctcgcccgga tccaaaaaaa tggtgagtaa aggagaagaa cttttcactg    420
gagttgtccc aattcttgtt gaattagatg gtgatgttaa tgggcacaaa ttttctgtca    480
gtggagaggg tgaaggtgat gcaacatacg gaaaacttac ccttaaattt atttgcacta    540
ctggaaaact acctgttcca tggccaacac ttgtcactac tttcggttat ggtctacaat    600
gctttgctag atacccagat catatgaaac aacatgactt tttcaagagt gccatgcccg    660
aaggttatgt acaggaaaga actatatttt tcaaagatga cgggaactac aagacacgtg    720
ctgaagtcaa gtttgaaggt gatacccttg ttaatagaat cgagttaaaa ggtattgatt    780
ttaaagaaga tggaaacatt cttggacaca aattggaata actataac tcacacaatg     840 tatacatcat ggcagacaaa caaagaatgg aatcaaagt taacttcaaa attagacaca    900
acattgaaga tggaagcgtt caactagcag accattatca acaaaatact ccaattggcg    960
atggccctgt ccttttacca gacaaccatt acctgtccta tcaatctgcc ctttcgaaag   1020
atcccaacga aaagagagac cacatggtcc ttcttgagtt tgtaacagct gctgggatta   1080
```

-continued cactcggcat ggatgaacta tacaaataa                                         1109

<210> SEQ ID NO 129
<211> LENGTH: 1093
<212> TYPE: DNA
<213> ORGANISM: Artificial sequence
<220> FEATURE:
<223> OTHER INFORMATION: Synthetic

<400> SEQUENCE: 129
taaatctatc accgcaaggg ataaatatct aacaccgtgc gtgttgacta ttttacctct        60
ggcggtgata atggttgaag ctttaatgcg attagttttt tagccttatt tctggggtaa      120
ttaatcagcg aagcgatgat ttttgatcta ttaacagata tataaatgca aaaactgcat      180
aaccacttta actaatactt tcaacatttt cggtttgtat tacttcttat tcaaatgtaa      240
taaaagtatc aacaaaaaat tgttaatata cctctatact ttaacgtcaa ggagaaaaaa      300
ccccggatcg gactactagc agctgtaata cgactcacta tagggaatat taagctcgcc      360
cggatccaaa aaatggtga gtaaaggaga agaacttttc actggagttg tcccaattct       420
tgttgaatta gatggtgatg ttaatgggca caatttttct gtcagtggag agggtgaagg      480
tgatgcaaca tacggaaaac ttacccttaa atttatttgc actactggaa aactacctgt      540
tccatggcca acacttgtca ctactttcgg ttatggtcta caatgctttg ctagataccc      600
agatcatatg aaacaacatg acttttcaa gagtgccatg cccgaaggtt atgtacagga      660
aagaactata ttttcaaag atgacgggaa ctacaagaca cgtgctgaag tcaagtttga      720
aggtgatacc cttgttaata gaatcgagtt aaaaggtatt gatttaaag aagatggaaa      780
cattcttgga cacaaattgg aatacaacta taactcacac aatgtataca tcatggcaga      840
caaacaaaag aatggaatca agttaacttt caaaattaga cacaacattg aagatggaag      900
cgttcaacta gcagaccatt atcaacaaaa tactccaatt ggcgatggcc ctgtcctttt       960
accagacaac cattacctgt cctatcaatc tgccctttcg aaagatccca acgaaaagag     1020
agaccacatg gtccttcttg agtttgtaac agctgctggg attacactcg gcatggatga     1080
actatacaaa taa                                                        1093

<210> SEQ ID NO 130
<211> LENGTH: 1128
<212> TYPE: DNA
<213> ORGANISM: Artificial sequence
<220> FEATURE:
<223> OTHER INFORMATION: Synthetic

<400> SEQUENCE: 130
ccactcccta tcagtgatag agaaaagtcc actccctatc agtgatagag aaaagtccac        60
tccctatcag tgatagagaa agtccactc cctatcagtg atagagaaaa gtaagcttta       120
atgcgattag ttttttagcc ttatttctgg ggtaattaat cagcgaagcg atgattttg       180
atctattaac agatatataa atgcaaaaac tgcataacca ctttaactaa tactttcaac      240
attttcggtt tgtattactt cttattcaaa tgtaataaaa gtatcaacaa aaattgtta      300
atatacctct atactttaac gtcaaggaga aaaaccccg atcggacta ctagcagctg       360
taatacgact cactataggg aatattaagc tcgcccggat ccaaaaaaat ggtgagtaaa      420
ggagaagaac ttttcactgg agttgtccca attcttgttg aattagatgg tgatgttaat      480
gggcacaaat tttctgtcag tggagagggt gaaggtgatg caacatacgg aaaacttacc      540
cttaaattta tttgcactac tggaaaacta cctgttccat ggccaacact tgtcactact      600

```
ttcggttatg gtctacaatg ctttgctaga tacccagatc atatgaaaca acatgacttt    660
ttcaagagtg ccatgcccga aggttatgta caggaaagaa ctatattttt caaagatgac    720
gggaactaca agacacgtgc tgaagtcaag tttgaaggtg ataccttgt taatagaatc     780 gagttaaaag gtattgattt taaagaagat ggaaacattt tggacacaa attggaatac     840 aactataact cacacaatgt atacatcatg gcagacaaac aaaagaatgg aatcaaagtt    900
aacttcaaaa ttagacacaa cattgaagat ggaagcgttc aactagcaga ccattatcaa    960
caaaatactc caattggcga tggccctgtc cttttaccag acaaccatta cctgtcctat   1020
caatctgccc tttcgaaaga tcccaacgaa aagagagacc acatggtcct tcttgagttt   1080
gtaacagctg ctgggattac actcggcatg gatgaactat acaaataa                1128
```

<210> SEQ ID NO 131
<211> LENGTH: 2592
<212> TYPE: DNA
<213> ORGANISM: Artificial sequence
<220> FEATURE:
<223> OTHER INFORMATION: Synthetic

<400> SEQUENCE: 131

```
atgaagctac tgtcttctat cgaacaagca tgcgatattt gccgacttaa aaagctcaag     60
tgctccaaag aaaaaccgaa gtgcgccaag tgtctgaaga caactggga gtgtcgctac    120 tctcccaaaa ccaaaaggtc tccgctgact agggcacatc tgacagaagt ggaatcaagg    180 ctagaaaagac tggaaagatc catcgccacc agatctcata cgctctacgc tcccggcggt    240
tatgacatta tgggctatct gattcagatt atgaagaggc aaacccccca gtagaactg     300 ggacctgttg acacgtcagt tgctctgatt ctgtgcgacc tgaagcaaaa agacacgcca    360
attgtgtacg cctcggaagc ttttctctat atgacaggat acagcaatgc ggaggtcttg    420
gggagaaact gccgttttct tcagtcaccc gacggaatgg tcaagccgaa atcgacaagg    480
aagtacgtcg actccaacac gatcaatacg atgaggaaag cgattgatag aacgccgag     540 gtgcaggttg aggtggtcaa ttttaagaag aacggccaac ggtttgtcaa cttcttgacg    600
atgattccgg tgcgagatga aacaggggaa taccggtaca gcatgggttt ccagtgcgaa    660
acggaactgc agtacccata cgatgttcca gattacgctg aattccagta cctgccagat    720
acagacgatc gtcaccggat tgaggagaaa cgtaaaagga catatgagac cttcaagagc    780
atcatgaaga gagtcctttt cagcggaccc accgaccccc ggcctccacc tcgacgcatt    840
gctgtgcctt cccgcagctc agcttctgtc cccaagccag caccccagcc ctatcccttt    900
acgtcatccc tgagcaccat caactatgat gagtttccca ccatggtgtt tccttctggg    960
cagatcagcc aggcctcggc cttggcccgg gcccctcccc aagtcctgcc ccaggctcca   1020
gcccctgccc ctgctccagc catggtatca gctctggccc aggcccagc ccctgtccca   1080 gtcctagccc caggccctcc tcaggctgtg gccccacctg cccccaagcc cacccaggct   1140
ggggaaggaa cgctgtcaga ggccctgctg cagctgcagt ttgatgatga agacctgggg   1200
gccttgcttg gcaacagcac agaccccagct gtgttcacag acctggcatc cgtcgacaac   1260
tccgagtttc agcagctgct gaaccagggc atacctgtgg cccccacac aactgagccc   1320 atgctgatgg agtaccctga ggctataact cgcctagtga gggggcccca gaggcccccc   1380
gacccagctc ctgctccact ggggccccg gggctcccca tggcctcct ttcaggagat    1440 gaagacttct cctccattgc ggacatggac ttctcagccc tgctgagtca gatcagctcc   1500
```

-continued

```
acgcgtcgtc ctgcttgtaa gattcctaat gacaagcaga aggttatgaa tcacatgagg   1560
cctgaatgtg tcatacagga gcccagtaaa aataaagaca ggcaaagaca aagaaaagac   1620
aaaggaatat tattacctgt tagtacgacc acagtcgaag accacatgcc cccgatcatg   1680
caatgtgatc cacctccgcc cgaggccgcc aggattcacg aagtcgtccc gaggtatctt   1740
tcggagaagc tgatggagca gaacaggcag aagaacatac caccattgtc ggcgaatcag   1800
aagtctctga tcgcgaggct cgtgtggtac caggagggat atgagcagcc ctccgacgag   1860
gatctcaaaa gagtaacgca gacttggcag tcggatgaag aggacgagga atccgatcta   1920
cccttccgcc agatcacgga gatgacgatc ttaacggtcc agttgatcgt cgagttcgcc   1980
aagggtctac cgggcttttc gaagatatca cagtctgatc aaatcacctt attaaaagcc   2040
tcgtccagcg aggtgatgat gctgcggg tg gcgaggcgat acgacgccgc gtccgacagc   2100
attctgttcg ccaacaacaa ggcgtacacg cgcgacaact accgcaaggc gggcatggcc   2160
gaggtcatcg aagacctcct acacttctgc cggtgcatgt tcgcgatggg catggacaat   2220
gtgcactttg cactgctcac ggccatcgtt atattctcag atcggccgg gctcgagcag   2280
ccgtcgctgg tagaagagat ccagagatac tacctgaaca cgttgcgaat ttacatcatc   2340
aaccagaaca gcgcgtcgtc gcgctgcgcc gtgatctacg caggatcct gagcgtgctg   2400
accgagctac gcacgctcgg cacgcaaaac tccaacatgt gcatctcgct gaagctgaag   2460
aacaggaagc tgccgccgtt cctcgaggag atctgggacg tggcggaggt ggccacgacg   2520
catcccacgg tgctgccgcc caccaacccg gtggtgctaa ctagtgacta caaagacgat   2580
gatgacaagt aa                                                      2592
```

<210> SEQ ID NO 132
<211> LENGTH: 863
<212> TYPE: PRT
<213> ORGANISM: Artificial sequence
<220> FEATURE:
<223> OTHER INFORMATION: Synthetic

<400> SEQUENCE: 132

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
```

```
                    165                 170                 175
Arg Asn Ala Glu Val Gln Val Glu Val Val Asn Phe Lys Lys Asn Gly
                180                 185                 190

Gln Arg Phe Val Asn Phe Leu Thr Met Ile Pro Val Arg Asp Glu Thr
            195                 200                 205

Gly Glu Tyr Arg Tyr Ser Met Gly Phe Gln Cys Glu Thr Glu Leu Gln
        210                 215                 220

Tyr Pro Tyr Asp Val Pro Asp Tyr Ala Glu Phe Gln Tyr Leu Pro Asp
225                 230                 235                 240

Thr Asp Asp Arg His Arg Ile Glu Glu Lys Arg Lys Arg Thr Tyr Glu
                245                 250                 255

Thr Phe Lys Ser Ile Met Lys Lys Ser Pro Phe Ser Gly Pro Thr Asp
                260                 265                 270

Pro Arg Pro Pro Arg Arg Ile Ala Val Pro Ser Arg Ser Ser Ala
            275                 280                 285

Ser Val Pro Lys Pro Ala Pro Gln Pro Tyr Pro Phe Thr Ser Ser Leu
        290                 295                 300

Ser Thr Ile Asn Tyr Asp Glu Phe Pro Thr Met Val Phe Pro Ser Gly
305                 310                 315                 320

Gln Ile Ser Gln Ala Ser Ala Leu Ala Pro Ala Pro Gln Val Leu
                325                 330                 335

Pro Gln Ala Pro Ala Pro Ala Pro Ala Pro Ala Met Val Ser Ala Leu
            340                 345                 350

Ala Gln Ala Pro Ala Pro Val Pro Val Leu Ala Pro Gly Pro Pro Gln
        355                 360                 365

Ala Val Ala Pro Pro Ala Pro Lys Pro Thr Gln Ala Gly Glu Gly Thr
370                 375                 380

Leu Ser Glu Ala Leu Leu Gln Leu Gln Phe Asp Asp Glu Asp Leu Gly
385                 390                 395                 400

Ala Leu Leu Gly Asn Ser Thr Asp Pro Ala Val Phe Thr Asp Leu Ala
                405                 410                 415

Ser Val Asp Asn Ser Glu Phe Gln Gln Leu Leu Asn Gln Gly Ile Pro
            420                 425                 430

Val Ala Pro His Thr Thr Glu Pro Met Leu Met Glu Tyr Pro Glu Ala
        435                 440                 445

Ile Thr Arg Leu Val Thr Gly Ala Gln Arg Pro Pro Asp Pro Ala Pro
450                 455                 460

Ala Pro Leu Gly Ala Pro Gly Leu Pro Asn Gly Leu Leu Ser Gly Asp
465                 470                 475                 480

Glu Asp Phe Ser Ser Ile Ala Asp Met Asp Phe Ser Ala Leu Leu Ser
                485                 490                 495

Gln Ile Ser Ser Thr Arg Arg Pro Ala Cys Lys Ile Pro Asn Asp Lys
            500                 505                 510

Gln Lys Val Met Asn His Met Arg Pro Glu Cys Val Ile Gln Glu Pro
        515                 520                 525

Ser Lys Asn Lys Asp Arg Gln Arg Lys Lys Asp Lys Gly Ile Leu
530                 535                 540

Leu Pro Val Ser Thr Thr Thr Val Glu Asp His Met Pro Pro Ile Met
545                 550                 555                 560

Gln Cys Asp Pro Pro Pro Glu Ala Ala Arg Ile His Glu Val Val
                565                 570                 575

Pro Arg Tyr Leu Ser Glu Lys Leu Met Glu Gln Asn Arg Gln Lys Asn
            580                 585                 590
```

```
Ile Pro Pro Leu Ser Ala Asn Gln Lys Ser Leu Ile Ala Arg Leu Val
        595                 600                 605

Trp Tyr Gln Glu Gly Tyr Glu Gln Pro Ser Asp Glu Asp Leu Lys Arg
    610                 615                 620

Val Thr Gln Thr Trp Gln Ser Asp Glu Glu Glu Ser Asp Leu
625                 630                 635                 640

Pro Phe Arg Gln Ile Thr Glu Met Thr Ile Leu Thr Val Gln Leu Ile
            645                 650                 655

Val Glu Phe Ala Lys Gly Leu Pro Gly Phe Ser Lys Ile Ser Gln Ser
                660                 665                 670

Asp Gln Ile Thr Leu Leu Lys Ala Ser Ser Ser Glu Val Met Met Leu
            675                 680                 685

Arg Val Ala Arg Arg Tyr Asp Ala Ala Ser Asp Ser Ile Leu Phe Ala
    690                 695                 700

Asn Asn Lys Ala Tyr Thr Arg Asp Asn Tyr Arg Lys Ala Gly Met Ala
705                 710                 715                 720

Glu Val Ile Glu Asp Leu Leu His Phe Cys Arg Cys Met Phe Ala Met
            725                 730                 735

Gly Met Asp Asn Val His Phe Ala Leu Leu Thr Ala Ile Val Ile Phe
                740                 745                 750

Ser Asp Arg Pro Gly Leu Glu Gln Pro Ser Leu Val Glu Glu Ile Gln
            755                 760                 765

Arg Tyr Tyr Leu Asn Thr Leu Arg Ile Tyr Ile Ile Asn Gln Asn Ser
    770                 775                 780

Ala Ser Ser Arg Cys Ala Val Ile Tyr Gly Arg Ile Leu Ser Val Leu
785                 790                 795                 800

Thr Glu Leu Arg Thr Leu Gly Thr Gln Asn Ser Asn Met Cys Ile Ser
            805                 810                 815

Leu Lys Leu Lys Asn Arg Lys Leu Pro Pro Phe Leu Glu Glu Ile Trp
            820                 825                 830

Asp Val Ala Glu Val Ala Thr Thr His Pro Thr Val Leu Pro Pro Thr
    835                 840                 845

Asn Pro Val Val Leu Thr Ser Asp Tyr Lys Asp Asp Asp Lys
    850                 855                 860
```

<210> SEQ ID NO 133
<211> LENGTH: 2532
<212> TYPE: DNA
<213> ORGANISM: Artificial sequence
<220> FEATURE:
<223> OTHER INFORMATION: Synthetic

<400> SEQUENCE: 133

```
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaagaggc aaaccccca agtagaactg      300 ggacctgttg acacgtcagt tgctctgatt ctgtgcgacc tgaagcaaaa agacacgcca     360
attgtgtacg cctcggaagc tttctctat atgacaggat acagcaatgc ggaggtcttg      420
gggagaaact gccgttttct tcagtcaccc gacggaatgg tcaagccgaa atcgacaagg     480
aagtacgtcg actccaacac gatcaatacg atgaggaaag cgattgatag gaacgccgag     540
```

```
gtgcaggttg aggtggtcaa ttttaagaag aacggccaac ggtttgtcaa cttcttgacg    600
atgattccgg tgcgagatga acaggggaa taccggtaca gcatgggttt ccagtgcgaa    660
acggaactgc agtacccata cgatgttcca gattacgctg aattccagta cctgccagat    720
acagacgatc gtcaccggat tgaggagaaa cgtaaaagga catatgagac cttcaagagc    780
atcatgaaga agagtccttt cagcggaccc accgaccccc ggcctccacc tcgacgcatt    840
gctgtgcctt cccgcagctc agcttctgtc cccaagccag caccccagcc ctatcccttt    900
acgtcatccc tgagcaccat caactatgat gagtttccca ccatggtgtt ccttctgggg    960
cagatcagcc aggcctcggc cttggccccg gcccctcccc aagtcctgcc ccaggctcca   1020 gccccctgccc ctgctccagc catggtatca gctctggccc aggccccagc cctgtcccca  1080
gtcctagccc caggccctcc tcaggctgtg gccccacctg cccccaagcc cacccaggct   1140
ggggaaggaa cgctgtcaga ggccctgctg cagctgcagt ttgatgatga agacctgggg   1200
gccttgcttg gcaacagcac agacccagct gtgttcacag acctggcatc cgtcgacaac   1260
tccgagtttc agcagctgct gaaccagggc atacctgtgg ccccccacac aactgagccc   1320
atgctgatgg agtaccctga ggctataact cgcctagtga caggggccca gaggccccca   1380
gacccagctc ctgctccact gggggccccg gggctcccca atggcctcct ttcaggagat   1440
gaagacttct cctccattgc ggacatggac ttctcagccc tgctgagtca gatcagctcc   1500
acgcgtcgtc ctgcttgtaa gattcctaat gacctcaagc agaaggttat gaatcactct   1560
gctggagaca tgagagctgc caacctttgg ccaagcccgc tcatgatcaa acgctctaag   1620
aagaacagcc tggccttgtc cctgacggcc gaccagatgg tcagtgcctt gttggatgct   1680 gagccccca tactctattc cgagtatgat cctaccagac ccttcagtga agcttcgatg   1740
atgggcttac tgaccaacct ggcagacagg gagctggttc acatgatcaa ctgggcgaag   1800
agggtgccag gctttgtgga tttgaccctc catgatcagg tccaccttct agaatgtgcc   1860
tggctagaga tcctgatgat tggtctcgtc tggcgctcca tggagcaccc agtgaagcta   1920
ctgtttgctc ctaacttgct cttggacagg aaccagggaa aatgtgtaga gggcatggtg   1980
gagatcttcg acatgctgct ggctacatca tctcggttcc gcatgatgaa tctgcaggga   2040
gaggagtttg tgtgcctcaa atctattatt ttgcttaatt ctggagtgta cacatttctg   2100
tccagcaccc tgaagtctct ggaagagaag gaccatatcc accgagtcct ggacaagatc   2160
acagacactt tgatccacct gatggccaag gcaggcctga ccctgcagca gcagcaccag   2220
cggctggccc agtcctcct catcctctcc cacatcaggc acatgagtaa caaaggcatg   2280
gagcatctgt acagcatgaa gtgcaagaac gtggtgcccc tctatgacct gctgctggag   2340
gcggcggacg cccaccgcct acatgcgccc actagccgtg gaggggcatc cgtggaggag   2400
acggaccaaa gccacttggc cactgcgggc tctacttcat cgcattcctt gcaaaagtat   2460
tacatcacgg gggaggcaga gggtttccct gccacagcta ctagtgacta caaagacgat   2520
gatgacaagt aa                                                       2532
```

<210> SEQ ID NO 134
<211> LENGTH: 843
<212> TYPE: PRT
<213> ORGANISM: Artificial sequence
<220> FEATURE:
<223> OTHER INFORMATION: Synthetic

<400> SEQUENCE: 134

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
                35                  40                  45

Leu Thr Arg Ala His Leu Thr Glu Val Glu Ser Arg Leu Glu Arg Leu
        50                  55                  60

Glu Arg Ser Ile Ala Thr Arg Ser His Thr Leu Tyr Ala Pro Gly Gly
65                      70                  75                  80

Tyr Asp Ile Met Gly Tyr Leu Ile Gln Ile Met Lys Arg Pro Asn Pro
                    85                  90                  95

Gln Val Glu Leu Gly Pro Val Asp Thr Ser Val Ala Leu Ile Leu Cys
                100                 105                 110

Asp Leu Lys Gln Lys Asp Thr Pro Ile Val Tyr Ala Ser Glu Ala Phe
            115                 120                 125

Leu Tyr Met Thr Gly Tyr Ser Asn Ala Glu Val Leu Gly Arg Asn Cys
        130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
                180                 185                 190

Gln Arg Phe Val Asn Phe Leu Thr Met Ile Pro Val Arg Asp Glu Thr
                195                 200                 205

Gly Glu Tyr Arg Tyr Ser Met Gly Phe Gln Cys Glu Thr Glu Leu Gln
        210                 215                 220

Tyr Pro Tyr Asp Val Pro Asp Tyr Ala Glu Phe Gln Tyr Leu Pro Asp
225                 230                 235                 240

Thr Asp Asp Arg His Arg Ile Glu Glu Lys Arg Lys Arg Thr Tyr Glu
                245                 250                 255

Thr Phe Lys Ser Ile Met Lys Lys Ser Pro Phe Ser Gly Pro Thr Asp
                260                 265                 270

Pro Arg Pro Pro Arg Arg Ile Ala Val Pro Ser Arg Ser Ser Ala
        275                 280                 285

Ser Val Pro Lys Pro Ala Pro Gln Pro Tyr Pro Phe Thr Ser Ser Leu
        290                 295                 300

Ser Thr Ile Asn Tyr Asp Glu Phe Pro Thr Met Val Phe Pro Ser Gly
305                 310                 315                 320

Gln Ile Ser Gln Ala Ser Ala Leu Ala Pro Ala Pro Pro Gln Val Leu
            325                 330                 335

Pro Gln Ala Pro Ala Pro Ala Pro Ala Met Val Ser Ala Leu
            340                 345                 350

Ala Gln Ala Pro Ala Pro Val Pro Val Leu Ala Pro Gly Pro Pro Gln
            355                 360                 365

Ala Val Ala Pro Pro Ala Pro Lys Pro Thr Gln Ala Gly Glu Gly Thr
        370                 375                 380

Leu Ser Glu Ala Leu Leu Gln Leu Gln Phe Asp Asp Glu Asp Leu Gly
385                 390                 395                 400

Ala Leu Leu Gly Asn Ser Thr Asp Pro Ala Val Phe Thr Asp Leu Ala
                405                 410                 415

Ser Val Asp Asn Ser Glu Phe Gln Gln Leu Leu Asn Gln Gly Ile Pro
```

```
            420                 425                 430
Val Ala Pro His Thr Glu Pro Met Leu Met Glu Tyr Pro Glu Ala
            435                 440                 445
Ile Thr Arg Leu Val Thr Gly Ala Gln Arg Pro Pro Asp Pro Ala Pro
450                 455                 460
Ala Pro Leu Gly Ala Pro Gly Leu Pro Asn Gly Leu Leu Ser Gly Asp
465                 470                 475                 480
Glu Asp Phe Ser Ser Ile Ala Asp Met Asp Phe Ser Ala Leu Leu Ser
                485                 490                 495
Gln Ile Ser Ser Thr Arg Arg Pro Ala Cys Lys Ile Pro Asn Asp Leu
            500                 505                 510
Lys Gln Lys Val Met Asn His Ser Ala Gly Asp Met Arg Ala Ala Asn
            515                 520                 525
Leu Trp Pro Ser Pro Leu Met Ile Lys Arg Ser Lys Lys Asn Ser Leu
            530                 535                 540
Ala Leu Ser Leu Thr Ala Asp Gln Met Val Ser Ala Leu Leu Asp Ala
545                 550                 555                 560
Glu Pro Pro Ile Leu Tyr Ser Glu Tyr Asp Pro Thr Arg Pro Phe Ser
                565                 570                 575
Glu Ala Ser Met Met Gly Leu Leu Thr Asn Leu Ala Asp Arg Glu Leu
            580                 585                 590
Val His Met Ile Asn Trp Ala Lys Arg Val Pro Gly Phe Val Asp Leu
            595                 600                 605
Thr Leu His Asp Gln Val His Leu Leu Glu Cys Ala Trp Leu Glu Ile
            610                 615                 620
Leu Met Ile Gly Leu Val Trp Arg Ser Met Glu His Pro Val Lys Leu
625                 630                 635                 640
Leu Phe Ala Pro Asn Leu Leu Leu Asp Arg Asn Gln Gly Lys Cys Val
                645                 650                 655
Glu Gly Met Val Glu Ile Phe Asp Met Leu Leu Ala Thr Ser Ser Arg
            660                 665                 670
Phe Arg Met Met Asn Leu Gln Gly Glu Glu Phe Val Cys Leu Lys Ser
            675                 680                 685
Ile Ile Leu Leu Asn Ser Gly Val Tyr Thr Phe Leu Ser Ser Thr Leu
            690                 695                 700
Lys Ser Leu Glu Glu Lys Asp His Ile His Arg Val Leu Asp Lys Ile
705                 710                 715                 720
Thr Asp Thr Leu Ile His Leu Met Ala Lys Ala Gly Leu Thr Leu Gln
                725                 730                 735
Gln Gln His Gln Arg Leu Ala Gln Leu Leu Leu Ile Leu Ser His Ile
            740                 745                 750
Arg His Met Ser Asn Lys Gly Met Glu His Leu Tyr Ser Met Lys Cys
            755                 760                 765
Lys Asn Val Val Pro Leu Tyr Asp Leu Leu Leu Glu Ala Ala Asp Ala
            770                 775                 780
His Arg Leu His Ala Pro Thr Ser Arg Gly Gly Ala Ser Val Glu Glu
785                 790                 795                 800
Thr Asp Gln Ser His Leu Ala Thr Ala Gly Ser Thr Ser Ser His Ser
                805                 810                 815
Leu Gln Lys Tyr Tyr Ile Thr Gly Glu Ala Glu Gly Phe Pro Ala Thr
            820                 825                 830
Ala Thr Ser Asp Tyr Lys Asp Asp Asp Lys
            835                 840
```

<210> SEQ ID NO 135
<211> LENGTH: 2412
<212> TYPE: DNA
<213> ORGANISM: Artificial sequence
<220> FEATURE:
<223> OTHER INFORMATION: Synthetic

<400> SEQUENCE: 135

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaaagatc catcgccacc agatctcata cgctctacgc tcccggcggt     240
tatgacatta tgggctatct gattcagatt atgaagaggc aaaccccca agtagaactg      300
ggacctgttg acacgtcagt tgctctgatt ctgtgcgacc tgaagcaaaa agacacgcca     360
attgtgtacg cctcggaagc ttttctctat atgacaggat acagcaatgc ggaggtcttg     420
gggagaaact gccgttttct tcagtcaccc gacggaatgg tcaagccgaa atcgacaagg     480
aagtacgtcg actccaacac gatcaatacg atgaggaaag cgattgatag gaacgccgag     540
gtgcaggttg aggtggtcaa ttttaagaag aacggccaac ggtttgtcaa cttcttgacg     600
atgattccgg tgcgagatga acaggggaa taccggtaca gcatgggttt ccagtgcgaa      660
acggaactgc agtacccata cgatgttcca gattacgctg aattccagta cctgccagat     720
acagacgatc gtcaccggat tgaggagaaa cgtaaaagga catatgagac cttcaagagc     780
atcatgaaga gagtcctttt cagcggaccc accgaccccc ggcctccacc tcgacgcatt     840
gctgtgcctt cccgcagctc agcttctgtc cccaagccag caccccagcc ctatcccttt     900
acgtcatccc tgagcaccat caactatgat gagtttccca ccatggtgtt tccttctggg     960
cagatcagcc aggcctcggc cttggccccg cccctcccc aagtcctgcc ccaggctcca    1020
gccctgccc ctgctccagc catggtatca gctctggccc aggcccagc ccctgtccca     1080
gtcctagccc caggccctcc tcaggctgtg gccccacctg ccccaagcc cacccaggct    1140
ggggaaggaa cgctgtcaga ggccctgctg cagctgcagt ttgatgatga agacctgggg    1200
gccttgcttg gcaacagcac agaccccagct gtgttcacag acctggcatc cgtcgacaac    1260
tccgagtttc agcagctgct gaaccagggc atacctgtgg cccccacac aactgagccc    1320
atgctgatgg agtaccctga ggctataact cgcctagtga caggggccca gaggccccc     1380
gacccagctc ctgctccact gggggccccg ggctcccca atggcctcct ttcaggagat    1440
gaagacttct cctccattgc ggacatggac ttctcagccc tgctgagtca gatcagctcc    1500
acgcgtcgtc ctgcttgtaa gattcctaat gacaagcaga aggttatgaa tcacaaaaag    1560
ttcaataaag tcagagttgt gagagcactg gatgctgttg ctctcccaca gccagtgggc    1620
gttccaaatg aaagccaagc cctaagccag agattcactt tttccaccagg tcaagacata    1680
cagttgattc caccactgat caacctgtta atgagcattg aaccagatgt gatctatgca    1740
ggacatgaca acacaaaacc tgacacctcc agttctttgc tgacaagtct taatcaacta    1800
ggcgagaggc aacttcttc agtagtcaag tggtctaaat cattgccagg ttttcgaaac    1860
ttacatattg atgaccagat aactctcatt cagtattctt ggatgagctt aatggtgttt    1920
ggtctaggat ggagatccta caaacacgtc agtgggcaga tgctgtattt tgcacctgat    1980
ctaatactaa atgaacagcg gatgaaagaa tcatcattct attcattatg ccttaccatg    2040
```

```
tggcagatcc cacaggagtt tgtcaagctt caagttagcc aagaagagtt cctctgtatg    2100
aaagtattgt tacttcttaa tacaattcct ttggaagggc tacgaagtca aacccagttt    2160
gaggagatga ggtcaagcta cattagagag ctcatcaagg caattggttt gaggcaaaaa    2220
ggagttgtgt cgagctcaca gcgtttctat caacttacaa aacttcttga taacttgcat    2280
gatcttgtca acaacttca tctgtactgc ttgaatacat ttatccagtc ccgggcactg    2340
agtgttgaat ttccagaaat gatgtctgaa gttattgcta ctagtgacta caaagacgat    2400
gatgacaagt aa                                                        2412
```

<210> SEQ ID NO 136
<211> LENGTH: 803
<212> TYPE: PRT
<213> ORGANISM: Artificial sequence
<220> FEATURE:
<223> OTHER INFORMATION: Synthetic

<400> SEQUENCE: 136

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Arg Ser Ile Ala Thr Arg Ser His Thr Leu Tyr Ala Pro Gly Gly
65                  70                  75                  80

Tyr Asp Ile Met Gly Tyr Leu Ile Gln Ile Met Lys Arg Pro Asn Pro
                85                  90                  95

Gln Val Glu Leu Gly Pro Val Asp Thr Ser Val Ala Leu Ile Leu Cys
            100                 105                 110

Asp Leu Lys Gln Lys Asp Thr Pro Ile Val Tyr Ala Ser Glu Ala Phe
        115                 120                 125

Leu Tyr Met Thr Gly Tyr Ser Asn Ala Glu Val Leu Gly Arg Asn Cys
    130                 135                 140

Arg Phe Leu Gln Ser Pro Asp Gly Met Val Lys Pro Lys Ser Thr Arg
145                 150                 155                 160

Lys Tyr Val Asp Ser Asn Thr Ile Asn Thr Met Arg Lys Ala Ile Asp
                165                 170                 175

Arg Asn Ala Glu Val Gln Val Glu Val Val Asn Phe Lys Lys Asn Gly
            180                 185                 190

Gln Arg Phe Val Asn Phe Leu Thr Met Ile Pro Val Arg Asp Glu Thr
        195                 200                 205

Gly Glu Tyr Arg Tyr Ser Met Gly Phe Gln Cys Glu Thr Glu Leu Gln
    210                 215                 220

Tyr Pro Tyr Asp Val Pro Asp Tyr Ala Glu Phe Gln Tyr Leu Pro Asp
225                 230                 235                 240

Thr Asp Asp Arg His Arg Ile Glu Glu Lys Arg Lys Arg Thr Tyr Glu
                245                 250                 255

Thr Phe Lys Ser Ile Met Lys Lys Ser Pro Phe Ser Gly Pro Thr Asp
            260                 265                 270

Pro Arg Pro Pro Pro Arg Arg Ile Ala Val Pro Ser Arg Ser Ser Ala
        275                 280                 285

Ser Val Pro Lys Pro Ala Pro Gln Pro Tyr Pro Phe Thr Ser Ser Leu
```

```
                290                 295                 300
Ser Thr Ile Asn Tyr Asp Glu Phe Pro Thr Met Val Phe Pro Ser Gly
305                 310                 315                 320

Gln Ile Ser Gln Ala Ser Ala Leu Ala Pro Ala Pro Gln Val Leu
                325                 330                 335

Pro Gln Ala Pro Ala Pro Ala Pro Ala Met Val Ser Ala Leu
                340                 345                 350

Ala Gln Ala Pro Ala Pro Val Pro Val Leu Ala Pro Gly Pro Pro Gln
                355                 360                 365

Ala Val Ala Pro Pro Ala Pro Lys Pro Thr Gln Ala Gly Glu Gly Thr
370                 375                 380

Leu Ser Glu Ala Leu Leu Gln Leu Gln Phe Asp Asp Glu Asp Leu Gly
385                 390                 395                 400

Ala Leu Leu Gly Asn Ser Thr Asp Pro Ala Val Phe Thr Asp Leu Ala
                405                 410                 415

Ser Val Asp Asn Ser Glu Phe Gln Gln Leu Leu Asn Gln Gly Ile Pro
                420                 425                 430

Val Ala Pro His Thr Thr Glu Pro Met Leu Met Glu Tyr Pro Glu Ala
                435                 440                 445

Ile Thr Arg Leu Val Thr Gly Ala Gln Arg Pro Pro Asp Pro Ala Pro
450                 455                 460

Ala Pro Leu Gly Ala Pro Gly Leu Pro Asn Gly Leu Leu Ser Gly Asp
465                 470                 475                 480

Glu Asp Phe Ser Ser Ile Ala Asp Met Asp Phe Ser Ala Leu Leu Ser
                485                 490                 495

Gln Ile Ser Ser Thr Arg Arg Pro Ala Cys Lys Ile Pro Asn Asp Lys
                500                 505                 510

Gln Lys Val Met Asn His Lys Lys Phe Asn Lys Val Arg Val Val Arg
                515                 520                 525

Ala Leu Asp Ala Val Ala Leu Pro Gln Pro Val Gly Val Pro Asn Glu
                530                 535                 540

Ser Gln Ala Leu Ser Gln Arg Phe Thr Phe Ser Pro Gly Gln Asp Ile
545                 550                 555                 560

Gln Leu Ile Pro Pro Leu Ile Asn Leu Leu Met Ser Ile Glu Pro Asp
                565                 570                 575

Val Ile Tyr Ala Gly His Asp Asn Thr Lys Pro Asp Thr Ser Ser Ser
                580                 585                 590

Leu Leu Thr Ser Leu Asn Gln Leu Gly Glu Arg Gln Leu Leu Ser Val
                595                 600                 605

Val Lys Trp Ser Lys Ser Leu Pro Gly Phe Arg Asn Leu His Ile Asp
                610                 615                 620

Asp Gln Ile Thr Leu Ile Gln Tyr Ser Trp Met Ser Leu Met Val Phe
625                 630                 635                 640

Gly Leu Gly Trp Arg Ser Tyr Lys His Val Ser Gly Gln Met Leu Tyr
                645                 650                 655

Phe Ala Pro Asp Leu Ile Leu Asn Glu Gln Arg Met Lys Glu Ser Ser
                660                 665                 670

Phe Tyr Ser Leu Cys Leu Thr Met Trp Gln Ile Pro Gln Glu Phe Val
                675                 680                 685

Lys Leu Gln Val Ser Gln Glu Glu Phe Leu Cys Met Lys Val Leu Leu
                690                 695                 700

Leu Leu Asn Thr Ile Pro Leu Glu Gly Leu Arg Ser Gln Thr Gln Phe
705                 710                 715                 720
```

```
Glu Glu Met Arg Ser Ser Tyr Ile Arg Glu Leu Ile Lys Ala Ile Gly
            725                 730                 735

Leu Arg Gln Lys Gly Val Val Ser Ser Gln Arg Phe Tyr Gln Leu
        740                 745                 750

Thr Lys Leu Leu Asp Asn Leu His Asp Leu Val Lys Gln Leu His Leu
        755                 760                 765

Tyr Cys Leu Asn Thr Phe Ile Gln Ser Arg Ala Leu Ser Val Glu Phe
    770                 775                 780

Pro Glu Met Met Ser Glu Val Ile Ala Thr Ser Asp Tyr Lys Asp Asp
785                 790                 795                 800

Asp Asp Lys
```

<210> SEQ ID NO 137
<211> LENGTH: 44
<212> TYPE: DNA
<213> ORGANISM: Artificial sequence
<220> FEATURE:
<223> OTHER INFORMATION: Synthetic

<400> SEQUENCE: 137
cttttggatc caagcgctat gaagctactg tcttctatcg aaca           44

<210> SEQ ID NO 138
<211> LENGTH: 45
<212> TYPE: DNA
<213> ORGANISM: Artificial sequence
<220> FEATURE:
<223> OTHER INFORMATION: Synthetic

<400> SEQUENCE: 138
agatctggtg gcgatggatc tttccagtct ttctagcctt gattc          45

<210> SEQ ID NO 139
<211> LENGTH: 50
<212> TYPE: DNA
<213> ORGANISM: Artificial sequence
<220> FEATURE:
<223> OTHER INFORMATION: Synthetic

<400> SEQUENCE: 139
cagtacccat acgatgttcc agattacgct gaattcccgg ggatctcgac     50

<210> SEQ ID NO 140
<211> LENGTH: 33
<212> TYPE: DNA
<213> ORGANISM: Artificial sequence
<220> FEATURE:
<223> OTHER INFORMATION: Synthetic

<400> SEQUENCE: 140
agaaattcga atgtacatgg cgatcccgga ccc                       33

<210> SEQ ID NO 141
<211> LENGTH: 40
<212> TYPE: DNA
<213> ORGANISM: Artificial sequence
<220> FEATURE:
<223> OTHER INFORMATION: Synthetic

<400> SEQUENCE: 141
agatccatcg ccaccagatc tcatacgctc tacgctcccg               40

```
<210> SEQ ID NO 142
<211> LENGTH: 46
<212> TYPE: DNA
<213> ORGANISM: Artificial sequence
<220> FEATURE:
<223> OTHER INFORMATION: Synthetic

<400> SEQUENCE: 142
tctggaacat cgtatgggta ctgcagttcc gtttcgcact ggaaac         46

<210> SEQ ID NO 143
<211> LENGTH: 30
<212> TYPE: DNA
<213> ORGANISM: Artificial sequence
<220> FEATURE:
<223> OTHER INFORMATION: Synthetic

<400> SEQUENCE: 143
caataccact atgaccctcg aaccgcgccc                             30

<210> SEQ ID NO 144
<211> LENGTH: 30
<212> TYPE: DNA
<213> ORGANISM: Artificial sequence
<220> FEATURE:
<223> OTHER INFORMATION: Synthetic

<400> SEQUENCE: 144
ctgatacgcc tcaacctccc atgggttcat                             30

<210> SEQ ID NO 145
<211> LENGTH: 28
<212> TYPE: DNA
<213> ORGANISM: Artificial sequence
<220> FEATURE:
<223> OTHER INFORMATION: Synthetic

<400> SEQUENCE: 145
attcagatta tgaacaggcc aaacccccc                              28

<210> SEQ ID NO 146
<211> LENGTH: 28
<212> TYPE: DNA
<213> ORGANISM: Artificial sequence
<220> FEATURE:
<223> OTHER INFORMATION: Synthetic

<400> SEQUENCE: 146
cagatagccc ataatgtcat aaccgccg                               28

<210> SEQ ID NO 147
<211> LENGTH: 25
<212> TYPE: DNA
<213> ORGANISM: Artificial sequence
<220> FEATURE:
<223> OTHER INFORMATION: Synthetic

<400> SEQUENCE: 147
gaattccagt acctgccaga tacag                                  25

<210> SEQ ID NO 148
<211> LENGTH: 30
<212> TYPE: DNA
<213> ORGANISM: Artificial sequence
<220> FEATURE:
<223> OTHER INFORMATION: Synthetic
```

```
<400> SEQUENCE: 148
tgtacattag gagctgatct gactcagcag                              30

<210> SEQ ID NO 149
<211> LENGTH: 19
<212> TYPE: DNA
<213> ORGANISM: Artificial sequence
<220> FEATURE:
<223> OTHER INFORMATION: Synthetic

<400> SEQUENCE: 149
gttgctctga ttctgtgcg                                          19

<210> SEQ ID NO 150
<211> LENGTH: 19
<212> TYPE: DNA
<213> ORGANISM: Artificial sequence
<220> FEATURE:
<223> OTHER INFORMATION: Synthetic

<400> SEQUENCE: 150
tgacgtgtca acaggtccc                                          19

<210> SEQ ID NO 151
<211> LENGTH: 23
<212> TYPE: DNA
<213> ORGANISM: Artificial sequence
<220> FEATURE:
<223> OTHER INFORMATION: Synthetic

<400> SEQUENCE: 151
gctgattcag attatgaaca ggc                                     23

<210> SEQ ID NO 152
<211> LENGTH: 22
<212> TYPE: DNA
<213> ORGANISM: Artificial sequence
<220> FEATURE:
<223> OTHER INFORMATION: Synthetic

<400> SEQUENCE: 152
cagcccataa tgtcataacc gc                                      22

<210> SEQ ID NO 153
<211> LENGTH: 20
<212> TYPE: DNA
<213> ORGANISM: Artificial sequence
<220> FEATURE:
<223> OTHER INFORMATION: Synthetic

<400> SEQUENCE: 153
gaggccaaac ccccaagtag                                         20

<210> SEQ ID NO 154
<211> LENGTH: 24
<212> TYPE: DNA
<213> ORGANISM: Artificial sequence
<220> FEATURE:
<223> OTHER INFORMATION: Synthetic

<400> SEQUENCE: 154
ttcataatct gaatcagata gccc                                    24

<210> SEQ ID NO 155
<211> LENGTH: 32
```

```
<212> TYPE: DNA
<213> ORGANISM: Artificial sequence
<220> FEATURE:
<223> OTHER INFORMATION: Synthetic

<400> SEQUENCE: 155
ctttagatct ttcttggcta ctacacttga ac                          32

<210> SEQ ID NO 156
<211> LENGTH: 43
<212> TYPE: DNA
<213> ORGANISM: Artificial sequence
<220> FEATURE:
<223> OTHER INFORMATION: Synthetic

<400> SEQUENCE: 156
ctttgaattc acctgatccg ccaccaagtt cttttgccgc ctc              43

<210> SEQ ID NO 157
<211> LENGTH: 31
<212> TYPE: DNA
<213> ORGANISM: Artificial sequence
<220> FEATURE:
<223> OTHER INFORMATION: Synthetic

<400> SEQUENCE: 157
ctttagatct cagaattttg tgataactga t                           31

<210> SEQ ID NO 158
<211> LENGTH: 31
<212> TYPE: DNA
<213> ORGANISM: Artificial sequence
<220> FEATURE:
<223> OTHER INFORMATION: Synthetic

<400> SEQUENCE: 158
ctttgaattc cactagcaac ttggcgtaat c                           31

<210> SEQ ID NO 159
<211> LENGTH: 40
<212> TYPE: DNA
<213> ORGANISM: Artificial sequence
<220> FEATURE:
<223> OTHER INFORMATION: Synthetic

<400> SEQUENCE: 159
agatccatcg ccaccagatc tcatacgctc tacgctcccg                  40

<210> SEQ ID NO 160
<211> LENGTH: 25
<212> TYPE: DNA
<213> ORGANISM: Artificial sequence
<220> FEATURE:
<223> OTHER INFORMATION: Synthetic

<400> SEQUENCE: 160
cttccagtct ttctagcctt gattc                                  25

<210> SEQ ID NO 161
<211> LENGTH: 40
<212> TYPE: DNA
<213> ORGANISM: Artificial sequence
<220> FEATURE:
<223> OTHER INFORMATION: Synthetic

<400> SEQUENCE: 161
```
agatccatcg ccaccagatc tcatacgctc tacgctcccg                40

<210> SEQ ID NO 162
<211> LENGTH: 39
<212> TYPE: DNA
<213> ORGANISM: Artificial sequence
<220> FEATURE:
<223> OTHER INFORMATION: Synthetic

<400> SEQUENCE: 162
ggatcctcca ccaccttcca gtctttctag ccttgattc                 39

<210> SEQ ID NO 163
<211> LENGTH: 39
<212> TYPE: DNA
<213> ORGANISM: Artificial sequence
<220> FEATURE:
<223> OTHER INFORMATION: Synthetic

<400> SEQUENCE: 163
tcatgaacca cagatctcat acgctctacg ctcccggcg                 39

<210> SEQ ID NO 164
<211> LENGTH: 39
<212> TYPE: DNA
<213> ORGANISM: Artificial sequence
<220> FEATURE:
<223> OTHER INFORMATION: Synthetic

<400> SEQUENCE: 164
ctttctgttt caggtcgttt tccagtcttt ctagccttg                 39

<210> SEQ ID NO 165
<211> LENGTH: 36
<212> TYPE: DNA
<213> ORGANISM: Artificial sequence
<220> FEATURE:
<223> OTHER INFORMATION: Synthetic

<400> SEQUENCE: 165
cttaagcttg ccaccatggt gagcaagcag atcctg                    36

<210> SEQ ID NO 166
<211> LENGTH: 29
<212> TYPE: DNA
<213> ORGANISM: Artificial sequence
<220> FEATURE:
<223> OTHER INFORMATION: Synthetic

<400> SEQUENCE: 166
caaggatcct tacacccact cgtgcaggc                            29

<210> SEQ ID NO 167
<211> LENGTH: 33
<212> TYPE: DNA
<213> ORGANISM: Artificial sequence
<220> FEATURE:
<223> OTHER INFORMATION: Synthetic

<400> SEQUENCE: 167
cttaagcttg ccaccatggt gagcaagggc gag                       33

<210> SEQ ID NO 168
<211> LENGTH: 31
<212> TYPE: DNA
<213> ORGANISM: Artificial sequence
<220> FEATURE:
<223> OTHER INFORMATION: Synthetic

<400> SEQUENCE: 168
caaggatccc tacttgtaca gctcgtccat g                                           31

<210> SEQ ID NO 169
<211> LENGTH: 37
<212> TYPE: DNA
<213> ORGANISM: Artificial sequence
<220> FEATURE:
<223> OTHER INFORMATION: Synthetic

<400> SEQUENCE: 169
tcgataggta ccctgtggaa tgtgtgtcag ttagggt                                     37

<210> SEQ ID NO 170
<211> LENGTH: 43
<212> TYPE: DNA
<213> ORGANISM: Artificial sequence
<220> FEATURE:
<223> OTHER INFORMATION: Synthetic

<400> SEQUENCE: 170
tccgtctaga aactcggtac cagctttttg caaaagccta ggc                              43

<210> SEQ ID NO 171
<211> LENGTH: 30
<212> TYPE: DNA
<213> ORGANISM: Artificial sequence
<220> FEATURE:
<223> OTHER INFORMATION: Synthetic

<400> SEQUENCE: 171
aggatcctga gctcgagctg cagatgaatc                                             30

<210> SEQ ID NO 172
<211> LENGTH: 27
<212> TYPE: DNA
<213> ORGANISM: Artificial sequence
<220> FEATURE:
<223> OTHER INFORMATION: Synthetic

<400> SEQUENCE: 172
catctttgca aagcttggag ttgattg                                                27

<210> SEQ ID NO 173
<211> LENGTH: 29
<212> TYPE: DNA
<213> ORGANISM: Artificial sequence
<220> FEATURE:
<223> OTHER INFORMATION: Synthetic

<400> SEQUENCE: 173
agctttgcaa agatgaagct actgtcttc                                              29

<210> SEQ ID NO 174
<211> LENGTH: 30
<212> TYPE: DNA
<213> ORGANISM: Artificial sequence
<220> FEATURE:
<223> OTHER INFORMATION: Synthetic

<400> SEQUENCE: 174
cgagctcagg atccttccgt ttcgcactgg                                             30

<210> SEQ ID NO 175
<211> LENGTH: 41
<212> TYPE: DNA
<213> ORGANISM: Artificial sequence
<220> FEATURE:
<223> OTHER INFORMATION: Synthetic

<400> SEQUENCE: 175
cccggatccg gtggaggtgg ctccaattt aatcaaagtg g              41

<210> SEQ ID NO 176
<211> LENGTH: 42
<212> TYPE: DNA
<213> ORGANISM: Artificial sequence
<220> FEATURE:
<223> OTHER INFORMATION: Synthetic

<400> SEQUENCE: 176
cccggatccg gcggtggtgg atcaggtgga ggtggctcca at             42

<210> SEQ ID NO 177
<211> LENGTH: 32
<212> TYPE: DNA
<213> ORGANISM: Artificial sequence
<220> FEATURE:
<223> OTHER INFORMATION: Synthetic

<400> SEQUENCE: 177
gggctcgagt tactctttt ttgggtttgg tg                        32

<210> SEQ ID NO 178
<211> LENGTH: 32
<212> TYPE: DNA
<213> ORGANISM: Artificial sequence
<220> FEATURE:
<223> OTHER INFORMATION: Synthetic

<400> SEQUENCE: 178
agctttgcaa agatggccat ggaggccagt ga                       32

<210> SEQ ID NO 179
<211> LENGTH: 34
<212> TYPE: DNA
<213> ORGANISM: Artificial sequence
<220> FEATURE:
<223> OTHER INFORMATION: Synthetic

<400> SEQUENCE: 179
catgcaagca acgaagcatc tgtgcttcat tttg                     34

<210> SEQ ID NO 180
<211> LENGTH: 32
<212> TYPE: DNA
<213> ORGANISM: Artificial sequence
<220> FEATURE:
<223> OTHER INFORMATION: Synthetic

<400> SEQUENCE: 180
ttcgttgctt gcatggccaa gcttcctgaa ac                       32

<210> SEQ ID NO 181
<211> LENGTH: 35
<212> TYPE: DNA
<213> ORGANISM: Artificial sequence
<220> FEATURE:
<223> OTHER INFORMATION: Synthetic

<400> SEQUENCE: 181
catctttgca aagctgctgg ggtatatttt ttttc            35

<210> SEQ ID NO 182
<211> LENGTH: 30
<212> TYPE: DNA
<213> ORGANISM: Artificial sequence
<220> FEATURE:
<223> OTHER INFORMATION: Synthetic

<400> SEQUENCE: 182
aggatcctga gctcgagctg cagatgaatc                  30

<210> SEQ ID NO 183
<211> LENGTH: 23
<212> TYPE: DNA
<213> ORGANISM: Artificial sequence
<220> FEATURE:
<223> OTHER INFORMATION: Synthetic

<400> SEQUENCE: 183
catctttgca aagctgctgg ggt                         23

<210> SEQ ID NO 184
<211> LENGTH: 41
<212> TYPE: DNA
<213> ORGANISM: Artificial sequence
<220> FEATURE:
<223> OTHER INFORMATION: Synthetic

<400> SEQUENCE: 184
cccggatccg gtggaggtgg ctccaattttt aatcaaagtg g    41

<210> SEQ ID NO 185
<211> LENGTH: 42
<212> TYPE: DNA
<213> ORGANISM: Artificial sequence
<220> FEATURE:
<223> OTHER INFORMATION: Synthetic

<400> SEQUENCE: 185
cccggatccg gcggtggtgg atcaggtgga ggtggctcca at    42

<210> SEQ ID NO 186
<211> LENGTH: 26
<212> TYPE: DNA
<213> ORGANISM: Artificial sequence
<220> FEATURE:
<223> OTHER INFORMATION: Synthetic

<400> SEQUENCE: 186
cccggatccg gtggatcagg tggagg                      26

<210> SEQ ID NO 187
<211> LENGTH: 32
<212> TYPE: DNA
<213> ORGANISM: Artificial sequence
<220> FEATURE:
<223> OTHER INFORMATION: Synthetic

<400> SEQUENCE: 187
cccggatccg gaagcggcgg tggtggatca gg               32

<210> SEQ ID NO 188

<210> SEQ ID NO 188
<211> LENGTH: 34
<212> TYPE: DNA
<213> ORGANISM: Artificial sequence
<220> FEATURE:
<223> OTHER INFORMATION: Synthetic

<400> SEQUENCE: 188
cccggatccg gtggcggcgg aagcggcggt ggtg                          34

<210> SEQ ID NO 189
<211> LENGTH: 41
<212> TYPE: DNA
<213> ORGANISM: Artificial sequence
<220> FEATURE:
<223> OTHER INFORMATION: Synthetic

<400> SEQUENCE: 189
cccggatccg gcggaggtgg gggctccggt ggcggcggaa g                  41

<210> SEQ ID NO 190
<211> LENGTH: 32
<212> TYPE: DNA
<213> ORGANISM: Artificial sequence
<220> FEATURE:
<223> OTHER INFORMATION: Synthetic

<400> SEQUENCE: 190
gggctcgagt tactcttttt ttgggtttgg tg                            32

<210> SEQ ID NO 191
<211> LENGTH: 37
<212> TYPE: DNA
<213> ORGANISM: Artificial sequence
<220> FEATURE:
<223> OTHER INFORMATION: Synthetic

<400> SEQUENCE: 191
ggtggctctg gaggcatgaa agcgttaacg gccaggc                       37

<210> SEQ ID NO 192
<211> LENGTH: 27
<212> TYPE: DNA
<213> ORGANISM: Artificial sequence
<220> FEATURE:
<223> OTHER INFORMATION: Synthetic

<400> SEQUENCE: 192
agatctcggt tcaccggcag ccacacg                                  27

<210> SEQ ID NO 193
<211> LENGTH: 33
<212> TYPE: DNA
<213> ORGANISM: Artificial sequence
<220> FEATURE:
<223> OTHER INFORMATION: Synthetic

<400> SEQUENCE: 193
ggtgaaccga gatctcatac gctctacgct ccc                           33

<210> SEQ ID NO 194
<211> LENGTH: 30
<212> TYPE: DNA
<213> ORGANISM: Artificial sequence
<220> FEATURE:
<223> OTHER INFORMATION: Synthetic

<400> SEQUENCE: 194
cgagctcagg atccttccgt ttcgcactgg                                    30

<210> SEQ ID NO 195
<211> LENGTH: 39
<212> TYPE: DNA
<213> ORGANISM: Artificial sequence
<220> FEATURE:
<223> OTHER INFORMATION: Synthetic

<400> SEQUENCE: 195
cccgaattct gcaaagatgg ataaagcgga attaattcc                          39

<210> SEQ ID NO 196
<211> LENGTH: 31
<212> TYPE: DNA
<213> ORGANISM: Artificial sequence
<220> FEATURE:
<223> OTHER INFORMATION: Synthetic

<400> SEQUENCE: 196
gcctccagag ccaccaccgg cggcggtacc c                                  31

<210> SEQ ID NO 197
<211> LENGTH: 26
<212> TYPE: DNA
<213> ORGANISM: Artificial sequence
<220> FEATURE:
<223> OTHER INFORMATION: Synthetic

<400> SEQUENCE: 197
cccggatccg gcggtggtgg atcagg                                        26

<210> SEQ ID NO 198
<211> LENGTH: 29
<212> TYPE: DNA
<213> ORGANISM: Artificial sequence
<220> FEATURE:
<223> OTHER INFORMATION: Synthetic

<400> SEQUENCE: 198
cccgaattcg ctggggtata ttttttttc                                     29

<210> SEQ ID NO 199
<211> LENGTH: 33
<212> TYPE: DNA
<213> ORGANISM: Artificial sequence
<220> FEATURE:
<223> OTHER INFORMATION: Synthetic

<400> SEQUENCE: 199
ggctctggag gcatgaaacc agtaacgtta tac                                33

<210> SEQ ID NO 200
<211> LENGTH: 28
<212> TYPE: DNA
<213> ORGANISM: Artificial sequence
<220> FEATURE:
<223> OTHER INFORMATION: Synthetic

<400> SEQUENCE: 200
cccagatctc aacgactgtt tgcccgcc                                      28

<210> SEQ ID NO 201
<211> LENGTH: 32
<212> TYPE: DNA

<213> ORGANISM: Artificial sequence
<220> FEATURE:
<223> OTHER INFORMATION: Synthetic

<400> SEQUENCE: 201
cccgaattca tggataaagc ggaattaatt cc         32

<210> SEQ ID NO 202
<211> LENGTH: 32
<212> TYPE: DNA
<213> ORGANISM: Artificial sequence
<220> FEATURE:
<223> OTHER INFORMATION: Synthetic

<400> SEQUENCE: 202
cctccagagc caccgaaccg gcggcggtac cc         32

<210> SEQ ID NO 203
<211> LENGTH: 34
<212> TYPE: DNA
<213> ORGANISM: Artificial sequence
<220> FEATURE:
<223> OTHER INFORMATION: Synthetic

<400> SEQUENCE: 203
ggtggctctg gaggcatgtc taccaagaag aaac       34

<210> SEQ ID NO 204
<211> LENGTH: 29
<212> TYPE: DNA
<213> ORGANISM: Artificial sequence
<220> FEATURE:
<223> OTHER INFORMATION: Synthetic

<400> SEQUENCE: 204
cccagatcta tattctgacc tcaaagacg             29

<210> SEQ ID NO 205
<211> LENGTH: 39
<212> TYPE: DNA
<213> ORGANISM: Artificial sequence
<220> FEATURE:
<223> OTHER INFORMATION: Synthetic

<400> SEQUENCE: 205
cccgaattct gcaaagatgg ataaagcgga attaattcc  39

<210> SEQ ID NO 206
<211> LENGTH: 31
<212> TYPE: DNA
<213> ORGANISM: Artificial sequence
<220> FEATURE:
<223> OTHER INFORMATION: Synthetic

<400> SEQUENCE: 206
gcctccagag ccaccaccgg cggcggtacc c          31

<210> SEQ ID NO 207
<211> LENGTH: 33
<212> TYPE: DNA
<213> ORGANISM: Artificial sequence
<220> FEATURE:
<223> OTHER INFORMATION: Synthetic

<400> SEQUENCE: 207
ggtggctctg gaggcatgtc taggctagat aag        33

<210> SEQ ID NO 208
<211> LENGTH: 33
<212> TYPE: DNA
<213> ORGANISM: Artificial sequence
<220> FEATURE:
<223> OTHER INFORMATION: Synthetic

<400> SEQUENCE: 208
cccagatctg gtgccgtgtc tatccagcat ctc    33

<210> SEQ ID NO 209
<211> LENGTH: 39
<212> TYPE: DNA
<213> ORGANISM: Artificial sequence
<220> FEATURE:
<223> OTHER INFORMATION: Synthetic

<400> SEQUENCE: 209
cccgaattct gcaaagatgg ataaagcgga attaattcc    39

<210> SEQ ID NO 210
<211> LENGTH: 31
<212> TYPE: DNA
<213> ORGANISM: Artificial sequence
<220> FEATURE:
<223> OTHER INFORMATION: Synthetic

<400> SEQUENCE: 210
gcctccagag ccaccaccgg cggcggtacc c    31

<210> SEQ ID NO 211
<211> LENGTH: 28
<212> TYPE: DNA
<213> ORGANISM: Artificial sequence
<220> FEATURE:
<223> OTHER INFORMATION: Synthetic

<400> SEQUENCE: 211
gggagatctc atacgctcta cgctcccg    28

<210> SEQ ID NO 212
<211> LENGTH: 30
<212> TYPE: DNA
<213> ORGANISM: Artificial sequence
<220> FEATURE:
<223> OTHER INFORMATION: Synthetic

<400> SEQUENCE: 212
cgagctcagg atccttccgt ttcgcactgg    30

<210> SEQ ID NO 213
<211> LENGTH: 27
<212> TYPE: DNA
<213> ORGANISM: Artificial sequence
<220> FEATURE:
<223> OTHER INFORMATION: Synthetic

<400> SEQUENCE: 213
cccagatctt tcttggctac tacactt    27

<210> SEQ ID NO 214
<211> LENGTH: 27
<212> TYPE: DNA
<213> ORGANISM: Artificial sequence
<220> FEATURE:

<223> OTHER INFORMATION: Synthetic

<400> SEQUENCE: 214
cccggatcca agttcttttg ccgcctc						27

<210> SEQ ID NO 215
<211> LENGTH: 28
<212> TYPE: DNA
<213> ORGANISM: Artificial sequence
<220> FEATURE:
<223> OTHER INFORMATION: Synthetic

<400> SEQUENCE: 215
gggagatctc atacgctcta cgctcccg						28

<210> SEQ ID NO 216
<211> LENGTH: 28
<212> TYPE: DNA
<213> ORGANISM: Artificial sequence
<220> FEATURE:
<223> OTHER INFORMATION: Synthetic

<400> SEQUENCE: 216
gggagatctc atacgctcta cgctcccg						28

<210> SEQ ID NO 217
<211> LENGTH: 30
<212> TYPE: DNA
<213> ORGANISM: Artificial sequence
<220> FEATURE:
<223> OTHER INFORMATION: Synthetic

<400> SEQUENCE: 217
cccgaattca tgtccgaata tcagccaagt						30

<210> SEQ ID NO 218
<211> LENGTH: 30
<212> TYPE: DNA
<213> ORGANISM: Artificial sequence
<220> FEATURE:
<223> OTHER INFORMATION: Synthetic

<400> SEQUENCE: 218
gggctcgagt taggattcaa ttgccttatc						30

<210> SEQ ID NO 219
<211> LENGTH: 30
<212> TYPE: DNA
<213> ORGANISM: Artificial sequence
<220> FEATURE:
<223> OTHER INFORMATION: Synthetic

<400> SEQUENCE: 219
aggatcctga gctcgagctg cagatgaatc						30

<210> SEQ ID NO 220
<211> LENGTH: 32
<212> TYPE: DNA
<213> ORGANISM: Artificial sequence
<220> FEATURE:
<223> OTHER INFORMATION: Synthetic

<400> SEQUENCE: 220
cccgaattcg gagccacctc cacctgatcc ac					32

```
<210> SEQ ID NO 221
<211> LENGTH: 30
<212> TYPE: DNA
<213> ORGANISM: Artificial sequence
<220> FEATURE:
<223> OTHER INFORMATION: Synthetic

<400> SEQUENCE: 221
cccgaattca gggcgagctt cgaggtcacc                                    30

<210> SEQ ID NO 222
<211> LENGTH: 33
<212> TYPE: DNA
<213> ORGANISM: Artificial sequence
<220> FEATURE:
<223> OTHER INFORMATION: Synthetic

<400> SEQUENCE: 222
cccggatccg ggcgagctta atattcccta tag                                33

<210> SEQ ID NO 223
<211> LENGTH: 31
<212> TYPE: DNA
<213> ORGANISM: Artificial sequence
<220> FEATURE:
<223> OTHER INFORMATION: Synthetic

<400> SEQUENCE: 223
cccggatcca aaaaatggt gagtaaagga g                                   31

<210> SEQ ID NO 224
<211> LENGTH: 27
<212> TYPE: DNA
<213> ORGANISM: Artificial sequence
<220> FEATURE:
<223> OTHER INFORMATION: Synthetic

<400> SEQUENCE: 224
ggggaattct tatttgtata gttcatc                                       27

<210> SEQ ID NO 225
<211> LENGTH: 25
<212> TYPE: DNA
<213> ORGANISM: Artificial sequence
<220> FEATURE:
<223> OTHER INFORMATION: Synthetic

<400> SEQUENCE: 225
tactagtgga tcatccccac gcgcc                                         25

<210> SEQ ID NO 226
<211> LENGTH: 28
<212> TYPE: DNA
<213> ORGANISM: Artificial sequence
<220> FEATURE:
<223> OTHER INFORMATION: Synthetic

<400> SEQUENCE: 226
agcgggtgac agccctccga aggaagac                                      28

<210> SEQ ID NO 227
<211> LENGTH: 28
<212> TYPE: DNA
<213> ORGANISM: Artificial sequence
<220> FEATURE:
<223> OTHER INFORMATION: Synthetic
```

<400> SEQUENCE: 227
acggaagact ctcctccgtg cgtcctcg                                          28

<210> SEQ ID NO 228
<211> LENGTH: 27
<212> TYPE: DNA
<213> ORGANISM: Artificial sequence
<220> FEATURE:
<223> OTHER INFORMATION: Synthetic

<400> SEQUENCE: 228
gaaacgcaga tgtgcctcgc gccgcac                                           27

<210> SEQ ID NO 229
<211> LENGTH: 29
<212> TYPE: DNA
<213> ORGANISM: Artificial sequence
<220> FEATURE:
<223> OTHER INFORMATION: Synthetic

<400> SEQUENCE: 229
cccaagcttt aatgcgatta gttttttag                                         29

<210> SEQ ID NO 230
<211> LENGTH: 29
<212> TYPE: DNA
<213> ORGANISM: Artificial sequence
<220> FEATURE:
<223> OTHER INFORMATION: Synthetic

<400> SEQUENCE: 230
taggctcgag cccacgcgcc ctgtagcgc                                         29

<210> SEQ ID NO 231
<211> LENGTH: 126
<212> TYPE: DNA
<213> ORGANISM: Artificial sequence
<220> FEATURE:
<223> OTHER INFORMATION: Synthetic

<400> SEQUENCE: 231
tcgagggcgt tcgtcctcac tgtatgatca tacagtctgt atatatatac agtactgtat       60
gatcatacag gttcctgaaa cgcagatgtg cctactgtat atatatacag taacaataaa     120
gattca                                                                 126

<210> SEQ ID NO 232
<211> LENGTH: 126
<212> TYPE: DNA
<213> ORGANISM: Artificial sequence
<220> FEATURE:
<223> OTHER INFORMATION: Synthetic

<400> SEQUENCE: 232
agcttgaatc tttattgtta ctgtatatat atacagtagg cacatctgcg tttcaggaac       60
ctgtatgatc atacagtact gtatatatat acagactgta tgatcataca gtgaggacga     120
acgccc                                                                 126

<210> SEQ ID NO 233
<211> LENGTH: 99
<212> TYPE: DNA
<213> ORGANISM: Artificial sequence
<220> FEATURE:
<223> OTHER INFORMATION: Synthetic

<400> SEQUENCE: 233
tcgagaattg tgagcggata acaattgtaa ttgtgagcgg ataacaatta tttgaattgt    60
gagcggataa caattgtaat tgtgagcgga taacaatta                          99

<210> SEQ ID NO 234
<211> LENGTH: 99
<212> TYPE: DNA
<213> ORGANISM: Artificial sequence
<220> FEATURE:
<223> OTHER INFORMATION: Synthetic

<400> SEQUENCE: 234
agcttaattg ttatccgctc acaattacaa ttgttatccg ctcacaattc aaataattgt    60
tatccgctca caattacaat tgttatccgc tcacaattc                          99

<210> SEQ ID NO 235
<211> LENGTH: 83
<212> TYPE: DNA
<213> ORGANISM: Artificial sequence
<220> FEATURE:
<223> OTHER INFORMATION: Synthetic

<400> SEQUENCE: 235
tcgagtaaat ctatcaccgc aagggataaa tatctaacac cgtgcgtgtt gactatttta    60
cctctggcgg tgataatggt tga                                           83

<210> SEQ ID NO 236
<211> LENGTH: 83
<212> TYPE: DNA
<213> ORGANISM: Artificial sequence
<220> FEATURE:
<223> OTHER INFORMATION: Synthetic

<400> SEQUENCE: 236
agcttcaacc attatcaccg ccagaggtaa aatagtcaac acgcacggtg ttagatattt    60
atcccttgcg gtgatagatt tac                                           83

<210> SEQ ID NO 237
<211> LENGTH: 118
<212> TYPE: DNA
<213> ORGANISM: Artificial sequence
<220> FEATURE:
<223> OTHER INFORMATION: Synthetic

<400> SEQUENCE: 237
tcgagccact ccctatcagt gatagagaaa agtccactcc ctatcagtga tagagaaaag    60
tccactccct atcagtgata gagaaaagtc cactccctat cagtgataga gaaaagta    118

<210> SEQ ID NO 238
<211> LENGTH: 117
<212> TYPE: DNA
<213> ORGANISM: Artificial sequence
<220> FEATURE:
<223> OTHER INFORMATION: Synthetic

<400> SEQUENCE: 238
gcttactttt ctctatcact gatagggagt ggactttttct ctatcactga tagggagtgg    60
acttttctct atcactgata gggagtggac ttttctctat cactgatagg gagtggc     117

```
<210> SEQ ID NO 239
<211> LENGTH: 34
<212> TYPE: DNA
<213> ORGANISM: Artificial sequence
<220> FEATURE:
<223> OTHER INFORMATION: Synthetic

<400> SEQUENCE: 239
gactacgcgt atgaggcctg aatgtgtcat acag                              34

<210> SEQ ID NO 240
<211> LENGTH: 29
<212> TYPE: DNA
<213> ORGANISM: Artificial sequence
<220> FEATURE:
<223> OTHER INFORMATION: Synthetic

<400> SEQUENCE: 240
gactactagt tagcaccacc gggttggtg                                    29

<210> SEQ ID NO 241
<211> LENGTH: 32
<212> TYPE: DNA
<213> ORGANISM: Artificial sequence
<220> FEATURE:
<223> OTHER INFORMATION: Synthetic

<400> SEQUENCE: 241
gactacgcgt tctgctggag acatgagagc tg                                32

<210> SEQ ID NO 242
<211> LENGTH: 29
<212> TYPE: DNA
<213> ORGANISM: Artificial sequence
<220> FEATURE:
<223> OTHER INFORMATION: Synthetic

<400> SEQUENCE: 242
gactactagt agctgtggca gggaaaccc                                    29

<210> SEQ ID NO 243
<211> LENGTH: 37
<212> TYPE: DNA
<213> ORGANISM: Artificial sequence
<220> FEATURE:
<223> OTHER INFORMATION: Synthetic

<400> SEQUENCE: 243
gactacgcgt aaaaagttca ataaagtcag agttgtg                           37

<210> SEQ ID NO 244
<211> LENGTH: 36
<212> TYPE: DNA
<213> ORGANISM: Artificial sequence
<220> FEATURE:
<223> OTHER INFORMATION: Synthetic

<400> SEQUENCE: 244
gactactagt agcaataact tcagacatca tttctg                            36

<210> SEQ ID NO 245
<211> LENGTH: 20
<212> TYPE: DNA
<213> ORGANISM: Artificial sequence
<220> FEATURE:
<223> OTHER INFORMATION: Synthetic
```

```
<400> SEQUENCE: 245
gagatacgcc ctggttcctg                                                    20

<210> SEQ ID NO 246
<211> LENGTH: 21
<212> TYPE: DNA
<213> ORGANISM: Artificial sequence
<220> FEATURE:
<223> OTHER INFORMATION: Synthetic

<400> SEQUENCE: 246
cgaaatgccc atactgttga g                                                  21

<210> SEQ ID NO 247
<211> LENGTH: 21
<212> TYPE: DNA
<213> ORGANISM: Artificial sequence
<220> FEATURE:
<223> OTHER INFORMATION: Synthetic

<400> SEQUENCE: 247
catgtacgtt gctatccagg c                                                  21

<210> SEQ ID NO 248
<211> LENGTH: 21
<212> TYPE: DNA
<213> ORGANISM: Artificial sequence
<220> FEATURE:
<223> OTHER INFORMATION: Synthetic

<400> SEQUENCE: 248
ctccttaatg tcacgcacga t                                                  21

<210> SEQ ID NO 249
<211> LENGTH: 35
<212> TYPE: DNA
<213> ORGANISM: Artificial sequence
<220> FEATURE:
<223> OTHER INFORMATION: Synthetic

<400> SEQUENCE: 249
ctttcatatg atgaagctac tgtcttctat cgaac                                   35

<210> SEQ ID NO 250
<211> LENGTH: 38
<212> TYPE: DNA
<213> ORGANISM: Artificial sequence
<220> FEATURE:
<223> OTHER INFORMATION: Synthetic

<400> SEQUENCE: 250
ctttctcgag ttattccgtt tcgcactgga aacccatg                                38
```

LIGHT-SWITCHABLE GENE EXPRESSION SYSTEM

CROSS REFERENCE TO RELATED PATENT APPLICATION

The present application is the US national stage of PCT/CN2012/071679 filed on Feb. 27, 2012, which claims the priority of the Chinese patent application No. 201110048142.1 filed on Feb. 28, 2011, which application is incorporated herein by reference.

FIELD OF INVENTION

The invention relates to the fields of genetic engineering and synthetic biology, especially, relates to gene expression, and more especially, relates to an inducible gene expression system based on light-switchable proteins and a method of regulating the gene expression in host cells by using this expression system.

BACKGROUND OF INVENTION

In the field of genetic engineering, precise controlling gene expression provides a valuable tool for studying and manipulating development and other physiological processes. Gene expression is a complex biological progress in which many specific protein-protein interactions are involved. The first step is the transcription of DNA into RNA, which needs the delivery of transcription factors to the promoter of gene. Transcription factor, also known as a sequence-specific DNA binding protein, is a kind of protein or protein complex which is capable of binding specific DNA sequence of promoter to initiate or prevent the transcription of downstream gene into RNA by recognizing/binding to the promoter. There are two kinds of transcription factors, termed as transcriptional activator and transcriptional repressor. In general, a transcription factor contains at least a DNA binding domain which can recruit cofactor(s), also named as co-activators, to bind proper locus of the promoter together so as to initiate the gene transcription. Besides, a transcription factor also contains a transcriptional activation domain or a transcriptional repression domain; the transcriptional activation domain may be in a certain distance from the DNA binding domain. Conventional transgenic method for heterologous gene expression usually uses universal promoter or cell type-specific promoter. The construct with a target gene and a corresponding promoter is transfected into host cells or integrated into the genome, and the target gene is transcribed and further translated into the corresponding protein in specific cell type when binding the transcription factor to the promoter.

An alternative way to regulate heterologous gene expression in host cells is using inducible promoters, which includes two categories: 1) Chemical substance inducible promoter and gene expression systems, and 2) physical methods inducible promoter and gene expression systems. Chemical substance inducers include small molecule drugs, a typical example is antibiotics such as tetracycline [Gossen, M. and H. Bujard, Proc Natl Acad Sci USA, 1992, 89 (12): 5547-5551—Gossen, M., etc., Science, 1995, 268 (5218): 1766-1769], and streptomycin [M. etc., Nat Biotechnology, 2000, 18 (11): 1203-1208]; hormone [Wang, Y, Proc Natl Acad Sci USA, 1994. 91 (17): 8180-8184] and its analogues and other inducers such as acetaldehyde [Weber, W., etc. NAT Biotechnol, 2004, 22 (11): 1440-1444]. Physical methods inducible promoters and gene expression system include ultraviolet (UV)-regulated "cage" (Caged) technology [Keyes, W M and A A Mills, Trends Biotechnology, 2003, 21 (2): 53-55]; and far-infrared light controlled heat shock effect mediated gene expression system [Kamei, Y., etc., Nat Methods, 2009, 6 (1): 79-81].

Although many of those methods have been widely used, there exist some potential problems, such as (1) pleiotropic effect of the inducers may interfere with endogenous gene expression, which may lead to a complicated result. For example, in heavy metal ions-induced gene expression systems, heavy metal ions are not only able to induce target gene expression but also cause other heavy metal ion-induced endogenous gene expression; (2) some inducers have potential toxicity which can affect the functions of other genes, e.g., the cytotoxicity of heavy metal ions impedes their use in animals or humans; (3) Many promoter systems have a high leakage expression in the absence of inducers, thus the gene expression cannot be in a completely off state and the ratio of gene expression level before and after adding the inducers (also termed as induction ratio) is low, such as hormone-induced gene expression system [Wang, Y., and so on. Proc Natl Acad Sci USA, 1994, 91 (17): 8180-8184]. Those promoter systems are not suitable for expressing toxic genes or genes for that low expression level can cause significant biological effects; (4) Some chemical-induced gene expression systems consist of two or more proteins, such as the gene expression system based on FKBP-FRAP, and they have lower transfection efficiency than the single transcription factor [Rivem, V M, etc., Nat Med, 1996 2 (9): 1028-1032]. (5) Chemicals can temporally but not spatially regulate gene expression in specific cells and tissues. (6) Most physical methods have a strong toxicity to cells, e.g., the UV-induced cage technology may cause irreversible damage to cells, the inducible expression system based on far-infrared laser-controlled heat shock may activate endogenous gene expression, and the device is complex and expensive [Kamei, Y., etc., Nat Methods, 2009, 6 (1): 79-81].

However, light is a non-toxic inducer, which can be spatiotemporally controlled. One feasible way is introducing heterogenous light-regulated proteins (also known as photosensitive protein) into eukaryotic cells and reconstructing them to be light-regulated transcription factors which can regulate gene expression via light irradiation. These proteins are expected not to interfere with the physiological processes of eukaryotic cells, and they would not cause pleiotropic effects or non-specific effects in eukaryotic cells. However, studies on light-regulated transcription factors have been rarely reported. Shimizu-Sato et al. reported a light-switchable gene expression system in yeast cells [Shimizu-Sato S. et al, NAT Biotechnology, 2002 20 (10): 1041-1044]. U.S. Pat. No. 6,858,429 described using genetic engineering techniques to combine plant protein phytochrome (abbreviated as Phy) and Phytochrome interacting factor 3 (abbreviated as PIF3) with yeast Gal4 DNA binding domain and Gal4 transactivation domain of the yeast two-hybridization system to obtain fusion proteins Gal4-Phy and PIF3-GAD, respectively. Gal4-Phy interacts with PIF3-GAD and recruits PIF3-GAD to the target promoter to initiate gene transcription by red light illumination; while far-red light irradiation causes dissociation of the conjugate of Gal4-Phy and PIF3-GAD thus the AD domain of Gal4 cannot bind to the promoter and the transcription of target gene is terminated. This light-induced promoter system is reversible and has a high expression lever. However, the interaction of phytochrome Phy and PIF3 needs the existence of phycocyanobilin, the chromophore of PIF3, which needs to be added exogenously into yeast and mammalian cells since it does not exist in these cells. In addition, this system is based on yeast two-hybridization system in which the transcription factor consists of two proteins, and the resulting big construct is difficult to be introduced into host cells, thus limiting the wide usage of this system.

There are some other known photosensitive proteins: the photosensitive proteins using flavin as the chromophore (also called flavin-containing protein family blue light receptor), which can be divided into three groups: First is photoreceptors with light-oxygen-voltage (LOV) domain, such as phytochrome; the second is photolyase-like cryptochromes; the third is blue light using FAD (BLUF) family that is found in recent years. Phytochrome is the most common photoreceptor containing LOV domain, such as phototropin 1, white collar-1 (WC-1), white collar-2 (WC-2), photoactive yellow protein (PYP), Phy3, VVD, etc. Phytochrome is usually a membrane-coupled kinase which can autophosphorylate and alter its activity to regulate specific physiological processes upon blue light exposure. Most phytochromes have Serine/Threonine kinase domain at the C-terminal and two LOV domains with flavin at the N-terminal. With the illumination of blue light, the LOV domain and flavin bind covalently to form a cysteinyl-flavin adduct which can cause the conformation change of flavin-binding pocket and then enable the kinase domain at the C-terminal to alter the kinase activity. This process is reversible. In addition, LOV2 domain is more sensitive than LOV1. Based on the interaction of *Arabidopsis* FKF1 (flavin-binding, kelch repeat, f box 1) and GI (GIGANTEA) protein upon blue light irradiation, Masayuki Yazaw et al. fused FKF1 and GI to DNA binding domain of Gal4 and the transactivation domain AD of herpes simplex virus VP16 to form transcription factors Gal4-FKF1 and VP16-GI, respectively [Yazawa, M., et al., Nat Biotechnology, 2009. 27(10): 941-945]. Upon blue light illumination, VP16-GI can interact with Gal4-FKF1 (specifically, the interaction happens between FKF1 and GI which has bound to the promoter region, and initiate the transcription of target gene. The drawbacks of this system are that the large constructs containing FKF1 or GI gene are difficult to be transfected into cells, and the induction ratio is very low (the highest one is only 5-fold). Cryptochromes from *Arabidopsis thaliana* are the first separated blue light photosensitive plant proteins, of which some have been well studied, such as cryptochrome1 (CRY1), cryptochrome 2 (CRY2), phytochrome A (phyA) and phytochrome B (phyB). Based on the interaction of *Arabidopsis* CRY2 and CIB1 (CRY-interacting bHLH1) protein upon blue light illumination, researchers fused CRY2 and CIB1 to Gal4 DNA binding domain and Gal4 transactivation domain of the yeast two hybridization system to construct transcription factors Gal4-CRY2 and CIB1-GAD, respectively. CIB1-GAD interacts with Gal4-CRY2 which has bound to the promoter, and initiate the expression of target gene [Kennedy, M J. et al. Nat Methods 2010.7 (12):973-975]. Although it is unnecessary for this system to add an exogenous chromophore, it is still difficult to manipulate since the system contains two fusion proteins on the basis of the two-hybridization system. Furthermore, there is some leaky expression in the absence of light. All these drawbacks limit the wide application of this system. Difference between blue light photoreceptor proteins with BLUF domain and photo-receptor proteins with LOV domain is that no adduct is generated between BLUF and flavin after light irradiation, but it will lead to 10 nm red-shift absorbance due to the conformation change of chromophore. The most well studied BLUF domain containing photoreceptor is AppA, which is a repressor of anti-transcription from *Rhodobacter sphaeroides*. AppA and transcription factor PpsR combine to form AppA-PpsR2 complex and enable PpsR not to bind with DNA in darkness; bright blue light irradiation may enable AppA to dissociate from the complex, and the released PpsR forms a tetramer and bind to a specific DNA sequence to repress the gene transcription.

In previous studies, hormone receptors or receptor mutants can be used to regulate gene functions and activities of transcription factors. For example, in Cre/LoxP system, we can reconstruct Cre recombinase to regulate its nucleus localization by fusing ER, PR or GR to it; thus the reconstructed Cre recombinase can play its function roles in the nucleus with the existence of corresponding ligand. Fusing a hormone receptor to a transcription factor can enable the transcription factor to function under the regulation of hormone, for example, a hormone-tetracycline co-regulated gene expression system in which tetracycline-regulated transcription factor is fused with EcR or GR, thus the gene expression is regulated by both the hormone and tetracycline.

As described above, the most widely used gene expression systems today utilize chemical substances as the inducers, which have reasonable desirable induction performance, low leakage expression and high expression levels. However, many of gene expression systems have side-effect and potential toxicity due to their pleiotropic effect. Besides, the chemical inducers cannot precisely control gene expression at high spatial resolution. Up to now, there are only a few of gene expression systems controlled by physical methods although they have the capability of spatial regulating gene expression in specific cells and tissues, their toxicity to host cells may cause irreversible damage or hard manipulation. Few photosensitive protein based gene expression systems have been developed, but the poor induction capacity, the requirement for exogenous chemicals, the difficulty for the transcription factor containing more than one protein to be introduced into host cells may limit their wide application. The applicants consider that a more excellent gene expression system can be created using a novel method to overcome the shortcomings of previous studies, and it can be widely used in biomedical sciences and technology researches. After painstaking studies, the applicant has invented a novel light-controllable gene expression system, which consists of two parts: a recombinant light-switchable transcription factor and a target transcription unit. It has excellent capacity to control gene expression and it can spatiotemporally regulate gene expression. Furthermore, in order to satisfy more complex synthetic biology research, we have modified the recombinant light-switchable transcription factor into a recombinant light-hormone dual regulated transcription factor which can regulate gene expression by both light and hormone.

Accordingly, the first object of the present invention is to provide a novel light-controllable gene expression system.

A second object of the present invention is to provide a light and hormone dual-regulated gene expression system.

A third object of the present invention is to provide a eukaryotic expression vector containing said light-controllable gene expression system.

A fourth object of the present invention is to provide a method of the regulation of gene expression by said light-controllable gene expression system in the host cell.

A fifth object of the present invention is to provide a kit containing components of the light controllable gene expression system.

A sixth object of the present invention is to provide a gene therapy method using the light-controllable gene expression system.

SUMMARY OF INVENTION

The present invention relates to a light-switchable gene expression system, comprising two parts: a) a gene encoding a recombinant light-switchable transcription factor, said recombinant light-switchable transcription factor including the first polypeptide as DNA-binding domain, the second polypeptide as light-switchable domain and the third polypeptide as transcriptional regulatory domain; b) a target transcription unit, including at least one reaction element recognized/bound by the first polypeptide, promoter connected thereto and the nucleic acid sequence to be transcribed.

In the first part of the light-switchable gene expression system according to the invention, the first polypeptide in the recombinant light-switchable transcription factor is a DNA-binding domain which is able to specifically recognize said reaction element, but unable to bind the reaction element or only have a weak binding affinity. The binding to the reaction element needs the assistance of the second polypeptide. The first polypeptide can be selected from the helix-turn-helix DNA-binding domain, zinc finger motif or zinc cluster DNA-binding domain, leucine zipper DNA-binding domain, winged helix DNA-binding domain, winged helix-turn-helix DNA-binding domain, helix-loop-helix DNA-binding domain, high mobility family DNA-binding domain and B3 DNA-binding domain. The second polypeptide is a light-switchable domain usually derived from the class of the photosensitive proteins containing flavin chromophore. The third polypeptide is a transcriptional regulatory domain including the transcriptional activation domain and the transcriptional repression domain.

The first polypeptide, the second polypeptide and the third polypeptide can be linked directly or operatively via a linker peptide. The amino acid number of the linker peptide is variable, such as 0, 1, 2, 3, 4, 5, 6, 7, 8, 9, 10 or more.

The first polypeptide and the second polypeptide can constitute a fusion protein of the light-switchable DNA-binding-protein (abbreviated as a light-switchable DNA binding protein), and can be used for in vitro researches for DNA binding characteristics of the recombinant light-switchable transcription factor. In the second portion (i.e. target transcription unit) of the light-switchable gene expression system, the reaction element, the promoter and the nucleic acid sequence to be transcribed can also be linked each other directly or operatively.

In the first portion of the light-switchable gene expression system, the recombinant light-switchable transcription factor can further comprise additional polypeptides, such as the fourth polypeptide (i.e. nuclear localization signal peptide) which can promote the transportation of the recombinant light-switchable transcription factor fusion protein into the nucleus; and/or the fifth polypeptide regulated by hormones. The fourth or the fifth polypeptide can be linked directly or via a linker peptide, with the first, the second, or the third polypeptides.

The present invention also relates to a eukaryotic expression vector containing the light-switchable gene expression system. The eukaryotic expression vector can only contain the gene encoding the recombinant light-switchable transcriptional factor, or only contain the target transcription unit containing the reaction element-promoter but leaving a vacancy for the nucleic acid sequence to be transcribed. Otherwise, the eukaryotic expression vectors can contain both the gene encoding the recombinant light-switchable transcriptional factor and the reaction element-promoter in the target transcription unit.

The present invention also relates to a method for the regulation of gene expression in the host cells by using the light-switchable gene expression system, comprising the following steps:

a) constructing the light-switchable gene expression system in the eukaryotic plasmid expression vectors;

b) introducing the construct into the host cells containing said gene being regulated; and c) inducing the host cells via illumination to express said gene being regulated.

In the above method, the illumination comprises the selection and the control of the light sources. The light sources include, but are not limited to, LED lamp, incandescent lamp, fluorescent lamp and laser; and the illumination method includes the selection of the quantity, time, intensity and frequency of the illumination. The spatial expression control of the target gene, using scan, projection, optical molds, etc., also falls into the range of the invention.

The present invention further relates to a kit containing the eukaryotic expression vector comprising the light-switchable gene expression system and/or the mammalian cells transfected by the eukaryotic expression vectors containing the transcription factor, as well as the directions, The kit can also contain the eukaryotic expression vector comprising the target transcription unit composed of the reaction element-promoter but leaving a vacancy for the nucleic acid sequence to be transcribed The present invention further relates to a method for the gene therapy using the light-switchable gene expression system.

DETAILED DESCRIPTION OF INVENTION

The invention provides a photosensitive polypeptide-based light-switchable gene expression system useful for the regulation of target gene expression with high spatiotemporal resolution in eukaryotic host cells. The light-switchable gene expression system of the invention relates to at least two portions. The first portion is a nucleotide sequence (encoding the recombinant light-switchable transcription factor fusion protein) being able to express in the host cells. This fusion protein is composed of three or four or five polypeptides, wherein the first polypeptide is its DNA-binding domain, the second polypeptide is a light-switchable domain, the third polypeptide is a transcriptional regulatory domain, the fourth polypeptide is a nuclear localization signal peptide, and the fifth polypeptide is a polypeptide regulated by hormone. The second portion is a nucleotide sequence of the target transcription unit composed of a reaction element-promoter-nucleotide sequence to be transcribed, wherein the reaction element is a DNA nucleotide motif recognized/bound by the first polypeptide in the above-mentioned recombinant light-switchable transcription factor fusion protein; and the promoter is usually minimal promoter or other complete promoter. The three or four or five polypeptide in the first portion is preferred to be a truncated functional active fragment (i.e. Domain) of the proteins involved. The first and second portions of the light-switchable gene expression system can be constructed in one or two eukaryotic expression vectors, respectively. These vector(s) will be introduced into host cells, by using different conventional methods for particular host cells, to express the recombinant light-switchable transcription factor fusion protein. The illumination of appropriate wavelength light can result in the change of dimerization ability of the light-switchable second polypeptide, then the change of dimerization ability of the whole recombinant light-switchable transcription factor. The dimerized transcription factor can bind to the reaction element in the second portion, i.e., target transcription unit nucleotide sequence, to regulate (initiate/repress) the transcription and expression of the target gene via the synergistic effect on the promoter in the target transcription unit by the transcriptional activation/repression domain of the third polypeptide in this fusion protein and other transcriptional co-factors derived from the recruitment host cells. The light-switchable gene expression system of the invention can utilize the illumination which is hardly damaging cells or the body, to regulate the target gene expression in eukaryotic host cells at high spatiotemporal resolution.

The light-switchable gene expression system can utilize different light sources and illumination conditions to regulate the target gene expression in eukaryotic host cells in the space. The used light is cheap, easy to be obtained and non-toxic to cells.

Definition and Explanation of Terms Used Herein

"light-switchable", "photosensitive" and "light-switchable" proteins have the same meaning and can be used interchangeably herein, refers these proteins which are sensitive to illumination and their activities (including activation, enhancement or repression) can be influenced by adjusting their conformations or configurations through being applied corresponding wavelength light in different intensities or different frequencies "Host" refers to the eukaryotes, including unicellular eukaryotes such as yeast and multicellular eukaryotes such as plants and animals, especially mammals, including humans.

"Host cells" refer to the cells of the constituted eukaryote tissues or the established eukaryotic cell lines and, as long as these cells or cell lines are compatible with the target protein to be expressed, the used screening system or the fermentation and culture system; comprising: unicellular eukaryotic cells such as cultured BY4741 and AH109 *Saccharomyces cerevisiae* yeast, fission yeast, *P. pastoris yeast, klebsiella lactate, H. polymorpha* yeast cells (for its review, see Fleer et al., Curr Opin Biotechnol, 1992, 3(5):486-489) and fungal cells. The nonrestrictive examples of the established subculturing in vitro immortal mammalian cell lines comprising: human embryonic kidney epithelial cells (HEK293), African green monkey kidney fibroblast COS-7, human cervix carcinoma cells (Hela), mouse fibroblasts (NIH3T3), etc. The host cells also include normal cells such as ex vivo transgenic or homologous recombinant animal embryo cells for the purpose of gene therapy. The particular value cell types for the purpose of gene therapy comprising: hematopoietic stem cells, osteoplasts, hepatocytes, leukocytes, neuronal cells, skin epithelium and airway epithelium cells; ex vivo transgenic or homologous recombinant animal embryo stem cells and fertilized egg cells. The host cells also comprising non-mammalian eukaryotic cells such as bacterial, fungal, yeast, plant, *drosophila*, inset, zebra fish, nematode, animal and mammalian cells. The above-mentioned transgenic cells include these cells transferred thereto by the inventive recombinant light-switchable transcription factor gene and/or the target transcription unit containing target protein gene. The inventive recombinant light-switchable transcription factor can well regulate the target gene expression in these cells via controllable light irradiation. The expression in insect cells can be performed with baculovirus expression vectors (see, for example, O'Reilly et al. (1992) "Baculovirus expression vectors: A laboratory manual", Stockton Press), available baculovirus vectors include pAc series (Smith, G. E., M. D. Summers, and M. J. Fraser, Mol Cell Biol, 1983. 3(12): 2156-2165) and pVL series ((Luckow, V. A. and M. D. Summers, Virology, 1989. 170(1): 31-39).

"Target protein" is also known as "interested protein" and refers to any useful protein, for example, useful eukaryotic protein, including natural or artificial modification or mutation proteins in need of expression in eukaryotic host cells for the preventive or therapeutic or other purposes, in particular, these proteins which must be modified after translation (such as glycosylation, amidation modification etc.) to obtain their activities, and they will be expressed in eukaryotic cells to obtain such modifications.

"Report protein", one of target proteins, refers to a useful protein which expression is easy to be detected. In order to facilitate the detection for effect of the inventive photosensitive polypeptide-based light-switchable target gene expression system, the known widely used report proteins can be selected as following: firefly luciferase (Fluc), green fluorescent protein (GFP), chloramphenicol acetyltransferase (CAT), β-galactosidase (LacZ), etc. However, the light-switchable target protein gene expression system is not limited to express a report protein, but may be used for the expression of any useful target protein.

"Gene", "encoding nucleotide sequence" and "sequence to be transcribed" of a protein, as used herein, have the same meaning. They can be used interchangeably and refer to the natural or recombinant codon DNA sequence carrying the amino acid sequence information, and also refers to the DNA sequence encoding a functional RNA such as antisense RNA.

"Gene of a target protein", "encoding nucleotide sequence of a target protein", "nucleotide sequence encoding target protein" and its abbreviation "target gene", as used herein, have the same meaning. They can be used interchangeably and refer to the gene encoding target protein, generally double-strands DNA sequence. This gene can be contained in the chromosomal DNA sequence of the host cells or in artificial expression vectors, such as the target transcription unit sequence of the invention. Similarly, "report gene" means a gene encoding a report protein.

"Transcription" as used herein specifically refers to a process wherein a target gene is transcribed by RNA polymerase to produce RNA carrying this gene information in the eukaryote host cells. The transcription of the eukaryote gene is much more complex than that of the prokaryote gene. In eukaryotes, there are three RNA polymerases, I, II and III, respectively for the transcription of three eukaryotic genes, resulting in three RNAs (rRNA, mRNA, tRNA) and antisense RNA. The transcription process, from DNA into mRNA, regulated by the transcription factor is the transcription started by RNA polymerase II.

"Transcriptional regulation" used herein refers to the regulation of eukaryotic gene transcription, including the transcriptional start or repression, enhancement or inhibition, upward or downward regulation.

"Expression", "gene expression of a target protein" and "gene expression", as used herein, have the same meaning. They can be used interchangeably and refer to both a target gene DNA sequence being transcribed to RNA (mRNA or antisense RNA) carrying this gene information and the information carried by this RNA being translated to produce the target protein, that is, both the messenger RNA production via transcription and the target protein production via translation are called as expression. As herein, these two meanings are included, mainly referring to produce the target protein.

"Transcription factor" and "transcription factor fusion protein" as herein have the same meaning. They can be used interchangeably, and refer to the eukaryote transcription factor. It is not a protein, but a general term for several interacting proteins or polypeptides. It may be natural or artificially modified or fused proteins composed of the polypeptide able to recognize/bind to the reaction element nucleotide sequence in the target transcription unit and the polypeptide able to recruit other transcriptional activation/repression cofactors. It can start and regulate the gene transcription of protein by binding to and interacting with the reaction element in the target transcription unit, as well as its acting on upstream promoter of the nucleic acid sequence together with other recruitment transcriptional activation or repression cofactors. Depending on the different composition, the transcription factors can be divided into "transcriptional activation factor" and "transcriptional repression factor".

"Target transcription unit" refers to a artificial DNA sequence composed of a reaction element, a promoter and a nucleic acid sequence to be transcribed (not a protein), wherein the reaction element is usually located upstream of the promoter, sometime may also be located downstream of the promoter; and the nucleic acid sequence to be transcribed is located downstream of the reaction element and the promoter. The reaction element, promoter and nucleic acid sequence to be transcribed can be connected directly or operatively, i.e., separated by several nucleotides.

"Reaction element" refers to one or more cis-DNA motifs recognized/bound specifically by a transcription factor. Different transcription factors have their corresponding different reaction elements; and the binding domain contained in the transcription factor can bind to this DNA motif. When a transcription factor has bound specifically to its corresponding reaction element, the third polypeptide in the transcription factor can recruit co-factors to effect synergically on the promoter for activation or repression of downstream target gene transcription in order to produce the corresponding RNA. According to the invention, the reaction refers to a DNA motif able to be recognized/bound specifically by the first polypeptide in the recombinant light-switchable transcription factor, for example, a Gal4 reaction element is the long 17 bp DNA motif (Sequence 67).

"Promoter" refers to a DNA sequence which can start and lead to its downstream gene transcription to produce RNA. Promoter may be a naturally or artificially modified promoter. The different promoter may guide the gene transcription in different developmental stages of different tissues or cells, or the gene expression in response to different environmental or physiological conditions. Promoters are usually divided into "constitutive promoter", "inducible promoter and "regulatory promoter"; or divided into "cell-specific promoter", "tissue-specific promoter", "developmental-specific promoter" and "cell-differentiation-specific promoter" based on tissues and cells. The upstream gene of the expressible natural cellular structure protein has its matching promoter; and DNA fragment of different genes may have the same promoter. The non-restrictive examples of the common constitutive promoters available for the expression of the recombinant light-switchable transcription factor are the promoters derived from polyoma virus, adenovirus 2, cytomegalovirus (CMV) and simian virus 40 (SV40). The non-restrictive examples of tissue-specific promoters available for the expession of the recombinant light-switchable transcription factor also include: the albumin promoter (liver-specific, Pinkert, C. A. et al, Genes Dev, 1987. 1(3): 268-276), lymphoid-specific promoter (Calame, K. and S. Eaton, Adv Immunol, 1988. 43: 235-275), in particular, T-cell receptor promoter (Winoto, A. and D. Baltimore, EMBO J, 1989. 8(3): 729-733), immune-globulin promoter (Banerji, J., L. Olson and W. Schaffner, Cell, 1983. 33(3): 729-740; Queen, C. and D. Baltimore, Cell, 1983. 33(3): 741-748), neuron-specific promoter (for example, nerve fibers promoter, Talbott, R. L., et al., Proc Natl Acad Sci USA, 1989. 86(15): 5743-5747), pancreas-specific promoter (Edlund, T. et al., Science, 1985. 230(4728): 912-916) and mammalian gland-specific promoter (such as milk whey promoter, U.S. Pat. No. 4,873, 316). The developmental regulatory promoters are also included, such as murine hox promoters (Kessel, M. and P. Gruss, Science, 1990. 249(4967): 374-379) and α-fetoprotein promoter (Camper, S. A. and S. M. Tilghman, Genes Dev, 1989. 3(4): 537-546). AT-rich region located in about −25 to −30 nucleotide upstream of the transcription initiation point in most eukaryotic genes is called as TATA box, as herein known as "minimal promoter" which determines the transcription start site, but itself is not sufficient to effectively start gene transcription. In upstream of TATA box, there are other necessary nucleotide motifs for transcription, i.e., the reaction element recognized/bound specifically by the transcription factor described herein. When this reaction element is bound by its corresponding transcription factor, the reactivity is communicated to the minimal promoter, and the minimal promoter is activated in the synergistic assistant of the transcription factor-recruitment co-factors, finally resulting in the transcription of downstream gene to produce corresponding RNA.

"Vector", "expression vector", "gene expression vector" and "recombinant gene expression vector" have the same meaning. They can be used interchangeably and refer to a vector able to express recombinant target proteins in eukaryotic cells. This vector may be an artificial plasmid or a recombinant virus vector.

"Transfection" refers to a process that the host cells uptake the exogenous gene-carrying expression vector through physical or chemical methods such as electroporation, calcium phosphate co-precipitation, lipofection amine or DEAE-dextran mediated transfection, DNA particle bombardment and microinjection, etc., or the gene-carrying expression vectors delivery into the host cells through a biological medium, such as retrovirus vector, adenovirus vector and receptor-mediated DNA uptake. These vectors entered into host cells can reside in the cytoplasm as episomes, or be integrated into the chromosome of the cells. These cells can transiently or long-termly express the protein or functional RNA encoded by the vector-carried gene. Such host cells are called as vector-transfected cells. The methods for the host cells transfected with the expression vectors can be found in Sambrooka et al (Molecular Cloning, A laboratory Manual, Second Edition, Cold Spring Harbor Press (1989) and other related textbooks.

The recombinant light-switchable transcription factor in the first portion of the photosensitive polypeptide-based light-switchable gene expression system of the invention is a fusion protein formed by tandem connection of three or four or five functional polypeptide fragments via direct peptide bonds or via a linker peptide. Under illumination of an appropriate wavelength light, such fusion protein can bind to the reaction element in the second portion, i.e., target transcription unit nucleotide sequence of the system, so as to initiate or repress the expression of the target protein gene in the transcription unit via the synergistic effect on the promoter in the target transcription unit by its transcriptional activation/repression domain and the transcriptional co-factors derived from the recruitment host cells themselves.

As used herein, "recombinant light-switchable transcription factor fusion protein" and "recombinant light-switchable transcription factor" have the same meaning and can be used interchangeably.

The recombinant light-switchable transcription factor of the invention comprises the first polypeptide which is able to specifically recognize said reaction element in the target transcription unit nucleotide sequence, but unable to bind the reaction component or only have a weak binding affinity. The first polypeptide can only bind to the reaction component after homogenous dimerization of the transcription factor occurring with the assistance of the second polypeptide. The first polypeptide can be selected from: the helix-turn-helix DNA-binding domain, zinc finger motif or zinc cluster DNA-binding domain, leucine zipper DNA-binding domain, winged helix DNA-binding domain, winged helix-turn-helix DNA-binding domain, helix-loop-helix DNA-binding domain, high mobility family DNA-binding domain and B3 DNA-binding domain. Based on the related literature analysis, the useful first polypeptide of the invention includes, but not limited to DNA-binding domain of Gal4 protein, DNA-binding domain of LexA protein, DNA-binding domain of Lac repression protein (Lac1), DNA-binding domain of λphage cl repression protein, DNA-binding domain of tetracycline repression protein (TetR), DNA-binding domain of tryptophan repression protein (TrpR) etc., more preferably DNA-binding domains of Gal4 protein and LexA protein. Gal4 is a transcriptional activation domain of *Saccharomyces cerevisiae*, and it is able to recognize/bind to the upstream reaction element-UAS$_G$ motif (SEQ. ID. NO:67). 1-94 Amino acids of the N-terminal of Gal4 protein is its DNA-binding domain (a zinc cluster DNA-binding domain), wherein 1-65 amino acid are useful for specific recognition of DNA, and 66-94 amino acids, useful for dimerization. Gal4 plays its role to bind to the reaction element in need of the formation of a homogeneous dimer [Marmorstein, R. et al., Nature, 1992. 356 (6368): 408-411]. Gal4/UAS-based double hybrid system is an effective tool for researching the gene expression. For example, this Gal4/UAS system has been used in CheckMate™ Mammalian Two-Hybrid System (Promega). LexA protein is a transcriptional repression protein present in *E. Coli* cells, and it can regulate the transcription of more than 20 genes and recognize/bind to palindromic structure of upstream reaction element (SEQ. ID. NO:68) of gene promoter to prevent the downstream gene transcription by RNA polymerase. LexA contains 202 amino acids with a winged helix-turn-helix DNA-binding domain, wherein the 1-87 amino acids are useful for specific recognition of DNA and the 88-202 amino acids, useful for dimerization. Only dimerized LexA can specifically bind to the corresponding reaction element. LexA exists in the dimeric form in normal cells. When the cells are stimulated by an internal or external SOS signal, the dimerized LexA is cut by certain enzymes in vivo and dissociated from the DNA, resulting in the activation of the gene previously repressed by LexA [Fogh, R. H. et al., EMBO J, 1994. 13 (17), 3936-3944]. LexA-based double hybrid system has also been used for researching the interaction of gene expression and proteins. For example, MATCHMAKER™ yeast LexA Two-Hybrid System (Clontech) is based on this system. LacI repression protein can recognize/bind to the operon of lactose system to regulate the transcription of the corresponding genes. Lac protein has a helix-turn-helix DNA-binding domain with 1-62 amino acids for the specific recognition of DNA, and its specifically recognizing/binding conserved sequence is shown as SEQ. ID. NO:69. Only dimerized or tetromerized LacI can bind to the DNA, but monomer LacI almost can not [Lewis, M. et al., Science, 1996. 271 (5253), 1247-1254]. The cI protein is a transcription repression protein encoded by λ phage cI gene, and it can prevent the transcription activity of λ left and right early promoters, resulting in the production of protein unable to perform cell duplication and cell division. The cI protein contains 236 amino acids with a helix-turn-helix DNA-binding domain, wherein 1-102 amino acids are useful for specific recognition of DNA and 132-236 amino acids, useful for dimerization. Only dimerized cI can specifically bind to the corresponding reaction element. The homogenous dimer of cI protein can recognize/bind to two operon sequences, $P_L$ and $P_R$, each contains three recognition/binding sites, OL1, OL2 and OL3 for $P_L$, and OR1, OR2 and OR3 for $P_R$, respectively. The cI protein has stronger ability to bind to OR1. The conserved DNA sequence is showed as SEQ. ID. NO:71. The monomer cI protein almost has no such binding ability [Burz, D. S., Beckett, D., Benson, N. and Ackers, G. K., Biochemistry, 1994. 33(28), 8399-8405, Hu, J. C., O'Shea, E. K., Kim, P. S. and Sauer, R. T., Science, 1990. 250 (4986), 1400-1403]. Tetracycline repression protein (TetR), a transcription factor resided in many Gram-negative bacteria, represses the transcription of corresponding genes via the bind to specific DNA motifs. TetR protein has a helix-turn-helix DNA-binding domain. The monomer of TetR protein can form the homogenous dimer for recognition/binding to the operon containing a specific DNA sequence (SEQ. ID. NO:70), but the monomer of TetR protein itself almost has no such binding ability [Wissmann, A. et al., EMBO J, 1991.10 (13), 4145-4152, Ramos, J. L. and, Microbiol Mol Biol Rev, 2005. 69(2), 326-356].

In a preferred embodiment of the invention, the first polypeptide is the 1-65 amino acid sequence of DNA-binding domain of Gal4 protein (its nucleic acid and protein sequences are SEQ. ID. NO:1 and SEQ. ID. NO:2, respectively), i.e., truncated DNA-binding domain which can not bind to the reaction element alone. In another preferred embodiment of the invention, the first polypeptide is the 1-87 amino acid sequence of DNA-binding domain of LexA protein (its nucleic acid and protein sequences are SEQ. ID. NO:5 and SEQ. ID. NO:6, respectively), i.e., truncated DNA-binding domain which can not bind to the reaction element alone. In another preferred embodiment of the invention, the first polypeptide is the 1-62 amino acid sequence of DNA-binding domain of LacI protein (its nucleic acid and protein sequences are SEQ. ID. NO:9 and SEQ. ID. NO:10, respectively), i.e., truncated DNA-binding domain which can not bind to the reaction element alone. In another preferred embodiment of the invention, the first polypeptide is the 1-63 amino acid sequence of DNA-binding domain of TetR protein (its nucleic acid and protein sequences are SEQ. ID. NO:13 and SEQ. ID. NO:14, respectively), i.e., truncated DNA-binding domain which can not bind to the reaction element alone. In another preferred embodiment of the invention, the first polypeptide is the 1-102 amino acid sequence of DNA-binding domain of cI protein (its nucleic acid and protein sequences are SEQ. ID. NO:17 and SEQ. ID. NO:18, respectively), i.e., truncated DNA-binding domain which also can not bind to the reaction element alone.

The second polypeptide in the recombinant light-switchable transcription factor fusion protein is a photosensitive polypeptide derived from the photosensitive domain containing flavin chromophore (FMN or FAD). For example, the photosensitive protein contains light-O-voltage (LOV) domain, the photolyase-like cryptochromes and the blue light protein using FAD (BLUF), preferably, the photosensitive protein contains LOV domain. After the illumination with the appropriate wavelength light, the dimerization ability of the second polypeptide has been changed to alter the dimerization ability of the transcription factor, then the dimer of the transcription factor can bind to the corresponding reaction element, thereby to regulate the expression level of the target genes. The invention includes, but is not limited to, several preferred photosensitive proteins or their functionally active truncated fragments described below.

The most preferred second polypeptide of the invention is the light-switchable domain of *Neurospora crassa* VIVID protein and its mutants. VIVID exists in the cells of *Neurospora crassa* and it is a photosensitive protein involved in cellular signaling pathway regulated by blue-light. Under the illumination of blue light, it can form a dimer with flavin adenine dinucleotide (FAD) in an intermolecular reaction. Full-length VIVID protein contains 186 amino acids with only one photosensitive LOV domain. Studies have showed that VIVID-36, the truncated protein of VIVID protein (missing 36 amino acid sequence in the N-terminal), were more stable than the full-length VIVID protein, Meanwhile, without illumination, the half-life of VIVID-36 dimer formed by illumination with blue light for regaining its monomeric form is 180000 s; the VIVID-36 containing point mutation C71V has more strong dimerization ability. In a preferred embodiment of the invention, the second polypeptide is selected from one point-mutation-containing and 1-36 amino acid sequence deleted VIVID (C71V), VIVID (N56K) and VIVID (Y50W) mutants (their nucleic acid sequences are SEQ. ID. NO:23, 25 and 29, respectively; their amino acid sequences are SEQ. ID. NO:24, 26 and 30, respectively). In a more preferred embodiment of the invention, the second polypeptide is two point-mutation-containing and 1-36 amino acid sequence deleted VIVID (N56K+C71V) mutants (The nucleic acid and protein sequences are SEQ. ID. NO:27 and SEQ. ID. NO:28, respectively).

The secondly preferred second polypeptide of the invention is LOV2 domain of *Avena sativa* phytochrome 1 (abbreviated as AsLOV2) [Peter, E., B. Dick, and S. A. Baeurle, Nat Commun, 2010. 1(8): 122]. The N-terminal of phytochrome 1 of *Avena sativa* is light-O-voltage (LOV) domain, LOV1 or LOV2, which can bind to flavin mononucleotide (FMN) to produce an additional compound under illumination of blue light. In the invention, LOV2 domain is linked to the first polypeptide, thus successfully resulting in the ability to bind to the corresponding reaction element for the first polypeptide in the transcription factor. The second polypeptide in the transcription factor GALP containing AsLOV2 domain (its nucleic acid and protein sequences are SEQ. ID. NO:41 and SEQ. ID. NO:42, respectively) can bind to its corresponding reaction element in dark, resulting in the expression of target gene, whereas this binding is weakening under illumination, resulting in the down-regulation of target gene expression level.

The thirdly preferred second polypeptide of the invention is LOV domain (abbreviated as AuLOV, its nucleic acid and protein sequences are SEQ. ID. NO:45 and SEQ. ID. NO:46 respectively) in the C-terminal of aureochrome1 of *Stramenopile algae Vaucheria frigida* [Takahashi, F. et al, Proc Natl Acad Sci USA, 2007. 104(49): 19625-19630]. The dimerization ability of the second polypeptide in the transcription factor GAAP containing AuLOV domain has been enhanced after illumination, thus resulting in the up-regulation of target gene expression level.

The dimerization of the recombinant light-switchable transcription factor constituted from VIVID or AuLOV is enhanced by the illumination of a light with an appropriate wavelength thus resulting in the bind of the second polypeptide to the reaction element to start or up-regulate the transcription. However, the light-switchable transcription factor containing AsLOV2 is dimerized in the dark, and binds to the reaction element, but the illumination depolymerizes the dimer to be monomer, thus weakening the bind or make it no more, thus repressing or down-regulating the transcription.

The homology of six different LOV domains derived from photosensitive proteins was analysed by using Accelry Discovery Studio 2.1. These LOV domains are derived from VIVID (Nc_VVD), White-collar-1 (Nc_Wc1), FKF1 (At_FKF1), aureochrome1 (Vf_Aureo1_LOV), oat phototropin 1 (As_phot_LOV1 and As_phot_LOV2). Results showed that these proteins have about 15% identical amino acids and about 36% similar sequences (FIG. 1).

The first polypeptide and the second polypeptide can constitute a light-switchable DNA-binding fusion protein (abbreviated as DNA-binding protein). Light-switchable DNA-binding proteins can be used to research DNA-binding abilities of various recombinant light-switchable transcription factors of the invention, especially, in vitro researches of DNA-binding ability of the complete DNA-binding domain constructed by the first polypeptide and the second polypeptide and its binding properties such as binding constants, the kinetics of the recovery of dimer to monomer, etc. The selected DNA-binding proteins are used to connect to the third polypeptide to constitute the transcription factors. In a particular embodiment, the first polypeptide in the light-switchable DNA-binding protein is Gal4 (1-65), the second polypeptide is wild type VIVID-36, Gal4-VIVID (WT) fusion protein (abbreviated as GAV (WT) (its nucleic acid and amino acid sequences are SEQ. ID. NO:84 and SEQ. ID. NO:85, respectively) has spectral properties similar to those of VIVID protein, and its DNA-binding ability is regulated by illumination. Its DNA-binding levels before and after illumination are significantly different, that is, the fusion protein in a high concentration can bind to the probe with a weak binding affinity in the dark, but it shows binding ability to the probe in all used protein concentration range after illumination.

The recombinant light-switchable transcription factor can contain the third polypeptide which is a transcriptional regulatory domain, a transcriptional activation domain (abbreviated as AD) or a transcriptional repression domain. The third polypeptide of the invention is used as a transcriptional activation domain or a transcriptional repression domain including, but not limited to, acidic amino acid-rich transcriptional activation domain (such as AD of VP16 and Gal4), proline-rich transcriptional activation domain (such as 399-499 amino acid residues of CTF/NF1), serine/threonine-rich transcriptional activation domain (such as 1-427 amino acid residues of ITF1) and glutamine-rich transcriptional activation domain (175-269 amino acid residues of Oct1), of which amino acid sequences and other useful transcriptional activation domains was described by Seipei et al [Seipel, K., Georgiev, O. and Schaffner, W., EMBO J, 1992. 11(13), 4961-4968 (1992)]. In addition, the sequence of Kruppel related box (KRAB) transcriptional repression domain has been reported [Peng, H. et al, J Biol Chem, 2000. 275(24): 18000-18010].

In embodiments of the invention, the third polypeptide is selected from VP16 transcriptional activation domain (abbreviated as VP16AD, its nucleic acid and protein sequence are SEQ. ID. NO:51 and SEQ. ID. NO:52, respectively), Gal4 transcriptional activation domain (abbreviated as Gal4AD, its nucleic acid and protein sequence are SEQ. ID. NO:53 and SEQ. ID. NO:54, respectively), the transcriptional activation domain of the general control protein (Gcn4AD, its nucleic acid and protein sequence are SEQ. ID. NO:95 and SEQ. ID. NO:96, respectively), the transcriptional activation domain of NF-κB p65 protein (abbreviated as p65AD, its nucleic acid and protein sequence are SEQ. ID. NO:49 and SEQ. ID. NO:50, respectively) and KRAB transcriptional repression domain of zinc finger protein 354A (its nucleic acid and protein sequence are SEQ. ID. NO:55 and SEQ. ID. NO:56, respectively). The two subunits of NF-κB protein often form homogeneous or heterogeneous dimer, most commonly, p65/p50 dimer or p65/p65 dimer; and the transcriptional activation domain of p65 subunit has been widely used to constitute various systems to induce gene expression with good effect [Wang, Y. et al., Gene Ther 1997.4(5), 432-441]. The transcriptional activation domain (AD) of Gal4 protein is mainly located in 768-881 amino acids of the C-terminal, among which many acidic amino acids can recruit other transcription accessory proteins in *Saccharomyces cerevisiae* cells to co-active the promoter, thus resulting in the transcription of the related gene [Shimizu-Sato, S., Huq, E., Tepperman, J. M., and Quail, P. H., Nat Biotechnol, 2002.20 (10), 1041-1044]. The transcriptional activation domain of yeast Gcn4 is mainly located in 1-144 amino acids of the N-terminal of Gcn4 protein, and it recruits other transcription accessory proteins in *Saccharomyces cerevisiae* cells to co-active the promoter, thus resulting in the transcription of the related gene [Drysdale, C. M. et al., Mol Cell Biol, 1995. 15(3):1220-1233]. VP16 is a viral intermediate layer protein composed of 490 amino acid residues expressed by UL48 structural gene in herpes simplex virus HSV-1. The acidic amino acid-rich C-terminal of VP16 is a transcriptional activation domain which has been successfully used in a variety of gene expression systems [Gossen, M. and H. Bujard et al., Proc Natl Acad Sci USA, 1992. 89(12): 5547-5551]. In preferred embodiments of the invention, transcriptional activation domains of VP16, NF-κB p65, Gal4 and Gcn4, and KBAB transcriptional repression domain of zinc finger protein 254A are used as the third polypeptide, respectively.

The recombinant light-switchable transcription factor fusion protein can also contain the fourth polypeptide, which is a nuclear localization signal peptide useful for promoting the transportation of the fusion protein into the nucleus. If all the first, second and third polypeptides contain no nuclear localization signal (NLS), the fourth polypeptide can be added. The nuclear localization signal peptide typically comprises a basic amino acid segment. The preferable nuclear localization signal peptide is that of Simian vacuoles virus 40 (SV40 NLS) [Fanara, P. et al., J Biol Chem, 2000. 275 (28): 21218-21223]. In one specific embodiment, the first polypeptide of the recombinant light-switchable transcription factor comprises Gal4 protein as a nuclear localization signal peptide, thus the fusion protein contains no the fourth polypeptide. In another specific embodiment, the fourth polypeptide link, directly or via a linker, with the first, the second, or the third polypeptides.

The recombinant light-switchable transcription factor fusion protein can further contain the fifth polypeptide, and the fifth polypeptide-containing recombinant light-switchable transcription factor fusion protein is also known as recombinant light-hormone double regulating transcription factor. In most cases, the fifth polypeptide is used to regulate the ability entering into nucleus, thus regulating the target gene expression in combination with illumination. The fifth polypeptide links, directly or via a linker, to the first, the second, or the third polypeptides. The fifth polypeptide includes, but not limited to, ecdysone receptor and its mutants, glucocorticoid receptor and its mutants, estrogen receptor and its mutants, and progesterone receptor and its mutants; preferably, *drosophila* ecdysone receptor and its mutants, *bombyx mori* ecdysone receptor and its mutants, human glucocorticoid receptor and its mutants, human estrogen receptor and its mutants, and human progesterone receptor and its mutants; more preferably, *bombyx mori* ecdysone receptor (V454I/Y474E) mutant, and human estrogen receptor (G400V/M543A/L544A) mutant. In one specific embodiment, the fifth polypeptide in the recombinant light-switchable transcription factor is the 272-606 amino acid sequence of *bombyx mori* ecdysone receptor (V454I/Y474E) mutant. In another specific embodiment, the fifth polypeptide is the 282-594 amino acid sequence of human estrogen receptor. In another specific embodiment, the fifth polypeptide is the 640-914 amino acid sequence of progesterone receptor.

As described above, there are various options for each of the third, fourth and fifth polypeptides contained in the recombinant light-switchable transcription factor and various combination options for the third, fourth and fifth polypeptides to be connected to become a fusion protein. The fragments of the functional domain of each polypeptide with good activity are preferably used for the preparation of the recombinant light-switchable transcription factor fusion protein. Recombinant light-switchable transcription factor with strong regulatory ability (i.e. large differences of its gene expression level during the illumination and in the dark), selected by the expression in mammalian cells or yeast cells, are used to regulate the expression of the nucleic acid sequence to be transcribed. Whatever choices and combinations are, they fall into the range of the invention provided the gene expression regulated by illumination is achieved.

The second portion of the photosensitive polypeptide-based light-switchable gene expression system is a target transcription unit (nucleotide sequence) composed of the reaction element (specifically recognized/bound by the transcription factor)-promoter-nucleotide sequence to be transcribed. Specifically, the reaction element, a nucleotide motif, is dependent on the first polypeptide selected to be used in the recombinant light-switchable transcription factor fusion protein. In other words, the reaction element, specific to the first polypeptide, must be selected based on the first polypeptide. For example, when the first polypeptide is the DNA recognition/binding domain of Gal4, LexA, LacI, TetR or cI proteins, the corresponding reaction element should be a motif of SEQ. ID. NO:67, 68, 69, 70 or 71. Target transcription unit contains one or more reaction elements, e.g., 1, 2, 3, 4 or 5 reaction elements, in specific embodiments. If the effect of more reaction elements is better, more reaction elements are selected.

The reaction element is usually linked operatively with a minimal promoter which is not enough to initiate gene transcription effectively. The minimal promoter, together with its upstream reaction element, must interact with members of transcription factors, so as to activate or up-regulate the transcription of the downstream target gene. Based on the analysis of related literatures, the available minimal promoters include, but not be limited to, the major late promoter of adenovirus (its nucleic acid sequence is SEQ. ID. NO:72), the minimal promoter of cytomegalovirus (CMV) (SEQ. ID. NO:75), GaL1 gene promoter of yeast (its nucleic acid sequence is SEQ. ID. NO:74). In specific embodiments of the invention, the minimal promoter is the major late promoter of adenovirus and GaL1 gene promoter of yeast, but other minimal promoters may also be used. The promoter linked operatively with the reaction element can also be a complete promoter, such promoter itself has the ability to initiate gene transcription, binding of transcription factor to the reaction element can enhance or repress the expression of downstream nucleic acid sequence to be transcribed. In another specific embodiment, the promoter is SV40 promoter (its nucleic acid sequence is SEQ. ID. NO:73). The person skilled in the art knows that so-called "operatively link" refers the connection between the reaction element and the promoter or among reaction elements is not a direct connection, but spaced by several nucleotides, provided the synergistic effect still exists.

In the target transcription unit of the invention, the downstream nucleotide sequence is a nucleotide sequence to be transcribed, a nucleotide sequence encoding the target protein or functional RNA. As above-mentioned, the target protein can be any useful protein. In order to verify the effects of the present system and to facilitate the detection, following exemplary report proteins have been used as target protein in the examples: firefly luciferase (Fluc, its nuclei acid and amino acid sequence are SEQ. ID. NO:76 and SEQ. ID. NO:77, respectively), Gaussian luciferase (Gluc, its nuclei acid and protein sequence are SEQ. ID. NO:78 and SEQ. ID. NO:79, respectively), Red fluorescent protein mCherry (its nuclei acid and protein sequence are SEQ. ID. NO:80 and SEQ. ID. NO:81, respectively), Green fluorescent protein (hrGFP, its nuclei acid and protein sequence are SEQ. ID. NO:82 and SEQ. ID. NO:83, respectively), yellow fluorescent protein (EYFP, its nuclei acid and protein sequence are SEQ. ID. NO:91 and SEQ. ID. NO:92, respectively), β-galactosidase (LacZ, its nuclei acid and protein sequence are SEQ. ID. NO:93 and SEQ. ID. NO:94, respectively). However, the target protein of the invention is not limited to these report proteins. The nucleotide sequence to be transcribed can also encode functional RNA molecules, such as antisense RNA molecule. Functional RNA molecules expressed in host or animal cells can regulate some activities within the host cells, for example, inhibit the mRNA translation, thus preventing the expression of target protein.

The first portion and the second portion of the light-switchable target protein gene expression system of the invention can be constituted in one eukaryotic expression vector or in two eukaryotic expression vectors, respectively, by using standard recombinant DNA technique. Such expression vectors can be introduced into various eukaryotic host cell population to express the interested target proteins, or introduced into various eukaryotic host cell population such as animal embryonic germ cells or plant germ cells to further selectively produce useful transgenic organisms such as transgenic goats, sheep, pigs, cattle or other livestock, or transgenic plants.

The expression system of the invention may be used for the expression of the endogenous or foreign proteins in the eukaryotic cells, for gene therapy and gene expression in transgenic or homologous recombinant organisms (e.g., animal or plant).

The present invention provides recombinant light-switchable transcription factor fusion proteins composed of three or four or five polypeptides, the encoding nucleic acids and the eukaryotic expression vectors containing same. In one embodiment of the invention, provided are the encoding nucleic acid sequence (SEQ. ID. NO:3), amino acid sequence (SEQ. ID. NO:4) and mammalian cell expression vector pGAVV (WT) of the recombinant light-switchable transcription factor Gal4-VIVID-VP16 (abbreviated as GAVV (WT). In another embodiment of the invention, provided are the encoding nucleic acid sequence (SEQ. ID. NO:31), amino acid sequence (SEQ. ID. NO:32) and mammalian cell expression vector pGAVP (WT) of the recombinant light-switchable transcription factor Gal4-VIVID-p65 (abbreviated as GAVP). In a preferable embodiment of the invention, provided are the encoding nucleic acid sequences (SEQ. ID. NO:33, 35, 39), amino acid sequences (SEQ. ID. NO:34, 36, 40) and mammalian cell expression vectors pGAVP(C71V), pGAVP (N56K) and pGAVP (Y50W) of three recombinant light-switchable transcription factors Gal4-VIVID-p65 wherein brackets are the mutation sites in VIVID. In another preferable embodiment of the invention, provided are the encoding nucleic acid sequence (SEQ. ID. NO:37), amino acid sequence (SEQ. ID. NO:38) and mammalian cell expression vector pGAVP (N56K+C71V) of the recombinant light-switchable transcription factor Gal4-VIVD-p65 containing double mutants in VIVID. In another embodiment of the invention, provided are the encoding nucleic acid sequence (SEQ. ID. NO:43), amino acid sequence (SEQ. ID. NO:44) and mammalian cell expression vector pGALP of the recombinant light-switchable transcription factor Gal4-AsLOV2-p65 (abbreviated as GALP). In another embodiment of the invention, provided are the encoding nucleic acid sequence (SEQ. ID. NO:47), amino acid sequence (SEQ. ID. NO:48) and mammalian cell expression vector pGAAP of the recombinant light-switchable transcription factor Gal4-AuLOV-p65 (abbreviated as GAAP). In another preferable embodiment of the invention, provided are the encoding nucleic acid sequences (SEQ. ID. NO:59, 61, 63), amino acid sequences (SEQ. ID. NO:60, 62, 64) and mammalian cell expression vectors pGAVP-9, pGAVP-11 and pGAVP-12 (wherein 9, 11, 12 represent different linker peptides) of three recombinant light-switchable transcription factors Gal4-VIVID-p65, wherein the connection between the first polypeptide and the second polypeptide is via different linker peptides. In another embodiment of the invention, provided are the encoding nucleic acid sequence (SEQ. ID. NO:57), amino acid sequence (SEQ. ID. NO:58) and mammalian cell expression vector pGAVK (C71V) of the recombinant light-switchable transcription factor Gal4-VIVID-KRAB (C71V) (abbreviated as GAVK(C71V)). In another embodiment of the invention, provided are the encoding nucleic acid sequence (SEQ. ID. NO:97, 99, 101, 103, 105 and 107, respectively), amino acid sequence (SEQ. ID. NO:98, 100, 102, 104, 106 and 108, respectively) and mammalian cell expression vector pGPMA-GVG-Ln (N56KC71V) of a group of the recombinant light-switchable transcription factor Gal4-VIVID-Gal4AD-Ln (N56K+C71V), wherein n is 1, 2, 3, 4, 5 or 6. In another embodiment of the invention, provided are the encoding nucleic acid sequence (SEQ. ID. NO:109), amino acid sequence (SEQ. ID. NO:110) and *Saccharomyces cerevisiae* expression vector pGPMA-GVVP(N56K+C71V) of the recombinant light-switchable transcription factor Gal4-

VIVID-VP16 (N56K+C71V) (abbreviated as GVVP (N56K+C71V)). In another embodiment of the invention, provided are the encoding nucleic acid sequence (SEQ. ID. NO:111), amino acid sequence (SEQ. ID. NO:112) and *Saccharomyces cerevisiae* expression vector pGPMA-GVGc (N56K+C71V) of the recombinant light-switchable transcription factor Gal4-VIVID-Gcn4 (N56K+C71V) (abbreviated as GVGc (N56K+C71V)). In another embodiment of the invention, provided are encoding nucleic acid sequences (SEQ. ID. NO:113, 115, 117, respectively), amino acid sequence (SEQ. ID. NO:114, 116, 118, respectively) and *Saccharomyces cerevisiae* expression vector pGPMA-GVG (WT), pGPMA-GVG (C71V) and pGPMA-GVG (Y50W) of a group of the recombinant light-switchable transcription factor Gal4-VIVID-Gal4AD containing a point mutation in VIVID. In another embodiment of the invention, provided are the encoding nucleic acid sequence (SEQ. ID. NO:119), amino acid sequence (SEQ. ID. NO:120) and *Saccharomyces cerevisiae* expression vector pGPMA-GLG of the recombinant light-switchable transcription factor Gal4-AsLOV2-Gal4AD (abbreviated as GLG). In another embodiment of the invention, provided are the encoding nucleic acid sequence (SEQ. ID. NO:7), amino acid sequence (SEQ. ID. NO:8) and *Saccharomyces cerevisiae* expression vector pGPMA-NLVG (N56K+C71V) of the recombinant light-switchable transcription factor NLS-LexA-VIVID-Gal4AD (N56K+C71V) containing the fourth polypeptide (abbreviated as NLVG (N56K+C71V)). In another embodiment of the invention, provided are the encoding nucleic acid sequence (SEQ. ID. NO:19), amino acid sequence (SEQ. ID. NO:20) and *Saccharomyces cerevisiae* expression vector pGPMA-NCVG (N56K+C71V) of the recombinant light-switchable transcription factor NLS-cI-VIVID-Gal4AD (N56K+C71V) containing the fourth polypeptide (abbreviated as NCVG (N56K+C71V)). In another embodiment of the invention, provided are the encoding nucleic acid sequence (SEQ. ID. NO:11), amino acid sequence (SEQ. ID. NO:12) and *Saccharomyces cerevisiae* expression vector pGPMA-NLcVG (N56K+C71V) of the recombinant light-switchable transcription factor NLS-LacI-VIVID-Gal4AD (N56K+C71V) containing the fourth polypeptide (abbreviated as NLcVG (N56K+C71V)). In another embodiment of the invention, provided are the encoding nucleic acid sequence (SEQ. ID. NO:15), amino acid sequence (SEQ. ID. NO:16) and *Saccharomyces cerevisiae* expression vector pGPMA-NTVG (N56K+C71V) of the recombinant light-switchable transcription factor NLS-TetR-VIVID-Gal4AD (N56K+C71V) containing the fourth polypeptide (abbreviated as NTVG (N56K+C71V)). It is known in the art that the codons of amino acid, nucleotides, have degeneracy, i.e. certain amino acids have two or three or four codons which are known as degenerate codons of amino acid. The present invention includes all the respective degenerate nucleotide sequences. In the case of the amino acid sequences of above-mentioned various recombinant light-switchable transcription factors, the present invention includes all their respective amino acid sequence analogs containing conserved deletions, additions, substitutions modified but still retains their original function and activation.

The invention also provides the eukaryotic expression vector containing the reaction element-promoter but leaving a vacancy for the nucleic acid sequence to be transcribed. This vacant location for the nucleic acid sequence can be replaced with the interested nucleotide sequence selected by the user himself, such as the gene encoding the target protein which is inserted into the expression vector of the invention by using standard recombinant DNA techniques, then this expression vector and above-mentioned expression vector containing the gene of the recombinant light-switchable transcription factor are used to co-transfect host cells for the regulation of the expression of the nucleotide sequence (gene) to be transcribed.

The invention also provides mammalian cells transfected with eukaryotic expression vectors containing genes encoding various recombinant light-switchable transcription factors, and provides eukaryotic expression vectors containing the target transcription unit composed of the reaction component-promoter, but leaving an vacancy for the nucleotide sequence to be transcribed. The nucleotide sequence to be transcribed (target protein gene) selected by the user himself can be inserted into said vector by using standard recombinant DNA techniques, then this re-constructed vector can be used to transfect mammalian cells already transfected by the eukaryotic expression vector containing the recombinant light-switchable transcription factor. These mammalian cells can be cultured to express the interested gene or to study how to regulate the expression of the target gene.

The present invention further provides a kit containing the expression vectors comprising two portions of the gene expression regulation system of the invention or the mammalian cells already transfected by these vectors. In one embodiment, some containers in the kit are filled, respectively, with the eukaryotic expression vector(s) containing one or more recombinant light-switchable transcription factor genes. In another embodiment, some containers in the kit are filled, respectively, with the eukaryotic expression vector(s) containing one or more recombinant light-switchable transcription factor genes, other containers are filled with the eukaryotic expression vector(s) containing the target transcription unit composed of the corresponding reaction component-promoter but leaving a vacancy for the nucleotide sequence to be transcribed. In a further embodiment, some containers in the kit are filled with mammalian cells already transfected with eukaryotic expression vectors containing the recombinant light-switchable transcription factor genes, other containers are filled with eukaryotic expression vectors containing the target transcription unit composed of the corresponding reaction component-promoter but leaving a vacancy for the nucleotide sequence to be transcribed.

The kit of the invention can also contain appropriate illumination control devices, such as LED lamp and its control devices. All kits of the invention will be equipped with a direction for the description of each component, its intended use and methods of application and provide relevant reference catalog.

The invention further provides a method for the regulation of gene expression in host cells using the light-switchable gene expression system, comprising following steps:

a) constructing the light-switchable gene expression system in eukaryotic plasmid expression vectors;

b) introducing the construct into host cells containing the gene being regulated; and c) inducing host cells via illumination to express the nucleotide being regulated.

The illumination method for inducing the gene expression in host cells comprising: selection and application of light sources. The light sources include, but not are limited to, LED lamp, incandescent lamp, fluorescent lamp and laser. In one embodiment of the invention, blue LED (460-470 nm) is selected as the light source. The illumination methods include illumination quantity, time, intensity and frequency as well as the spatial expression control of the target gene via scan, projection, optical molds, etc. They are also comprised in the range of the invention. In one embodiment of the invention, the illumination intensities are varying within 0-0.8 W/m². In another embodiment of the invention, the total illumination quantity are different, i.e., when the illumination intensity and total illumination time are identical, illumination induction are carried out for 1 s illumination every 30 s, is illumination every 60 s and 1 s every 120 s, respectively. In another embodiment of the invention, the cellular target gene expression in different locations is regulated in the space using the printing projection film as a light mold. In another embodiment of the invention, the cellular target gene expression in different locations is regulated in the space using the neutral gray film as a light mold.

The invention further provides a method for the gene therapy of type I diabetes, comprising treating a mammal (including a human) in need of treatment with the light-switchable gene expression system of the invention.

PREFERABLE EMBODIMENTS

Figures 1, 2:
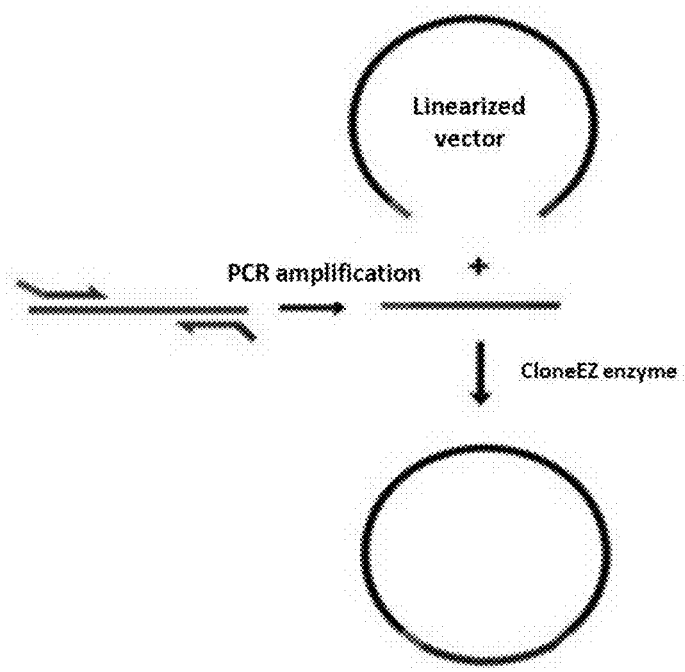
FIG. 1 shows homology analysis of LOV domains derived from six photosensitive proteins, wherein the black color represents 100% homologous amino acid sequence, the dark grey represents the higher homologous sequences and french gray represents the medium homologous Sequences.
FIG. 2 is a schematic diagram of homologous recombination ligation.

The invention will be described in detail by using following examples. These examples are only used for the illustration of the invention without any restriction on the scope of protection. It is not difficult for those skilled in the art to successfully implement the invention on the basis of the examples with some modifications or alternatives. All these modifications or alternatives are within the scope of the attached claims.

Methods, Equipment and Regents Used in the Examples

The methods used in the samples were the routine methods of molecular biology cloning in genetic engineering and cell biology field, such as: 《Lab Ref: A handbook of Recipes, Reagents, and Other Reference Tools for Use at the Bench》 written by Roskams, J. et al, 《Molecular Cloning: A Laboratory Manual》 (the third edition, August in 2002, Science press, Beijing) written by Sambrook J and Russell D W, and translated by Peitang Huang et al.; Chapters in book 《Short protocols in Protein Science》 (Science press, background) written by Coligan J. E. et al, and translated by Shentao Li et al.

Eukaryotic expression vectors pEGFP-N1, pGADT7 and pGBKT7 were purchased from Clontech; pcDNA3.1 (+)-hygro and pYES2.1 TOPO were purchased from Invitrogen; and pG5luc, pBIND and pACT were purchased from Promega. pcDNA3.1 (+)-hygro and pEGFP-N1, both containing CMV promoter, were used to construct eukaryotic expression vectors that could express target gene in mammalian cells, pcDNA3.1 (+)-hygro had hygromycin resistance while pEGFP-N1 had neomycin resistance. pGADT7 contained the gene of Gal4 transcriptional activation domain, pBIND contained the gene of DNA binding domain of Gal4 from yeast, and pACT contained the gene of VP16 transcriptional activation domain. pG5luc contained Gal4 operon, TATA minimal promoter and firefly luciferase Fluc gene. pIRES-hrGFP (purchased from Stratagene) contained hrGFP gene, pGluc-basic from NEB contained Gluc gene, pTRIPZ from Openbiosystem contained the sequence of SV40 promoter and pCDFDuet1 from Novagen contained LacI gene.

All the primers were synthesized, purified and identified via mass spectrometry by Shanghai Generay Biotech Co. Ltd. All the vectors obtained in the examples were verified via sequencing by BGI Company. Taq DNA polymerase used in the examples was purchased from DongSheng Biotech Company; pfu DNA polymerase was purchased from TianGen Biotech (Beijing) Co. LtD., and PrimeStar DNA polymerase was purchased from TaKaRa. All the three polymerases contained corresponding buffer and dNTP when purchased. Restriction enzyme such as BsrGI, Eco47III, BglII, PstI, HindIII, BamHI, et al., T4 ligase and T4 phosphatase (T4 PNK) were purchased, together with 10×Tango™ buffer, from Fermentas. CloneEZ PCR clone kit was purchased from GenScript (Nanjing). Unless otherwise mentioned, inorganic salt chemical reagents were purchased from Sinopharm Chemical Reagent Co.; Kanamycin, Ampicillin, PNPG, Streptozotocin (STZ) and Dithiothreitol (DTT) were purchased from Ameresco; Flavin adenosine dinucleotide (FAD), ATP and Imidazole were purchased from Alfa; Gluc-detecting kit was purchased from NEB. Potassium Salt of D-Luciferin was purchased from Synchem; EGTA was purchased from BBI; Trizol regent, Trpsin-EDTA, FBS, Lipofectamine2000, L-glutamine, sodium pyruvate, Opti-mem medium, Penicillin/Streptomycin-resistant antibiotics were purchased from Invitrogen; and amino acids was purchased from Sinopharm Chemical Reagent Co. unless mentioned, disposable equipments for cell culture were purchased from Corning. 20 mm diameter dishes for cell culture with glass bottom were purchased from NEST; 384 well white plates for luminescence detection and 384 well black plates for fluorescene detection were purchased from Grenier; and 96 well quadrate plates for cell culture was purchased from GE.

The kit for DNA purification was purchased from BBI (Canada); common plasmid kit was purchased from TianGen Biotech (Beijing) Co. LtD.; transfection grade plasmid kit was purchased from Omega; RNA extraction kit was purchased from TianGen Biotech (Beijing) Co. LtD.; ImpromIIreverse transcription kit was purchased from Promega company; DC protein assay kit was purchased from Bio-rad; E. coli strain Mach1 was purchased from Invitrogen; E. coli strain JM109 was purchased from Promega; E. coli strain BL21(DE3) was purchased from Novagen; and HEK293, COS-7 and NIH3T3 cell lines were purchased from American Type Culture Collection (ATCC). Neurospora crassa was a gift of Bin Chen from School of Resources and Environment Science in Guangxi Normal University. AH109 strain was purchased from Clontech; BY4741 strain was purchased from Openbiosystem Company; Tebufenozide and 4-OHTamxoifen was purchased from Sigma and Mifepristone was purchased from Cayman.

Main equipments: Biotek Synergy 2 multi-mode microplate reader (BioTek, US), X-15Rhigh speed refriger (Beckman, US), Microfuge22Rhigh speed refriger (Beckman, US), PCR Amplifier (Biometra, Germany), In-Vivo Multispectral System FX (Kodak, US), Luminometer (Sanwa, Japan), electrophoresis apparatus (shanghai Biocolor BioScience & Technology Co.), Eclipse Ti inverted microscope system (Nikon, Japan), four-use ultraviolet analyzer (Shanghai Jiapeng Co.), ACCU-CHEK Integra Glucose Meter (Roche).

The meaning of abbreviations: h=hour, min=minute, s=second, μL=microliter, mL=milliliter, L=liter, bp=base pair, mM=millimole, μM=Micromolar.

Some sequences used in the examples were obtained from NCBI (National Center for Biotechnology Information) or official websites or websites of companies selling commercial vectors with corresponding genes. Websites for searching gene sequences are as follows:

Gluc (Gaussia luciferase): (http://www.ncbi.nlm.nih.gov/protein/AAG54095.1);

hrGFP (humanized Renilla Green Fluorescent Protein): (http://www.ncbi.nlm.nih.gov/nuccore/AY613996.1);

Fluc (firefly luciferase): (http://www.promega.com/vectors/pG5luc.txt);

Gal4: (http://www.ncbi.nlm.nih.gov/nuccore/NC_001148?report=genbank&from=79711&to=82356&strand=true)

VP16 (herpes simplex virus VP16 protein): (http://www.promega.com/vectors/pACT.txt);

NF-κB p65: (http://www.ncbi.nlm.nih.gov/nuccore/23958349?report=GenBank);

VIVID: (http://www.ncbi.nlm.nih.gov/nuccore/AF338412.1);

Phototropin1: (http://www.ncbi.nlm.nih.gov/nucleotide/2754822?report=genbank&log$=nucltop&blast_rank=1&RID=P49RPCAR01S);

Aureochrome1: (http://www.ncbi.nlm.nih.gov/nuccore/AB252504.1);

Gcn4: (http://www.ncbi.nlm.nih.gov/nuccore/NC_001137?report=genbank&from=138918&to=139763&strand=true);

LacI (repressor from Lac operon): (http://www.ncbi.nlm.nih.gov/nuccore/NC000913?report=genbank&from=365652&to=366734&strand=true);

LexA: (http://biocyc.org/ecoli/sequence?type=GENE&object=EG10533);

EYFP (enhanced yellow fluorescent protein): (http://www.ncbi.nlm.nih.gov/protein/37551795);

BmEcR (Bombyx mori ecdysone receptor):
http://www.ncbi.nlm.nih.gov/nucleotide/290560663?report=genbank&log$=nuchop&blast_rank=2&RID=K3Z8WXTW01R;

hPR (human progesterone receptor):
http://www.ncbi.nlm.nih.gov/nucleotide/321117149?report=genbank&log$=nucltop&blast_rank=1&RID=K3ZDKTB901R; and ER (estrogen receptor):
http://www.ncbi.nlm.nih.gov/nucleotide/170295798?report=genbank&log$=nuchop&blast_rank=1&RID=K3ZPW1MT01R.

Other gene sequences used in the examples were obtained from NCBI (National Center for Biotechnology Information) or Uniprot (Universal Protein Resource), and then were transferred to nucleotide sequences according to the codon preference of each species using software DNA design 2.0. Websites of searching gene sequences are:

cI (repressor of λ operon) (http://www.uniprot.org/uniprot/P03034);

TetR (Tn10 B class) (http://www.uniprot.org/uniprot/P04483); and mCherry (http://www.ncbi.nlm.nih.gov/nuccore/AY678264.1).

Figure 3:
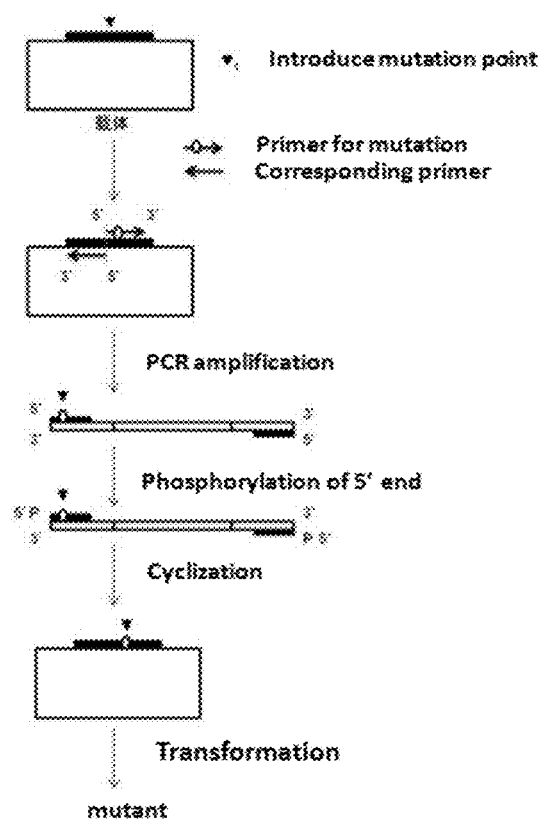
FIG. 3 shows the principle of reverse PCR.
Figure 4:
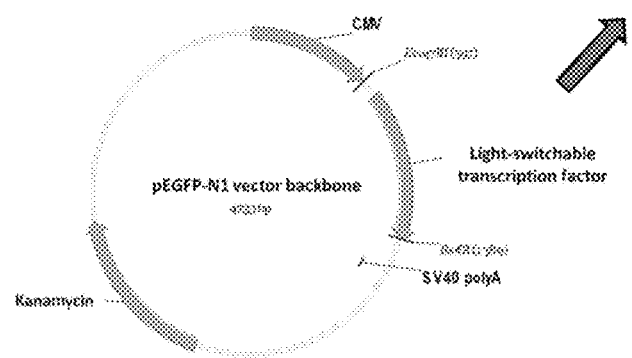
FIG. 4 is a schematic diagram of construction of mammalian cell expression vectors containing the light-switchable transcription factor. Top panel is schematic diagram of the light-switchable transcription factor fusion protein. Bottom panel is schematic diagram of orbicular expression vectors, wherein the backbone of these vectors is pGFP-N1, and the intrinsic EGFP gene was replaced with the light-switchable transcription factor gene. * represents the different linker peptides for two polypeptides.

Example 1: Construction of Mammalian Cell Expression Vectors Containing the Recombinant Light-Switchable Transcription Factors Using VP16, p65 or KRAB as the Third Polypeptide Plasmids construction of this example is shown in FIG. 4. The Gal4 (1-65 amino acid) gene was amplified from pBIND (Promega) by PCR using primer P1, P2; The VP16 gene was amplified from pACT (Promega) by PCR using primer P3, P4. After extracting the genomic DNA of Neurospora crassa by using Trizol Kit (Invitrogen), the intact VIVID gene was amplified by using primers P5 and P6. The resulted VIVID gene contained two introns. Then introns were removed by reverse PCR (see FIG. 3) using primer P7, P8, P9 and P10 as primers to obtain cDNA (SEQ ID NO: 21). Gal4, VIVID-36 and VP16 genes were fused by overlap PCR (see FIG. 8), and inserted into pEGFP-N1 vector (Clontech) by Eco47III and BsrGI digestion, the resulted mammalian cell expression vectors was named pGAVV (WT), which contains the fusion protein gene of recombinant light-switchable transcription factor Gal4-VIVID-VP16 (GAVV(WT)) (SEQ. ID. No:3 (polynucleotide) and 4 (polypeptide)), of which VIVID was 1-36 amino acid truncation form VIVID-36, and the other place mentioned is truncation form VIVID-36 as well. There is a BglII site between Gal4 and VIVID, and an EcoRI site between VIVID and VP16.

Primers for the amplification of Gal4 gene:

```
Forward primer (P1):
5'-CTTTTGGATCCAAGCGCTATGAAGCTACTGTCTTCTATCGAACA-3'

Reverse primer (P2):
5'-AGATCTGGTGGCGATGGATCTTTCCAGTCTTTCTAGCCTTGATT
C-3'
```

Primers for the amplification of VP16 gene:

```
Forward primer (P3):
5'-CAGTACCCATACGATGTTCCAGATTACGCTGAATTCCCGGGGATCTC
GAC-3'

Reverse primer (P4):
5'-AGAAATTCGAATGTACATGGCGATCCCGGACCC-3'
```

Primers for the amplification of VIVID gene:

```
Forward primer (P5):
5'-AGATCCATCGCCACCAGATCTCATACGCTCTACGCTCCCG-3'

Reverse primer (P6):
5'-TCTGGAACATCGTATGGGTACTGCAGTTCCGTTTCGCACTGGAAA
C-3'
```

Primers for removing introns of VIVID gene:
Removing the first intron:

```
Forward primer (P7)
5'-CAATACCACTATGACCCTCGAACCGCGCCC-3'

Reverse primer (P8):
5'-CTGATACGCCTCAACCTCCCATGGGTTCAT-3'
```

Removing the second intron:

```
Forward primer (P9)
5'-ATTCAGATTATGAACAGGCCAAACCCCC-3'

Reverse primer (P10):
5'-CAGATAGCCCATAATGTCATAACCGCCG-3'
```

For subcloning the recombinant light-switchable transcription factor with p65 transcriptional activation domain as the third polypeptide, total mRNA was extracted from HEK293 cells by using Trizol reagent (Invitrogen) and converted into cDNA by using ImpromII reverse transcriptase (Promega). P65AD of NF-κB P65 gene was amplified by using primers P11 and P12 (see FIG. 9), and the plasmid pGAVV(WT) constructed in this sample was double digested by using EcoRI and BsrGI. Then the VP16 gene was replaced with p65AD gene, and the resulting mammalian cell expression vector was named pGAVP(WT), which contains the fusion protein gene of Gal4-VIVID-p65 (GAVP (WT)) (SEQ. ID. No:31 (polynucleotide) and 32 (polypeptide)).

Primers for the amplification of p65 gene:

```
Forward primer (P11):
5'-GAATTCCAGTACCTGCCAGATACAG-3'

Reverse primer (P12):
5'-TGTACATTAGGAGCTGATCTGACTCAGCAG-3'
```

The artificial KRAB gene with EcoRI and BsrGI sites was synthesized by Generay Company (Shanghai) for subcloning recombinant light-switchable transcription factor with KRAB transcription repression domain as the third polypeptide. P65AD of pGAVP(C71V) described in example 2 was substituted with KRAB gene by double digestion, resulting mammalian cell expression vector named pGAVK (C71V), which contains the fusion protein gene of recombinant light-switchable transcription factor Gal4-VIVID-KRAB (C71V) (GAVK(C71V)) (SEQ. ID. No:57 (polynucleotide) and 58 (polypeptide)).

All the constructs were verified by DNA sequencing. Plasmids were prepared in transfection grade.

Example 2: Construction of Mammalian Cell Expression Vectors Containing the Recombinant Light-Switchable Transcription Factors Using VIVID Mutants or AsLOV2 or AuLOV as the Second Polypeptide Refer to FIG. 4 for the plasmid construction of this example. VIVID of pGAVP (WT) described in example 1 was mutated into C71V or Y50W or N56K by reverse PCR using primers 13, 14, 15, 16, 17 and 18, the resulting mammalian cell expression vectors were named as pGAVP (C71V) (SEQ. ID. No:33 (polynucleotide) and 34 (polypeptide)), pGAVP (Y50W) (SEQ. ID. No:35 (polynucleotide) and 36 (polypeptide)) and pGAVP (N56K) (SEQ. ID. No:37 (polynucleotide) and 38 (polypeptide)), respectively.

Primer sequences was as follows:

```
pGAVP (C71V):
Forward primer (P13):
5'-GTTGCTCTGATTCTGTGCG-3'

Reverse primer (P14):
5'-TGACGTGTCAACAGGTCCC-3' pGAVP (Y50W):
Forward primer (P15):
5'-GCTGATTCAGATTATGAACAGGC-3'

Reverse primer (P16):
5'-CAGCCCATAATGTCATAACCGC-3' pGAVP (N56K):
Forward primer (P17):
5'-GAGGCCAAACCCCCAAGTAG-3'

Reverse primer (P18):
5'-TTCATAATCTGAATCAGATAGCCC-3'
```

GAVP (C71V) was constructed firstly and N56K mutation was introduced into VIVID (C71V) of GAVP (C71V) to obtain a double mutant-containing plasmid pGAVP (N56K+ C71V) Recombinant light-switchable transcription factor GAVP (C71V), GAVP (N56K), GAVP (N56K+C71V) and GAVP (Y50W) fusion proteins have sequences of polypeptide, SEQ. ID. No: 34, 36, 38, 40, respectively, and the corresponding sequences of polynucleotide are SEQ. ID. No: 33, 35, 37, 39, respectively.

Figures 8, 9, 10, 11:
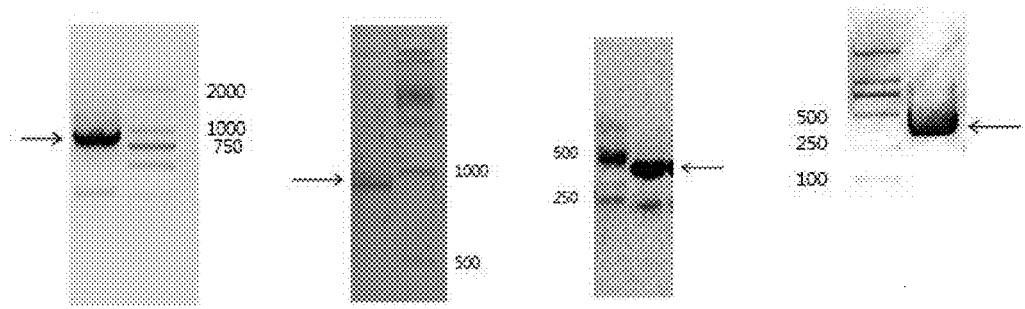
FIG. 8 is the agrose gel electrophoresis result of the overlap PCR product of Gal4, VIVID (WT) or VP16. Left arrow points to the target band of overlap PCR product, and the right bands are the DNA maker.
FIG. 9 is the agrose gel electrophoresis result of the p65AD amplified by PCR. The left arrow points to the target band of PCR product, and the right bands are the DNA maker.
FIG. 10 is the agrose electrophoresis result of the AsLOV2 amplified by PCR. The right arrow points to the target band of PCR product and the left bands are the DNA maker.
FIG. 11 is the agrose electrophoresis result of the AuLOV amplified by PCR. The right arrow points to the target band of PCR product, the left bands are the DNA maker.

For subcloning the recombinant light-switchable transcription factor with LOV2 domain of phototropin 1 (AsLOV2, a kind gift from Gardner lab, The University of Texas at Dallas) as the second polypeptide, AsLOV2 was PCR amplified using primers 19 and 20 (see FIG. 10). VIVID of pGAVP(WT) was replaced with AsLOV2 by using BglII and EcoRI digestion, and the resulting mammalian cell expression vector containing Gal4-AsLOV2-p65 fusion protein gene was named as pGALP (SEQ. ID. No:43 (polynucleotide) and 44 (polypeptide)).

Primers for the amplification of AsLOV2:

```
Forward primer (P19):
5'-CTTTAGATCTTTCTTGGCTACTACACTTGAAC-3'

Reverse primer (P20):
5'-CTTTGAATTCACCTGATCCGCCACCAAGTTCTTTTGCCGCCTC-3'
```

For subcloning the recombinant light-switchable transcription factor with LOV domain of Aureochrome (AuLOV, a kind gift from Hironao Kataoka lab, Ritsumeikan University) as the second polypeptide, AuLOV was PCR amplified by using primers 21 and 22 (see FIG. 11). VIVID of pGAVP (WT) was replaced by AuLOV by BglII and EcoRI digestion, the resulting mammalian cell expression vector was named as pGAAP, and the fusion protein was GAAP (SEQ. ID. No:47 (polynucleotide) and 48 (polypeptide)).

Primers for the amplification of AuLOV:

```
Forward primer (P21):
5'-CTTTAGATCTCAGAATTTTGTGATAACTGAT-3'

Reverse primer (P22):
5'-CTTTGAATTCCACTAGCAACTTGGCGTAATC-3'
```

Example 3: Construction of Mammalian Cell Expression Vectors Containing the Recombinant Light-Switchable Transcription Factors Using Different Linkers Between the First Polypeptide and Second Polypeptide Refer to FIG. 4 for the plasmid construction of this example. Linker between the first polypeptide and the second polypeptide of pGAVP (WT) described in Example 2 was optimized. pGAVP(WT) was amplified by reverse PCR using primers 23-28 to add different linkers between the first peptide and the second peptide, the resulting mammalian cell expression vectors were named as pGAVP(WT)-9, pGAVP(WT)-11 and pGAVP(WT)-12 containing recombinant light-switchable transcription factor GAVP(WT)-9 (SEQ. ID. No:59 (polynucleotide) and 60 (polypeptide)), pGAVP(WT)-11 (SEQ. ID. No:61 (polynucleotide) and 62(polypeptide)), pGAVP(WT)-12 (SEQ. ID. No:63 (polynucleotide) and 64 (polypeptide)), respectively.

Primer sequences were as follows:

```
pGAVP (WT)-9
Forward primer (P23):
5'-AGATCCATCGCCACCAGATCTCATACGCTCTACGCTCCCG-3'
```

```
-continued
Reverse primer (P24):
5'-CTTCCAGTCTTTCTAGCCTTGATTC-3' pGAVP (WT)-11
Forward primer (P25):
5'-AGATCCATCGCCACCAGATCTCATACGCTCTACGCTCCCG-3'

Reverse primer (P26):
5'-GGATCCTCCACCACCTTCCAGTCTTTCTAGCCTTGATTC-3' pGAVP (WT)-12
Forward primer (P27):
5'-TCATGAACCACAGATCTCATACGCTCTACGCTCCCGGCG-3'

Reverse primer (P28):
5'-CTTTCTGTTTCAGGTCGTTTTCCAGTCTTTCTAGCCTTG-3'
```

All the constructs were verified by DNA sequencing. Plasmids were prepared in transfection grade.

Example 4: Construction of Mammalian Cell Expression Vectors Containing Transcription Units (with Different Target Gene)

Figure 5:
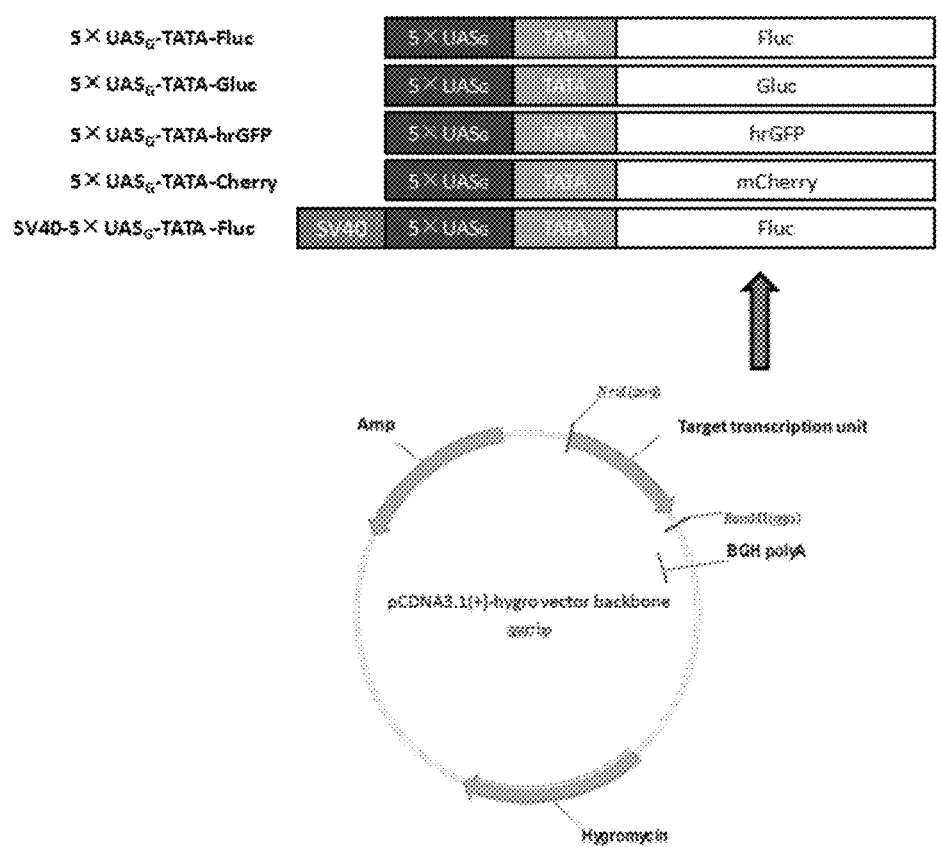
FIG. 5 is a schematic diagram of construction of mammalian cell expression vectors containing the target transcription unit. Top panel is a schematic diagram of respective target transcription units, and the bottom panel is a schematic diagram of orbicular expression vectors. The backbone of these vectors is pcDNA3.1 (+)-hygro, and the intrinsic CMV promoter and multiple clone sites were replaced with the target transcription units.

Refer to FIG. 5 for the plasmid construction of this example. For constructing expression vector containing the transcription unit with Gluc reporter gene, 5×UAS$_G$-TATA was amplified from pG5luc vector (Promega) (TATA is short for adenoviral E1b promoter) and Gluc gene was amplified from pGluc-basic (NEB), these two segment were fused by overlap PCR and ligated into NruI/BamHI site of pcDNA3.1 (+)-hygro by homologous recombination. At the meanwhile, the CMV promoter of pcDNA3.1(+)-hygro was removed, the resulting vector pU5Gluc contains the transcription unit 5×UAS$_G$-TATA-Gluc (SEQ. ID. No:89 (polynucleotide)).

Expression vectors containing transcription units having Fluc, green fluorescent protein hrGFP or red fluorescent protein mCherry reporter gene were constructed as follows:

Gluc gene of pU5Gluc vector has HindIII/BamHI restriction site at its two ends. Fluc gene of pG5luc was double digested by HindIII/BamHI and then ligated into pU5Gluc to obtain reporter vector pU5Fluc containing the transcription unit 5×UAS$_G$-TATA-Fluc with Fluc reporter gene (SEQ. ID. No:86 (polynucleotide)).

Similarly, hrGFP and mCherry genes were amplified from pIRES-hrGFP (Stratagene) and synthesized mCherry gene using primers P29-30 and P31-32, respectively, and inserted into pU5Gluc by HindIII/BamHI double digestion to obtain vectors pU5hrGFP and pU5mCherry, which contain transcription units 5×UAS$_G$-TATA-hrGFP and 5×UAS$_G$-TATA-mCherry (SEQ. ID. No:87 (polynucleotide) and SEQ. ID. No:88 (polynucleotide)), respectively.

Primers for the amplification of hrGFP:

```
Forward primer (P29):
5'-CTTAAGCTTGCCACCATGGTGAGCAAGCAGATCCTG-3'

Reverse primer (P30):
5'-CAAGGATCCTTACACCCACTCGTGCAGGC-3'
```

Primers for the amplification of mCherry:

```
Forward primer (P31):
5'-CTTAAGCTTGCCACCATGGTGAGCAAGGGCGAG-3'

Reverse primer (P32):
5'-CAAGGATCCCTACTTGTACAGCTCGTCCATG-3'
```

For constructing expression vector containing the transcription unit with Simian virus 40 (SV40) promoter, SV40 promoter was amplified from pTRIPZ vector (Openbiosystem) using primers 33 and 34, and the obtained SV40 promoter fragment was inserted into pG5luc vector, which was digested with KpnI, by homologous recombination. The resulting vector pSU5Fluc contains the transcription unit with SV40 promoter (SEQ. ID. No:90 (polynucleotide)).

```
Forward primer (P33):
5'-TCGATAGGTACCCTGTGGAATGTGTGTCAGTTAGGGT-3'

Reverse primer (P34):
5'-TCCGTCTAGAAACTCGGTACCAGCTTTTTGCAAAAGCCTAGGC-3'
```

For constructing the expression vector containing the transcription unit with Insulin gene, Insulin gene containing HindIII and BamHI sites at its two ends was synthesized by Shanghai Generay Biotech Co. Ltd. pU5GLuc constructed in this sample was double digested by HindIII/BamHI sites and then the Gluc gene was replaced with Insulin gene, resulting the vector named pU5-Insulin (SEQ. ID. No:137 (polynucleotide), SEQ. ID. No:138 (polypeptide)).

All the constructs were verified by DNA sequencing. Plasmids were prepared in transfection grade.

Figure 6:
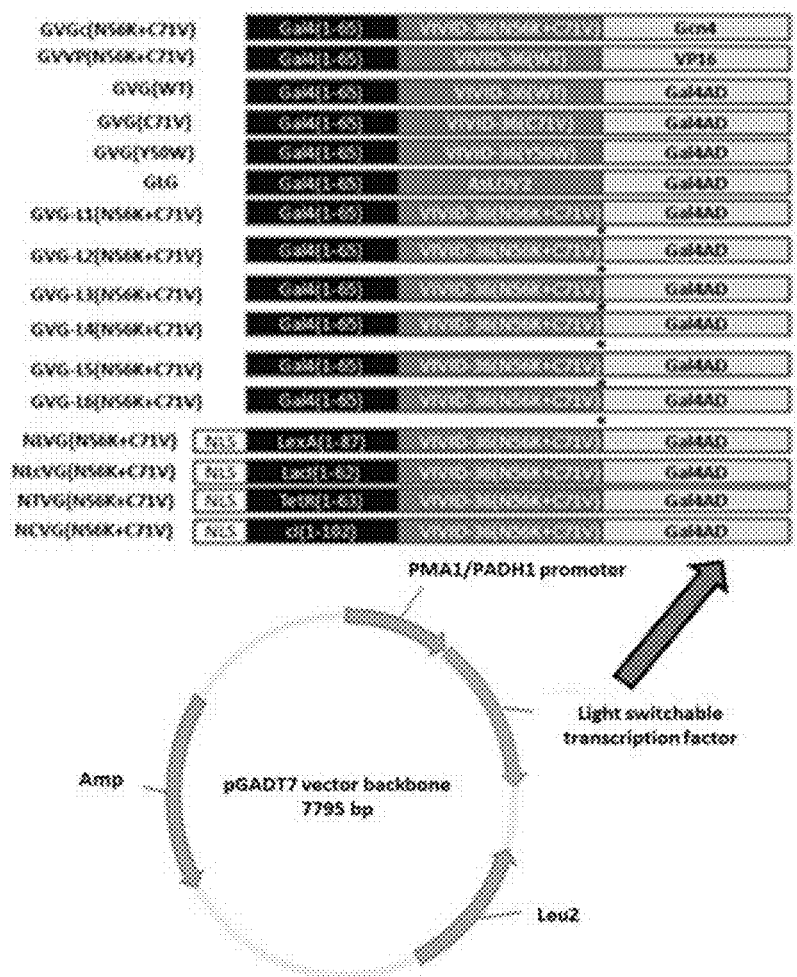
FIG. 6 is a schematic diagram of construction of yeast expression vectors containing the light-switchable transcription factor. Top panel is a schematic diagram of the light-switchable transcription factor fusion protein Bottom panel is a schematic diagram of orbicular expression vectors. The backbone of these vectors is pGADT7, and the intrinsic Gal4AD gene and multiple clone sites were replaced with the light-switchable transcription factor fusion protein gene. * represents the different linker peptide for two polypeptides.

Example 5: Construction of *Saccharomyces cerevisrae* Expression Vector Containing the Recombinant Light-Switchable Transcription Factor with Gal4, LexA, cI, TetR or Gcn4 as the First Polypeptide Plasmids construction of this example is shown in FIG. 6. To construct the vector containing the recombinant light-switchable transcription factor Gal4-VIVID-Gal4AD (N56K+C71V) with Gal4 as the first polypeptide, pGADT7 from the yeast hybrid system (Clontech company) was amplified by PCR using primers P35 and P36 to remove its multiple clone site (MCS region) and Gal4AD sequence. Gal4-VIVID (N56K+C71V) was amplified from pGAVP (N56K+C71V) described in sample 2 by PCR using primers P37 and P38 and inserted into the linearized pGADT7 to create pGAD-GV(N56K+C71V) vector by recombination. pGAD-GV (N56K+C71V) is a transitional vector that can be used to obtain yeast expression vectors containing recombinant light-switchable transcription factors with the third polypeptide (such as Gal4AD).

In the experiment of recombination, primers for removing the multiple clone site and Gal4AD sequence of pGADT7:

```
Forward primer (P35):
5'-AGGATCCTGAGCTCGAGCTGCAGATGAATC-3'

Reverse primer (P36):
5'-CATCTTTGCAAAGCTTGGAGTTGATTG-3'
```

Primers for amplifying Gal4-VIVID (N56K+C71V):

```
Forward primer (P37):
5'-AGCTTTGCAAAGATGAAGCTACTGTCTTC-3'

Reverse primer (P38):
5'-CGAGCTCAGGATCCTTCCGTTTCGCACTGG-3'
```

Gal4AD gene was amplified from pGADT7 (Clontech company) by PCR using primers P39, P40 (containing nucleotide sequences encoding two different lengths of linkers) and P41, the obtained Gal4AD sequences contained two linkers with different lengths and were ligated into pGAD-GV(N56K+C71V) by BamHI/XhoI double digestion, the resulting vectors were named pGAD-GVG-L1 (N56K+C71V) and pGAD-GVG-L2(N56K+C71V) containing Gal4-VIVID-Gal4AD-L1 (N56K+C71V) (SEQ. ID. No: 97 (polynucleotide), SEQ. ID. No:98 (polynucleotide)) and Gal4-VIVID-Gal4AD-L2(N56K+C71V) fusion protein genes (SEQ. ID. No:99 (polynucleotide), SEQ. ID. No:100 (polynucleotide)) with two different lengths of linkers, respectively (L1 and L2).

The forward primers for amplifying two Gal4AD sequences with different length of linkers:

```
Linker L1 (P39):
5'-CCCGGATCCGGTGGAGGTGGCTCCAATTTTAATCAAAGTGG-3'

Linker L2 (P40):
5'-CCCGGATCCGGTGGAGGTGGCTCCAATTTTAATCAAAGTGG-3'
```

The common reverse primer (P41):

```
5'-GGGCTCGAGTTACTCTTTTTTTGGGTTTGGTG-3'
```

To obtain pGPMA vector with a stronger promoter PMA1 that can increase the expression level of recombinant transcription factor, pGADT7 was amplified by PCR using primers P42 and P43 to generate the linearized fragment that lost PADH1 promoter sequence. At the meanwhile, PMA1 promoter fragment was amplified from pZF1/2-FRET (a gift from David J. Eide laboratory, University of Wisconsin-Madison, USA) by PCR using primers P44 and P45 and cloned into the linearized pGADT7 vector by recombination to obtain pGPMA. Construction of the following plasmids was based on pGPMA: pGPMA vector was amplified by PCR using primers P46 and P47, and then similarly to construction of pGAD-GV (N56K+C71V), Gal4-VIVID (N56K+C71V) gene fragment was cloned into the linearized pGPMA by recombination, the obtained pGPMA-GV (N56K+C71V) contains fusion protein gene Gal4-VIVID (N56K+C71V), which could be used to construct following yeast expression vectors.

To screen effective linkers for the following experiments, the effects of recombinant light-switchable factors with different linkers were determined. In detailed, Gal4AD was amplified from pGAD-GV (N56K+C71V) by PCR using primers P48-P54 that contain the nucleotide sequences encoding six kinds of linkers with different lengths, and then were ligated into pGPMA-GV(N56K+C71V) vector by BamHI/XhoI double digestion, the resulting vectors that contain fusion proteins Gal4-VIVID-Gal4AD-Ln(N56K+C71V) encoding genes with six kinds of linkers (L1, L2, L3, L4, L5 and L6) were named as pGPMA-GVG-L1 (N56K+C71V), pGPMA-GVG-L2 (N56K+C71V), pGPMA-GVG-L3 (N56K+C71V), pGPMA-GVG-L4 (N56K+C71V), pGPMA-GVG-L5 (N56K+C71V), pGPMA-GVG-L6 (N56K+C71V), respectively. Nucleotide sequences of these recombinant proteins are SEQ. ID. No:97, SEQ. ID. No:99, SEQ. ID. No:101, SEQ. ID. No:103, SEQ. ID. No:105 and SEQ. ID. No:107; Amino acid sequences were SEQ. ID. No:98, SEQ. ID. No:100, SEQ. ID. No:102, SEQ. ID. No:104, SEQ. ID. No:106 and SEQ. ID. No:108.

Primers for linearizing pGADT7 by PCR amplification:

```
Forward primer (P42):
5'-AGCTTTGCAAAGATGGCCATGGAGGCCAGTGA-3'

Reverse primer (P43):
5'-CATGCAAGCAACGAAGCATCTGTGCTTCATTTTG-3'
```

Primers for amplifying PMA1 promoter:

Forward primer (P44):
    5'-TTCGTTGCTTGCATGGCCAAGCTTCCTGAAAC-3'

Reverse primer (P45):
    5'-CATCTTTGCAAAGCTGCTGGGGTATATTTTTTTC-3'

Primers for linearizing pGPMA by PCR amplification:

Forward primer (P46):
    5'-AGGATCCTGAGCTCGAGCTGCAGATGAATC-3'

Reverse primer (P47):
    5'-CATCTTTGCAAAGCTGCTGGGGT-3'

Forward primers for amplifying Gal4AD with six kinds of length of linkers:

Linker L1 (P48):
5'-CCCGGATCCGGTGGAGGTGGCTCCAATTTTAATCAAAGTGG-3'

Linker L2 (P49):
5'-CCCGGATCCGGCGGTGGTGGATCAGGTGGAGGTGGCTCCAAT-3'

Linker L3 (P50):
5'-CCCGGATCCGGTGGATCAGGTGGAGG-3'

Linker L4 (P51):
5'-CCCGGATCCGGAAGCGGCGGTGGTGGATCAGG-3'

Linker L5 (P52):
5'-CCCGGATCCGGTGGCGGCGGAAGCGGCGGTGGTG-3'

Linker L6 (P53):
5'-CCCGGATCCGGCGGAGGTGGGGGCTCCGGTGGCGGCGGAAG-3'

The common reverse primer (P54) is:

5'-GGGCTCGAGTTACTCTTTTTTTGGGTTTGGTG-3'

Figures 12, 13, 14, 15, 16:
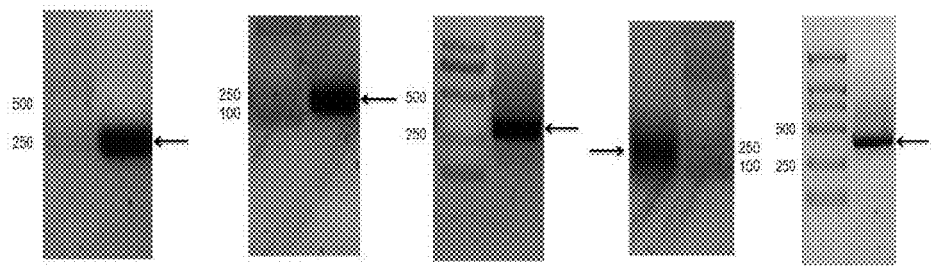
FIG. 12 is the agrose gel electrophoresis result of the LexA (1-87) amplified by PCR. The right arrow points to the target band of PCR product, and the left bands are the DNA maker.
FIG. 13 is the agrose gel electrophoresis result of the LacI (1-62) amplified by PCR. The right arrow points to the target band of PCR product and the left bands are the DNA maker.
FIG. 14 is the agrose gel electrophoresis result of the cI (1-102) amplified by PCR. The right arrow points to the target band of PCR product, and the left bands are the DNA maker.
FIG. 15 is the agrose gel electrophoresis result of the TetR (1-63) amplified by PCR. The right arrow points to the target band of PCR product, left band is the DNA maker.
FIG. 16 is the agrose gel electrophoresis result of the Gcn4 (1-144) amplified by PCR. The right arrow points to the target band of PCR product; and the left bands are the DNA makers.

To construct yeast expression vector that contains recombinant light-switchable transcription factor NLS-LexA-VIVID-Gal4AD (N56K+C71V) (abbreviated to NLVG (N56K+C71V)) with LexA as the first peptide, LexA (1-87) was amplified from the genome of E. coli strain BL21 by PCR using primers P55 and P56 (see FIG. 12), VIVID (N56K+C71V) was amplified from pGAVP (N56K+C71V) described in example 2 using primers P57 and P58. LexA (1-87) and VIVID (N56K+C71V) were overlapped by overlapping PCR to obtain LexA-VIVID (N56K+C71V) gene fragment. SV40 nuclear localization signal gene fragment was amplified from pGADT7 vector (Clontech company) by PCR using primers P59 and P60 and overlapped with LexA-VIVID (N56K+C71V) resulting in NLS-LexA-VIVID (N56K+C71V) gene fragment. pGPMA-GVG-L2 (N56K+C71V) described in this example was amplified by PCR using primers P61 and P62, the linearized vector was ligated with NLS-LexA-VIVID (N56K+C71V) by EcoRI/BamHI double digestion, the resulting vector was named as pGPMA-NLVG (N56K+C71V) which contains recombinant protein gene NLVG (N56K+C71V) (SEQ. ID. No:7 (polynucleotide) and SEQ. ID. No:8 (polypeptide)).

Primers for amplifying LexA (1-87):

Forward primer (P55):
    5'-GGTGGCTCTGGAGGCATGAAAGCGTTAACGCCAGGC-3'

Reverse primer (P56):
    5'-AGATCTCGGTTCACCGGCAGCCACACG-3'

Primers for amplifying VIVID (N56K+C71V):

Forward primer (P57):
    5'-GGTGAACCGAGATCTCATACGCTCTACGCTCCC-3'

Reverse primer (P58):
    5'-CGAGCTCAGGATCCTTCCGTTTCGCACTGG-3'

Primers for amplifying NLS:

Forward primer (P59):
    5'-CCCGAATTCTGCAAAGATGGATAAAGCGGAATTAATTCC-3'

Reverse primer (P60):
    5'-GCCTCCAGAGCCACCACCGGCGGCGGTACCC-3'

Primers for linearizing pGPMA-GVG-L2 (N56K+C71V) by PCR amplification:

Forward primer (P61):
    5'-CCCGGATCCGGCGGTGGTGGATCAGG-3'

Reverse primer (P62):
    5'-CCCGAATTCGCTGGGGTATATTTTTTTC-3'

To construct yeast expression vector that contains recombinant light-switchable transcription factor NLS-LacI-VIVID-Gal4AD (N56K+C71V) (abbreviated to NLcVG (N56K+C71V)) with LacI as the first polypeptide, DNA binding domain of LacI (1-62 amino acid) was amplified from commercial vector pCDFDuet1 (Novagen) by PCR using primers P63 and P64 (see FIG. 13), NLS gene fragment was amplified from commercial pGADT7 vector by PCR using primers P65 and P66, then LacI and NLS gene fragments were ligated by overlapping PCR, the obtained NLS-LacI gene fragment was inserted into pGPMA-NLVG (N56K+C71V) described in this example by EcoRI/BglII double digestion. The resulting vector was named as pGPMA-NLcVG (N56K+C71V) containing the gene of recombinant light-switchable transcription factor NLcVG (N56K+C71V) (SEQ. ID. No:11 (polynucleotide) and 12 (polypeptide)).

Primers for amplifying the DNA binding domain of LacI:

Forward primer (P63):
    5'-GGCTCTGGAGGCATGAAACCAGTAACGTTATAC-3'

Reverse primer (P64):
    5'-CCCAGATCTCAACGACTGTTTGCCCGCC-3'

Primers for amplifying NLS:

Forward primer (P65):
    5'-CCCGAATTCATGGATAAAGCGGAATTAATTCC-3'

Reverse primer (P66):
    5'-CCTCCAGAGCCACCGAACCGGCGGCGGTACCC-3'

To construct yeast expression vector that contains recombinant light-switchable transcription factor NLS-cI-VIVID-Gal4AD(N56K+C71V) with cI as the first peptide, DNA binding domain of cI(1-102 amino acid) was synthesized by Shanghai Generay Biotech Co. Ltd. and amplified by PCR using primers P67 and P68 (see FIG. 14), NLS gene fragment was amplified from commercial pGADT7 vector by PCR using primers P69 and P70, cI and NLS gene fragments were ligated by overlapping PCR, the obtained NLS-cI fragment was inserted into pGPMA-NLVG(N56K+C71V) vector described in this example by EcoRI/BglII double digestion. The resulting vector was named as pGPMA-NCVG (N56K+C71V) containing the gene of recombinant light-switchable transcription factor NCVG (N56K+C71V) (SEQ. ID. No:19 (polynucleotide) and 20 (polypeptide)).

Primers for amplifying the DNA binding domain of cI:

```
Forward primer (P67):
5'-GGTGGCTCTGGAGGCATGTCTACCAAGAAGAAAC-3'

Reverse primer (P68):
5'-CCCAGATCTATATTCTGACCTCAAAGACG-3'
```

Primers for amplifying NLS:

```
Forward primer (P69):
5'-CCCGAATTCTGCAAAGATGGATAAAGCGGAATTAATTCC-3'

Reverse primer (P70):
5'-GCCTCCAGAGCCACCACCGGCGGCGGTACCC-3'
```

To construct yeast expression vector containing the recombinant light-switchable transcription factor NLS-TetR-VIVID-Gal4AD (N56K+C71V) (abbreviated to NTVG (N56K+C71V)) with TetR as the first peptide, DNA binding domain of TetR (1-63 amino acid) synthesized by Shanghai Generay Biotech Co. Ltd. was amplified by PCR using primers P71 and P72 (see FIG. 15), NLS gene fragment was amplified from commercial pGADT7 vector by PCR using primers P73 and P74, TetR and NLS gene fragments were ligated by overlapping PCR, the obtained NLS-TetR gene fragment was cloned into pGPMA-NLVG (N56K+C71V) described in this example by EcoRI/BglII double digestion. The resulting vector was named as pGPMA-NCVG (N56K+C71V) containing the gene of recombinant light-switchable transcription factor NTVG (N56K+C71V) (SEQ. ID. No:15 (polynucleotide) and 16 (polypeptide)).

Primers for amplifying the DNA binding domain of TetR:

```
Forward primer (P71):
5'-GGTGGCTCTGGAGGCATGTCTAGGCTAGATAAG-3'

Reverse primer (P72):
5'-CCCAGATCTGGTGCCGTGTCTATCCAGCATCTC-3'
```

Primers for amplifying NLS:

```
Forward primer (P73):
5'-CCCGAATTCTGCAAAGATGGATAAAGCGGAATTAATTCC-3'

Reverse primer (P74):
5'-GCCTCCAGAGCCACCACCGGCGGCGGTACCC-3'
```

All the constructs were verified by DNA sequencing. Plasmids were prepared for the following yeast transformation.

Example 6: Construction of *Saccharomyces cerevisiae* Expression Vectors Containing the Genes of Recombinant Light-Switchable Transcription Factors with VIVID Mutants or AsLOV2 as the Second Polypeptides Refer to FIG. 6 for the plasmid construction of this example. To construct vectors containing the genes of recombinant light-switchable transcription factors with VIVID mutants as the second polypeptide, pGPMA-GVG-L2(N56K+C71V) vector described in example 5 was double digested by BglII/BamHI sites to remove VIVID(N56K+C71V) sequence, VIVID(WT), VIVID(C71V) and VIVID (Y50W) gene fragments were amplified from pGAVP(WT), pGAVP(C71V) and pGAVP(Y50W) described in example 3 by PCR using primers P75 and P76, and then were ligated with pGPMA-GVG-L2(N56K+C71V) vector whose VIVID (N56K+C71V) gene fragment has been removed, the resulting vectors were named as pGPMA-GVG(WT), pGPMA-GVG(C71V) or pGPMA-GVG(Y50W) containing the genes of recombinant protein Gal4-VIVID-Gal4AD(WT) (abbreviated to GVG(WT), (SEQ. ID. No:113 (polynucleotide) and 114 (polypeptide)), Gal4-VIVID-Gal4AD (C71V) (abbreviated to GVG(C71V), (SEQ. ID. No:115 (polynucleotide) and 116 (polypeptide))) or Gal4-VIVID-Gal4AD (Y50W) (abbreviated to GVG(Y50W), SEQ. ID. No:117 (polynucleotide) and 118 (polypeptide)), respectively.

Primers for amplifying VIVID or its mutants:

```
Forward primer (P75):
5'-GGGAGATCTCATACGCTCTACGCTCCCG-3'

Reverse primer (P76):
5'-CGAGCTCAGGATCCTTCCGTTTCGCACTGG-3'
```

To construct yeast expression vector containing the gene of recombinant light-switchable transcription factor Gal4-AsLOV2-Gal4AD (abbreviated to GLG) with AsLOV2 as the second polypeptide, pGPMA-GVG-L2(N56K+C71V) vector described in example 6 was double digested by BglII/BamHI to remove the VIVID(N56K+C71V) gene fragment, AsLOV2 gene was amplified from pGALP described in example 2 by PCR using primers P77 and P78 and ligated with pGPMA-GVG-L2(N56K+C71V) whose VIVID(N56K+C71V) gene fragment has been removed, the obtained expression vector was named as pGPMA-GLG containing the gene of recombinant light-switchable transcription factor GLG (SEQ. ID. No:119 (polynucleotide) and 120 (polypeptide)).

Primers for amplifying AsLOV2:

```
Forward primer (P77):
5'-CCCAGATCTTTCTTGGCTACTACACTT-3'

Reverse primer (P78):
5'-CCCGGATCCAAGTTCTTTTGCCGCCTC-3'
```

All the constructs were verified by DNA sequencing. Plasmids were prepared for the following yeast transformation.

Example 7: Construction of *Saccharomyces cerevisiae* Expression Vectors Containing the Gene of Recombinant Light-Switchable Transcription Factor with VP16 or Gcn4 as the Third Polypeptide Plasmids construction of this example is shown in FIG. 6. To construct yeast expression vector containing the gene of recombinant light-switchable transcription factor Gal4-VIVID-VP16 (N56K+C71V) (abbreviated to GVVP (N56K+C71V)) with VP16 as the third polypeptide, VIVID-VP16 (N56K+C71V) gene fragment was amplified from pGAVV (WT) constructed in sample 2 by PCR using primers P79 and P80, and then was ligated with pGPMA-GVG-L2 (N56K+C71V) described in example 5 by BglII/XhoI double digestion. The obtained vector was named as pGPMA-GVG-L2 (N56K+C71V) containing the gene of recombinant light-switchable transcription factor GAVE (N56K+C71V) (SEQ. ID. No:109 (polynucleotide) and 110 (polypeptide)).

Primers for amplifying VIVID-VP16 (N56K+C71V):

```
Forward primer (P79):
5'-GGGAGATCTCATACGCTCTACGCTCCCG-3'

Reverse primer (P80):
5'-GGGCTCGAGTGGCGATCCCGGACCCGGG-3'
```

To construct yeast expression vector containing the gene of recombinant light-switchable transcription factor Gal4-VIVID-Gcn4 (N56K+C71V) (abbreviated to GVGc(N56K+C71V)) with Gcn4 as the third polypeptide, the gene fragment of Gcn4 transcriptional activation domain was amplified from the genome of yeast strain BY4741 by PCR using primers P81 and P82 (see FIG. 16), pGPMA-GVG-L2(N56K+C71V) vector was amplified by PCR using primers P83 and P84, the obtained linearized vector contained EcoRI and XhoI sites at the two ends, then Gcn4 gene fragment was ligated into the linearized pGPMA-GVG-L2 (N56K+C71V) by EcoRI/XhoI double digestion. The obtained vector was named as pMPMA-GVGc (N56K+C71V) that contains the gene encoding recombinant light-switchable transcription factor GVGc (N56K+C71V) (SEQ. ID. No:111 (polynucleotide) and 112 (polypeptide)).

Primers for amplifying Gcn4:

```
Forward primer (P81):
5'-CCCGAATTCATGTCCGAATATCAGCCAAGT-3'

Reverse primer (P82):
5'-GGGCTCGAGTTAGGATTCAATTGCCTTATC-3'
```

Primers for amplifying pGPMA-GVG-L2 (N56K+C71V):

```
Forward primer (P83):
5'-AGGATCCTGAGCTCGAGCTGCAGATGAATC-3'

Reverse primer (P84):
5'-CCCGAATTCGGAGCCACCTCCACCTGATCCAC-3'
```

All the constructs were verified by DNA sequencing. Plasmids were prepared for the following yeast transformation.

Example 8: Construction of *Saccharomyces cerevisiae* Expression Vectors Containing Target Transcription Units with the Reaction Elements of Gal4, LexA, CI, TetR or Gcn4

Figure 7:
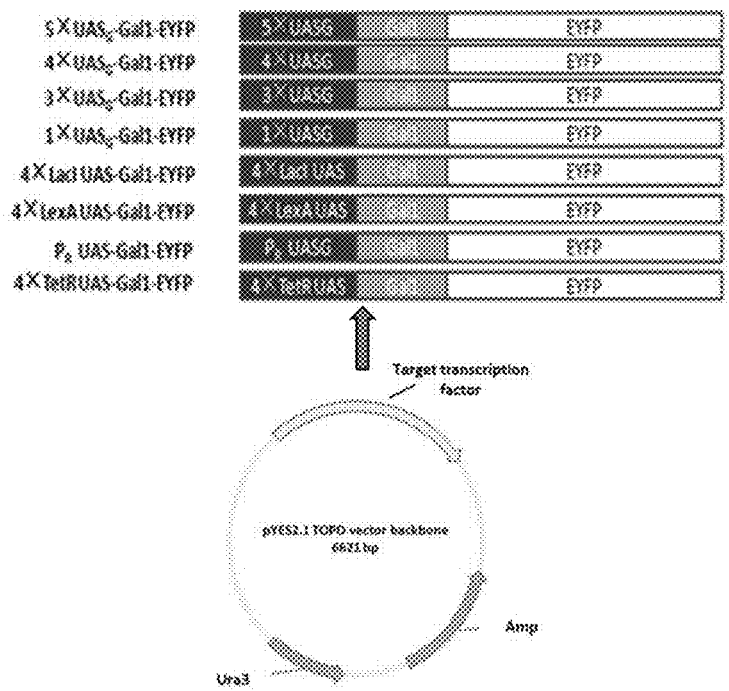
FIG. 7 is a schematic diagram of construction of yeast expression vectors containing the target transcription unit. Top panel is a schematic diagram of respective target transcription units, and the bottom panel is a schematic diagram of orbicular expression vectors. The backbone of these vectors is pYES2.1 TOPO.

Plasmid construction of this example is shown in FIG. 7. To detect the effect of recombinant light-switchable transcription factor with Gal4 as the first peptide on the transcriptional regulation of EYFP gene, *Saccharomyces cerevisiae* expression vector containing the target transcription unit with Gal4 reaction element and fluorescent protein reporter gene was constructed. PYES2.1 TOPO (Invitrogen) was amplified by PCR using primers P85 and P86, the obtained linearized vector backbone contained BamHI and EcoRI sites. EYFP gene was amplified from pZF1/2-FRET (a gift from David J. Eide lab, Wisconsin university in Madison in USA) by PCR using primers P87 and P88 and ligated with the linearized pYES2.1 TOPO by BamHI/EcoRI double digestion. The obtained vector pYE-EYFP contains the target transcription unit 5×UAS$_G$-Gal1-EYFP (SEQ. ID. No:121 (polynucleotide))

Primers for linearizing pYES2.1 TOPO by PCR amplification:

```
Forward primer (P85):
5'-CCCGAATTCAGGGCGAGCTTCGAGGTCACC-3'

Reverse primer (P86):
5'-CCCGGATCCGGGCGAGCTTAATATTCCCTATAG-3'
```

Primers for amplifying EYFP:

```
Forward primer (P87):
5'-CCCGGATCCAAAAAAATGGTGAGTAAAGGAG-3'

Reverse primer (P88):
5'-GGGGAATTCTTATTTGTATAGTTCATC-3'
```

To detect the effects of target transcription units with different number of Gal4 reaction elements on the recombinant light-switchable transcription factor regulated EYFP gene transcription, yeast expression vectors containing target transcription units with different number of Gal4 reaction elements were constructed. pYE-EYFP constructed in this example contains five Gal4 reaction elements, i.e. 5×UAS$_G$. pYE-EYFP was amplified by PCR using primers P89-P92, the obtained three pYE-EYFP vectors lacked one, two or four Gal4 recognition/binding sites in the target transcription unit, and were named as pYE-EYFP(1× UAS$_G$), pYE-EYFP(3×UAS$_G$) or pYE-EYFP(4×UAS$_G$) containing the transcription unit 1×UAS$_G$-Gal1-EYFP (SEQ. ID. No:122 (polynucleotide)), 3×UAS$_G$-Gal1-EYFP (SEQ. ID. No: 123 (polynucleotide)) and 4×UAS$_G$-Gal1-EYFP (SEQ. ID. No:124 (polynucleotide)), respectively. The forward primers for amplification are different, while the reverse primers are the same, their sequences are as following:

```
Common reverse primer (P89):
5'-TACTAGTGGATCATCCCCACGCGCC-3'

Forward primer 1(90):
5'-CCCGAATTCAGGGCGAGCTTCGAGGTCACC-3'

Forward primer 2(P91):
5'-CCCGAATTCAGGGCGAGCTTCGAGGTCACC-3'

Forward primer 3(P92):
5'-CCCGAATTCAGGGCGAGCTTCGAGGTCACC-3'
```

To detect the effect of recombinant light-switchable transcription factor with LexA as the first polypeptide, *Saccharomyces cerevisiae* expression vector containing target transcription unit with the LexA reaction element was constructed. pYE-EYFP in this example was amplified by PCR using primers P93 and P94 to remove the 5×UAS$_G$ sequence, the linearized vector was double digested by XhoI/HindIII sites and ligated with the fragment from the annealing product of primers P95 and P96. The resulting vector was named as pYEL4-EYFP containing the target transcription unit 4×LexA UAS-Gal1-EYFP (SEQ. ID. No:125 (polynucleotide)).

Primers for linearizing pYE-EYFP by PCR amplification:

```
Forward primer (P93):
5'-CCCAAGCTTTAATGCGATTAGTTTTTTAG-3'

Reverse primer (P94):
5'-TAGGCTCGAGCCCACGCGCCCTGTAGCGC-3'
```

Primers for annealing:

```
Forward primer (P95):
5'-TCGAGGGCGTTCGTCCTCACTGTATGATCATACAGTCTGTATATAT

ATACAGTACTGTATGATCATACAGGTTCCTGAAACGCAGATGTGCCTAC

TGTATATATATACAGTAACAATAAAGATTCA-3'

Reverse primer (P96):
5'-AGCTTGAATCTTTATTGTTACTGTATATATATACAGTAGGCACATC

TGCGTTTCAGGAACCTGTATGATCATACAGTACTGTATATATATACAGA

CTGTATGATCATACAGTGAGGACGAACGCCC-3'
```

To detect the effect of recombinant light-switchable transcription factor with LacI as the first polypeptide, *Saccharomyces cerevisiae* expression vector containing target transcription unit with the LacI reaction element was constructed. pYEL4-EYFP in this example was double digested by XhoI/HindIII sites and ligated with the fragment from the annealing product of primers P97 and P98, the resulting vector was named as pYELc4-EYFP that contains the target transcription unit 4×LacI UAS-Gal1-EYFP (SEQ. ID. No: 126 (polynucleotide)).

Primers for annealing:

```
Forward primer (P97):
5'-TCGAGAATTGTGAGCGGATAACAATTGTAATTGTGAGCGGATAACA

ATTATTTGAATTGTGAGCGGATAACAATTGTAATTGTGAGCGGATAACA

ATTA-3'

Reverse primer (P98):
5'-AGCTTAATTGTTATCCGCTCACAATTACAATTGTTATCCGCTCACA

ATTCAAATAATTGTTATCCGCTCACAATTACAATTGTTATCCGCTCACA

ATTC-3'
```

To detect the effect of recombinant light-switchable transcription factor with cI as the first polypeptide of cI, *Saccharomyces cerevisiae* expression vector containing target transcription unit with the cI reaction element was constructed. pYEL4-EYFP in this example was double digested by XhoI/HindIII sites and ligated with the fragment from the annealing product of primers P99 and P100, the resulting vector was named as pYEP$_R$-EYFP that contains the target transcription unit P$_R$UAS-Gal1-EYFP (SEQ. ID. No:127 (polynucleotide)).

Primers for annealing:

```
Forward primer (P99):
5'-TCGAGTAAATCTATCACCGCAAGGGATAAATATCTAACACCGTGCG

TGTTGACTATTTTACCTCTGGCGGTGATAATGGTTGA-3'

Reverse primer (P100):
5'-AGCTTCAACCATTATCACCGCCAGAGGTAAAATAGTCAACACGC

ACGGTGTTAGATATTTATCCCTTGCGGTGATAGATTTAC-3'
```

To detect the effect of recombinant light-switchable transcription factor with TetR as the first polypeptide, *Saccharomyces cerevisiae* expression vector containing target transcription unit with the TetR reaction element was constructed. pYEL4-EYFP in this example was double digested by XhoI/HindIII sites and ligated with the fragment from the annealing product of primers P101 and P102, the resulting vector was named as pYET4-EYFP that contains the transcription unit 4×TetR UAS-Gal1-EYFP (SEQ. ID. No:128 (polynucleotide)).

Primers for annealing:

```
Forward primer (P101):
5'-TCGAGCCACTCCCTATCAGTGATAGAGAAAAGTCCACTCCCTATCA

GTGATAGAGAAAAGTCCACTCCCTATCAGTGATAGAGAAAAGTCCACTC

CCTATCAGTGATAGAGAAAAGTA-3'

Reverse primer (P102):
5'-AGCTTACTTTTCTCTATCACTGATAGGGAGTGGACTTTTCTCTATC

ACTGATAGGGAGTGGACTTTTCTCTATCACTGATAGGGAGTGGACTTTT

CTCTATCACTGATAGGGAGTGGC-3'
```

Example 9: Construction of Mammalian Cell Expression Vectors Containing Recombinant Hormone and Light Dual-Regulated Transcription Factors with Different Fifth Polypeptides Refer to FIG. 4 for the plasmid construction of this example. The 272-606 amino acid ligand-binding domain of EcR (*Bombyx mori* ecdysone receptor) gene was amplified from pCS2-GVVEcR F' (a kind gift from James K Chen lab, Stanford University School of Medicine in California) by PCR using primers 103 and 104; ER (estrogen receptor, ligand-binding domain 282-595 amino acid) gene was amplified from ER-CRE vector (a kind gift from Zhiqi Xiong lab, Shanghai Institutes for Biological Sciences) by PCR using primer 105 and 106; hPR (human progesterone receptor 640-891 amino acid) gene was amplified from pSwitch (Invitrogen) by PCR using primer 107 and 108. EcR, ER or hPR gene was ligated into pGAVP (N56K+C71V) by MluI/SpeI double digestion to obtain recombinant hormone and light dual-regulated transcription factor GAVPEcR (SEQ. ID. No:131 (polynucleotide) and 132 (polypeptide), GAVPER (SEQ. ID. No:133 (polynucleotide) and 134 (polypeptide) or GAVPhPR (SEQ. ID. No:135 (polynucleotide) and 136 (polypeptide), the resulting mammalian cell expression vectors were named as pGAVPEcR, pGAVPER and pGAVPhPR, respectively.

Primer sequences were as following:

```
pGAVPEcR:
Forward primer (P103):
GACTACGCGTATGAGGCCTGAATGTGTCATACAG

Reverse primer (P104):
GACTACTAGTTAGCACCACCGGGTTGGTG pGAVPER:
Forward primer (P105):
GACTACGCGTTCTGCTGGAGACATGAGAGCTG Reverse primer (P106):
GACTACTAGTAGCTGTGGCAGGGAAACCC pGAVPhPR:
Forward primer (P107):
GACTACGCGTAAAAAGTTCAATAAAGTCAGAGTTGTG Reverse primer (P108):
GACTACTAGTAGCAATAACTTCAGACATCATTTCTG
```

Example 10: Regulation of Gene Expression by Recombinant Light-Switchable Transcription Factor in Mammalian Cells All of cell lines used in this example were cultured in $CO_2$ incubator in DMEM containing 10% fetal bovine serum (FBS) and penicillin-streptomycin, and subcultured when cell density reach 80-90% confluence. Transfection was carried out by following the Lipofectamine 2000 manual. Fluc assay was carried out refer to "Molecular biology experiment reference manual" (Jane Roskams); Gluc activity was determined by using BioLux® Gaussia Luciferase Assay Kit (NEB) according to the manufacturer's instruction. Sample 11, 13, 14 and 15 also utilized the same experiment methods.

Figure 17:
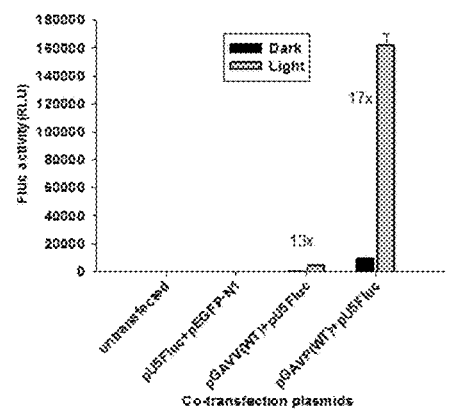
FIG. 17 shows the Fluc expression levels regulated by illuminating mammalian cells transfected by the transcription factors containing several different transcriptional activation domains as the third polypeptide respectively.
Figure 18:
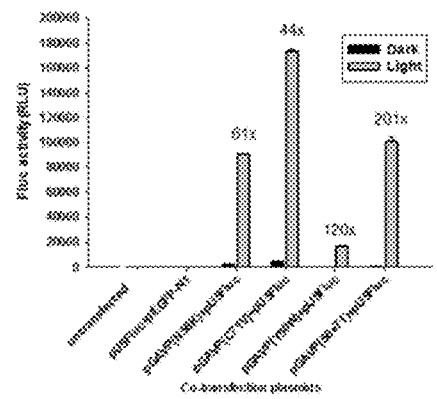
FIG. 18 shows the Fluc expression levels regulated by illuminating mammalian cells transfected by the transcription factors containing several VIVID mutants as the second polypeptide respectively.

Fluc was used as the reporter gene to test light-regulated gene expression by recombinant light-switchable transcription factor with VIVID and its mutants as the second polypeptide. HEK293 cells with 90-95% density were seeded into two identical 48 well plates 16 h before transfection, pU5Fluc described in sample 4 with pGAVV(WT) or pGAVP(WT) or pGAVP(C71V) or pGAVP(Y50W) or pGAVP(N56K) or pGAVP(C71V+N56K) or pEGFP-N1 described in sample 2 was co-transfected into HEK293 cells, manipulation of the two plates was the same. Then one plate was cultured in darkness, while the other was illuminated for 1 s every 30 s 6 h after transfection, the light source was blue LED above mentioned, Fluc activity was determined 22 h after illumination. The result showed that Fluc activity of cells without recombinant light-switchable transcription factor and dark group cells with light-switchable transcription factor almost equaled to untransfected cells, while light group cells expressing these recombinant light-switchable transcription factors showed higher Fluc expression than dark group, which indicated that these light-switchable transcription factors could regulate the target gene expression level in cells. In detailed, the target gene expression in cells expressing GAVP(WT) after illumination was 13-fold greater than the dark group; light-regulated Fluc expression level mediated by GAVP(WT) was dozen of times than GAVV(WT), indicating GAVP(WT) transcription factor with p65AD as the third polypeptide had stronger induction capacity (FIG. 17). Induction ratios of recombinant light-switchable transcription factors GAVP(C71V), GAVP(N56K), GAVP(Y50W), GAVP(N56K+C71V), containing different mutants of VIVID, were higher than GAVP(WT) with wild type VIVID in different degree; the recombinant light-switchable transcription factor GAVP(N56K+C71V) with double mutations had the highest induction ratio which could achieve 200-fold (FIG. 18). We concluded that all of light-switchable transcription factors with VIVID or its mutants as the second polypeptide may activate gene expression after blue light illumination.

Figure 19:
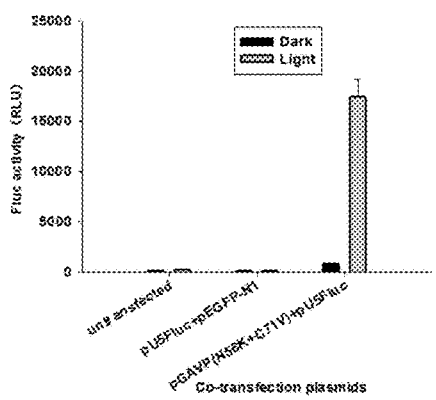
FIG. 19 shows Fluc expression levels regulated by illuminating NIH3T3 cells transfected by the light-switchable transcription factor GAVP (N56K+C71V).
Figure 20:
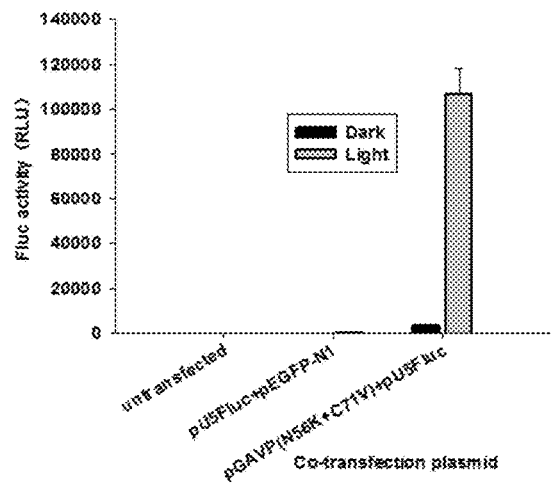
FIG. 20 shows Fluc expression levels regulated by illuminating COS-7 cells transfected by the light-switchable transcription factor GAVP (N56K+C71V).
Figure 21:
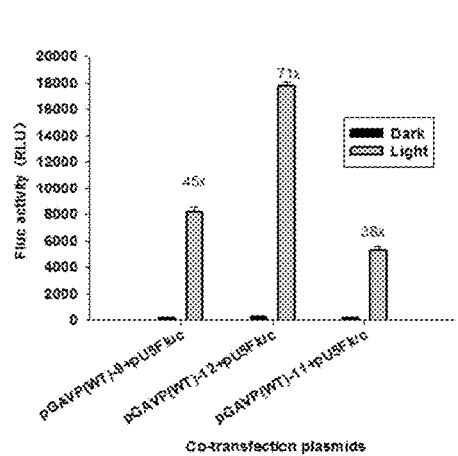
FIG. 21 shows the Fluc expression levels regulated by illuminating mammalian cells transfected by the recombinant light-switchable transcription factor GAVP(WT) containing different linkers between the first polypeptide and the second polypeptide.

The system in the invention can be applied to a variety of mammalian cells. Fluc was used as the reporter gene, pGAVP(N56K+C71V) and pU5Fluc vectors were co-transfected into NIH3T3 or COS-7 cell lines, cells culture, transfection, blue light induction, cell manipulation and determination of the expressed Fluc were the same as the description in the first paragraph of this example. The result indicated that the cell expressing GAVP (N56K+C71V) could activate the target gene (Fluc) expression after light irradiation in NIH3T3 or COS-7 cell lines (FIG. 19, 20). Fluc was used as the reporter gene to detect the regulation of recombinant light-switchable transcription factor with different linkers between the first peptide and second peptide on the target gene expression after light illumination, pU5Fluc with pGAVP(WT)-9 or pGAVP(WT)-11 or pGAVP (WT)-12 described in sample 2 were co-transfected into HEK293 cells, cells culture, transfection, blue light induction, cell manipulation and determination of the expressed Fluc were the same as the description in the first paragraph of this example. The result showed that light-switchable transcription factors GAVP(WT)-9, GAVP(WT)-11 and GAVP(WT)-12 could activate Fluc expression after light illumination, but the induction ratios were different, GAVP (WT)-12 had the highest induction ratio (FIG. 21).

Figure 22:
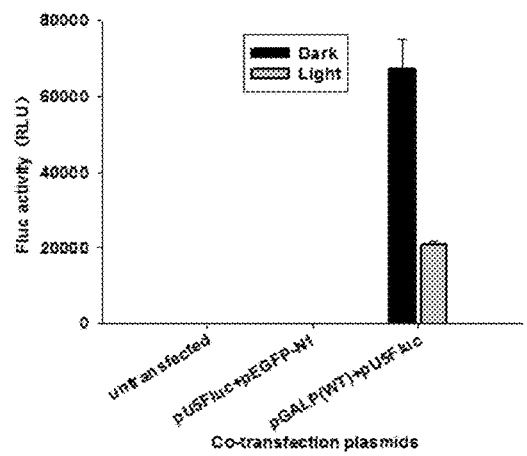
FIG. 22 shows the Fluc expression levels regulated by illuminating mammalian cells transfected by the transcription factor containing AsLOV2 as the second polypeptide.

To detect the regulation of gene expression by recombinant light-switchable transcription factor with AsLOV2 as the second polypeptide in mammalian cells, Fluc was used as the reporter gene to detect the regulation of gene expression by the recombinant light-switchable transcription factor Gal4-AsLOV2-p65 (abbreviated to GALP). pU5Fluc with pGALP constructed in sample 2 were co-transfect into HEK293, cells culture, transfection, blue light induction, cell manipulation and determination of the expressed Fluc were the same as the description in the first paragraph of this example. The result showed that Fluc expression of light group was lower that dark group, which was approximately half of the dark group, indicating that the recombinant light-switchable transcription factor GALP could decrease the target gene expression after light illumination (FIG. 22).

Figure 23:
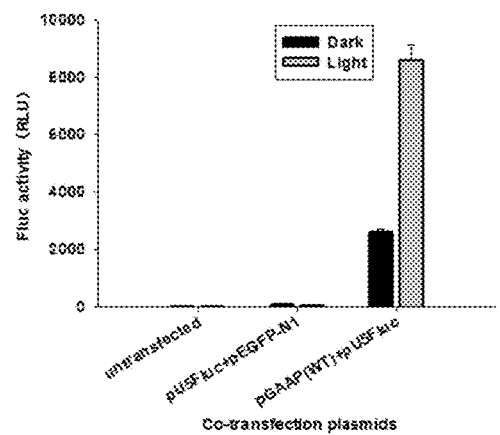
FIG. 23 shows the Fluc expression levels regulated by illuminating mammalian cells transfected by the transcription factor containing AuLOV as the second polypeptide.

To detect the regulation of gene expression by recombinant light-switchable transcription factor with AuLOV as the second polypeptide in mammalian cells, Fluc was used as the reporter gene to detect the regulation of gene expression by the recombinant light-switchable transcription factor Gal4-AuLOV-p65 (abbreviated to GAAP). pU5Fluc with pGAAP constructed in sample 2 were co-transfect into HEK293, cells culture, transfection, blue light induction, cell manipulation and determination of the expressed Fluc were the same as the description in the first paragraph of this example. The result showed that Fluc gene expression of light group was higher that dark group, indicating that the recombinant light-switchable transcription factor GAAP could increase the target gene expression after light illumination (FIG. 23).

Figure 24:
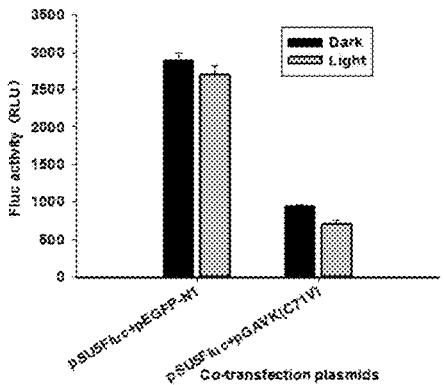
FIG. 24 shows the Fluc expression levels regulated by illuminating mammalian cells transfected by the transcription factor containing KRAB as the third polypeptide.

To detect the regulation of gene expression by recombinant light-switchable transcription factor with KRAB as the third polypeptide in mammalian cells, the effect of recombinant light-switchable transcription factor GAVK (C71V) on gene expression upon light exposure was detected. pU5Fluc vector constructed in sample 4 and pGAVK (C71V) vector constructed in sample 1 were co-transfected into HEK293 cells, cells culture, transfection, blue light induction, cell manipulation and determination of the expressed Fluc were the same as the description in the first paragraph of this example. The result indicated that the recombinant light-switchable transcription factor GAVK (C71V) could decrease Fluc expression level after light illumination (FIG. 24).

Figure 25:
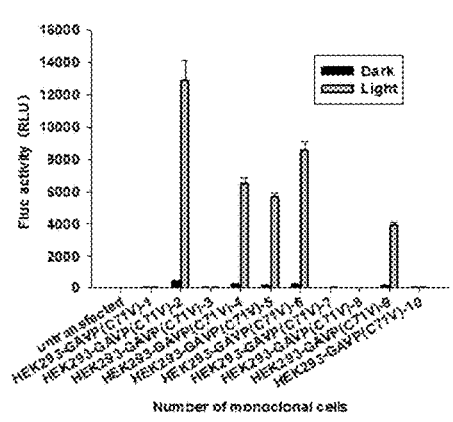
FIG. 25 shows the clone screening of HEK293 cells expressing the recombinant light-switchable transcription factor GAVP (C71V).

Example 11: Regulation of Gene Expression by Recombinant Light-Switchable Transactivation Factor in Stable Cell Line To establish stable cell line expressing light-switchable transcription factor GAVP (C71V), pGAVP(C71V) vector described in example 2 was transfected into HEK293 cells, cells were and seeded into 100 mm dish 48 h after transfection. 24 h later, media was refreshed using medium with additional 600 µg/mL G418 and repeated every two days in the following 3 weeks. After that, 10 monoclonal cell lines were selected by serial dilution in the survival cells. These monoclonal cell lines were seeded into 48 well plate, and transfected with pU5Fluc vector constructed in sample 4 to detect whether these cell lines expressed the recombinant light-switchable transcription factor, if yes, cells could express Fluc gene after light illumination. Blue light induction, cell manipulation and determination of the expressed Fluc were the same as sample 10. The result showed that, clone 2, 4, 5, 6, 9 contained the recombinant light-switchable transcription factor; clone 2 showed the highest Fluc expression level after illumination, the induction ratio was approximate 30-fold which was similar to transient transfection of the recombinant light-switchable transcription factor. These results indicated that the recombinant light-switchable transcription factor gene integrated into the genome could regulate the expression level of target gene (FIG. 25).

Figure 26:
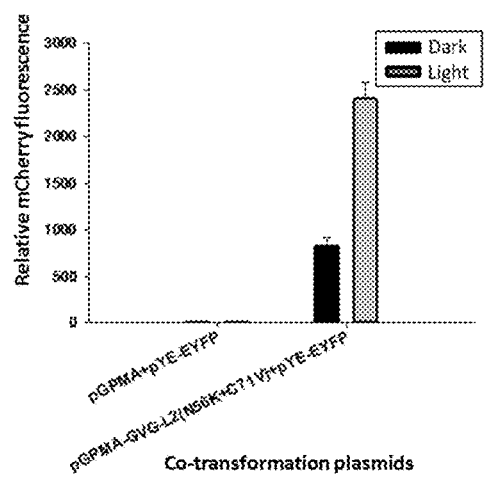
FIG. 26 shows the EYFP expression level regulated by illuminating *Saccharomyces cerevisiae* AH109 cells transfected by the recombinant light-switchable transcription factor GVG (N56K+C71V).

Example 12: Regulation of Gene Expression by Recombinant Light-Switchable Transcription Factors in *Saccharomyces cerevisiae* Cells Protocol for the detection of fluorescent protein EYFP expressed by yeast cells: clones on the transformed plate were picked and incubated at 240 rpm and 30° C. in incubator shakers under darkness. 500 μl of the overnight cultured cells was diluted into two tubes with 4.5 mL fresh YPDA medium, one was illuminated by blue light exposure while the other was kept in darkness, the cells were kept at 240 rpm and 30° C. until the OD600 reached 0.8-1.0. 500 μl of the cultured cells was harvested in 1.5 mL tube and centrifuged at 4000 rpm for 5 min, then the supernatant was discarded and cells were washed with 1 mL PBS for twice. The cells were suspended to the OD600 around 0.5 using PBS. (Ensure the accuracy of the fluorescence determination). 100 μl of the supernatant was added to the 96-well black plate, the fluorescence was measured by Synergy 2 multi-mode microplate reader (BioTek) with excitation wavelength of 485±20 nm and emission wavelength of 528±20 nm. Each data point represents the average of 3 replicates. To detect the effect of recombinant light-switchable transcription factor GVG-L2 (N56K+C71V) constructed in sample 5 on regulation of gene expression in yeast cells, the effect of GVG-L2 (N56K+C71V) on the expression of EYFP upon blue light exposure was measured. pGPMA-GVG-L2(N56K+C71V) constructed in example 5 and pYE-EYFP constructed in example 8 were co-transformed into AH109 strain, co-transformation of empty pGPMA vector and pYE-EYFP into AH109 cell was used as the control. The EYFP fluorescence of the cells upon blue light exposure or under darkness was measured; the result indicated that the recombinant light-switchable transcription factor GVG-L2 (N56K+C71V) could increase the expression level of EYFP in AH109 cells upon blue light exposure (FIG. 26).

Figure 27:
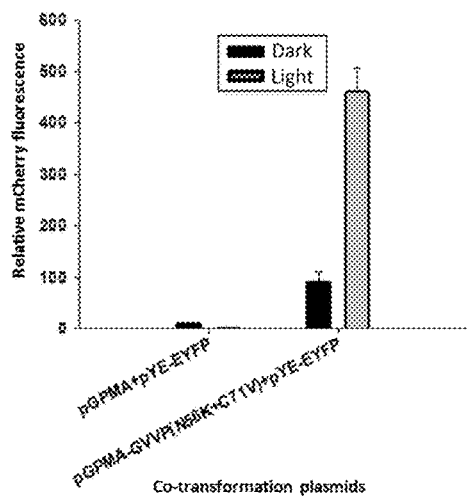
FIG. 27 shows the EYFP expression level regulated by illuminating Saccharomyces cerevisiae AH109 cells transfected by the recombinant light-switchable transcription factor GVVP (N56K+C71V).

To detect the effect of recombinant light-switchable transcription factor GVVP (N56K+C71V) on the regulation of gene expression in yeast cells, the effect of GVVP (N56K+C71V) described in example 7 on the expression of EYFP upon blue light exposure was measured. pGPMA-GVVP (N56K+C71V) described in example 7 and pYE-EYFP described in example 8 were co-transformed into AH109 strain, co-transformation of empty pGPMA vector and pYE-EYFP into AH109 cell was used as the control. The EYFP fluorescence of the cells upon blue light exposure or under darkness was measured. The result showed that the recombinant light-switchable transcription factor GVVP (N56K+C71V could effectively increase the expression level of EYFP in AH109 cells upon blue light exposure (FIG. 27).

Figure 28:
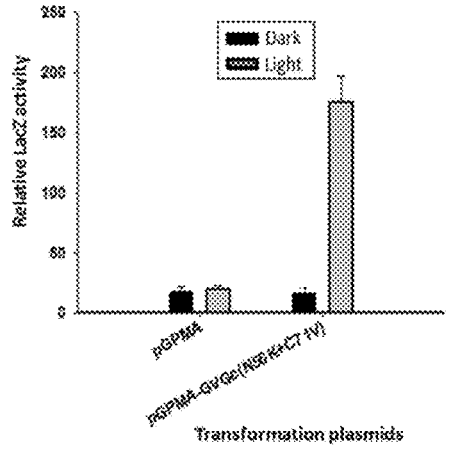
FIG. 28 shows the LacZ expression level regulated by illuminating Saccharomyces cerevisiae AH109 cells transfected by the recombinant light-switchable transcription factor GVGc (N56K+C71V).

To detect the effect of recombinant light-switchable transcription factor GVGc (N56K+C71V) on the regulation of gene expression in yeast cells, the effect of GVGc (N56K+C71V) described in example 7 on the expression of LacZ upon blue light exposure was measured. pGPMA-GVGc (N56K+C71V) described in example 7 was transformed into AH109 strain, transformation of empty pGPMA vector into AH109 cell was used as the control. The expression level of LacZ of the cells upon blue light exposure or under darkness was measured according to the 《Yeast protocols handbook》 from Clontech Company. The result indicated that the recombinant light-switchable transcription factor GVGc (N56K+C71V) effectively increased the expression level of LacZ in AH109 cells, the induction ratio could reach nearly 10 folds (FIG. 28).

Figure 29:
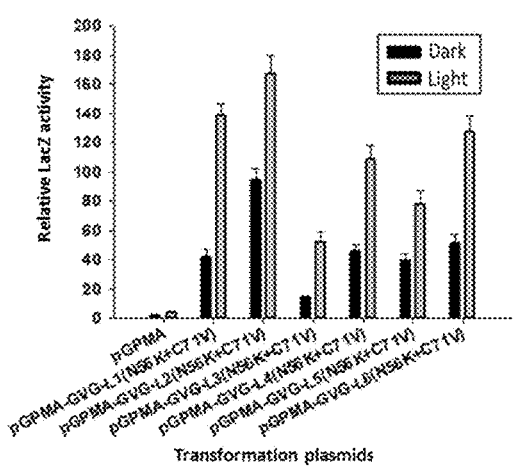
FIG. 29 shows the LacZ expression level regulated by illuminating Saccharomyces cerevisiae AH109 cells transfected by the recombinant light-switchable transcription factor GVG (N56K+C71V) containing different linkers between the second polypeptide and the third polypeptide.

To detect the effects of recombinant light-switchable transcription factor GVG(N56K+C17V) containing different linkers on the regulation of gene expression in yeast cells, pGPMA-GVG-L1 (N56K+C71V), pGPMA-GVG-L2 (N56K+C71V), pGPMA-GVG-L3 (N56K+C71V), pGPMA-GVG-L4 (N56K+C71V), pGPMA-GVG-L5 (N56K+C71V) or pGPMA-GVG-L6 (N56K+C71V) was transformed into AH109 strain, transformation of empty pGPMA vector into AH109 cell was used as the control. The expression level of LacZ of the cells upon blue light exposure or under darkness was measured. The results showed that all the recombinant light-switchable factor GVG (N56K+C17V) with different linkers could regulate the LacZ expression but had different expression level of LacZ, recombinant light-switchable factors with linker L1, L3 and L6 had the higher expression level of LacZ, i.e. they had the highest activation capacity after light illumination. (FIG. 29).

Figure 30:
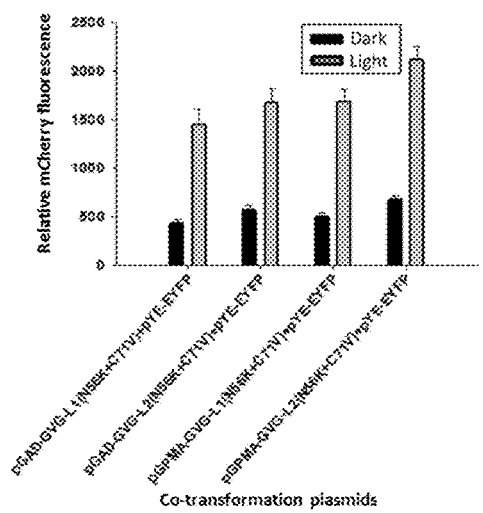
FIG. 30 shows the detection of the target gene expression regulated by different expression level of the recombinant light-switchable transcription factor Gal4-VIVID-Gal4AD in Saccharomyces cerevisiae cells.

To detect the effects of different expression levels of recombinant light-switchable transcription factor Gal4-VIVID-Gal4AD on the regulation of gene expression in yeast cells, pGAD-GVG-L1 (N56K+C71V), pGAD-GVG-L2 (N56K+C71V), pGPMA-GVG-L1 (N56K+C71V) or pGPMA-GVG-L2 (N56K+C71V) was co-transformed with pYE-EYFP described in example 8 into AH109 strain, The EYFP fluorescence of the cells upon blue light exposure or under darkness was measured. The EYFP expression level regulated by Gal4-VIVID-Gal4AD under PMA1 promoter was higher than ADH1 promoter probably due to that PMA promoter had stronger initiation capacity than ADH1 promoter. The result indicated more Gal4-VIVID-Gal4AD resulted in higher expression level of EYFP in AH109 cells at the same conditions (FIG. 30).

Figure 31:
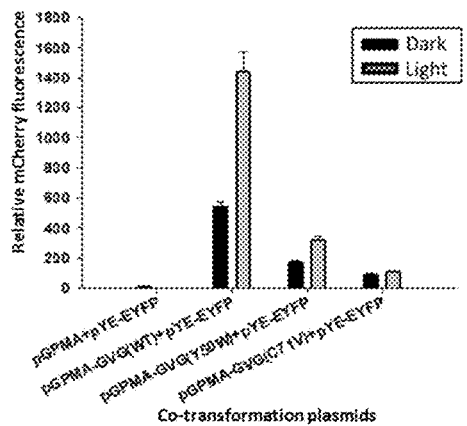
FIG. 31 shows the EYFP expression levels regulated by illuminating Saccharomyces cerevisiae AH109 cells transfected by the transcription factors containing several different VIVID mutants as the second polypeptide respectively.

To detect the effects of the recombinant light-switchable transcription factors Gal4-VIVID-Gal4AD with VIVID mutants on the regulation of gene expression in yeast cells, pGPMA-GVG (WT), pGPMA-GVG(C71V) or pGPMA-GVG(Y50W) was co-transformed with pYE-EYFP described in example 8 into AH109 cells, co-transformation of empty pGPMA vector and pYE-EYFP into AH109 cell was used as the control. The EYFP fluorescence of the cells upon blue light exposure or under darkness was measured. The results showed that all the recombinant light-switchable transcription factors Gal4-VIVID-Gal4AD with different VIVID mutants we tested could increase the expression level of EYFP (FIG. 31).

Figure 32:
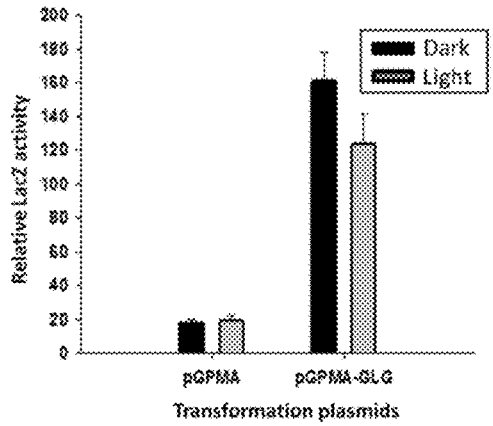
FIG. 32 shows the EYFP expression level regulated by illuminating saccharomyces cerevisiae AH109 cells transfected by the transcription factor containing AsLOV2 as the second polypeptide upon blue light exposure.

To detect the effect of the recombinant light-switchable transcription factor GLG on the regulation of gene expression in yeast cells, pGPMA-GLG described in example 6 was transformed into AH109 strain, transformation of empty pGPMA vector into AH109 cell was used as the control. The expression level of LacZ of the cells upon blue light exposure or under darkness was measured. The result demonstrated that GLG could decrease the expression level of LacZ in AH109 cells; the induction ratio was about 0.8 fold (FIG. 32).

Figures 33, 34:
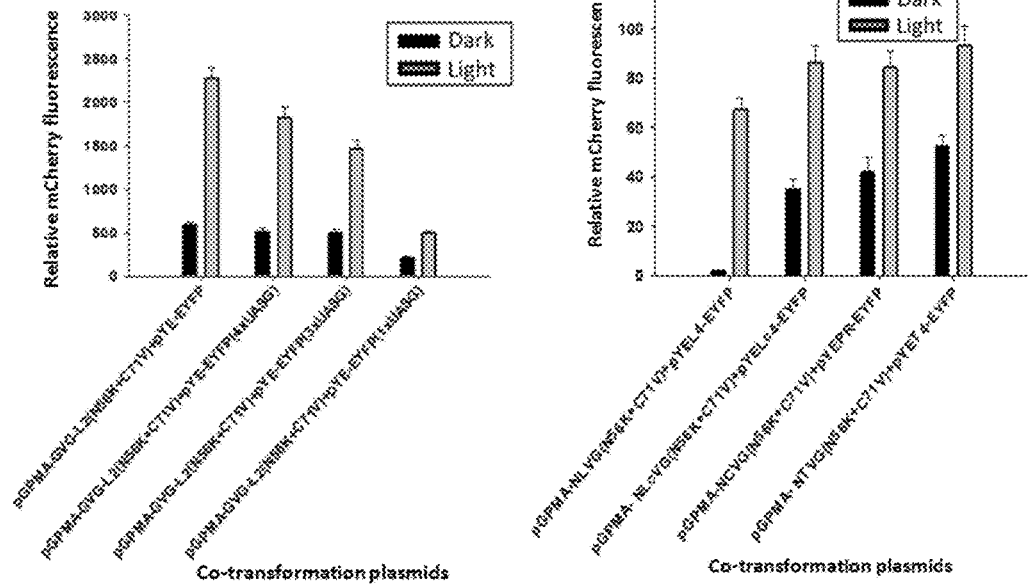
FIG. 33 shows the EYFP expression difference of the target transcription units containing different numbers of Gal4 reaction elements regulated by the recombinant light-switchable transcription factor.
FIG. 34 shows the EYFP expression levels regulated by illuminating saccharomyces cerevisiae AH109 cells transfected by the recombinant light-switchable transcription factors containing LexA, LacI, cI or TetR as first polypeptide respectively.

To detect the effects of recombinant light-switchable transcription factor on the regulation of EYFP expression when the target transcription unit contained different number of Gal4 reaction element, pYE-EYFP(1×UAS$_G$), pYE-EYFP(3×UAS$_G$), pYE-EYFP(4×UAS$_G$) or pYE-EYFP were co-transformed with pGPMA-GVG(N56K+C71V) described in example 5 into BY4741 strain. The EYFP fluorescence of the cells upon blue light exposure or under darkness was measured. The result indicated that the EYFP expression level decreased along with the reduced number of Gal4 recognition elements at the same conditions, but the induction ratio remained almost the same (FIG. 33).

To detect the effects of recombinant light-switchable transcription factors NLVG(N56K+C71V), NLcVG(N56K+C71V), NCVG(N56K+C71V) or NTVG(N56K+C71V) on the regulation of gene expression in yeast cells, pGPMA-NLVG(N56K+C71V), pGPMA-NLcVG(N56K+C71V), pGPMA-NCVG(N56K+C71V) or pGPMA-NTVG(N56K+C71V) were co-transformed with pYEL4-EYFP, pYELc4-EYFP, pYEP$_R$-EYFP or pYET4-EYFP into AH109 cells, respectively. The EYFP fluorescence of the cells upon blue light exposure or under darkness was measured. The result showed that all the four recombinant light-switchable transcription factors could increase the expression level of EYFP after blue light illumination while NLVG (N56K+C71V) had the highest induction ratio (FIG. 34).

Figure 35:
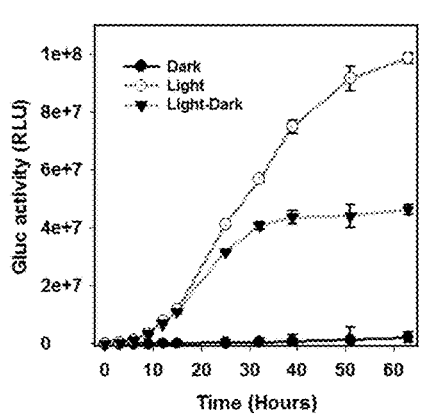
FIG. 35 shows the kinetics and reversible process of light-induced target gene expression in mammalian cells transfected by the recombinant light-switchable transcription factor GAVP (N56K+C71V).

Example 13: Characteristics of Gene Expression Regulation by the Recombinant Light-Switchable Transcription Factor Upon Light Illumination Time course and reversibility of light-switchable transcription factor regulated gene expression were tested by co-transfection of pGAVP (N56K+C71V) constructed in sample 2 and pU5Gluc constructed in sample 4 into HEK293 cells, cells were seeded into 3 plates and their culture and transfection were the same. Two of the three plates were given illumination 10 h after transfection for 1 s every 30 s, and one of the two plates was transferred to darkness 15 h after illumination for reversibility study. The last one was kept in dark all the time as dark group sample. Samples were collected for Gluc assay at indicated time under red LED light according to sample 11. The result showed that Gluc expression level increased significantly after light illumination in recombinant light-switchable transcription factor GAVP (N56K+C71V) expressing cells. The induction ratio could achieve 30-fold, 100-fold after 3 h, 12 h illumination, respectively. For the reversibility sample (light-dark), Gluc expression gradually decreased and stopped 15 h after turning the light off (FIG. 35). These results indicated that the expression level of target gene induced by the light-switchable transcription factor in this invention increased along with the raising time, gene expression gradually stopped after removal of light, demonstrating this process is reversible.

Figure 36:
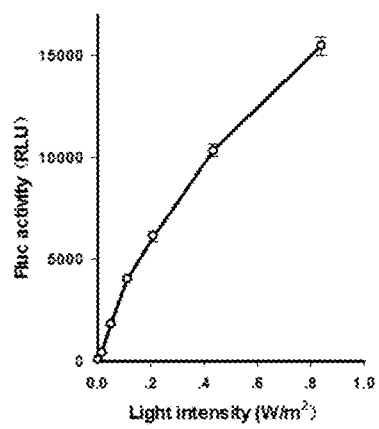
FIG. 36 shows the target gene expression levels regulated by illuminating with different intensities in cells expressing the recombinant light-switchable transcription factor GAVP (N56K+C71V).

To evaluate the gene expression regulated by light-switchable transcription factor in different light irradiance, pGAVP (N56K+C71V) constructed in sample 3 and pU5Fluc vector were co-transfected into HEK293 cells, the cells were divided into two plates, cell sample at the same conditions had three replicates, one plate was illuminated 6 h after transfection for 1 s every 30 s, neutral density filters were used to adjust the light intensity (Light intensity determine by a laminator (Sanwa)). 22 h after illumination, the cells were lysed and Fluc activity was determined. The result showed that recombinant light-switchable transcription factor GAVP(N56K+C71V) induced Fluc expression level depended on light intensity, demonstrating that gene expression level regulated by the recombinant light-switchable transcription factor in this invention depended on light intensity (FIG. 36).

Figure 37:
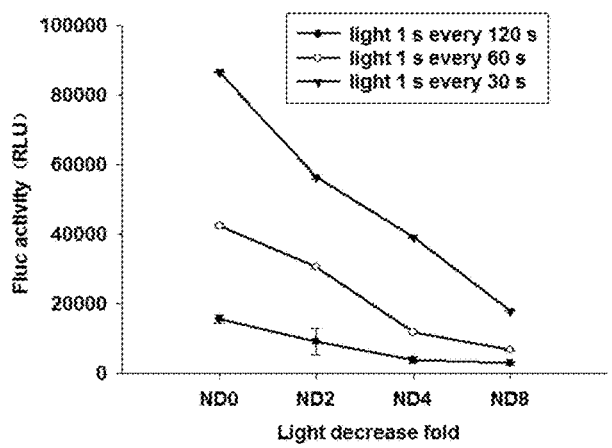
FIG. 37 shows the target gene expression levels regulated by the different total illumination dose (illumination frequency) in cells expressing the recombinant light-switchable transcription factor GAVP (N56K+C71V).

To evaluate the gene expression regulated by light-switchable transcription factor in different illumination frequencies, pGAVP (N56K+C71V) vector and pU5Fluc vector were co-transfected into HEK293 cells, the cells were divided into three plates, cell sample at the same conditions had three replicates. Cells were illuminated 6 h after transfection for 1 s every 30 s, 1 s every 60 s, 1 s every 120 s, respectively. 22 h after illumination, the cells were lysed and Fluc activity was determined. The result showed that Fluc activity was the highest when illuminated is every 30 s and was the lowest when illuminated 1 s every 120 s, indicating that higher frequency of light illumination could result in higher gene expression level when the light intensity was the same (FIG. 37).

Figure 38:
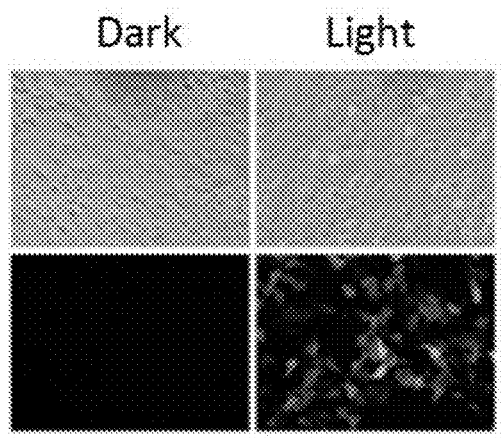
FIG. 38 is the microscopic image of mCherry fluorescence (red fluorescent protein) expression regulated by illuminating cells expressing the recombinant light-switchable transcription factor GAVP (N56K+C71V). Top panel is a phase contrast image, and bottom panel is a fluorescence image.
Figure 39:
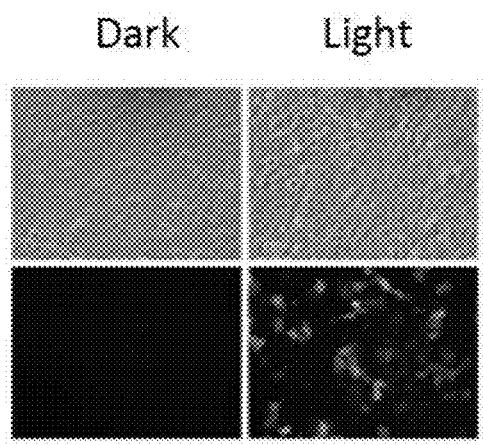
FIG. 39 is the microscopic image of hrGFP fluorescence (green fluorescent protein) expression regulated by illuminating cells expressing the recombinant light-switchable transcription factor GAVP (N56K+C71V). Top panel is a phase contrast image, and bottom panel is a fluorescence image.
Figure 40:
FIG. 40 shows the determination of the fluorescent protein expression using non-reducing polyacrylamide gel electrophoresis. The target band in top panel is hrGFP (green fluorescent protein), and the target band in bottom panel is mCherry (red fluorescent protein).

To observe recombinant light-switchable transcription factor regulated gene expression, mCherry and hrGFP were used as the reporter genes, pGAVP (N56K+C71V) and pU5mCherry or pU5hrGFP were co-transfected into HEK293 cells. 10 h after transfection, cells were illuminated for 20 s every 10 min. 24 h later, images were taken using an Eclipse Ti inverted microscope system (Nikon). The results were shown in FIG. 38 and FIG. 39, cells expressing mCherry or hrGFP reporter gene were in normal morphology before and after light illumination. Cells expressing fluorescent protein mCherry increased after light illumination which could reach more than 50% of the total cells, and its fluorescence intensity was higher than background. To directly observe fluorescent protein expression regulated by recombinant light-switchable transcription factor GAVP (N56K+C71V), the cells used for imaging were lysed by adding 280 μl cell lysis buffer, then the protein concentration of each sample was determined using DC protein assay kit; after that, equal amounts of cell lysate (10 mg) were loaded on 15% native PAGE and ran for 2 h in 20 mA constant current. The gel was imaged with 4×4 binning in Kodak In-Vivo Multispectral System FX (for mCherry, ex 550 nm/em 600 nm; for hrGFP, ex 480 nm/em 535 nm). The method of native PAGE can be seen in 《Short protocols in Protein Science》 written by Coligan J. E. et al, and translated by Shentao Li et al, page 303-307. The result was shown in FIG. 40, "+" referred to "yes", i.e. using corresponding condition or eukaryotic expression vector, "−" referred to "no". The result showed nearly no fluorescent protein expressed in cells only containing target transcription unit but without recombinant light-switchable transcription factor both in darkness and upon light exposure, while the cells expressing both target transcription unit and recombinant light-switchable transcription factor showed higher fluorescent protein (mCherry or hrGFP) expression upon light illumination than in the darkness, nearly no fluorescence was observed in cells kept in darkness, indicating the recombinant light-switchable transcription factor GAVP (N56K+C71V) had low leak expression and high induction capacity.

Transcription level of recombinant light-switchable transcription factor induced gene transcription was evaluated by RT-PCR (reverse transcriptional PCR). pGAVP (N56K+

Figure 41:
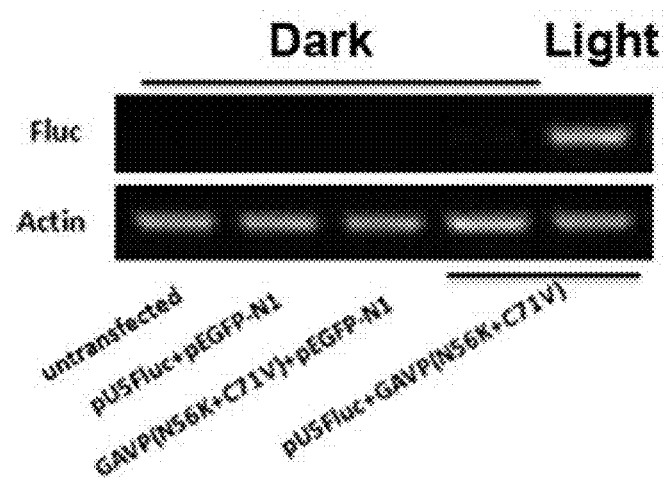
FIG. 41 shows Fluc expression identification under blue light illumination or darkness using RT-PCR.

C71V) constructed in sample 2 and pU5Fluc constructed in sample 4 were co-transfected into HEK293 cells in 24 well plates, cell culture, transfection and induction method were the same as described in example 10. Total RNA of these samples was extracted using RNA isolation kit according to the instructions (Tiangen). RNA concentration was determined and 0.5 μg RNA was reverse transcribed into cDNA using ImpromII reverse transcriptase. Refer to P109 and P110 for primers for Flue, and refer to P111 and P112 for primers for internal reference gene actin. Approach of RT-PCR was the same as routine PCR using Taq DNA polymerase with 1 kb/min for 28 cycles. The result showed that no visible band was observed when cells transfected with pU5Fluc or pGAVP (N56K+C71V) alone, and a bright band existed in co-transfection and light irradiation cells but only a faint band in dark cells, indicating that recombinant light-switchable transcription factor GAVP (N56K+C71V) could activate gene transcription after light illumination, there was significant difference between samples kept in darkness and in light (FIG. 41).

RT-PCR primer for Flue gene:

```
Forward primer (P109):
5'-GAGATACGCCCTGGTTCCTG-3'

Reverse primer (P110):
5'-CGAAATGCCCATACTGTTGAG-3'
```

RT-PCR primer for Actin gene:

```
Forward primer (P111):
5'-CATGTACGTTGCTATCCAGGC-3'

Reverse primer (P112):
5'-CTCCTTAATGTCACGCACGAT-3'
```

Figure 42:
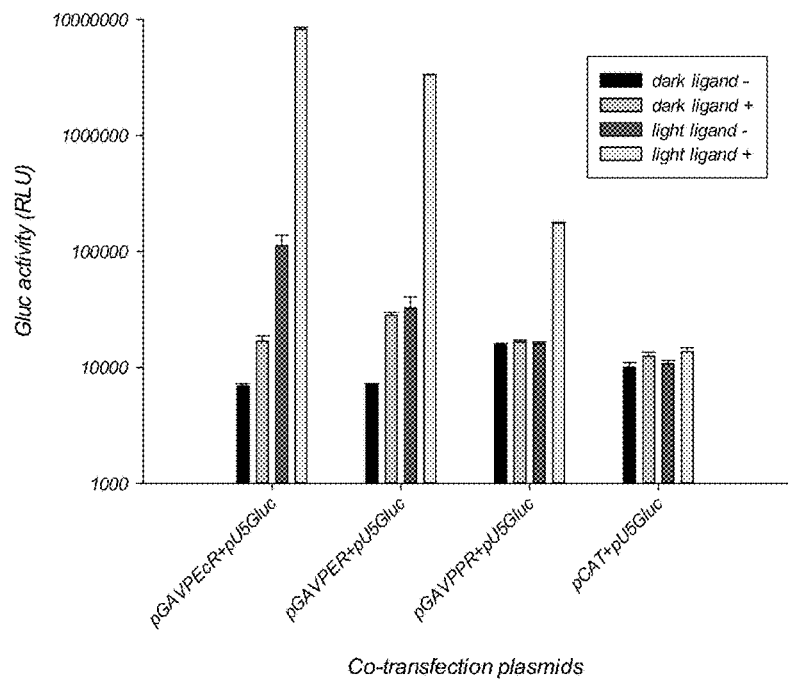
FIG. 42 shows the Gluc expression level regulated by illuminating mammalian cells transfected by the recombinant light-hormone co-regulated light-switchable transcription factor.

Example 14: Regulation Gene Expression by Recombinant Light-Hormone Dual-Regulated Transcription Factors in Mammalian Cells To evaluate gene expression regulated by recombinant light-hormone dual-regulated transcription factors, Gluc was used as the reporter gene to detect the gene expression regulated by light and ligand of EcR, ER or hPR in HEK293 cells. pU5Gluc with pGAVPEcR, pGAVPER or pGAVPhPR constructed in sample 9 were co-transfected into two identical plates of HEK293 cells. Cells were cultured in the dark for 8 hours, ligands of receptors (EcR: Tebufenozide; ER: 4-OHTamxoifen; the hPR: Mifepristone) were added at the final concentration of 1 μM under red light illumination; then one plate was wrapped in aluminum foil and placed in dark while the other was illuminated for 1 s every 30 s. After 22 h induction, medium was collected and Gluc activity was analyzed. Cells transfected with pU5Gluc and pEGFP-N1 containing no recombinant light-switchable transcription factor was used as negative control. The result showed that Gluc activity of cells in negative control group was very low both in dark and in light conditions, Gluc activity of cells with those three recombinant light-hormone dual-regulated transcription factors were higher in the presence of both light and hormone than cells in dark condition without ligand or cells in dark condition with ligand or cells in light condition without ligand, indicating the recombinant light-hormone dual-regulated transcription factors could utilize light and hormone to co-regulated gene expression in cells. In detailed, Gluc activity of cells transfected with pGAVPEcR, pGAVPER or pGAVPhPR in the absence of ligand and in dark conditions was extremely low and was similar to the cells containing no recombinant light-hormone dual-regulated transcription factors, Gluc activity in HEK293 cells increased 4-5 folds with light illumination but no ligand or in the presence of ligand but without light, while in the presence of both light and ligand (EcR: Tebufenozide; ER: 4-OHTamxoifen; hPR: Mifepriston), Gluc activity increased 1000, 500, 60 folds in pGAVPEcR, pGAVPER, pGAVPhPR expressing cells respectively (FIG. 42), indicating that recombinant light-hormone dual-regulated transcription factor could regulate gene expression in mammalian cells.

Figure 43:
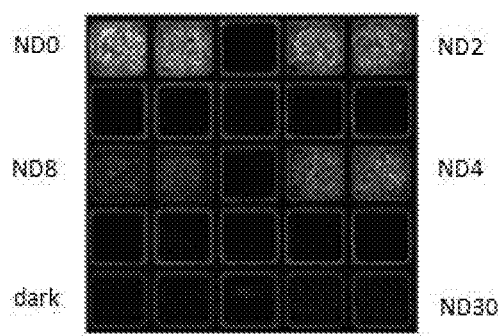
FIG. 43 shows the spatial fluorescent protein expression regulated by illuminating cells transfected with the recombinant light-switchable transcription factor GAVP (N56K+C71V) cultured in 96 well microplate with neutral gray filter.

Example 15: Spatiotemporally Regulate Gene Expression by Recombinant Light-Switchable Transcription Factors in Mammalian Cells On the one hand, neutral density filter as photomask was used to study recombinant light-switchable transcription factors regulated gene expression in spatiotemporal resolution. mCherry was used as the reporter gene, pU5mCherry vector and pGAVP (N56K+C71V) vector were co-transfected into HEK293 cells in 96 quadrate well plate. 10 h after transfection, cells were illuminated by blue light for 1 s every 30 s, graded light intensity was adjusted by neutral density filter. 24 h after illumination, the medium was removed and the imaging was conducted using the In-Vivo Multispectral System FX (Kodak) with 550 nm excitation and 600 nm emission filters for the mCherry, image was collected in 4×4 binning for 5 min exposure. The result indicated that cells showed graded expression level by neutral density filter adjustment, and mCherry achieved the highest expression level when no neutral density filter was added (FIG. 43).

On the other hand, to display spatiotemporally regulated gene expression capacity, printed laser transparency film was used as photomask to "take photos" for cells. A "ECUST" pattern was printed and a gradient slider on laser transparency film using a laser printer was used as photomask, the light intensity of transparent space detected by a luminator was 30 times more than the black space. HEK293 cells were seeded in glass bottom dish (NEST), pU5mCherry with pGAVP (N56K+C71V) were co-transfected and the photomask was pasted on the bottom of the dish, the cells were illuminated 10 h after transfection for 1 s every 30 s. 24 h after illumination, the medium was removed and the imaging was conducted using the In-Vivo Multispectral System FX (Kodak) with 550 nm excitation and 600 nm emission filters for the mCherry, image was collected in 4×4 binning for 5 min exposure. The result showed that the mCherry fluorescence image of the cells had the pattern of the original image used as the mask, that was an "ECUST" and a gradient slider (FIG. 44), indicating that the system could spatiotemporally regulate gene expression.

Example 16: Characteristics of Recombinant Light-Switchable DNA Binding Protein and DNA Recognition/Binding Analysis To evaluate spectrum and DNA binding capacity of the recombinant light-switchable DNA binding protein in this invention, the recombinant light-switchable DNA binding protein was purified first. Gal4-VIVID(WT) was amplified from pGAVP(WT) described in sample 2 by PCR using primers P113 and P114 and ligated into pET28a by NdeI/XhoI digestion, the resulting vector was named as pET28a-

GAV(WT) containing recombinant protein GAV(WT), there is a His-tag in its N-terminal for nickel ion affinity chromatograph.

```
Forward primer (P113):
5'-CTTTCATATGATGAAGCTACTGTCTTCTATCGAAC-3'

Figures 44, 45:
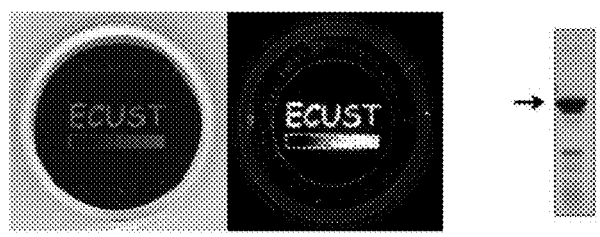
FIG. 44 is the ECUST pattern obtained from "taking photograph" of the cells expressing the recombinant light-switchable transcription factor GAVP (N56K+C71V) using a printed patterns projection film. The left panel is the photograph of culture dish affixed with projection film, and the right panel is the image of fluorescent cells.
FIG. 45 is the purity of purified DNA-binding protein GAV (WT). The arrow points to the target protein band.

Reverse primer (P114):
5'-CTTTCTCGAGTTATTCCGTTTCGCACTGGAAACCCATG-3'
``` pET28a-GAV (WT) was transformed into JM109 (DE3) competent cell, a positive clone was picked for GAV (WT) expression, the expressed protein was purified using 1 ml Hitrap column (GE Healthcare), and further desalting by 5 ml Hitrap Desalting column (GE Healthcare). The purified protein with 90% purity identified by SDS-PAGE was kept in 20 mM Hepes, 150 mM NaCl, 20 μM $ZnCl_2$, 10% glycerol, pH7.5 and in dark at 4° C. (FIG. 45).

Figure 46:
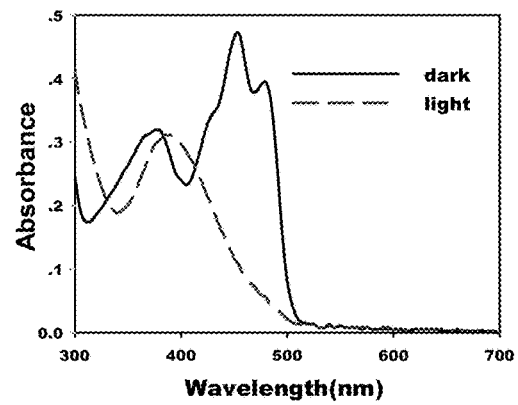
FIG. 46 shows the spectrum characteristics of the light-switchable DNA-binding protein GAV (WT).

For analysis of the spectrum of GAV (WT), protein was kept at 4° C. for 30 h for recovering back to the dark state. 40 μL sample was added into 384 UV-star plate in dim red light (light intensity<0.05 $W/cm^2$), absorbance spectrum was determined from 300 nm to 700 nm by Synergy 2 multi-mode microplate reader (BioTek). Then the sample was irradiated by blue light (460-470 nm, 0.4 $W/cm^2$) for 5 min and the spectrum was determined. It has been reported that dark state of wild type VIVID-36 has peaks in 428 nm, 450 nm, 478 nm and only a 390 nm peak in light state [Zoltowski, B. D. et al, Science 316 (5827), 1054-1057 (2007)]. The result showed that spectrum of GAV (WT) was similar to VIVID-36, indicating that recombinant protein GAV (WT) retained the absorbance spectrum of wild-type VIVID-36 (FIG. 46).

DNA recognization/binding capacity of recombinant protein GAV(WT) was evaluated by EMSA, protein was kept in 4° C. for 30 h for recovering back to the dark state. DNA probe was as follows:

```
Sense strand (P105):
5'-TCTTCGGAGGGCTGTCACCCGAATATA-3',

Anti-sense strand (P106):
5'-ACCGGAGGACAGTCCTCCGG-3',
```

Figure 47:
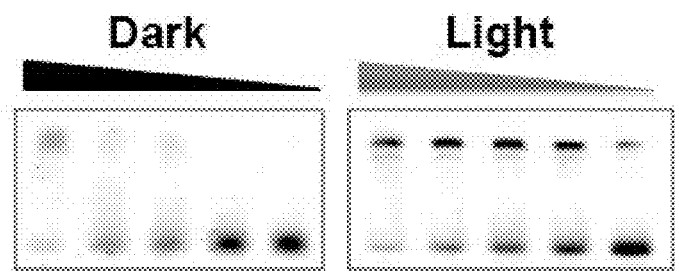
FIG. 47 shows the result of the electrophoresis mobility shift assay for the light-switchable DNA-binding protein GAV (WT). Each GAV (WT) protein concentration is 5.5 µM, 2.8 µM, 1.4 µM, 0.7 µM, 0.35 µM, respectively from the left to the right; and all probe concentrations are 125 nM.

To obtain double strand DNA probe, DNA was diluted to 10 μM, 1:1 mixed and annealed in PCR instrument which began from 95° C. for 5 min and reduced 1° C. every minute from 95° C. to 25° C. GAV (WT) protein was diluted in RnB (20 mM Hepes 7.5, 50 mM NaCl, 100 μg/mL BSA) by 2 fold serial dilution. Protein and DNA (125 μM) were mixed with an additional 5% w/v Ficol and divided into two replicates, one was illuminated by blue light and the other was kept in darkness at room temperature for 30 min. After incubation, the two samples were loaded onto two 6% polyacryamide gel in 0.5× Tris-borate-EDTA (TBE) buffer and run at 100V for 30-50 min at 4° C. upon light exposure or in darkness, then the gels were stained by Gelred nucleic acid gel stain. The result was shown in FIG. 47, GAV (WT) bound with probe shifted slowly and located in the top band due to its high molecular weight, while GAV (WT) bound with no probe shifted fast and located in the bellow band due to its small molecular weight. The left figure showed that GAV (WT) could bind probe only at high concentration in the darkness, the right figure showed GAV (WT) could bind probe at all concentration used after blue light exposure, indicating that blue light could regulate the binding of recombinant GAV (WT) with DNA probe.

Sample 17: The Study of Light-Switchable Gene Expression System on the Gene Therapy of Type I Diabetic Mice 1. Establishment of Type I diabetic mice models induced by Streptozotocin (STZ).

(1) Male Kunming (KM) mice (Four-week-old, ~20 g body weight, FUDAN University) were dealt with sufficient water but no food overnight, and were weighed and labeled the next day.

(2) Citrate solution (0.1 M, pH 5) was prepared as injection solution of STZ and placed on ice away from light.

(3) Streptozotocin (STZ) was intraperitoneally injected into the mice at a dose of 150 mg·$kg^{-1}$ body weight.

(4) The mice were fed with sufficient water and food and 10% sugar solution overnight.

(5) The mice were fed with sufficient water and food without 10% sugar solution in the next two weeks.

(6) After 5-7 days, the glucose levels of each mouse were determined using the ACCU-CHEK Integra Glucose Meter (Roche), and mice with glucose levels of approximately 30 mM (Type I diabetic mice) were selected for use in the following experiment.

2. Drug administration: 20 μg of pU5-insulin described in example 4 and 10 μg of pGAVP (C71V+N56K) described in example 2 were tail intravenously injected into the selected mice in 5-7 seconds (the injection volume was 0.12 ml/g, about 3 mL each mice), the vectors were dissolved in Ringer's solution (147 mM NaCl, 4 mM KCl, 1.13 mM $CaCl_2$). The control vector was pGAVPO (C108S) described in example 2.

3. Determination of blood glucose levels: a shaver was utilized to shave off most of the fur firstly, and then cotton ball was dipped with 8% sodium sulfide to remove the residual fur. The residual sodium sulfide was washed off with warm water and dried the skin of abdomen. The mice were illuminated under blue light with 90 mW $cm^{-2}$ intensity without food for 8 h, and then the mice were allowed to rest in darkness for another 4 hours with sufficient food. The blood glucose levels of each mouse were determined using the ACCU-CHEK Integra Glucose Meter (Roche).

Figure 48:
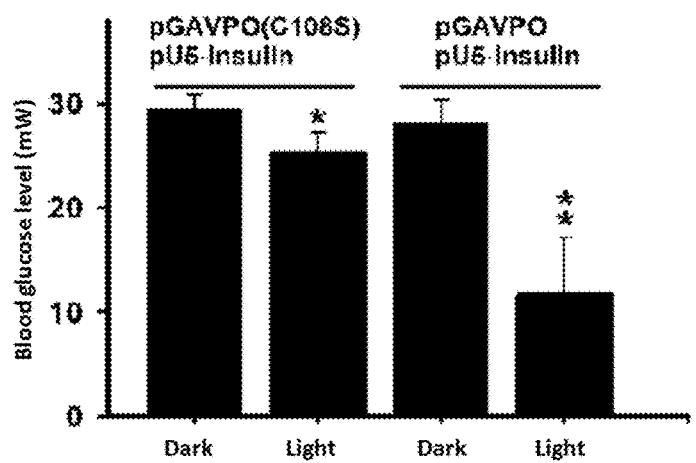
FIG. 48 shows the result of gene therapy in type I diabetic mice using the light-switchable gene expression system.

FIG. 48 indicated that the expression of insulin could significantly decrease the blood glucose levels upon blue light exposure, while the mice kept in darkness or the control group (got injection of control vector pGAVP (C108S)) decreased insignificantly. So the light-switchable gene expression system could be used in gene therapy of Type I diabetic mice.

It will be understood that the dosages, reaction conditions, etc., in the examples are approximate values unless noted otherwise, and they can be exactly changed base on the situations to obtain similar results. All of the professional terms used in the Description, except those specially defined, have identical meanings to those known by persons skilled in the art. All the references referred to are incorporated into the application as a whole. The preferable embodiments are only exemplified for the illustration of the invention. Those skilled in the art can adopt similar methods or materials to obtain similar results. All the changes and modifications are within the scope of the attached claims.

REFERENCES

1. Gossen, M. and H. Bujard, Tight control of gene expression in mammalian cells by tetracycline-responsive promoters. Proc Natl Acad Sci USA, 1992. 89(12): p. 5547-51.

2. Gossen, M., et al., Transcriptional activation by tetracyclines in mammalian cells. Science, 1995. 268(5218): p. 1766-9.
3. Fussenegger, M., et al., Streptogramin-based gene regulation systems for mammalian cells. Nat Biotechnol, 2000. 18(11): p. 1203-8.
4. Wang, Y., et al., A regulatory system for use in gene transfer. Proc Natl Acad Sci USA, 1994. 91(17): p. 8180-4.
5. Weber, W., et al., Gas-inducible transgene expression in mammalian cells and mice. Nat Biotechnol, 2004. 22(11): p. 1440-4.
6. Keyes, W. M. and A. A. Mills, Inducible systems see the light. Trends Biotechnol, 2003. 21(2): p. 53-5.
7. Kamei, Y., et al., Infrared laser-mediated gene induction in targeted single cells in vivo. Nat Methods, 2009. 6(1): p. 79-81.
8. Rivera, V. M., et al., A humanized system for pharmacologic control of gene expression. Nat Med, 1996. 2(9): p. 1028-32.
9. Shimizu-Sato, S., et al., A light-switchable gene promoter system. Nat Biotechnol, 2002. 20(10): p. 1041-4.
10. Yazawa, M., et al., Induction of protein-protein interactions in live cells using light. Nat Biotechnol, 2009. 27(10): p. 941-5.
11. Kennedy, M. J., et al., Rapid blue-light-mediated induction of protein interactions in living cells. Nat Methods, 2010.
12. Fleer, R., Engineering yeast for high level expression. Curr Opin Biotechnol, 1992. 3(5): p. 486-96.
13. Smith, G. E., M. D. Summers, and M. J. Fraser, Production of human beta interferon in insect cells infected with a baculovirus expression vector. Mol Cell Biol, 1983. 3(12): p. 2156-65.
14. Luckow, V. A. and M. D. Summers, High level expression of nonfused foreign genes with *Autographa californica* nuclear polyhedrosis virus expression vectors. Virology, 1989. 170(1): p. 31-9.
15. Pinkert, C. A., et al., An albumin enhancer located 10 kb upstream functions along with its promoter to direct efficient, liver-specific expression in transgenic mice. Genes Dev, 1987. 1(3): p. 268-76.
16. Calame, K. and S. Eaton, Transcriptional controlling elements in the immunoglobulin and T cell receptor loci. Adv Immunol, 1988. 43: p. 235-75.
17. Winoto, A. and D. Baltimore, A novel, inducible and T cell-specific enhancer located at the 3' end of the T cell receptor alpha locus. EMBO J, 1989. 8(3): p. 729-33.
18. Banerji, J., L. Olson, and W. Schaffner, A lymphocyte-specific cellular enhancer is located downstream of the joining region in immunoglobulin heavy chain genes. Cell, 1983. 33(3): p. 729-40.
19. Queen, C. and D. Baltimore, Immunoglobulin gene transcription is activated by downstream sequence elements. Cell, 1983. 33(3): p. 741-8.
20. Talbott, R. L., et al., Nucleotide sequence and genomic organization of feline immunodeficiency virus. Proc Natl Acad Sci USA, 1989. 86(15): p. 5743-7.
21. Edlund, T., et al., Cell-specific expression of the rat insulin gene: evidence for role of two distinct 5' flanking elements. Science, 1985. 230(4728): p. 912-6.
22. Kessel, M. and P. Gruss, Murine developmental control genes. Science, 1990. 249(4967): p. 374-9.
23. Camper, S. A. and S. M. Tilghman, Postnatal repression of the alpha-fetoprotein gene is enhancer independent. Genes Dev, 1989. 3(4): p. 537-46.
24. Marmorstein, R., et al., DNA recognition by GAL4: structure of a protein-DNA complex. Nature, 1992. 356 (6368): p. 408-14.
25. Fogh, R. H., et al., Solution structure of the LexA repressor DNA binding domain determined by 1H NMR spectroscopy. EMBO J, 1994. 13(17): p. 3936-44.
26. Lewis, M., et al., Crystal structure of the lactose operon repressor and its complexes with DNA and inducer. Science, 1996. 271(5253): p. 1247-54.
27. Burz, D. S., et al., Self-assembly of bacteriophage lambda cI repressor: effects of single-site mutations on the monomer-dimer equilibrium. Biochemistry, 1994. 33(28): p. 8399-405.
28. Hu, J. C., et al., Sequence requirements for coiled-coils: analysis with lambda repressor-GCN4 leucine zipper fusions. Science, 1990. 250(4986): p. 1400-3.
29. Wissmann, A., et al., Amino acids determining operator binding specificity in the helix-turn-helix motif of Tn10 Tet repressor. EMBO J, 1991. 10(13): p. 4145-52.
30. Ramos, J. L., et al., The TetR family of transcriptional repressors. Microbiol Mol Biol Rev, 2005. 69(2): p. 326-56.
31. Peter, E., B. Dick, and S. A. Baeurle, Mechanism of signal transduction of the LOV2-Jalpha photosensor from *Avena sativa*. Nat Commun, 2010. 1(8): p. 122.
32. Takahashi, F., et al., AUREOCHROME, a photoreceptor required for photomorphogenesis in stramenopiles. Proc Natl Acad Sci USA, 2007. 104(49): p. 19625-30.
33. Seipel, K., O. Georgiev, and W. Schaffner, Different activation domains stimulate transcription from remote ('enhancer') and proximal ('promoter') positions. EMBO J, 1992. 11(13): p. 4961-8.
34. Peng, H., et al., Biochemical analysis of the Kruppel-associated box (KRAB) transcriptional repression domain. J Biol Chem, 2000. 275(24): p. 18000-10.
35. Wang, Y., et al., Positive and negative regulation of gene expression in eukaryotic cells with an inducible transcriptional regulator. Gene Ther, 1997. 4(5): p. 432-41.
36. Drysdale, C. M., et al., The transcriptional activator GCN4 contains multiple activation domains that are critically dependent on hydrophobic amino acids. Mol Cell Biol, 1995. 15(3): p. 1220-33.
37. Fanara, P., et al., Quantitative analysis of nuclear localization signal (NLS)-importin alpha interaction through fluorescence depolarization. Evidence for auto-inhibitory regulation of NLS binding. J Biol Chem, 2000. 275(28): p. 21218-23.
38. Zoltowski, B. D., et al., Conformational switching in the fungal light sensor Vivid. Science, 2007. 316(5827): p. 1054-7.

What is claimed is:

1. A light-switchable gene expression system, comprising: a) a gene encoding a photosensitive recombinant light-switchable eukaryotic transcription factor, said recombinant light-switchable eukaryotic transcription factor is one protein including a first polypeptide as DNA-binding domain, a second polypeptide as light-switchable domain and a third polypeptide as transcriptional regulatory domain; b) a target transcription unit, including at least one reaction element recognized/bound by the first polypeptide, a promoter regulated by the third polypeptide and a nucleic acid sequence to be transcribed; wherein said second polypeptide is selected from LOV2 domain of *Neurospora crassa* VIVID, AsLOV2 domain of oat phytochrome gene 1 and AuLOV domain in Aureochrome1 of *Stramenopile algae Vaucheria frigida*.

2. The light-switchable gene expression system according to claim 1, wherein said first polypeptide, second polypeptide and third polypeptide were linked each other operatively and/or wherein said reaction element, promoter and nucleic acid sequence to be transcribed were linked each other operatively.

3. The light-switchable gene expression system according to claim 1, wherein said first polypeptide is selected from helix-turn-helix DNA-binding domain, zinc finger motif or zinc cluster DNA-binding domain, leucine zipper DNA-binding domain, winged helix DNA-binding domain, winged helix-turn-helix DNA-binding domain, helix-loop-helix DNA-binding domain, high mobility family DNA-binding domain and B3 DNA-binding domain.

4. The light-switchable gene expression system according to claim 3, wherein said first polypeptide is selected from DNA binding domain of yeast Gal4 protein.

5. The light-switchable gene expression system according to claim 1, wherein said third polypeptide is selected from transcriptional activation domains rich in acidic amino acids, transcriptional activation domains rich in proline, transcriptional activation domains rich in serine/threonine and transcriptional activation domains rich in glutamine, and Kruppel-retated box transcriptional repression domain.

6. The light-switchable gene expression system according to claim 5, wherein the third polypeptide is selected from transcriptional activation domains of the herpes simplex virus VP16 particle protein, transcriptional activation domains of yeast Gal4 protein, transcriptional activation domains of NF-κB p65 subunit, transcriptional activation domains of yeast general control protein 4, and Kruppel-retated box transcriptional repression domain of the zinc finger 354A protein.

7. The light-switchable gene expression system according to claim 1, further comprising a fourth polypeptide, i.e., nuclear localization signal peptide, which can promote the transportation of the recombinant light-switchable transcription factor into the nucleus, said fourth polypeptide links with the first, the second and the third polypeptides directly or via a linker peptide.

8. The light-switchable gene expression system according to claim 1, further comprising a fifth polypeptide regulated by hormones, said fifth polypeptide links with the first, the second and the third polypeptides directly or via a linker peptide.

9. The light-switchable gene expression system according to claim 1, wherein said reaction element is a DNA motif which can be specifically recognized and bound by the first polypeptide.

10. The light-switchable gene expression system according to claim 9, wherein said reaction element is selected from Gal4 binding element.

11. The light-switchable gene expression system according to claim 1, wherein the promoter is selected from the adenovirus late promoter, cytomegalovirus (CMV) minimal promoter, yeast Gal1 gene promoter and SV40 promoter.

12. The light-switchable gene expression system according to claim 1, wherein said first polypeptide and said second polypeptide constitute a light-switchable DNA-binding protein.

* * * * *